United States Patent
Tamai et al.

(10) Patent No.: US 8,648,075 B2
(45) Date of Patent: Feb. 11, 2014

(54) SUBSTITUTED PYRIDO[2,3-B]PYRAZINES AND AN AGROCHEMICAL COMPOSITION THEREOF

(71) Applicants: Kumiai Chemical Industry Co., Ltd., Tokyo (JP); Ihara Chemical Industry Co., Ltd., Tokyo (JP)

(72) Inventors: Ryuji Tamai, Shizuoka (JP); Minoru Ito, Shizuoka (JP); Masami Kobayashi, Tokyo (JP); Takashi Mitsunari, Tokyo (JP); Yuki Nakano, Tokyo (JP)

(73) Assignees: Kumiai Chemical Industry Co., Ltd., Tokyo (JP); Ihara Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 13/743,574

(22) Filed: Jan. 17, 2013

(65) Prior Publication Data
US 2013/0137577 A1 May 30, 2013

Related U.S. Application Data

(62) Division of application No. 12/671,411, filed as application No. PCT/JP2008/002055 on Jul. 31, 2008, now Pat. No. 8,389,523.

(30) Foreign Application Priority Data

Aug. 1, 2007 (JP) ................................ 2007-201387

(51) Int. Cl.
A61K 31/495 (2006.01)
(52) U.S. Cl.
USPC .......................................... 514/249; 544/350
(58) Field of Classification Search
USPC .......................................... 514/249; 544/350
See application file for complete search history.

(56) References Cited

U.S. PATENT DOCUMENTS

| | | | |
|---|---|---|---|
| 3,997,535 | A | 12/1976 | Collins et al. |
| 4,181,724 | A | 1/1980 | Hall et al. |
| 4,800,223 | A | 1/1989 | Ohkura |
| 6,380,384 | B1 | 4/2002 | Nakazato et al. |
| 2006/0270666 | A1 | 11/2006 | Bladh et al. |

FOREIGN PATENT DOCUMENTS

| | | |
|---|---|---|
| CA | 1026333 A1 | 2/1978 |
| CA | 2313055 A1 | 6/1999 |
| CN | 1269794 A | 10/2000 |
| CN | 1280569 A | 1/2001 |
| CN | 1845909 A | 10/2006 |
| EP | 283261 A2 | 9/1988 |
| EP | 1 020 453 A1 | 7/2000 |
| EP | 1 048 655 A1 | 11/2000 |
| JP | 50-29583 | 3/1975 |
| JP | 4-5287 | 1/1992 |
| JP | 11-236375 A | 8/1999 |
| JP | 2000-80085 | 3/2000 |
| JP | 2007-504127 | 3/2007 |
| WO | 2005/021512 A1 | 3/2005 |

OTHER PUBLICATIONS

Clark-Lewis, et al. Journal of the Chemical Society, 1957, 430-439.*
Ahmad et al., "Preparation of 3-Substituted 6,7-Dimetoxyquinoxquinoxalin-2(1H)-ones and Studies of Their Potential as Fluoroinophores", Tetrahedron, 1995, vol. 51, No. 47, pp. 12899-12910.
Ahmad et al., Quinoxaline Derivatives VII. The Mechanism of the Formation of 6-Chloro-1,2,3,4,2',3'-hexahydro-4,1'-dimethoxy-3,2'-dioxoquinoxaline-2-spiro-3'-indole from a Quinoxaline N-Oxide Derivative by Nucleophilic Chlorination, Bulletin of the Chemical Society of Japan, 1965, vol. 38, No. 10, pp. 1659-1663.
Sonna et al., "Synthesis of substituted 2-ethoxycarbonyl- and 2-carboxyquinoxalin-3-ones for evaluation of antimicrobial and anti-cancer activity", IL Farmaco, 1998, vol. 53, No. 7, pp. 455-461.
Savelli et al., "Synhesis of 1H-Pyrazino [1,2-a] pyrido [2,3e] pyrazine and 2H-Pyrano [2,3-b] pyrido [2,3-e] pyazine Derivatives", Journal of Heterocyclic Chemistry, 1996, vol. 33, No. 6, pp. 1737-1742.
Database Caplus on STN, AN 1965:3098, DN 62:3098, Ahmad et al., Quinoxaline derivatives. I. Intramolecular rearrangement of certain quinoxalinecarboxanilides to spiroindoles, Journal of the Chemical Society, 1964, pp. 4053-4056.

(Continued)

Primary Examiner — Douglas M Willis
(74) Attorney, Agent, or Firm — Edwards Wildman Palmer LLP; Peter F. Corless; Christine C. O'Day

(57) ABSTRACT

The present invention is to provide an oxopyrazine derivative having an excellent herbicidal activity and besides exhibiting high safety for useful crops and the like, or a salt thereof, and a herbicide containing the same.
The present invention relates to an oxopyrazine derivative represented by formula [I]:

[Chemical Formula 39]

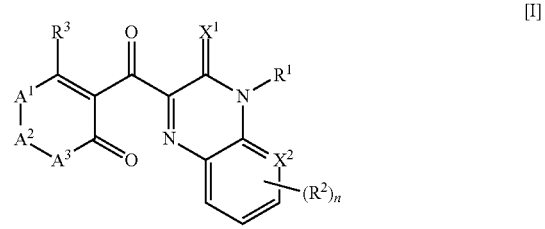

wherein $X^1$ represents an oxygen atom or a sulfur atom; $X^2$ represents CH or $N(O)_m$; m represents an integer of 0 or 1; $R^1$ represents a hydrogen atom, a $C_1$-$C_{12}$ alkyl group and the like; $R^2$ represents a halogen atom, a cyano group and the like; $R^3$ is a hydroxyl group, a halogen atom and the like; $A^1$ represents $C(R^4R^5)$; $A^2$ represents $C(R^6R^7)$ or C=O; $A^3$ represents $C(R^8R^9)$; $R^4$ to $R^9$ represent a hydrogen atom or an alkyl group,
  or a salt thereof, and a herbicide containing these compounds.

13 Claims, No Drawings

(56) References Cited

OTHER PUBLICATIONS

XP-002601979—Database Accession No. 1961:8147—Abstract: M.S. Habib et al., "reduction of 3-hydroxyquinoxaline-2-carboxylic acid and derivatives with sodium dithionite", Chemical Abstracts Service—Database CA (Online), Journal of the Chemical Society, 2384-6 Coden: JCSOA9; ISSN: 0368-1769 (1960).

Chem. Abstracts Accession No. 1952:48667: F.E. King et al., "constitution of the products formed from o-phenylanediamines and alioxan in neutral solution" Journal of the Chemical Society, pp. 3379-3382 (1951).

* cited by examiner

SUBSTITUTED PYRIDO[2,3-B]PYRAZINES AND AN AGROCHEMICAL COMPOSITION THEREOF

BACKGROUND OF THE INVENTION

1. Field of the Invention

The present invention relates to a novel oxopyrazine derivative or a salt thereof, a herbicide containing the same as an active ingredient, and a method of using the same.

2. Description of Related Art

BACKGROUND ART

Several compounds among the 1,3-cyclohexanedione derivatives which have been acylated at the 2-position with an arylcarbonyl group, have already been commercially available as agrochemicals. For example, mesotrione is attracting public attention as a foliar applied herbicide for corn having a new mechanism of action. A 1,3-cyclohexanedione is a tautomer, which exists also as 1-hydroxycyclohexene-3-one which is an enol form thereof, and this derivative has been developed as a compound for various agrochemical uses.

For example, a derivative having the aryl group of the arylcarbonyl group substituting at the 2-position changed to various heteroaryl or cycloalkyl groups such as pyrazine (see, Patent Document 1), a derivative having the 1,3-cyclohexanedione ring fused at the 4- and 5-positions with a cyclopropane ring (see, Patent Document 2), a derivative having the arylcarbonyl group at the 2-position changed to a pyrimidin-5-ylcarbonyl group derivative (see, Patent Document 3), a derivative having the arylcarbonyl group at the 2-position changed to a pyrazin-2-ylcarbonyl group derivative (see, Patent Document 4), a derivative having the arylcarbonyl group at the 2-position changed to a 1,2,3-thiadiazol-5-ylcarbonyl group derivative (see, Patent Document 5), derivatives having the arylcarbonyl group at the 2-position changed to a pyridinecarbonyl group derivative (see, Patent Documents 2, 6, 7, 8, 9 and 10), derivatives having the arylcarbonyl group at the 2-position changed to a quinolinecarbonyl group derivative (see, Patent Documents 11 and 12), a derivative having the arylcarbonyl group at the 2-position changed to a heteroarylcarbonyl group formed from a benzazole (see, Patent Document 13), a derivative having the arylcarbonyl group at the 2-position changed to an azolecarbonyl group derivative formed from an 1,2-azole (see, Patent Document 14), and the like have been reported. Furthermore, derivatives in which the 4-position and the 6-position of the 1,3-cyclohexanedione ring are crosslinked by an alkylene group such as an ethylene group, have also been reported (see, Patent Documents 8, 11, 12, 13, 14, 15 and 16). In addition, it has also been reported to have a 3,5-cyclohexanedione-1-thione ring in which the 5-position of the 1,3-cyclohexanedione ring has been changed to an oxo group, and the 1-position has been changed to a thiocarbonyl group (see, Patent Document 17).

As such, a large number of cyclohexanedione compounds having herbicidal activity have been reported, but there is no known cyclohexanedione compound having a dihydropyrazine ring substituted with an oxo group or a thioxo group (in the present specification, these may be generically called (thio)oxo), such as the compound of the present invention represented by the following formula [I].

Patent Document 1: EP-283261
Patent Document 2: WO 91/00260
Patent Document 3: U.S. Pat. No. 4,708,732
Patent Document 4: DE-3902818
Patent Document 5: EP-338525
Patent Document 6: JP-A No. 2-78662
Patent Document 7: JP-A No. 3-52862
Patent Document 8: JP-A No. 4-29973
Patent Document 9: WO 96/14285
Patent Document 10: WO 2000/39094
Patent Document 11: JP-A No. 2000-16982
Patent Document 12: WO 2000/14069
Patent Document 13: WO 2000/68210
Patent Document 14: JP-A No. 2005-200401
Patent Document 15: WO 2005/058831
Patent Document 16: WO 2006/066871
Patent Document 17: DE 10256354

BRIEF SUMMARY OF THE INVENTION

As discussed in the above, 1,3-cyclohexanedione compounds substituted with a specific heteroarylcarbonyl group are known to have an herbicidal activity, but since these compounds need to be applied in high doses, they are not satisfactory as herbicides. Thus, there has been a demand for the development of a herbicide showing excellent properties in lower doses.

The present invention has been achieved under such circumstances, and an object of the present invention is to provide a compound having a herbicidal activity which has no drug-induced damages against useful plants and useful crops, and can control various weeds growing in upland fields, orchards, paddy fields and non-agricultural lands at low doses, and a herbicide containing the compound.

DETAILED DESCRIPTION OF THE INVENTION

In order to achieve the above-described purpose, the inventors of the present invention devotedly conducted research on the chemical structure and herbicidal activity of cyclohexanedione compounds. As a result, they found that a cyclohexanedione compound having a pyrazine ring substituted with an oxo group or a thioxo group can control various weeds growing in upland fields, orchards, paddy fields and non-agricultural lands for a long time, and exhibits high safety against useful plants, useful crops and the like, thus completing the present invention.

Thus, the present invention is characterized in that for a 2-heteroarylcarbonyl-1,3-cyclohexanedione compound having a herbicidal activity, a 2-(thio)oxopyrazin-3-yl group which may be substituted, and preferably a 2-(thio)oxobenzopyrazin-3-yl group which may be substituted or a 2-(thio)oxopyridopyrazine-3-yl group which may be substituted, is used as the heteroaryl group.

More specifically, the present invention relates to the following (1) to (7).

(1) An oxopyrazine derivative represented by formula [I], or an agrochemically acceptable salt thereof:

[Chemical Formula 1]

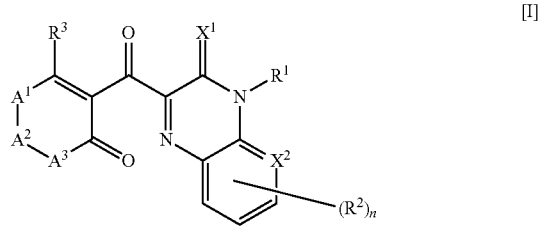

wherein $X^1$ represents an oxygen atom or a sulfur atom;

$X^2$ represents CH (the carbon atom may be substituted with $R^2$), that is, CH which may be substituted with a substituent $R^2$, or $N(O)_m$;

m represents an integer of 0 or 1;

$R^1$ represents a hydrogen atom; a $C_1$-$C_{12}$ alkyl group; a $C_2$-$C_6$ alkenyl group; a $C_2$-$C_6$ alkynyl group; a $C_3$-$C_8$ cycloalkyl group; a $C_3$-$C_8$ cycloalkyl-$C_1$-$C_6$ alkyl group; a $C_1$-$C_6$ haloalkyl group; a $C_2$-$C_6$ haloalkenyl group; a $C_2$-$C_6$ haloalkynyl group; a $C_3$-$C_8$ halocycloalkyl group; a $C_3$-$C_8$ halocycloalkyl-$C_1$-$C_6$ alkyl group; an amino-$C_1$-$C_6$ alkyl group; a nitro-$C_1$-$C_6$ alkyl group; a mono($C_1$-$C_6$ alkyl)amino-$C_1$-$C_6$ alkyl group; a di($C_1$-$C_6$ alkyl)amino-$C_1$-$C_6$ alkyl group; a $C_1$-$C_6$ alkylthio-$C_1$-$C_6$ alkyl group; a $C_1$-$C_6$ alkylsulfinyl-$C_1$-$C_6$ alkyl group; a $C_1$-$C_6$ alkylsulfonyl-$C_1$-$C_6$ alkyl group; a $C_1$-$C_6$ haloalkylthio-$C_1$-$C_6$ alkyl group; a $C_1$-$C_6$ haloalkylsulfinyl-$C_1$-$C_6$ alkyl group; a $C_1$-$C_6$ haloalkylsulfonyl-$C_1$-$C_6$ alkyl group; a $C_1$-$C_6$ alkoxy-$C_1$-$C_6$ alkyl group; a hydroxy-$C_1$-$C_6$ alkyl group; a phenyl-$C_1$-$C_6$ alkoxy-$C_1$-$C_6$ alkyl group (the phenyl moiety of the group may be substituted with one or two or more identical or different $R^4$s), that is, a phenyl-$C_1$-$C_6$ alkoxy-$C_1$-$C_6$ alkyl group in which the phenyl group may be substituted with one or more identical or different $R^4$s; a $C_1$-$C_6$ alkoxy-$C_1$-$C_6$ alkoxy-$C_1$-$C_6$ alkyl group; a $C_3$-$C_8$ cycloalkyloxy-$C_1$-$C_6$ alkyl group; a $C_3$-$C_8$ cycloalkyl-$C_1$-$C_6$ alkoxy-$C_1$-$C_6$ alkyl group; a phenyloxy-$C_1$-$C_6$ alkyl group (the phenyl moiety of the group may be substituted with one or two or more identical or different $R^4$s), that is, a phenyloxy-$C_1$-$C_6$ alkyl group in which the phenyl group may be substituted with one or two or more identical or different $R^4$s; a heterocyclic-oxy-$C_1$-$C_6$ alkyl group in which the heterocyclic moiety has 2 to 10 carbon atoms and 1 to 5 heteroatoms selected from an oxygen atom, a sulfur atom and a nitrogen atom (the heterocyclic moiety having 2 to 10 carbon atoms and having 1 to 5 heteroatoms selected from an oxygen atom, a sulfur atom and a nitrogen atom in the group, may be substituted with one or two or more identical or different $R^5$s), that is, a heterocyclic-oxy-$C_1$-$C_6$ alkyl group in which the heterocyclic moiety has 2 to 10 carbon atoms and 1 to 5 heteroatoms selected from an oxygen atom, a sulfur atom and a nitrogen atom, and may be substituted with one or two or more identical or different $R^5$s; a phenylthio-$C_1$-$C_6$ alkyl group (the phenyl moiety of the group may be substituted with one or two or more identical or different $R^4$s), that is, a phenylthio-$C_1$-$C_6$ alkyl group in which the phenyl group may be substituted with one or two or more identical or different $R^4$s; a phenylsulfinyl-$C_1$-$C_6$ alkyl group (a phenyl of the group may be substituted with one or two or more identical or different $R^4$s), that is, a phenyl group may be substituted with one or two or more identical or different $R^4$s; a phenylsulfonyl-$C_1$-$C_6$ alkyl group (a phenyl of the group may be substituted with one or two or more identical or different $R^4$s), that is, a phenyl group may be substituted with one or two or more identical or different $R^4$s; a $C_1$-$C_6$ haloalkoxy-$C_1$-$C_6$ alkyl group; a heterocyclic-$C_1$-$C_6$ alkoxy-$C_1$-$C_6$ alkyl group in which the heterocyclic moiety has 2 to 10 carbon atoms and 1 to 5 heteroatoms selected from an oxygen atom, a sulfur atom and a nitrogen atom (the heterocyclic moiety having 2 to 10 carbon atoms and having 1 to 5 heteroatoms selected from an oxygen atom, a sulfur atom and a nitrogen atom in the group, may be substituted with one or two or more identical or different $R^5$s), that is, a heterocyclic-$C_1$-$C_6$ alkoxy-$C_1$-$C_6$ alkyl group in which the heterocyclic moiety has 2 to 10 carbon atoms and 1 to 5 heteroatoms selected from an oxygen atom, a sulfur atom and a nitrogen atom, and may be substituted with one or two or more identical or different $R^5$s; a $C_1$-$C_6$ alkylthio-$C_1$-$C_6$ alkoxy-$C_1$-$C_6$ alkyl group; a $C_1$-$C_6$ alkylsulfinyl $C_1$-$C_6$ alkoxy-$C_1$-$C_6$ alkyl group; a $C_1$-$C_6$ alkylsulfonyl-$C_1$-$C_6$ alkoxy-$C_1$-$C_6$ alkyl group; a cyano-$C_1$-$C_6$ alkoxy-$C_1$-$C_6$ alkyl group; a cyano-$C_1$-$C_6$ alkyl group; a $C_1$-$C_6$ alkylcarbonyloxy-$C_1$-$C_6$ alkyl group; a $C_1$-$C_6$ acyl-$C_1$-$C_6$ alkyl group; a $C_1$-$C_6$ acylamino group; a di($C_1$-$C_6$ alkoxy)-$C_1$-$C_6$ alkyl group; a $C_1$-$C_6$ alkoxycarbonyl-$C_1$-$C_6$ alkyl group; a $C_1$-$C_6$ alkoxyimino-$C_1$-$C_6$ alkyl group; a $C_1$-$C_6$ alkylideneaminooxy-$C_1$-$C_6$ alkyl group; a $(R^6R^7N$—$C$=$O)$—$C_1$-$C_6$ alkyl group; a $C_6$-$C_{10}$ aryl-$C_1$-$C_6$ alkyl group (the aryl moiety of the group may be substituted with one or two or more identical or different $R^8$s), that is, a $C_6$-$C_{10}$ aryl-$C_1$-$C_6$ alkyl group in which the aryl group may be substituted with one or two or more identical or different $R^8$s; a heterocyclic-$C_1$-$C_6$ alkyl group in which the heterocyclic moiety has 2 to 10 carbon atoms and 1 to 5 heteroatoms selected from an oxygen atom, a sulfur atom and a nitrogen atom (the heterocyclic moiety having 2 to 10 carbon atoms and 1 to 5 heteroatoms selected from an oxygen atom, a sulfur atom and a nitrogen atom in the group, may be substituted with one or two or more identical or different $R^9$s), that is, a heterocyclic-$C_1$-$C_6$ alkyl group in which the heterocyclic moiety has 2 to 10 carbon atoms and 1 to 5 heteroatoms selected from an oxygen atom, a sulfur atom and a nitrogen atom, and may be substituted with one or two or more identical or different $R^9$s; an $NR^{10}R^{11}$ group; a $C_1$-$C_6$ alkoxy group; a $C_6$-$C_{10}$ aryl group (the group may be substituted with one or two or more identical or different $R^{12}$s), that is, a $C_6$-$C_{10}$ aryl group which may be substituted with one or two or more identical or different $R^{12}$s; or a heterocyclic group having 2 to 10 carbon atoms and 1 to 5 heteroatoms selected from an oxygen atom, a sulfur atom and a nitrogen atom (the group may be substituted with one or two or more identical or different $R^{13}$s), that is, a heterocyclic group which has 2 to 10 carbon atoms and 1 to 5 heteroatoms selected from an oxygen atom, a sulfur atom and a nitrogen atom, and may be substituted with one or two or more identical or different $R^{13}$s;

$R^2$ represents a halogen atom; a hydroxyl group; a nitro group; a cyano group; a $C_1$-$C_6$ alkyl group; a $C_3$-$C_8$ cycloalkyl group; a $C_3$-$C_8$ cycloalkyl-$C_1$-$C_6$ alkyl group; a $C_2$-$C_6$ alkenyl group; a $C_2$-$C_6$ alkynyl group; a $C_1$-$C_6$ haloalkyl group; a $C_2$-$C_6$ haloalkenyl group; a $C_2$-$C_6$ haloalkynyl group; a $C_3$-$C_8$ halocycloalkyl group; a $C_3$-$C_8$ halocycloalkyl-$C_1$-$C_6$ alkyl group; a $C_1$-$C_6$ alkoxy group; a $C_3$-$C_8$ cycloalkyloxy group; a $C_3$-$C_8$ cycloalkyl-$C_1$-$C_6$ alkyloxy group; a $C_2$-$C_6$ alkenyloxy group; a $C_2$-$C_6$ alkynyloxy group; a $C_1$-$C_6$ haloalkoxy group; a $C_1$-$C_6$ alkoxy-$C_1$-$C_6$ alkoxy group; a $C_1$-$C_6$ alkylcarbonyloxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; an amino group; a mono($C_1$-$C_6$ alkyl)amino group; a di($C_1$-$C_6$ alkyl) amino group; a $C_1$-$C_6$ acylamino group; a hydroxy-$C_1$-$C_6$ alkyl group; a $C_1$-$C_6$ alkoxy-$C_1$-$C_6$ alkyl group; a $C_1$-$C_6$ alkylthio-$C_1$-$C_6$ alkyl group; a $C_1$-$C_6$ alkylsulfinyl-$C_1$-$C_6$ alkyl group; a $C_1$-$C_6$ alkylsulfonyl-$C_1$-$C_6$ alkyl group; a $C_1$-$C_6$ haloalkylthio-$C_1$-$C_6$ alkyl group; a $C_1$-$C_6$ haloalkylsulfinyl-$C_1$-$C_6$ alkyl group; a $C_1$-$C_6$ haloalkylsulfonyl-$C_1$-$C_6$ alkyl group; a cyano-$C_1$-$C_6$ alkyl group; a $C_1$-$C_6$ acyl group; a $C_1$-$C_6$ alkoxyimino-$C_1$-$C_6$ alkyl group; a carboxyl group; a $C_1$-$C_6$ alkoxycarbonyl group; a carbamoyl group; a mono($C_1$-$C_6$ alkyl)aminocarbonyl group; a di($C_1$-$C_6$ alkyl)aminocarbonyl group; or a heterocyclic group having 2 to 10 carbon atoms and 1 to 5 heteroatoms selected from an oxygen atom, a sulfur atom and a nitrogen atom (the heterocyclic moiety having 2 to 10 carbon atoms and 1 to 5 heteroatoms selected from an oxygen atom, a sulfur atom and a nitrogen atom in the group, may be substituted with one or two or more identical or different $R^{14}$s), that is, a heterocyclic group in which the heterocyclic moiety has 2 to 10 carbon atoms and 1 to 5 heteroatoms selected from an oxygen atom, a sulfur atom and a nitrogen atom, and may be substituted with one or two or more identical or different $R^{14}$s; and furthermore, two adjacent $R^2$s may be joined with the respective carbon atoms to which $R^2$s are directly bound, to form a 4- to 8-membered carbocyclic ring or a 4- to 8-membered heterocyclic ring having 1 to 4 heteroatoms selected from an oxygen atom, a sulfur atom and a nitrogen atom, and the ring thus formed may be substituted with a halogen atom, a cyano group, a nitro group, a $C_1$-$C_6$ alkyl group, a $C_1$-$C_6$ haloalkyl group, a $C_1$-$C_6$ alkoxy group, a $C_1$-$C_6$ haloalkoxy group or an oxo group;

n represents an integer from 0 to 4 when $X^2$ is CH (the group may be substituted with $R^2$), that is, when $X^2$ is CH which may be substituted with a substituent $R^2$, and n represents an integer from 0 to 3 when $X^2$ is $N(O)_m$;

$R^3$ represents a hydroxyl group; $O^-M^+$ (wherein $M^+$ is an alkali metal cation or an ammonium cation); an amino group; a halogen atom; a $C_1$-$C_6$ alkylsulfonyloxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; a $C_2$-$C_6$ alkenylthio group; a $C_2$-$C_6$ alkenylsulfinyl group; a $C_2$-$C_6$ alkenylsulfonyl group; a $C_2$-$C_6$ alkynylthio group; a $C_2$-$C_6$ alkynylsulfinyl group; a $C_2$-$C_6$ alkynylsulfonyl group; a $C_1$-$C_6$ alkylcarbonyloxy group; a $C_2$-$C_6$ alkenylcarbonyloxy group; a $C_2$-$C_6$ alkynylcarbonyloxy group; a phenoxy group (the group may be substituted with one or two or more identical or different $R^{14}$s), that is, a phenoxy group which may be substituted with one or two or more identical or different $R^{14}$s; a phenylthio group (the group may be substituted with one or two or more identical or different $R^{14}$s), that is, a phenylthio group which may be substituted with one or two or more identical or different $R^{14}$s; a phenylsulfinyl group (the group may be substituted with one or two or more identical or different $R^{14}$s), that is, a phenylsulfinyl group which may be substituted with one or two or more identical or different $R^{14}$s; a phenylsulfonyl group (the group may be substituted with one or two or more identical or different $R^{14}$s), that is, a phenylsulfonyl group which may be substituted with one or two or more identical or different $R^{14}$s; a phenylsulfonyloxy group (the group may be substituted with one or two or more identical or different $R^{14}$s), that is, a phenylsulfonyloxy group which may be substituted with one or two or more identical or different $R^{14}$s; a phenylcarbonyloxy group (the group may be substituted with one or two or more identical or different $R^{14}$s), that is, a phenyl carbonyloxy group which may be substituted with one or two or more identical or different $R^{14}$s; a 1,2,4-triazol-1-yl group; a 1,2,3-triazol-1-yl group; a 1,2,3-triazol-2-yl group; an imidazol-1-yl group; a pyrazol-1-yl group; a tetrazol-1-yl group; or a tetrazol-2-yl group;

$R^4$ represents a halogen atom; a nitro group; a cyano group; a $C_1$-$C_6$ alkyl group; a $C_2$-$C_6$ alkenyl group; a $C_2$-$C_6$ alkynyl group; a $C_3$-$C_8$ cycloalkyl group; a $C_1$-$C_6$ haloalkyl group; a $C_1$-$C_6$ alkoxy group; a $C_2$-$C_6$ alkenyloxy group; a $C_2$-$C_6$ alkynyloxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; a $C_1$-$C_6$ alkoxycarbonyl group; a $C_1$-$C_6$ acyl group; or a $C_1$-$C_6$ alkoxy-$C_1$-$C_6$ alkyl group;

$R^5$ represents an oxo group; a halogen atom; a nitro group; a cyano group; a $C_1$-$C_6$ alkyl group; a $C_2$-$C_6$ alkenyl group; a $C_2$-$C_6$ alkynyl group; a $C_3$-$C_8$ cycloalkyl group; a $C_1$-$C_6$ haloalkyl group; a $C_1$-$C_6$ alkoxy group; a $C_2$-$C_6$ alkenyloxy group; a $C_2$-$C_6$ alkynyloxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; a $C_1$-$C_6$ alkoxycarbonyl group; a $C_1$-$C_6$ acyl group; or a $C_1$-$C_6$ alkoxy-$C_1$-$C_6$ alkyl group;

$R^6$ and $R^7$ each independently represent a $C_1$-$C_6$ alkyl group, and furthermore, $R^6$ and $R^7$ may be joined with the nitrogen atom to which these are bound, to form a 5- to 6-membered ring, while the ring thus formed may have an oxygen atom interposed, in addition to the nitrogen atom to which $R^6$ and $R^7$ are bound;

$R^8$ represents a halogen atom; a nitro group; a cyano group; a $C_1$-$C_6$ alkyl group; a $C_2$-$C_6$ alkenyl group; a $C_2$-$C_6$ alkynyl group; a $C_3$-$C_8$ cycloalkyl group; a $C_1$-$C_6$ haloalkyl group; a $C_1$-$C_6$ alkoxy group; a $C_2$-$C_6$ alkenyloxy group; a $C_2$-$C_6$ alkynyloxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; a $C_1$-$C_6$ alkoxycarbonyl group; a $C_1$-$C_6$ acyl group; or a $C_1$-$C_6$ alkoxy-$C_1$-$C_6$ alkyl group;

$R^9$ represents an oxo group; a halogen atom; a nitro group; a cyano group; a $C_1$-$C_6$ alkyl group; a $C_2$-$C_6$ alkenyl group; a $C_2$-$C_6$ alkynyl group; a $C_3$-$C_8$ cycloalkyl group; a $C_1$-$C_6$ haloalkyl group; a $C_1$-$C_6$ alkoxy group; a $C_2$-$C_6$ alkenyloxy group; a $C_2$-$C_6$ alkynyloxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; a $C_1$-$C_6$ alkoxycarbonyl group; a $C_1$-$C_6$ acyl group; or a $C_1$-$C_6$ alkoxy-$C_1$-$C_6$ alkyl group;

$R^{10}$ and $R^{11}$ each independently represent a hydrogen atom; a $C_1$-$C_6$ alkyl group; or a $C_1$-$C_6$ alkoxycarbonyl group, and furthermore, $R^{10}$ and $R^{11}$ may be joined together with the nitrogen atom to which these are bound, to form a 5- to 6-membered ring, while the ring thus formed may have a sulfur atom and/or an oxygen atom interposed, in addition to the nitrogen atom to which $R^{10}$ and $R^{11}$ are bound;

$R^{12}$ represents a halogen atom; a hydroxyl group; a nitro group; a cyano group; a $C_1$-$C_6$ alkyl group; a $C_3$-$C_8$ cycloalkyl group; a $C_3$-$C_8$ cycloalkyl-$C_1$-$C_6$ alkyl group; a $C_2$-$C_6$ alkenyl group; a $C_2$-$C_6$ alkynyl group; a $C_1$-$C_6$ haloalkyl group; a $C_2$-$C_6$ haloalkenyl group; a $C_3$-$C_8$ halocycloalkyl group; a $C_3$-$C_8$ halocycloalkyl-$C_1$-$C_6$ alkyl group; a $C_1$-$C_6$ alkoxy group; a $C_3$-$C_8$ cycloalkyloxy group; a $C_2$-$C_6$ alkenyloxy group; a $C_2$-$C_6$ alkynyloxy group; a $C_1$-$C_6$ alkylcarbonyloxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; an amino group; a $C_1$-$C_6$ acylamino group; a mono($C_1$-$C_6$ alkyl)amino group; a di($C_1$-$C_6$ alkyl)amino group; a hydroxy-$C_1$-$C_6$ alkyl group; a $C_1$-$C_6$ alkoxy-$C_1$-$C_6$ alkyl group; a $C_1$-$C_6$ alkylthio-$C_1$-$C_6$ alkyl group; a $C_1$-$C_6$ alkylsulfinyl-$C_1$-$C_6$ alkyl group; a $C_1$-$C_6$ alkylsulfonyl-$C_1$-$C_6$ alkyl group; a $C_1$-$C_6$ haloalkylthio-$C_1$-$C_6$ alkyl group; a $C_1$-$C_6$ haloalkylsulfinyl-$C_1$-$C_6$ alkyl group; a $C_1$-$C_6$ haloalkylsulfonyl-$C_1$-$C_6$ alkyl group; a cyano-$C_1$-$C_6$ alkyl group; a $C_1$-$C_6$ alkoxy-$C_1$-$C_6$ alkoxy group; a $C_3$-$C_8$ cycloalkyl-$C_1$-$C_6$ alkyloxy group; a $C_1$-$C_6$ haloalkoxy-$C_1$-$C_6$ alkoxy group; a cyano-$C_1$-$C_6$ alkoxy group; a $C_1$-$C_6$ acyl group; a $C_1$-$C_6$ alkoxyimino-$C_1$-$C_6$ alkyl group; a carboxyl group; a $C_1$-$C_6$ alkoxycarbonyl group; a carbamoyl group; a mono($C_1$-$C_6$ alkyl)aminocarbonyl group; a di($C_1$-$C_6$ alkyl)aminocarbonyl group; a heterocyclic group having 2 to 10 carbon atoms and 1 to 5 heteroatoms selected from an oxygen atom, a sulfur atom and a nitrogen atom (the heterocyclic moiety of the group may be substituted with one or two or more identical or different $R^{14}$s), that is, a heterocyclic group which has 2 to 10 carbon atoms and 1 to 5 heteroatoms selected from an oxygen atom, a sulfur atom and a nitrogen atom, and may be substituted with one or two or more identical or different $R^{14}$s; or a heterocyclic-$C_1$-$C_6$ alkoxy group in which the heterocyclic moiety has 2 to 10 carbon atoms and 1 to 5 heteroatoms selected from an oxygen atom, a sulfur atom and a nitrogen atom (the heterocyclic moiety having 2 to 10 carbon atoms and having 1 to 5 heteroatoms selected from an oxygen atom, a sulfur atom and a nitrogen atom in the group, may be substituted with one or two or more identical or different $R^{14}$s), that is, a heterocyclic-$C_1$-$C_6$ alkoxy group in which the heterocyclic moiety has 2 to 10 carbon atoms and 1 to 5 heteroatoms selected from an oxygen atom, a sulfur atom and a nitrogen atom, and may be substituted with one or two or more identical or different $R^{14}$s, or two adjacent $R^{12}$s may be joined with the respective carbon atoms to which $R^{12}$s are directly bound, to form a 4- to 8-membered carbocyclic ring or a 4- to 8-membered heterocyclic ring having 1 to 4 heteroatoms selected from an oxygen atom, a sulfur atom and a nitrogen atom, while the ring thus formed may be substituted with a halogen atom, a cyano group, a nitro group, a $C_1$-$C_6$ alkyl group, a $C_1$-$C_6$ haloalkyl group, a $C_1$-$C_6$ alkoxy group, a $C_1$-$C_6$ haloalkoxy group or an oxo group;

$R^{13}$ represents an oxo group; a thioxo group; a hydroxyl group; a halogen atom; a nitro group; a cyano group; a $C_1$-$C_6$ alkyl group; a $C_2$-$C_6$ alkenyl group; a $C_2$-$C_6$ alkynyl group; a $C_3$-$C_8$ cycloalkyl group; a $C_3$-$C_8$ cycloalkyl-$C_1$-$C_6$ alkyl group; a $C_1$-$C_6$ haloalkyl group; a $C_2$-$C_6$ haloalkenyl group; a $C_3$-$C_8$ halocycloalkyl group; a $C_3$-$C_8$ halocycloalkyl-$C_1$-$C_6$ alkyl group; a $C_1$-$C_6$ alkoxy group; a $C_2$-$C_6$ alkenyloxy group; a $C_2$-$C_6$ alkynyloxy group; a $C_3$-$C_8$ cycloalkyloxy group; a $C_3$-$C_8$ cycloalkyl-$C_1$-$C_6$ alkyloxy group; a $C_1$-$C_6$ haloalkoxy group; a $C_1$-$C_6$ alkoxy-$C_1$-$C_6$ alkoxy group; a $C_1$-$C_6$ haloalkoxy-$C_1$-$C_6$ alkoxy group; a cyano-$C_1$-$C_6$ alkoxy group; a $C_1$-$C_6$ alkylcarbonyloxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; an amino group; a mono($C_1$-$C_6$ alkyl)amino group; a di($C_1$-$C_6$ alkyl) amino group; a $C_1$-$C_6$ acylamino group; a carboxyl group; a $C_1$-$C_6$ alkoxycarbonyl group; a carbamoyl group; a mono($C_1$-$C_6$ alkyl)aminocarbonyl group; a di($C_1$-$C_6$ alkyl)aminocarbonyl group; a $C_1$-$C_6$ acyl group; a $C_1$-$C_6$ alkoxyimino-$C_1$-$C_6$ alkyl group; a $C_1$-$C_6$ alkoxy-$C_1$-$C_6$ alkyl group; a $C_1$-$C_6$ alkylthio-$C_1$-$C_6$ alkyl group; a $C_1$-$C_6$ alkylsulfinyl-$C_1$-$C_6$ alkyl group; a $C_1$-$C_6$ alkylsulfonyl-$C_1$-$C_6$ alkyl group; a $C_1$-$C_6$ haloalkylthio-$C_1$-$C_6$ alkyl group; a $C_1$-$C_6$ haloalkylsulfinyl-$C_1$-$C_6$ alkyl group; a $C_1$-$C_6$ haloalkylsulfonyl-$C_1$-$C_6$ alkyl group; or a cyano-$C_1$-$C_6$ alkyl group; and further, two adjacent $R^{13}$s may be joined with the respective carbon atoms to which $R^{13}$s are directly bound, to form a 4- to 8-membered carbocyclic ring or a 4- to 8-membered heterocyclic ring having 1 to 4 heteroatoms selected from an oxygen atom, a sulfur atom and a nitrogen atom, while the ring thus formed may be substituted with a halogen atom, a cyano group, a nitro group, a $C_1$-$C_6$ alkyl group, a $C_1$-$C_6$ haloalkyl group, a $C_1$-$C_6$ alkoxy group, a $C_1$-$C_6$ haloalkoxy group or an oxo group;

$R^{14}$ represents a halogen atom; a nitro group; a cyano group; a $C_1$-$C_6$ alkyl group; a $C_1$-$C_6$ haloalkyl group, a $C_1$-$C_6$ alkoxy group, a $C_1$-$C_6$ haloalkoxy group;

$A^1$ represents $C(R^{15}R^{16})$;
$A^2$ represents $C(R^{17}R^{18})$, or C=O;
$A^3$ represents $C(R^{19}R^{20}$; and $R^{15}$, $R^{16}$, $R^{17}$, $R^{18}$, $R^{19}$ and $R^{20}$ each independently represent a hydrogen atom or a $C_1$-$C_6$ alkyl group, and $R^{15}$ and $R^{20}$ may be joined together to form a $C_2$-$C_5$ alkylene chain, and may constitute a ring together with adjacent carbon atoms.

(2) The oxopyrazine derivative or the agrochemically acceptable salt thereof according to (1) above, wherein in the formula [I], $X^2$ is CH (the group may be substituted with $R^2$), that is, CH which may be substituted with a substituent $R^2$.

(3) The oxopyrazine derivative or the agrochemically acceptable salt thereof according to (1) above, wherein in the formula [I], $X^2$ is $N(O)_m$.

(4) The oxopyrazine derivative or the agrochemically acceptable salt thereof according to claim 1, wherein in the formula [I], $R^3$ is hydroxyl group; or $O^-M^+$ (wherein $M^+$ is an alkali metal cation or an ammonium cation).

(5) The oxopyrazine derivative or the agrochemically acceptable salt thereof according to (1) above, wherein in the formula [I], $X^1$ is an oxygen atom or a sulfur atom;

$X^2$ is CH (the carbon atom may be substituted with $R^2$), that is, CH which may be substituted with a substituent $R^2$, or a nitrogen atom;

$R^1$ represents a hydrogen atom; a $C_1$-$C_{12}$ alkyl group; a $C_2$-$C_6$ alkenyl group; a $C_2$-$C_6$ alkynyl group; a $C_3$-$C_8$ cycloalkyl group; a $C_1$-$C_6$ haloalkyl group; a $C_2$-$C_6$ haloalkenyl group; a $C_1$-$C_6$ alkylthio-$C_1$-$C_6$ alkyl group; a $C_1$-$C_6$ alkylsulfonyl-$C_1$-$C_6$ alkyl group; a $C_1$-$C_6$ alkoxy-$C_1$-$C_6$ alkyl group; a $C_1$-$C_6$ alkoxy-$C_1$-$C_6$ alkoxy-$C_1$-$C_6$ alkyl group; a phenoxy-$C_1$-$C_6$ alkyl group; a $C_1$-$C_6$ haloalkoxy-$C_1$-$C_6$ alkyl group; a tetrahydrofuran-$C_1$-$C_6$ alkoxy-$C_1$-$C_6$ alkyl group; a $C_1$-$C_6$ alkylsulfonyl-$C_1$-$C_6$ alkoxy-$C_1$-$C_6$ alkyl group; a cyano-$C_1$-$C_6$ alkoxy-$C_1$-$C_6$ alkyl group; a cyano-$C_1$-$C_6$ alkyl group; a $C_1$-$C_6$ alkylcarbonyloxy-$C_1$-$C_6$ alkyl group; a $C_1$-$C_6$ acyl-$C_1$-$C_6$ alkyl group; a $C_1$-$C_6$ alkoxycarbonyl-$C_1$-$C_6$ alkyl group; a $(R^6R^7N—C=O)—C_1$-$C_6$ alkyl group; a $C_6$-$C_{10}$ aryl-$C_1$-$C_6$ alkyl group (the aryl moiety of the group may be substituted with one or two or more identical or different $R^8$s), that is, a $C_6$-$C_{10}$ aryl-$C_1$-$C_6$ alkyl group in which the aryl group may be substituted with one or two or more identical or different $R^8$s; a $Het^1$-$C_1$-$C_6$ alkyl group (the group may be substituted with one or two or more identical or different $R^9$s), that is, a $Het^1$-$C_1$-$C_6$ alkyl group which may be substituted with one or two or more identical or different $R^9$s; a $NR^{10}R^{11}$ group; a $C_6$-$C_{10}$ aryl group (the group may be substituted with one or two or more identical or different $R^{12}$s), that is, a $C_6$-$C_{10}$ aryl group which may be substituted with one or two or more identical or different $R^{12}$s; or a $Het^1$ group (the group may be substituted with one or two or more identical or different $R^{13}$s), that is, a $Het^1$ group which may be substituted with one or two or more identical or different $R^{13}$s, wherein $Het^1$ is tetrahydrofuran, tetrahydrothiophene, tetrahydrothiophene dioxide, tetrahydrothiopyrane, tetrahydrothiopyrane dioxide, 4,5-dihydroisoxazole, thiophene, pyrazole, oxazole, isoxazole, thiazole, isothiazole, 1,2,4-triazole, 1,2,4-oxadiazole, 1,3,4-thiadiazole, pyridine, pyridazine, pyrimidine, pyrazine, 2,3-dihydrobenzofuran, 1,3-benzodioxole, benzo-1,4-dioxane, benzofuran or indole;

$R^2$ is a halogen atom, a nitro group, a $C_1$-$C_6$ alkyl group, a $C_1$-$C_6$ haloalkyl group, a $C_1$-$C_6$ alkoxy group, a $C_1$-$C_6$ alkylthio group, a $C_1$-$C_6$ alkylsulfonyl group, or a $C_1$-$C_6$ alkoxy-$C_1$-$C_6$ alkyl group;

n represents an integer from 0 to 4 when $X^2$ is CH (the group may be substituted with $R^2$), that is, CH which may be substituted with $R^2$, and when $X^2$ is $N(O)_m$, n represents an integer from 0 to 3;

$R^3$ is a hydroxyl group;

$R^6$ and $R^7$ each independently represent a $C_1$-$C_6$ alkyl group;

or $R^6$ and $R^7$ may also be joined with the nitrogen atom to which they are bound, to form a 5- to 6-membered ring, while this ring may have an oxygen atom interposed, in addition to the nitrogen atom to which $R^6$ and $R^7$ are bound;

$R^8$ is a halogen atom, a $C_1$-$C_6$ haloalkyl group, a $C_1$-$C_6$ alkoxy group, or a $C_1$-$C_6$ haloalkoxy group;

$R^9$ is a $C_1$-$C_6$ alkyl group, a halogen atom, or a $C_1$-$C_6$ haloalkyl group;

$R^{10}$ and $R^{11}$ are each independently a $C_1$-$C_6$ alkyl group, or a $C_1$-$C_6$ alkoxycarbonyl group;

$R^{12}$ is a halogen atom, a hydroxyl group, a nitro group, a cyano group, a $C_1$-$C_6$ alkyl group, a $C_3$-$C_8$ cycloalkyl group, a $C_1$-$C_6$ haloalkyl group, a $C_1$-$C_6$ alkoxy group, a $C_2$-$C_6$ alkenyloxy group, a $C_2$-$C_6$ alkynyloxy group, a $C_1$-$C_6$ haloalkoxy group, a $C_1$-$C_6$ alkylthio group, a $C_1$-$C_6$ alkylsulfonyl group, a $C_1$-$C_6$ haloalkylthio group, a $C_1$-$C_6$ alkoxy-$C_1$-$C_6$ alkyl group, a $C_3$-$C_8$ cycloalkyl-$C_1$-$C_6$ alkyloxy group, a $C_1$-$C_6$ haloalkoxy-$C_1$-$C_6$ alkoxy group, a cyano-$C_1$-$C_6$ alkoxy group, a $C_1$-$C_6$ acyl group, a $C_1$-$C_6$ alkoxycarbonyl group, a di($C_1$-$C_6$ alkyl)amino group, or a $Het^1$-$C_1$-$C_6$ alkoxy group ($Het^1$ has the same meaning as defined above), or two adjacent $R^{12}$s may be joined with the respective carbon atoms to which they are directly bound, to form a 4- to 8-membered carbocyclic ring or a 4- to 8-membered heterocyclic ring having 1 to 4 heteroatoms selected from an oxygen atom, a sulfur atom and a nitrogen atom, while the ring thus formed may be substituted with a halogen atom, a $C_1$-$C_6$ alkyl group or an oxo group; and $R^{13}$ is an oxo group, a halogen atom, a $C_1$-$C_6$ alkyl group, a $C_1$-$C_6$ haloalkyl group, a $C_1$-$C_6$ alkoxy group, or a mono ($C_1$-$C_6$ alkyl)amino group.

(6) The oxopyrazine derivative or the agrochemically acceptable salt thereof according to any one of (1), (2), (4) and (5) above, wherein in the formula [I], $X^1$ represents an oxygen atom or a sulfur atom;

$X^2$ is CH (the group may be substituted with $R^2$), that is, CH which may be substituted with a substituent $R^2$;

$R^1$ is a hydrogen atom; a $C_1$-$C_{12}$ alkyl group; a $C_2$-$C_6$ alkenyl group; a $C_2$-$C_6$ alkynyl group; a $C_3$-$C_8$ cycloalkyl group; a $C_1$-$C_6$ haloalkyl group; a $C_1$-$C_6$ alkylthio-$C_1$-$C_6$ alkyl group; a $C_1$-$C_6$ alkylsulfonyl-$C_1$-$C_6$ alkyl group; a $C_1$-$C_6$ alkoxy-$C_1$-$C_6$ alkyl group; a $C_1$-$C_6$ alkoxy-$C_1$-$C_6$ alkoxy-$C_1$-$C_6$ alkyl group; a phenoxy-$C_1$-$C_6$ alkyl group; a $C_1$-$C_6$ haloalkoxy-$C_1$-$C_6$ alkyl group; a tetrahydrofuran-$C_1$-$C_6$ alkoxy-$C_1$-$C_6$ alkyl group; a $C_1$-$C_6$ alkylsulfonyl-$C_1$-$C_6$ alkoxy-$C_1$-$C_6$ alkyl group; a cyano-$C_1$-$C_6$ alkoxy-$C_1$-$C_6$ alkyl group; a cyano-$C_1$-$C_6$ alkyl group; a $C_1$-$C_6$ alkylcarbonyloxy-$C_1$-$C_6$ alkyl group; a $C_1$-$C_6$ acyl-$C_1$-$C_6$ alkyl group; a $C_1$-$C_6$ alkoxycarbonyl-$C_1$-$C_6$ alkyl group; a ($R^6R^7N$—C=O)—$C_1$-$C_6$ alkyl group; a $C_6$-$C_{10}$ aryl-$C_1$-$C_6$ alkyl group (the aryl moiety of the group may be substituted with one or two or more identical or different $R^8$s), that is, a $C_6$-$C_{10}$ aryl-$C_1$-$C_6$ alkyl group in which the aryl group may be substituted with one or two or more identical or different $R^8$s; a $Het^1$-$C_1$-$C_6$ alkyl group (the group may be substituted with one or two or more identical or different $R^9$s), that is, a $Het^1$-$C_1$-$C_6$ alkyl group which may be substituted with one or two or more identical or different $R^9$s; a $NR^{10}R^{11}$ group; a $C_6$-$C_{10}$ aryl group (the group may be substituted with one or two or more identical or different $R^{12}$s), that is, a $C_6$-$C_{10}$ aryl group which may be substituted with one or two or more identical or different $R^{12}$s; or a $Het^1$ group (the group may be substituted with one or two or more identical or different $R^{13}$s), that is, a $Het^1$ group which may be substituted with one or two or more identical or different $R^{13}$s, wherein $Het^1$ is tetrahydrofuran, tetrahydrothiophene, tetrahydrothiophene dioxide, tetrahydrothiopyrane, tetrahydrothiopyrane dioxide, 4,5-dihydroisoxazole, thiophene, pyrazole, oxazole, isoxazole, thiazole, isothiazole, 1,2,4-triazole, 1,2,4-oxadiazole, 1,3,4-thiadiazole, pyridine, pyridazine, pyrimidine, pyrazine, 2,3-dihydrobenzofuran, 1,3-benzodioxole, benzo-1,4-dioxane, benzofuran or indole;

$R^2$ is a halogen atom, a nitro group, a $C_1$-$C_6$ alkyl group, a $C_1$-$C_6$ haloalkyl group, a $C_1$-$C_6$ alkoxy group, a $C_1$-$C_6$ alkylthio group, a $C_1$-$C_6$ alkylsulfonyl group or a $C_1$-$C_6$ alkoxy-$C_1$-$C_6$ alkyl group;

n is an integer from 0 to 4;

$R^3$ is a hydroxyl group;

$R^6$ and $R^7$ each independently represent a $C_1$-$C_6$ alkyl group, or $R^6$ and $R^7$ may be joined with the nitrogen atom to which they are bound, to form a 5- to 6-membered ring, while the ring thus formed may have an oxygen atom interposed, in addition to the nitrogen atom to which $R^6$ and $R^7$ are bound;

$R^8$ is a halogen atom or a $C_1$-$C_6$ alkoxy group;

$R^9$ is a $C_1$-$C_6$ alkyl group;

$R^{10}$ and $R^{11}$ are each independently a $C_1$-$C_6$ alkyl group, or a $C_1$-$C_6$ alkoxycarbonyl group;

$R^{12}$ is a halogen atom, a hydroxyl group, a nitro group, a cyano group, a $C_1$-$C_6$ alkyl group, a $C_3$-$C_8$ cycloalkyl group, a $C_1$-$C_6$ haloalkyl group, a $C_1$-$C_6$ alkoxy group, a $C_2$-$C_6$ alkenyloxy group, a $C_2$-$C_6$ alkynyloxy group, a $C_1$-$C_6$ haloalkoxy group, a $C_1$-$C_6$ alkylthio group, a $C_1$-$C_6$ alkylsulfonyl group, a $C_1$-$C_6$ alkoxy-$C_1$-$C_6$ alkyl group, a $C_3$-$C_8$ cycloalkyl-$C_1$-$C_6$ alkyloxy group, a $C_1$-$C_6$ haloalkoxy-$C_1$-$C_6$ alkoxy group, a cyano-$C_1$-$C_6$ alkoxy group, a $C_1$-$C_6$ acyl group, a $C_1$-$C_6$ alkoxycarbonyl group, a di($C_1$-$C_6$ alkyl) amino group, or a $Het^1$-$C_1$-$C_6$ alkoxy group ($Het^1$ has the same meaning as defined above), or two adjacent $R^{12}$s may be joined with the respective carbon atoms to which they are directly bound, to form a 4- to 8-membered carbocyclic ring or a 4- to 8-membered heterocyclic ring having 1 to 4 heteroatoms selected from an oxygen atom, a sulfur atom and a nitrogen atom, while the ring thus formed may be substituted with a halogen atom, a $C_1$-$C_6$ alkyl group or an oxo group; and $R^{13}$ is an oxo group, a halogen atom, a $C_1$-$C_6$ alkyl group, a $C_1$-$C_6$ haloalkyl group, a $C_1$-$C_6$ alkoxy group, or a mono ($C_1$-$C_6$ alkyl)amino group.

(7) The oxopyrazine derivative or the agrochemically acceptable salt thereof according to any one of (1), (3), (4) and (5) above, wherein in the formula [I], $X^1$ is an oxygen atom;

$X^2$ is a nitrogen atom;

$R^1$ is a hydrogen atom; a $C_1$-$C_{12}$ alkyl group; a $C_2$-$C_6$ alkenyl group; a $C_2$-$C_6$ alkynyl group; a $C_1$-$C_6$ haloalkyl group; a $C_2$-$C_6$ haloalkenyl group; a $C_1$-$C_6$ alkylthio-$C_1$-$C_6$ alkyl group; a $C_1$-$C_6$ alkoxy-$C_1$-$C_6$ alkyl group; a $C_1$-$C_6$ haloalkoxy-$C_1$-$C_6$ alkyl group; a $C_1$-$C_6$ alkoxycarbonyl-$C_1$-$C_6$ alkyl group; a $C_6$-$C_{10}$ aryl-$C_1$-$C_6$ alkyl group (the aryl moiety of the group may be substituted with one or two or more identical or different $R^8$s), that is, a $C_6$-$C_{10}$ aryl-$C_1$-$C_6$ alkyl group in which the aryl group may be substituted with one or two or more identical or different $R^8$s; a $Het^2$-$C_1$-$C_6$ alkyl group (the group may be substituted with one or two or more identical or different $R^9$s), that is, a $Het^2$-$C_1$-$C_6$ alkyl group which may be substituted with one or two or more identical or different $R^9$s; a $C_6$-$C_{10}$ aryl group (the group may be substituted with one or two or more identical or different $R^{12}$s), that is, a $C_6$-$C_{10}$ aryl group which may be substituted with one or two or more identical or different $R^{12}$s; or a $Het^2$ group (the group may be substituted with one or two or more identical or different $R^{13}$s), that is, a $Het^2$ group which may be substituted with one or two or more identical or different $R^{13}$s; wherein Het$^2$ is 4,5-dihydroisoxazole, thiophene, pyrazole, isoxazole, pyridine, 2,3-dihydrobenzofuran, 1,3-benzodioxole or benzo-1,4-dioxane;

$R^2$ is a halogen atom, a $C_1$-$C_6$ alkyl group; $C_1$-$C_6$ alkylthio group or a $C_1$-$C_6$ alkoxy group;

n represents an integer from 0 to 4 wherein $X^2$ is CH (the group may be substituted with $R^2$), that is, CH which may be substituted with $R^2$, or represents an integer from 0 to 3 when $X^2$ is $N(O)_m$;

$R^3$ is a hydroxyl group;

$R^8$ is a halogen atom, a $C_1$-$C_6$ haloalkyl group, a $C_1$-$C_6$ alkoxy group, or a $C_1$-$C_6$ haloalkoxy group;

$R^9$ is a $C_1$-$C_6$ alkyl group, a halogen atom or a $C_1$-$C_6$ haloalkyl group;

$R^{12}$ is a halogen atom, a cyano group, a $C_1$-$C_6$ alkyl group, a $C_3$-$C_8$ cycloalkyl group, a $C_1$-$C_6$ haloalkyl group, a $C_1$-$C_6$ alkoxy group, a $C_1$-$C_6$ haloalkoxy group or a $C_1$-$C_6$ haloalkylthio group, or two adjacent $R^{12}$s may be joined with the respective carbon atoms to which they are directly bound, to form a 4- to 8-membered carbocyclic ring or a 4- to 8-membered heterocyclic ring having 1 to 4 heteroatoms selected from an oxygen atom, a sulfur atom and a nitrogen atom, while the ring thus formed may be substituted with a halogen atom; and $R^{13}$ is a halogen atom, a $C_1$-$C_6$ alkyl group, a $C_1$-$C_6$ haloalkyl group, or a $C_1$-$C_6$ alkoxy group.

(8) A compound represented by formula [J1]:

[Chemical Formula 2]

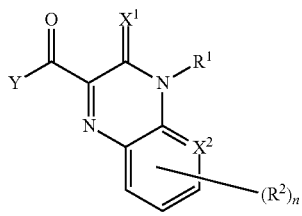

[J1]

wherein $X^1$ represents an oxygen atom or a sulfur atom;

$X^2$ represents CH (the carbon atom may be substituted with $R^2$) or a nitrogen atom;

$R^1$ represents a $C_1$-$C_{12}$ alkyl group; a $C_2$-$C_6$ alkenyl group; a $C_2$-$C_6$ alkynyl group; a $C_3$-$C_8$ cycloalkyl group; a $C_1$-$C_6$ haloalkyl group; a $C_2$-$C_6$ haloalkenyl group; a $C_1$-$C_6$ alkylthio-$C_1$-$C_6$ alkyl group; a $C_1$-$C_6$ alkylsulfonyl-$C_1$-$C_6$ alkyl group; a $C_1$-$C_6$ alkoxy-$C_1$-$C_6$ alkyl group; a $C_1$-$C_6$ alkoxy-$C_1$-$C_6$ alkoxy-$C_1$-$C_6$ alkyl group; a phenyloxy-$C_1$-$C_6$ alkyl group; a $C_1$-$C_6$ haloalkoxy-$C_1$-$C_6$ alkyl group; a tetrahydrofuran-$C_1$-$C_6$ alkoxy-$C_1$-$C_6$ alkyl group; a $C_1$-$C_6$ alkylsulfonyl-$C_1$-$C_6$ alkoxy-$C_1$-$C_6$ alkyl group; cyano-$C_1$-$C_6$ alkoxy-$C_1$-$C_6$ alkyl group; a cyano-$C_1$-$C_6$ alkyl group; a $C_1$-$C_6$ alkylcarbonyloxy-$C_1$-$C_6$ alkyl group; a $C_1$-$C_6$ acyl-$C_1$-$C_6$ alkyl group; a $C_1$-$C_6$ alkoxycarbonyl-$C_1$-$C_6$ alkyl group; a $(R^6R^7N\text{---}C\text{=}O)$-$C_1$-$C_6$ alkyl group; a $C_6$-$C_{10}$ aryl-$C_1$-$C_6$ alkyl group (the aryl moiety of the group may be substituted with one or two or more identical or different $R^8$s), that is, a $C_6$-$C_{10}$ aryl-$C_1$-$C_6$ alkyl group in which the aryl group may be substituted with one or two or more identical or different $R^8$s; a Het$^1$-$C_1$-$C_6$ alkyl group (the group may be substituted with one or two or more identical or different $R^9$s), that is, a Het$^1$-$C_1$-$C_6$ alkyl group which may be substituted with one or two or more identical or different $R^9$s; a $NR^{10}R^{11}$ group; a $C_6$-$C_{10}$ aryl group (the group may be substituted with one or two or more identical or different $R^{12}$s), that is, a $C_6$-$C_{10}$ aryl group which may be substituted with one or two or more identical or different $R^{12}$s; or a Het$^1$ group (the group may be substituted with one or two or more identical or different $R^{13}$s), that is, a Het$^1$ group which may be substituted with one or two or more identical or different $R^{13}$s;

$R^2$ represents a halogen atom; a nitro group; a $C_1$-$C_6$ alkyl group; a $C_1$-$C_6$ haloalkyl group; a $C_1$-$C_6$ alkoxy group; a $C_1$-$C_6$ alkylthio group; a $C_1$-$C_6$ alkylsulfonyl group; or a $C_1$-$C_6$ alkoxy-$C_1$-$C_6$ alkyl group;

n represents an integer from 0 to 4 when $X^2$ is CH (the group may be substituted with $R^2$), and n represents an integer from 0 to 3 when $X^2$ is nitrogen atom;

$R^6$ and $R^7$ each independently represent a $C_1$-$C_6$ alkyl group, and furthermore, $R^6$ and $R^7$ may be joined with the nitrogen atom to which these are bound, to form a 5- to 6-membered ring, while the ring thus formed may have an oxygen atom interposed, in addition to the nitrogen atom to which $R^6$ and $R^7$ are bound;

$R^8$ represents a halogen atom; a $C_1$-$C_6$ haloalkyl group; a $C_1$-$C_6$ alkoxy group; or a $C_1$-$C_6$ haloalkoxy group;

$R^9$ represents a $C_1$-$C_6$ alkyl group; a halogen atom; or a $C_1$-$C_6$ haloalkyl group;

$R^{10}$ and $R^{11}$ each independently represent a $C_1$-$C_6$ alkyl group; or a $C_1$-$C_6$ alkoxycarbonyl group;

$R^{12}$ represents a halogen atom; a hydroxyl group; a nitro group; a cyano group; a $C_1$-$C_6$ alkyl group; a $C_3$-$C_8$ cycloalkyl group; a $C_1$-$C_6$ haloalkyl group; a $C_1$-$C_6$ alkoxy group; a $C_2$-$C_6$ alkenyloxy group; a $C_2$-$C_6$ alkynyloxy group; a $C_1$-$C_6$ haloalkoxy group; a $C_1$-$C_6$ alkylthio group; a $C_1$-$C_6$ alkylsulfonyl group; a $C_1$-$C_6$ haloalkylthio group; a $C_1$-$C_6$ alkoxy-$C_1$-$C_6$ alkyl group; a $C_3$-$C_8$ cycloalkyl-$C_1$-$C_6$ alkyloxy group; a cyano-$C_1$-$C_6$ alkoxy group; a $C_1$-$C_6$ acyl group; a $C_1$-$C_6$ alkoxycarbonyl group; a di($C_1$-$C_6$ alkyl)amino group; or a Het$^1$-$C_1$-$C_6$ alkoxy group, and furthermore, two adjacent $R^{12}$s may be joined with the respective carbon atoms to which they are directly bound, to form a 4- to 8-membered carbocyclic ring or a 4- to 8-membered heterocyclic ring having 1 to 4 heteroatoms selected from an oxygen atom, a sulfur atom and a nitrogen atom, while the ring thus formed may be substituted with a halogen atom; a $C_1$-$C_6$ alkyl group; or an oxo group;

$R^{13}$ represents an oxo group; a halogen atom; a $C_1$-$C_6$ alkyl group; a $C_1$-$C_6$ haloalkyl group; a $C_1$-$C_6$ alkoxy group; or a mono($C_1$-$C_6$ alkyl)amino group;

Y represents a halogen atom or a cyano group; and

Het$^1$ represents tetrahydrothiophene, tetrahydrothiophene dioxide, tetrahydrothiopyrane, tetrahydrothiopyranedioxide, 4,5-dihydroisoxazole, thiophene, pyrazole, oxazole, isoxazole, thiazole, isothiazole, 1,2,4-triazole, 1,2,4-oxadiazole, 1,3,4-thiadiazole, pyridine, pyridazine, pyrimidine, pyrazine, 2,3-dihydrobenzofuran, 1,3-benzodioxole, benzo-1,4-dioxane, benzofuran or indole.

(9) A compound represented by formula [J2]:

[Chemical Formula 3]

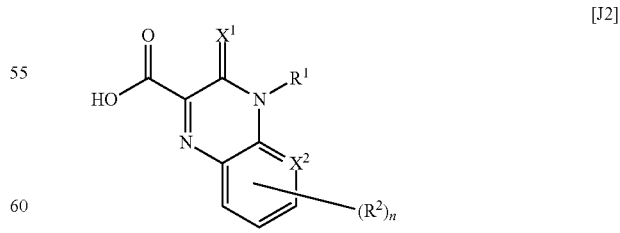

[J2]

wherein $X^1$ represents an oxygen atom or a sulfur atom;

$X^2$ represents CH (the carbon atom may be substituted with $R^2$) or a nitrogen atom;

$R^1$ represents a $C_1$-$C_{12}$ alkyl group; a $C_2$-$C_6$ alkenyl group; a $C_2$-$C_6$ alkynyl group; a $C_3$-$C_8$ cycloalkyl group; a $C_1$-$C_6$ haloalkyl group; a $C_2$-$C_6$ haloalkenyl group; a $C_1$-$C_6$ alkylthio-$C_1$-$C_6$ alkyl group; a $C_1$-$C_6$ alkylsulfonyl-$C_1$-$C_6$ alkyl group; a $C_1$-$C_6$ alkoxy-$C_1$-$C_6$ alkyl group; a $C_1$-$C_6$ alkoxy-$C_1$-$C_6$ alkoxy-$C_1$-$C_6$ alkyl group; a phenyloxy-$C_1$-$C_6$ alkyl group; a $C_1$-$C_6$ haloalkoxy-$C_1$-$C_6$ alkyl group; a tetrahydrofuran-$C_1$-$C_6$ alkoxy-$C_1$-$C_6$ alkyl group; a $C_1$-$C_6$ alkylsulfonyl-$C_1$-$C_6$ alkoxy-$C_1$-$C_6$ alkyl group; cyano-$C_1$-$C_6$ alkoxy-$C_1$-$C_6$ alkyl group; a cyano-$C_1$-$C_6$ alkyl group; a $C_1$-$C_6$ alkylcarbonyloxy-$C_1$-$C_6$ alkyl group; a $C_1$-$C_6$ acyl-$C_1$-$C_6$ alkyl group; a $C_1$-$C_6$ alkoxycarbonyl-$C_1$-$C_6$ alkyl group; a $(R^6R^7N-C=O)-C_1$-$C_6$ alkyl group; a $C_6$-$C_{10}$ aryl-$C_1$-$C_6$ alkyl group (the aryl moiety of the group may be substituted with one or two or more identical or different $R^8$s), that is, a $C_6$-$C_{10}$ aryl-$C_1$-$C_6$ alkyl group in which the aryl group may be substituted with one or two or more identical or different $R^8$s; a Het$^1$-$C_1$-$C_6$ alkyl group (the group may be substituted with one or two or more identical or different $R^9$s), that is, a Het$^1$-$C_1$-$C_6$ alkyl group which may be substituted with one or two or more identical or different $R^9$s; a NR$^{10}$R$^{11}$ group; a $C_6$-$C_{10}$ aryl group (the group may be substituted with one or two or more identical or different $R^{12}$s), that is, a $C_6$-$C_{10}$ aryl group which may be substituted with one or two or more identical or different $R^{12}$s; or a Het$^1$ group (the group may be substituted with one or two or more identical or different $R^{13}$s), that is, a Het$^1$ group which may be substituted with one or two or more identical or different $R^{13}$s;

$R^2$ represents a halogen atom; a nitro group; a $C_1$-$C_6$ alkyl group; a $C_1$-$C_6$ haloalkyl group; a $C_1$-$C_6$ alkoxy group; a $C_1$-$C_6$ alkylthio group; a $C_1$-$C_6$ alkylsulfonyl group; or a $C_1$-$C_6$ alkoxy-$C_1$-$C_6$ alkyl group;

n represents an integer from 0 to 4 when $X^2$ is CH (the group may be substituted with $R^2$), and n represents an integer from 0 to 3 when $X^2$ is nitrogen atom;

$R^6$ and $R^7$ each independently represent a $C_1$-$C_6$ alkyl group, and furthermore, $R^6$ and $R^7$ may be joined with the nitrogen atom to which these are bound, to form a 5- to 6-membered ring, while the ring thus formed may have an oxygen atom interposed, in addition to the nitrogen atom to which $R^6$ and $R^7$ are bound;

$R^8$ represents a halogen atom; a $C_1$-$C_6$ haloalkyl group; a $C_1$-$C_6$ alkoxy group; or a $C_1$-$C_6$ haloalkoxy group;

$R^9$ represents a $C_1$-$C_6$ alkyl group; a halogen atom; or a $C_1$-$C_6$ haloalkyl group;

$R^{10}$ and $R^{11}$ each independently represent a $C_1$-$C_6$ alkyl group; or a $C_1$-$C_6$ alkoxycarbonyl group;

$R^{12}$ represents a halogen atom; a hydroxyl group; a nitro group; a cyano group; a $C_1$-$C_6$ alkyl group; a $C_3$-$C_8$ cycloalkyl group; a $C_1$-$C_6$ haloalkyl group; a $C_1$-$C_6$ alkoxy group; a $C_2$-$C_6$ alkenyloxy group; a $C_2$-$C_6$ alkynyloxy group; a $C_1$-$C_6$ haloalkoxy group; a $C_1$-$C_6$ alkylthio group; a $C_1$-$C_6$ alkylsulfonyl group; a $C_1$-$C_6$ haloalkylthio group; a $C_1$-$C_6$ alkoxy-$C_1$-$C_6$ alkyl group; a $C_3$-$C_8$ cycloalkyl-$C_1$-$C_6$ alkyloxy group; a cyano-$C_1$-$C_6$ alkoxy group; a $C_1$-$C_6$ acyl group; a $C_1$-$C_6$ alkoxycarbonyl group; a di($C_1$-$C_6$ alkyl)amino group; or a a Het$^1$-$C_1$-$C_6$ alkoxy group, and furthermore, two adjacent $R^{12}$s may be joined with the respective carbon atoms to which they are directly bound, to form a 4- to 8-membered carbocyclic ring or a 4- to 8-membered heterocyclic ring having 1 to 4 heteroatoms selected from an oxygen atom, a sulfur atom and a nitrogen atom, while the ring thus formed may be substituted with a halogen atom; a $C_1$-$C_6$ alkyl group; or an oxo group;

$R^{13}$ represents an oxo group; a halogen atom; a $C_1$-$C_6$ alkyl group; a $C_1$-$C_6$ haloalkyl group; a $C_1$-$C_6$ alkoxy group; or a mono($C_1$-$C_6$ alkyl)amino group;

Het$^1$ represents tetrahydrothiophene, tetrahydrothiophene dioxide, tetrahydrothiopyrane, tetrahydrothiopyranedioxide, 4,5-dihydroisoxazole, thiophene, pyrazole, oxazole, isoxazole, thiazole, isothiazole, 1,2,4-triazole, 1,2,4-oxadiazole, 1,3,4-thiadiazole, pyridine, pyridazine, pyrimidine, pyrazine, 2,3-dihydrobenzofuran, 1,3-benzodioxole, benzo-1,4-dioxane, benzofuran or indole.

(10) The compound according to (9) above, wherein in the formula [J2], $R^1$ is a $C_2$-$C_6$ alkynyl group; a $C_3$-$C_8$ cycloalkyl group; a $C_1$-$C_6$ haloalkyl group; a $C_2$-$C_6$ haloalkeny group; a $C_1$-$C_6$ alkylthio-$C_1$-$C_6$ alkyl group; a $C_1$-$C_6$ alkylsulfonyl-$C_1$-$C_6$ alkyl group; a $C_1$-$C_6$ alkoxy-$C_1$-$C_6$ alkoxy-$C_1$-$C_6$ alkyl group; a phenyloxy-$C_1$-$C_6$ alkyl group; a $C_1$-$C_6$ haloalkoxy-$C_1$-$C_6$ alkyl group; a tetrahydrofuran-$C_1$-$C_6$ alkoxy-$C_1$-$C_6$ alkyl group; a $C_1$-$C_6$ alkylsulfonyl-$C_1$-$C_6$ alkoxy-$C_1$-$C_6$ alkyl group; a cyano-$C_1$-$C_6$ alkoxy-$C_1$-$C_6$ alkyl group; a cyano-$C_1$-$C_6$ alkyl group; a $C_1$-$C_6$ alkylcarbonyloxy-$C_1$-$C_6$ alkyl group; a $C_1$-$C_6$ acyl-$C_1$-$C_6$ alkyl group; a $C_1$-$C_6$ alkoxycarbonyl-$C_1$-$C_6$ alkyl group; a $(R^6R^7N-C=O)-C_1$-$C_6$ alkyl group; a $C_6$-$C_{10}$ aryl-$C_1$-$C_6$ alkyl group (the aryl moiety of the group may be substituted with one or two or more identical or different $R^8$s), a Het$^1$-$C_1$-$C_6$ alkyl group (the group may be substituted with one or two or more identical or different $R^9$s), that is, a Het$^1$-$C_1$-$C_6$ alkyl group which may be substituted with one or two or more identical or different $R^9$s; a NR$^{10}$R$^{11}$ group; or a Het$^1$ group (the group may be substituted with one or two or more identical or different $R^{13}$s), that is, a Het$^1$ group which may be substituted with one or two or more identical or different $R^{13}$s.

(11) The compound according to (9) above, wherein in the formula [J2], $X^2$ represents a nitrogen atom; and $R^1$ is a $C_6$-$C_{10}$ aryl group (the group may be substituted with one or two or more identical or different $R^{12}$s), that is, a $C_6$-$C_{10}$ aryl group which may be substituted with one or two or more identical or different $R^{12}$s.

(12) A herbicide characterized by comprising the oxopyrazine derivative according to anyone of (1) to (7) above or a salt thereof, as an active ingredient.

(13) A method of using a herbicide characterized by treating soil and/or plants with an effective amount of the herbicide according to (12) above.

(14) An agrochemical composition for herbicidal use, comprising the oxopyrazine derivative according to any one of (1) to (7) above or a salt thereof, and an agrochemically acceptable carrier.

(15) A method for suppressing the growth of weeds, the method including spreading an agrochemical composition containing an effective amount of the oxopyrazine derivative according to anyone of (1) to (7) above or a salt thereof, over a place where the weeds to be removed are growing.

The present invention also relates to the following (16) to (25).

(16) An oxopyrazine derivative represented by formula [X], or an agrochemically acceptable salt thereof:

[Chemical Formula 4]

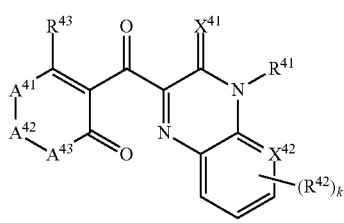

[X]

wherein $X^{41}$ represents an oxygen atom or a sulfur atom;

$X^{42}$ represents CH (the carbon atom may be substituted with $R^{42}$) or $N(O)_m$;

m represents an integer of 0 or 1;

$R^{41}$ represents a hydrogen atom; an amino group; a mono($C_1$-$C_6$ alkyl)amino group; a di($C_1$-$C_6$ alkyl)amino group; a $C_1$-$C_6$ alkoxy group; a $C_1$-$C_{12}$ alkyl group which may be substituted with any group selected from the substituent group α as shown below; a $C_3$-$C_6$ cycloalkyl group; a $C_2$-$C_6$ alkenyl group which may be substituted with a group selected from the substituent group a as shown below; a $C_2$-$C_6$ alkynyl group which may be substituted with a group selected from the substituent group α as shown below; a phenyl group which may be substituted with a group selected from the substituent group β as shown below; a phenyl-$C_1$-$C_3$ alkyl group which may be substituted with a group selected from the substituent group β as shown below; a heterocyclic group having 2 to 10 carbon atoms and 1 to 5 heteroatoms selected from an oxygen atom, a sulfur atom and a nitrogen atom (the group may be substituted with a group selected from the substituent group β as shown below); or a heterocyclic-$C_1$-$C_3$ alkyl group having 2 to 10 carbon atoms and 1 to 5 heteroatoms selected from an oxygen atom, a sulfur atom and a nitrogen atom (the group may be substituted with a group selected from the substituent group β as shown below);

$R^{42}$ represents a halogen atom, a hydroxyl group, a nitro group, a cyano group, a $C_1$-$C_6$ alkyl group, a $C_3$-$C_6$ cycloalkyl group, a $C_3$-$C_6$ cycloalkyl-$C_1$-$C_3$ alkyl group, a $C_2$-$C_6$ alkenyl group, a $C_2$-$C_6$ alkynyl group, a $C_1$-$C_6$ haloalkyl group, a $C_1$-$C_6$ alkoxy group, a $C_3$-$C_6$ cycloalkyloxy group, a $C_2$-$C_6$ alkenyloxy group, a $C_2$-$C_6$ alkynyloxy group, a $C_1$-$C_6$ haloalkoxy group, a $C_1$-$C_6$ alkylthio group, a $C_1$-$C_6$ alkylsulfinyl group, a $C_1$-$C_6$ alkylsulfonyl group, a $C_1$-$C_6$ haloalkylthio group, a $C_1$-$C_6$ haloalkylsulfinyl group, a $C_1$-$C_6$ haloalkylsulfonyl group, an amino group, a mono($C_1$-$C_6$ alkyl)amino group, a di($C_1$-$C_6$ alkyl)amino group, a $C_1$-$C_6$ alkoxy-$C_1$-$C_6$ alkyl group, a $C_1$-$C_6$ acyl group, a carboxyl group, a $C_1$-$C_6$ alkoxycarbonyl group, a mono($C_1$-$C_6$ alkyl)aminocarbonyl group, or a di($C_1$-$C_6$ alkyl)aminocarbonyl group;

n represents an integer from 0 to 4 when $X^{42}$ is CH (the group may be substituted with $R^{42}$), or n represents an integer from 0 to 3 when $X^{42}$ is $N(O)_m$;

$R^{43}$ represents a hydroxyl group, $O^-M^+$ (wherein $M^+$ represents an alkali metal cation or an ammonium cation), an amino group, a halogen atom, a $C_1$-$C_6$ alkylsulfonyloxy group, a $C_1$-$C_6$ alkylthio group, a $C_1$-$C_6$ alkylsulfinyl group, a $C_1$-$C_6$ alkylsulfonyl group, a $C_1$-$C_6$ haloalkylthio group, a $C_1$-$C_6$ haloalkylsulfinyl group, a $C_1$-$C_6$ haloalkylsulfonyl group, a $C_2$-$C_6$ alkenylthio group, a $C_2$-$C_6$ alkenylsulfinyl group, a $C_2$-$C_6$ alkenylsulfonyl group, a $C_2$-$C_6$ alkynylthio group, a $C_2$-$C_6$ alkynylsulfinyl group, a $C_2$-$C_6$ alkynylsulfonyl group, a $C_1$-$C_6$ alkylcarbonyloxy group, a $C_2$-$C_6$ alkenylcarbonyloxy group, a $C_2$-$C_6$ alkynylcarbonyloxy group, a phenoxy group which may be substituted with a group selected from the substituent group γ as shown below, a phenylthio group which may be substituted with a group selected from the substituent group γ as shown below, a phenylsulfinyl group which may be substituted with a group selected from the substituent group γ as shown below, a phenylsulfonyl group which may be substituted with a group selected from the substituent group γ as shown below, a phenylsulfonyloxy group which may be substituted with a group selected from the substituent group γ as shown below, a phenylcarbonyloxy group which may be substituted with a group selected from the substituent group γ as shown below, a 1,2,4-triazol-1-yl group, a 1,2,3-triazol-1-yl group, a 1,2,3-triazol-2-yl group, an imidazol-1-yl group, a pyrazol-1-yl group, a tetrazol-1-yl group or a tetrazol-2-yl group;

$A^{41}$ represents $C(R^{44}R^{45})$;

$A^{42}$ represents $C(R^{46}R^{47})$ or C=O;

$A^{43}$ represents $C(R^{48}R^{49})$; and $R^{44}$, $R^{45}$, $R^{46}$, $R^{47}$, $R^{48}$ and $R^{49}$ each independently represent a hydrogen atom or a $C_1$-$C_6$ alkyl group, or $R^{44}$ and $R^{49}$ may be joined by a $C_2$-$C_5$ alkylene chain to constitute a ring.

[Substituent Group α]

A group comprising a halogen atom, a hydroxyl group, a nitro group, a cyano group, a $C_1$-$C_6$ alkyl group, a $C_3$-$C_6$ cycloalkyl group, a $C_1$-$C_6$ haloalkyl group, a $C_1$-$C_6$ alkoxy group, a $C_3$-$C_6$ cycloalkyloxy group, a $C_1$-$C_6$ haloalkoxy group, a phenoxy group, a $C_1$-$C_6$ alkyl carbonyloxy group, a $C_1$-$C_6$ alkylthio group, a $C_1$-$C_6$ alkylsulfinyl group, a $C_1$-$C_6$ alkylsulfonyl group, an amino group, a mono($C_1$-$C_6$ alkyl)amino group, a di($C_1$-$C_6$ alkyl) amino group, a $C_1$-$C_6$ alkoxy-$C_1$-$C_6$ alkoxy group, a $C_1$-$C_6$ alkylsulfonyl-$C_1$-$C_6$ alkoxy group, a cyano-$C_1$-$C_6$ alkoxy group, a heterocyclic-$C_1$-$C_3$ alkoxy group having 2 to 10 carbon atoms and 1 to 5 heteroatoms arbitrarily selected from an oxygen atom, a sulfur atom and a nitrogen atom, a $C_1$-$C_6$ acyl group, a $C_1$-$C_6$ alkoxycarbonyl group, and a $R^{50}R^{51}N$—C=O group ($R^{50}$ and $R^{51}$ each independently represent a hydrogen atom or a $C_1$-$C_6$ alkyl group, or $R^{50}$ and $R^{51}$ may be joined with the nitrogen atom to which they are bound, to form a 5- to 6-membered ring, while this ring may have one or more atoms arbitrarily selected from the group of an oxygen atom, a nitrogen atom and a sulfur atom, interposed therein, in addition to the nitrogen atom to which $R^{50}$ and $R^{51}$ are bound).

[Substituent Group β]

A group comprising a halogen atom, a hydroxyl group, a nitro group, a cyano group, a $C_1$-$C_6$ alkyl group, a $C_3$-$C_6$ cycloalkyl group, a $C_3$-$C_6$ cycloalkyl-$C_1$-$C_3$ alkyl group, a $C_2$-$C_6$ alkenyl group, a $C_2$-$C_6$ alkynyl group, a $C_1$-$C_6$ haloalkyl group, a $C_1$-$C_6$ alkoxy group, a $C_3$-$C_6$ cycloalkyloxy group, a $C_2$-$C_6$ alkenyloxy group, a $C_2$-$C_6$ alkynyloxy group, a $C_1$-$C_6$ alkylcarbonyloxy group, a $C_1$-$C_6$ haloalkoxy group, a $C_1$-$C_6$ alkylthio group, a $C_1$-$C_6$ alkylsulfinyl group, a $C_1$-$C_6$ alkylsulfonyl group, a $C_1$-$C_6$ haloalkylthio group, a $C_1$-$C_6$ haloalkylsulfinyl group, a $C_1$-$C_6$ haloalkylsulfonyl group, an amino group, a mono($C_1$-$C_6$ alkyl)amino group, a di($C_1$-$C_6$ alkyl)amino group, a $C_1$-$C_3$ alkoxy-$C_1$-$C_3$ alkyl group, a $C_1$-$C_6$ alkoxy-$C_1$-$C_6$ alkoxy group, a $C_3$-$C_6$ cycloalkyl-$C_1$-$C_3$ alkyl oxy group, a cyano-$C_1$-$C_3$ alkoxy group, a $C_1$-$C_6$ acyl group, a carboxyl group, a $C_1$-$C_6$ alkoxycarbonyl group, a carbamoyl group, a mono($C_1$-$C_{10}$ alkyl) aminocarbonyl group, a di($C_1$-$C_{10}$ alkyl)aminocarbonyl group, and a heterocyclic-$C_1$-$C_3$ alkoxy group having 2 to 10 carbon atoms and 1 to 5 heteroatoms arbitrarily selected upon an oxygen atom, a sulfur atom and a nitrogen atom;

[Substituent Group γ]

A group comprising a halogen atom, a nitro group, a cyano group, a $C_1$-$C_6$ alkyl group, a $C_1$-$C_6$ haloalkyl group, a $C_1$-$C_6$ alkoxy group, and a $C_1$-$C_6$ haloalkoxy group.

(17) The oxopyrazine derivative or the agrochemically acceptable salt thereof according to (11) above, wherein in the formula [X], $X^{42}$ is CH (the carbon atom may be substituted with $R^{42}$).

(18) The oxopyrazine derivative or the agrochemically acceptable salt thereof according to (11) above, wherein in the formula [X], $X^{42}$ is $N(O)_m$.

(19) The oxopyrazine derivative or the agrochemically acceptable salt thereof according to (16) to (18) above, wherein in the formula [X], $X^{41}$ is an oxygen atom or a sulfur atom;

$X^{42}$ is CH (the carbon atom may be substituted with $R^{42}$) or a nitrogen atom;

$R^{41}$ is a hydrogen atom, a $C_1$-$C_{12}$ alkyl group which may be substituted with a group selected from the substituent group α as shown below, a $C_3$-$C_6$ cycloalkyl group, a $C_2$-$C_6$ alkenyl group, a $C_2$-$C_6$ alkynyl group, a phenyl group which may be substituted with a group selected from the substituent group β as shown below, a phenyl-$C_1$-$C_3$ alkyl group which may be substituted with a group selected from the substituent group β as shown below, a heterocyclic group selected from the heterocyclic ring group Z as shown below (the group may be substituted with a group selected from the substituent group β as shown below), or a heterocyclic-$C_1$-$C_3$ alkyl group in which the heterocyclic moiety is selected from the heterocyclic ring group Z as shown below (the group may be substituted with a group selected from the substituent group β as shown below);

$R^{42}$ is a halogen atom, a $C_1$-$C_6$ alkoxy group, a $C_1$-$C_6$ alkylthio group, or a $C_1$-$C_6$ alkylsulfonyl group;

n is an integer from 0 to 4 when $X^{42}$ is CH (the carbon atom may be substituted with $R^{42}$), or n is an integer from 0 to 3 when $X^{42}$ is a nitrogen atom; and $R^{43}$ is a hydroxyl group.

[Substituent Group α]

A group comprising a halogen atom, a cyano group, a $C_1$-$C_6$ alkoxy group, a $C_1$-$C_6$ haloalkoxy group, a $C_1$-$C_6$ alkoxy-$C_1$-$C_6$ alkoxy group, a $C_1$-$C_6$ alkylsulfonyl-$C_1$-$C_6$ alkoxy group, a cyano-$C_1$-$C_6$ alkoxy group, a phenoxy group, a $C_1$-$C_6$ alkylcarbonyloxy group, a heterocyclic-$C_1$-$C_6$ alkoxy group in which the heterocyclic moiety is selected from the heterocyclic ring group Z as shown below, a $C_1$-$C_6$ alkylthio group, a $C_1$-$C_6$ alkylsulfonyl group, a $C_1$-$C_6$ acyl group, a $C_1$-$C_6$ alkoxycarbonyl group, and a $R^{50}R^{51}N$—C=O group ($R^{50}$ and $R^{51}$ each independently represent a $C_1$-$C_6$ alkyl group, or $R^{50}$ and $R^{51}$ may be joined with the nitrogen atom to which they are bound, to form a 5- to 6-membered ring, while this ring may have an oxygen atom interposed, in addition to the nitrogen atom to which $R^{50}$ and $R^{51}$ are bound).

[Substituent Group β]

A group comprising a halogen atom, a hydroxyl group, a nitro group, a cyano group, a $C_1$-$C_6$ alkyl group, a $C_1$-$C_6$ haloalkyl group, a $C_1$-$C_6$ alkoxy group, a $C_1$-$C_6$ haloalkoxy group, a $C_2$-$C_6$ alkenyloxy group, a $C_2$-$C_6$ alkynyloxy group, a heterocyclic-$C_1$-$C_6$ alkoxy group in which the heterocyclic moiety is selected from the heterocyclic ring group Z as shown below, a $C_1$-$C_6$ alkylthio group, a $C_1$-$C_6$ alkylsulfonyl group, a $C_1$-$C_3$ alkoxy-$C_1$-$C_3$ alkyl group, a $C_3$-$C_6$ cycloalkyl-$C_1$-$C_3$ alkyloxy group, a cyano-$C_1$-$C_3$ alkoxy group, and a $C_1$-$C_6$ acyl group.

[Heterocyclic Ring Group Z]

A group comprising tetrahydrofuran, tetrahydrothiophene, tetrahydrothiophene dioxide, tetrahydrothiopyrane, tetrahydrothiopyrane dioxide, 4,5-dihydroisoxazole, thiophene, isoxazole, thiazole, isothiazole, 1,2,4-oxadiazole, pyridine, pyrimidine, 2,3-dihydrobenzofuran, 1,3-benzodioxole, and benzo-1,4-dioxane.

(20) The oxopyrazine derivative or the agrochemically acceptable salt thereof according to any one of (16) to (19) above, wherein in the formula [X], $X^{41}$ represents an oxygen atom or a sulfur atom, $X^{42}$ is CH (the group may be substituted with $R^{42}$), $R^{41}$ is a hydrogen atom, a $C_1$-$C_{12}$ alkyl group which may be substituted with a group selected from the substituent group α as shown below, a $C_3$-$C_6$ cycloalkyl group, a $C_2$-$C_6$ alkenyl group, a $C_2$-$C_6$ alkynyl group, a phenyl group which may be substituted with a group selected from the substituent group β as shown below, a phenyl-$C_1$-$C_3$ alkyl group which may be substituted with any group selected from the substituent group β as shown below, a heterocyclic group selected from the heterocyclic ring group Z as shown below (the group may be substituted with a group selected from the substituent group β as shown below), or a heterocyclic-$C_1$-$C_3$ alkyl group in which the heterocyclic moiety is selected from the following heterocyclic ring group Z (the group may be substituted with a group selected from the substituent group β as shown below);

$R^{42}$ is a halogen atom, a $C_1$-$C_6$ alkylthio group or a $C_1$-$C_6$ alkylsulfonyl group;

n is an integer from 0 to 4; and $R^{43}$ is a hydroxyl group.

[Substituent Group α]

A group comprising a halogen atom, a cyano group, a $C_1$-$C_6$ alkoxy group, a $C_1$-$C_6$ alkoxy-$C_1$-$C_6$ alkoxy group, a $C_1$-$C_6$ alkylsulfonyl-$C_1$-$C_6$ alkoxy group, a cyano-$C_1$-$C_6$ alkoxy group, a phenoxy group, a $C_1$-$C_6$ haloalkoxy group, a $C_1$-$C_6$ alkylcarbonyloxy group, a heterocyclic-$C_1$-$C_{10}$ alkoxy group in which the heterocyclic moiety is selected from the following heterocyclic ring group Z, a $C_1$-$C_6$ alkylthio group, a $C_1$-$C_6$ alkylsulfonyl group, a $C_1$-$C_6$ acyl group, a $C_1$-$C_6$ alkoxycarbonyl group, and a $R^{50}R^{51}N$—C=O group ($R^{50}$ and $R^{51}$ each independently represent a $C_1$-$C_6$ alkyl group, or $R^{50}$ and $R^{51}$ may be joined with the nitrogen atom to which they are bound, to form a 5- to 6-membered ring, while this ring may have an oxygen atom interposed, in addition to the nitrogen atom to which $R^{50}$ and $R^{51}$ are bound).

[Substituent Group β]

A group comprising a halogen atom, a hydroxyl group, a nitro group, a cyano group, a $C_1$-$C_6$ alkyl group, a $C_1$-$C_6$ haloalkyl group, a $C_1$-$C_6$ alkoxy group, a $C_1$-$C_6$ haloalkoxy group, a heterocyclic-$C_1$-$C_{10}$ alkoxy group in which the heterocyclic moiety is selected from the heterocyclic ring group Z as shown below, a $C_1$-$C_6$ alkylthio group, a $C_1$-$C_6$ alkylsulfonyl group, a $C_1$-$C_6$ alkoxy-$C_1$-$C_6$ alkyl group, a $C_3$-$C_6$ cycloalkyl-$C_1$-$C_3$ alkyloxy group, a cyano-$C_1$-$C_3$ alkoxy group, and a $C_1$-$C_6$ acyl group.

[Heterocyclic Ring Group Z]

A group comprising tetrahydrofuran, tetrahydrothiophene, tetrahydrothiophene dioxide, tetrahydrothiopyrane, tetrahydrothiopyrane dioxide, 4,5-dihydroisoxazole, thiophene, isoxazole, thiazole, isothiazole, 1,2,4-oxadiazole, pyridine, pyrimidine, 2,3-dihydrobenzofuran, 1,3-benzodioxole, and benzo-1,4-dioxane.

(21) The oxopyrazine derivative or the agrochemically acceptable salt thereof according to any one of (16) to (20) above, wherein in the formula [X], $X^{41}$ is an oxygen atom;

$X^{42}$ is a nitrogen atom;

$R^{41}$ is a $C_1$-$C_{12}$ alkyl group which may be substituted with any group selected from the following substituent group α, a $C_2$-$C_6$ alkenyl group, a $C_2$-$C_6$ alkynyl group, a phenyl group which may be substituted with any group selected from the following substituent group β, a phenyl-$C_1$-$C_3$ alkyl group, a heterocyclic group selected from the following heterocyclic group Z (the group may be substituted with any group selected from the following substituent group β), or a heterocyclic-$C_1$-$C_3$ alkyl group selected from the following heterocyclic group Z (the group may be substituted with any group selected from the following substituent group β);

$R^{42}$ is a halogen atom or a $C_1$-$C_6$ alkoxy group;

n is an integer from 0 to 3;

$R^{43}$ is a hydroxyl group;

$A^{41}$ is $CHR^{44}$;

$A^{42}$ is $CH_2$;

$A^{43}$ is $CHR^{49}$;

$R^{44}$ and $R^{49}$ are hydrogen atoms, or $R^{44}$ and $R^{49}$ may be joined by a $C_2$-$C_5$ alkylene chain to constitute a ring.

[Substituent Group α]

A group comprising a halogen atom, a $C_1$-$C_6$ alkoxy group, and a $C_1$-$C_6$ alkoxycarbonyl group.

[Substituent Group β]

A group comprising a halogen atom, a $C_1$-$C_6$ alkyl group, a $C_1$-$C_6$ haloalkyl group, and a $C_1$-$C_6$ alkoxy group.

[Heterocyclic Ring Group Z]

A group comprising 4,5-dihydroisoxazole, thiophene, isoxazole, pyridine, 1,3-benzodioxole, and benzo-1,4-dioxane.

(22) A herbicide characterized by comprising the oxopyrazine derivative according to anyone of (16) to (21) above or a salt thereof, as an active ingredient.

(23) A method of using a herbicide characterized by treating soil and/or plants with an effective amount of the herbicide according to (22) above.

(24) An agrochemical composition for herbicidal use, comprising the oxopyrazine derivative according to any one of (16) to (21) above or a salt thereof, and an agrochemically acceptable carrier thereof.

(25) A method for suppressing the growth of weeds, the method including spreading an agrochemical composition containing an effective amount of the oxopyrazine derivative according to any one of (16) to (21) above or a salt thereof, over a place where the weeds to be removed are growing.

The oxopyrazine derivative represented by the formula [I] or a salt thereof according to the present invention has been re-written on the basis of the description on the oxopyrazine derivative represented by the formula [X] or a salt thereof.

In the present specification, the entirety of the subject matters described in the specification of Japanese Patent Application No. 2007-201387, on the basis of which the present patent application claims priority, has been incorporated into the description of the present specification.

Effect of the Invention

The oxopyrazine derivative represented by formula [I] or an agrochemically acceptable salt thereof according to the present invention can control various weeds growing in upland fields, orchards, paddy fields and non-agricultural lands, and has excellent effects of action as an agrochemical, such as showing high safety against useful plants, useful crops and the like.

BEST MODE FOR CARRYING OUT THE INVENTION

The symbols and terms described in the present specification will be explained.

The halogen atom is a fluorine atom, a chlorine atom, a bromine atom or an iodine atom.

A notation showing elemental symbols and subscript numbers, such as in $C_1$-$C_3$, indicates that the number of elements of the group described subsequently to the notation is in the range indicated by the subscript numbers. For example, in this case, it is indicated that the carbon number is 1 to 3. The notation of $C_1$-$C_6$ indicates that the carbon number is 1 to 6, while the notation of $C_1$-$C_{12}$ indicates that the carbon number is 1 to 12.

The $C_1$-$C_6$ alkyl group represents, unless particularly limited, a straight-chained or branched alkyl group having 1 to 6 carbon atoms, and groups such as methyl, ethyl, n-propyl, isopropyl, n-butyl, sec-butyl, isobutyl, tert-butyl, n-pentyl, 1-methylbutyl, 2-methylbutyl, 3-methylbutyl, 1-ethylpropyl, 1,1-dimethylpropyl, 1,2-dimethylpropyl, neopentyl, n-hexyl, 1-methylpentyl, 2-methylpentyl, 3-methylpentyl, 4-methylpentyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, 1-ethyl-1-methylpropyl and 1-ethyl-2-methylpropyl may be included, for example. A preferred alkyl group having 1 to 6 carbon atoms may be exemplified by a straight-chained or branched alkyl group having 1 to 4, or 1 to 3, carbon atoms.

The $C_1$-$C_{12}$ alkyl group represents, unless particularly limited, a straight-chained or branched alkyl group having 1 to 12 carbon atoms, and in addition to the examples of the $C_1$-$C_6$ alkyl group, groups such as n-heptyl, 1-methylhexyl, 5-methylhexyl, 1,1-dimethylpentyl, 2,2-dimethylpentyl, 4,4-dimethylpentyl, 1-ethylpentyl, 2-ethylpentyl, 1,1,3-trimethylbutyl, 1,2,2-trimethylbutyl, 1,3,3-trimethylbutyl, 2,2,3-trimethylbutyl, 2,3,3-trimethylbutyl, 1-propylbutyl, 1,1,2,2-tetramethylpropyl, n-octyl, 1-methylheptyl, 3-methylheptyl, 6-methylheptyl, 2-ethylhexyl, 5,5-dimethylhexyl, 2,4,4-trimethylpentyl, 1-ethyl-1-methylpentyl, nonyl, 1-methyloctyl, 2-methyloctyl, 3-methyloctyl, 7-methyloctyl, 1-ethylheptyl, 1,1-dimethylheptyl, 6,6-dimethylheptyl, decyl, 1-methylnonyl, 2-methylnonyl, 6-methylnonyl, 1-ethyloctyl, 1-propylheptyl, n-nonyl, n-decyl, n-undecyl and n-dodecyl may be included, for example. A preferred alkyl group having 1 to 12 carbon atoms may be exemplified by a straight-chained or branched alkyl group having 1 to 8, 1 to 6, or 1 to 3, carbon atoms.

The $C_3$-$C_8$ cycloalkyl group represents, unless particularly limited, a cycloalkyl group having 3 to 8 carbon atoms, and groups such as cyclopropyl, cyclobutyl, cyclopentyl and cyclohexyl may be included, for example. A preferred cycloalkyl group having 3 to 8 carbon atoms may be exemplified by a cycloalkyl group having 3 to 6, or 4 to 6, carbon atoms.

The $C_3$-$C_8$ cycloalkyl-$C_1$-$C_6$ alkyl group represents, unless particularly limited, an alkyl group having 1 to 6 carbon atoms substituted with a cycloalkyl group having 3 to 8 carbon atoms, in which the cycloalkyl moiety and the alkyl moiety respectively have the same meanings as defined above, and groups such as cyclopropylmethyl, 1-cyclopropylethyl, 2-cyclopropylethyl, 1-cyclopropylpropyl, 2-cyclopropylpropyl, 3-cyclopropylpropyl, cyclobutylmethyl, cyclopentylmethyl and cyclohexylmethyl may be included, for example.

The $C_1$-$C_6$ haloalkyl group represents a straight-chained or branched alkyl group having 1 to 6 carbon atoms substituted with one or more, preferably 1 to 10, and more preferably 1 to 5, halogen atoms, and groups such as fluoromethyl, chloromethyl, bromomethyl, difluoromethyl, dichloromethyl, trifluoromethyl, trichloromethyl, chlorodifluoromethyl, bromodifluoromethyl, 2-fluoroethyl, 1-chloroethyl, 2-chloroethyl, 1-bromoethyl, 2-bromoethyl, 2,2-difluoroethyl, 1,2-dichloroethyl, 2,2-dichloroethyl, 2,2,2-trifluoroethyl, 2,2,2-trichloroethyl, 1,1,2,2-tetrafluoroethyl, pentafluoroethyl, 2-bromo-2-chloroethyl, 2-chloro-1,1,2,2-tetrafluoroethyl, 1-chloro-1,2,2,2-tetrafluoroethyl, 1-chloropropyl, 2-chloropropyl, 3-chloropropyl, 2-bromopropyl, 3-bromopropyl, 2-bromo-1-methylethyl, 3-iodopropyl, 2,3-dichloropropyl, 2,3-dibromopropyl, 3,3,3-trifluoropropyl, 3,3,3-trichloropropyl, 3-bromo-3,3-difluoropropyl, 3,3-dichloro-3-fluoropropyl, 2,2,3,3-tetrafluoropropyl, 1-bromo-3,3,3-trifluoropropyl, 2,2,3,3,3-pentafluoropropyl, 2,2,2-trifluoro-1-trifluoromethylethyl, heptafluoropropyl, 1,2,2,2-tetrafluoro-1-trifluoromethylethyl, 2,3-dichloro-1,1,2,3,3-pentafluoropropyl, 2-chlorobutyl, 3-chlorobutyl, 4-chlorobutyl, 2-chloro-1,1-dimethylethyl, 4-bromobutyl, 3-bromo-2-methylpropyl, 2-bromo-1,1-dimethylethyl, 2,2-dichloro-1,1-dimethylethyl, 2-chloro-1-chloromethyl-2-methylethyl, 4,4,4-trifluorobutyl, 3,3,3-trifluoro-1-methylpropyl, 3,3,3-trifluoro-2-methylpropyl, 2,3,4-trichlorobutyl, 2,2,2-trichloro-1,1-dimethylethyl, 4-chloro-4,4-difluorobutyl, 4,4-dichloro-4-fluorobutyl, 4-bromo-4,4-difluorobutyl, 2,4-dibromo-4,4-difluorobutyl, 3,4-dichloro-3,4,4-trifluorobutyl, 3,3-dichloro-4,4,4-trifluorobutyl, 4-bromo-3,3,4,4-tetrafluorobutyl, 4-bromo-3-chloro-3,4,4-trifluorobutyl, 2,2,3,3,4,4-hexafluorobutyl, 2,2,3,4,4,4-hexafluorobutyl, 2,2,2-trifluoro-1-methyl-1-trifluoromethylethyl, 3,3,3-trifluoro-2-trifluoromethylpropyl, 2,2,3,3,4,4,4-heptafluorobutyl, 2,3,3,3-tetrafluoro-2-trifluoromethylpropyl, 1,1,2,2,3,3,4,4-octafluorobutyl, nonafluorobutyl, 4-chloro-1,1,2,2,3,3,4,4-octafluorobutyl, 5-fluoropentyl, 5-chloropentyl, 5,5-difluoropentyl, 5,5-dichloropentyl, 5,5,5-trifluoropentyl, 6,6,6-trifluorohexyl and 5,5,5,6,6,6-hexafluorohexyl may be included, for example.

The $C_2$-$C_6$ alkenyl group represents, unless particularly limited, a straight-chained or branched alkenyl group having 2 to 6 carbon atoms, and groups such as vinyl, 1-propenyl, isopropenyl, 2-propenyl, 1-butenyl, 1-methyl-1-propenyl, 2-butenyl, 1-methyl-2-propenyl, 3-butenyl, 2-methyl-1-propenyl, 2-methyl-2-propenyl, 1,3-butadienyl, 1-pentenyl, 1-ethyl-2-propenyl, 2-pentenyl, 1-methyl-1-butenyl, 3-pentenyl, 1-methyl-2-butenyl, 4-pentenyl, 1-methyl-3-butenyl, 3-methyl-1-butenyl, 1,2-dimethyl-2-propenyl, 1,1-dimethyl-2-propenyl, 2-methyl-2-butenyl, 3-methyl-2-butenyl, 1,2-dimethyl-1-propenyl, 2-methyl-3-butenyl, 3-methyl-3-butenyl, 1,3-pentadienyl, 1-vinyl-2-propenyl, 1-hexenyl, 1-propyl-2-propenyl, 2-hexenyl, 1-methyl-1-pentenyl, 1-ethyl-2-butenyl, 3-hexenyl, 4-hexenyl, 5-hexenyl, 1-methyl-4-pentenyl, 1-ethyl-3-butenyl, 1-(isobutyl)vinyl, 1-ethyl-1-methyl-2-propenyl, 1-ethyl-2-methyl-2-propenyl, 1-(isopropyl)-2-propenyl, 2-methyl-2-pentenyl, 3-methyl-3-pentenyl, 4-methyl-3-pentenyl, 1,3-dimethyl-2-butenyl, 1,1-dimethyl-3-butenyl, 3-methyl-4-pentenyl, 4-methyl-4-pentenyl, 1,2-dimethyl-3-butenyl, 1,3-dimethyl-3-butenyl, 1,1,2-trimethyl-2-propenyl, 1,5-hexadienyl, 1-vinyl-3-butenyl and 2,4-hexadienyl may be included, for example. A preferred alkenyl group having 2 to 6 carbon atoms may be exemplified by a straight-chained or branched alkenyl group having 2 to 4 carbon atoms.

The $C_2$-$C_6$ alkynyl group represents, unless particularly limited, a straight-chained or branched alkynyl group having 2 to 6 carbon atoms, and groups such as ethynyl, 1-propynyl, 2-propynyl, 1-butynyl, 1-methyl-2-propynyl, 2-butynyl, 3-butynyl, 1-pentynyl, 1-ethyl-2-propynyl, 2-pentynyl, 3-pentynyl, 1-methyl-2-butynyl, 4-pentynyl, 1-methyl-3-butynyl, 2-methyl-3-butynyl, 1-hexynyl, 1-(n-propyl)-2-propynyl, 2-hexynyl, 1-ethyl-2-butynyl, 3-hexynyl, 1-methyl-2-pentynyl, 1-methyl-3-pentynyl, 4-methyl-1-pentynyl, 3-methyl-1-pentynyl, 5-hexynyl, 1-ethyl-3-butynyl, 1-ethyl-1-methyl-2-propynyl, 1-(isopropyl)-2-propynyl, 1,1-dimethyl-2-butynyl and 2,2-dimethyl-3-butynyl may be included, for example. A preferred alkynyl group having 2 to 6 carbon atoms may be exemplified by a straight-chained or branched alkynyl group having 2 to 4 carbon atoms.

The $C_1$-$C_6$ alkoxy group represents, unless particularly limited, a straight-chained or branched alkoxy group having 1 to 6 carbon atoms, and groups such as methoxy, ethoxy, propoxy, isopropoxy, butoxy, pentyloxy and hexyloxy may be included, for example. A preferred alkoxy group having 1 to 6 carbon atoms may be exemplified by a straight-chained or branched alkoxy group having 1 to 4, or 1 to 3, carbon atoms.

The $C_1$-$C_6$ alkoxy-$C_1$-$C_6$ alkyl group represents, unless particularly limited, an alkyl group having 1 to 6 carbon atoms substituted with an alkoxy group having 1 to 6 carbon atoms, in which the alkyl moiety and the alkoxy moiety respectively have the same meanings as defined above, and groups such as methoxymethyl, ethoxymethyl, isopropoxymethyl, pentyloxymethyl, methoxyethyl and butoxyethyl may be included, for example.

The $C_1$-$C_6$ alkoxy-$C_1$-$C_6$ alkoxy group represents an alkoxy group having 1 to 6 carbon atoms substituted with an alkoxy group having 1 to 6 carbon atoms, in which the alkoxy moiety has the same meaning as defined above, and groups such as methoxymethoxy, ethoxymethoxy, 2-methoxyethoxy and 2-ethoxyethoxy may be included, for example.

The $C_3$-$C_8$ cycloalkyl-$C_1$-$C_6$ alkyloxy group represents an (alkyl)-O— group having 1 to 6 carbon atoms substituted with a cycloalkyl group having 3 to 8 carbon atoms, in which the cycloalkyl moiety and the alkyl moiety respectively have the same meanings as defined above, and groups such as cyclopropylmethyloxy, cyclopropylethyloxy and cyclopentylmethyloxy may be included, for example. A preferred cycloalkyl group having 3 to 8 carbon atoms may be exemplified by a cycloalkyl group having 3 to 6 carbon atoms.

The cyano-$C_1$-$C_6$ alkoxy group represents an alkoxy group having 1 to 6 carbon atoms substituted with a cyano group, in which the alkoxy moiety has the same meaning as defined above, and groups such as 2-cyanoethoxy and 3-cyanopropoxy may be included, for example.

The $C_3$-$C_8$ cycloalkyloxy group represents, unless particularly limited, a (cycloalkyl)-O— group having 3 to 8 carbon atoms in which the cycloalkyl moiety has the same meaning as defined above, and groups such as cyclopropyloxy, cyclobutyloxy, cyclopentyloxy and cyclohexyloxy may be included, for example.

The $C_2$-$C_6$ alkenyloxy group represents, unless particularly limited, an (alkenyl)-O— group having 2 to 6 carbon atoms in which the alkenyl moiety has the same meaning as defined above, and groups such as 2-propenyloxy may be included, for example.

The $C_2$-$C_6$ alkynyloxy group represents, unless particularly limited, an (alkynyl)-O— group having 2 to 6 carbon atoms in which the alkynyl moiety has the same meaning as defined above, and groups such as 2-propynyloxy may be included, for example.

The $C_1$-$C_6$ alkylthio group represents an (alkyl)-S-group having 1 to 6 carbon atoms in which the alkyl moiety has the same meaning as defined above, and groups such as methylthio, ethylthio, n-propylthio and isopropylthio may be included, for example.

The $C_1$-$C_6$ alkylsulfinyl group represents an (alkyl)-SO— group having 1 to 6 carbon atoms in which the alkyl moiety has the same meaning as defined above, and groups such as methylsulfinyl, ethylsulfinyl, n-propylsulfinyl and isopropylsulfinyl may be included, for example.

The $C_1$-$C_6$ alkylsulfonyl group represents an (alkyl)-$SO_2$— group having 1 to 6 carbon atoms in which the alkyl moiety has the same meaning as defined above, and groups such as methylsulfonyl, ethylsulfonyl, n-propylsulfonyl and isopropylsulfonyl may be included, for example.

The $C_1$-$C_6$ alkylsulfonyloxy group represents an (alkyl)-$SO_2$—O— group having 1 to 6 carbon atoms in which the alkyl moiety has the same meaning as defined above, and groups such as methylsulfonyloxy and ethylsulfonyloxy may be included, for example.

The $C_1$-$C_6$ alkylsulfonyl-$C_1$-$C_6$ alkoxy group represents an alkoxy group having 1 to 6 carbon atoms substituted with an alkylsulfonyl group having 1 to 6 carbon atoms, in which the alkylsulfonyl moiety and the alkoxy moiety respectively have the same meanings as defined above, and groups such as 2-(methylsulfonyl)ethoxy and 2-(ethylsulfonyl)ethoxy may be included, for example.

The mono($C_1$-$C_6$ alkyl) amino group represents an (alkyl)-NH— group having 1 to 6 carbon atoms in which the alkyl moiety has the same meaning as defined above, and groups such as methylamino and ethylamino may be included, for example.

The di($C_1$-$C_6$ alkyl)amino group represents an (alkyl)$_2$N— group having 1 to 6 carbon atoms in which the alkyl moiety has the same meaning as defined above, and groups such as dimethylamino, diethylamino, methylethylamino, dipropylamino and dibutylamino may be included, for example.

The mono($C_1$-$C_6$ alkyl)aminocarbonyl group represents an (alkyl)-NH—C(=O)— group having 1 to 6 carbon atoms in which the alkyl moiety has the same meaning as defined above, and groups such as methylaminocarbonyl and ethylaminocarbonyl may be included, for example.

The di($C_1$-$C_6$ alkyl)aminocarbonyl group represents an (alkyl)$_2$N—C(=O)— group having 1 to 6 carbon atoms in which the alkyl moiety has the same meaning as defined above, and groups such as dimethylaminocarbonyl, diethylaminocarbonyl, methylethylaminocarbonyl, dipropylaminocarbonyl and dibutylaminocarbonyl may be included, for example.

The $C_1$-$C_6$ alkoxycarbonyl group represents an (alkyl)-OC(=O)— group having 1 to 6 carbon atoms in which the alkyl moiety has the same meaning as defined above, and groups such as methoxycarbonyl, ethoxycarbonyl, n-propoxycarbonyl and isopropoxycarbonyl may be included, for example.

The $C_1$-$C_6$ acyl group represents an acyl group derived from a straight-chained or branched aliphatic carboxylic acid having 1 to 6 carbon atoms, and groups such as formyl, acetyl, propionyl, isopropionyl, butyryl and pivaloyl may be included, for example.

The $C_1$-$C_6$ alkylcarbonyloxy group represents an (alkyl)-C(=O)—O— group having 1 to 6 carbon atoms in which the alkyl moiety has the same meaning as defined above, and groups such as acetoxy, propionyloxy, isopropionyloxy and pivaloyloxy may be included, for example.

The $C_2$-$C_6$ alkenylcarbonyloxy group represents an (alkenyl)-C(=O)—O— group having 2 to 6 carbon atoms in which the alkenyl moiety has the same meaning as defined above, and groups such as 1-propenylcarbonyloxy, 2-propenylcarbonyloxy, 1-butenylcarbonyloxy and 1-methyl-1-propenylcarbonyloxy may be included, for example.

The $C_2$-$C_6$ alkynylcarbonyloxy group represents an (alkynyl)-C(=O)—O— group having 2 to 6 carbon atoms in which the alkynyl moiety has the same meaning as defined above, and groups such as 1-propynylcarbonyloxy and 2-propynylcarbonyloxy may be included, for example.

The $C_1$-$C_6$ haloalkylthio group represents a (haloalkyl)-S— group having 1 to 6 carbon atoms in which the haloalkyl moiety has the same meaning as defined above, and groups such as difluoromethylthio and trifluoromethylthio may be included, for example.

The $C_1$-$C_6$ haloalkylsulfinyl group represents a (haloalkyl)-SO— group having 1 to 6 carbon atoms in which the haloalkyl moiety has the same meaning as defined above, and groups such as chloromethylsulfinyl, difluoromethylsulfinyl and trifluoromethylsulfinyl may be included, for example.

The $C_1$-$C_6$ haloalkylsulfonyl group represents a (haloalkyl)-SO$_2$— group having 1 to 6 carbon atoms in which the haloalkylmoiety has the same meaning as defined above, and groups such as chloromethylsulfonyl, difluoromethylsulfonyl and trifluoromethylsulfonyl may be included, for example.

The mono($C_1$-$C_6$ alkyl)aminocarbonyl group represents an (alkyl)NH—C(=O)— group having 1 to 6 carbon atoms in which the alkyl moiety has the same meaning as defined above, and groups such as methylaminocarbonyl and ethylaminocarbonyl may be included, for example.

The di($C_1$-$C_6$ alkyl)aminocarbonyl group represents an (alkyl)$_2$N—C(=O)— group in which the alkyl moiety has the same meaning as defined above, and groups such as dimethylaminocarbonyl, diethylaminocarbonyl, methylethylaminocarbonyl, dipropylaminocarbonyl and dibutylaminocarbonyl may be included, for example.

The $C_2$-$C_6$ alkenylthio group represents an (alkenyl)-S— group having 2 to 6 carbon atoms in which the alkenyl moiety has the same meaning as defined above, and groups such as allylthio may be included, for example.

The $C_2$-$C_6$ alkenylsulfinyl group represents an (alkenyl)-SO— group having 2 to 6 carbon atoms in which the alkenyl moiety has the same meaning as defined above, and groups such as allylsulfinyl may be included, for example.

The $C_2$-$C_6$ alkenylsulfonyl group represents an (alkenyl)-SO$_2$— group having 2 to 6 carbon atoms in which the alkenyl moiety has the same meaning as defined above, and groups such as allylsulfonyl may be included, for example.

The $C_2$-$C_6$ alkynylthio group represents an (alkynyl)-S— group having 2 to 6 carbon atoms in which the alkynyl moiety has the same meaning as defined above, and groups such as 2-propynylthio may be included, for example.

The $C_2$-$C_6$ alkynylsulfinyl group represents an (alkynyl)-SO— group having 2 to 6 carbon atoms in which the alkynyl moiety has the same meaning as defined above, and groups such as 2-propynylsulfinyl may be included, for example.

The $C_2$-$C_6$ alkynylsulfonyl group represents an (alkynyl)-SO$_2$— having 2 to 6 carbon atoms in which the alkynyl moiety has the same meaning as defined above, and groups such as 2-propynylsulfonyl may be included, for example.

The phenyl-$C_1$-$C_6$ alkyl group represents an alkyl group having 1 to 6 carbon atoms substituted with a phenyl group, in which the alkyl moiety has the same meaning as defined above, and groups such as benzyl, 1-phenylethyl and 2-phenylethyl may be included, for example.

The heterocyclic group having 2 to 10 carbon atoms and 1 to 5 heteroatoms selected from an oxygen atom, a sulfur atom and a nitrogen atom, represents, unless particularly limited, a monovalent group formed from a 3- to 8-membered, and preferably 5- to 7-membered monocyclic, polycyclic or fused-ring heterocyclic ring having 1 to 5, and preferably 1 to 3, heteroatoms selected from the group consisting of an oxygen atom, a sulfur atom and a nitrogen atom, and groups such as oxirane, tetrahydrofuran, pyrrolidine, tetrahydrothiophene, tetrahydrothiophene dioxide, tetrahydrothiopyrane, tetrahydrothiopyrane dioxide, 4,5-dihydroisoxazole, piperidine, piperazine, morpholine, furan, thiophene, pyrrole, pyrazole, imidazole, oxazole, isoxazole, thiazole, isothiazole, 1,3,4-oxadiazole, 1,3,4-thiadiazole, 1,3,4-triazole, 1,2,4-oxadiazole, 1,2,4-thiadiazole, 1,2,4-triazole, 1,2,3-oxadiazole, 1,2,3-thiadiazole, 1,2,3-triazole, tetrazole, pyridine, pyrimidine, pyrazine, pyridazine, 1,3,5-triazine, 1,2,4-triazine, benzothiophene, benzofuran, indole, benzoxazole, benzothiazole, benzimidazole, benzisoxazole, benzisothiazole, indazole, 1,3-benzodioxole, benzo-1,4-dioxane and 2,3-dihydrobenzofuran may be included, for example.

The heterocyclic-$C_1$-$C_6$ alkyl group in which the heterocyclic moiety has 2 to 10 carbon atoms and 1 to 5 heteroatoms selected from an oxygen atom, a sulfur atom and a nitrogen atom, represents, unless particularly limited, an alkyl group having 1 to 6 carbon atoms substituted with a heterocyclic group in which the alkyl moiety has the same meaning as defined above, and groups such as (tetrahydrofuran-2-yl)methyl, (4,5-dihydroisoxazol-5-yl)methyl, (isoxazol-5-yl)methyl and (thiophen-2-yl)methyl may be included, for example.

The heterocyclic-$C_1$-$C_6$ alkoxy group in which the heterocyclic moiety has 2 to 10 carbon atoms and 1 to 5 heteroatoms selected from an oxygen atom, a sulfur atom and a nitrogen atom, represents an alkoxy group having 1 to 6 carbon atoms substituted with a heterocyclic group having 2 to 10 carbon atoms and 1 to 5 heteroatoms selected from an oxygen atom, a sulfur atom and a nitrogen atom, in which the heterocyclic moiety having 2 to 10 carbon atoms and 1 to 5 heteroatoms selected from an oxygen atom, a sulfur atom and a nitrogen atom, and the alkoxy moiety respectively have the same meanings as defined above, and groups such as (tetrahydrofuran-2-yl)methoxy and (tetrahydrofuran-3-yl)methoxy may be included, for example.

The heterocyclic-$C_1$-$C_6$ alkoxy-$C_1$-$C_6$ alkyl group in which the heterocyclic moiety has 2 to 10 carbon atoms and 1 to 5 heteroatoms selected from an oxygen atom, a sulfur atom and a nitrogen atom, represents an alkyl group having 1 to 6 carbon atoms substituted with an alkoxy group having 1 to 6 carbon atoms, which is substituted with a heterocyclic group having 2 to 10 carbon atoms and 1 to 5 heteroatoms selected from an oxygen atom, a sulfur atom and a nitrogen atom, in which the heterocyclic moiety having 2 to 10 carbon atoms and 1 to 5 heteroatoms selected from an oxygen atom, a sulfur atom and a nitrogen atom, the alkoxy moiety and the alkyl moiety respectively have the same meanings as defined above. Groups such as (tetrahydrofuran-2-yl)methoxymethyl and (tetrahydrofuran-3-yl)methoxymethyl may be included, for example.

The $C_2$-$C_6$ haloalkenyl group represents, unless particularly limited, a straight-chained or branched alkenyl group having 2 to 6 carbon atoms substituted with 1 to 11, and preferably 1 to 5, halogen atoms, and groups such as 2-chlorovinyl, 2-bromovinyl, 2-iodovinyl, 3-chloro-2-propenyl, 3-bromo-2-propenyl, 1-chloromethylvinyl, 2-bromo-1-methylvinyl, 1-trifluoromethylvinyl, 3,3,3-trichloro-1-propenyl, 3-bromo-3,3-difluoro-1-propenyl, 2,3,3,3-tetrachloro-1-propenyl, 1-trifluoromethyl-2,2-difluorovinyl, 2-chloro-2-propenyl, 3,3-difluoro-2-propenyl, 2,3,3-trichloro-2-propenyl, 4-bromo-3-chloro-3,4,4-trifluoro-1-butenyl, 1-bromomethyl-2-propenyl, 3-chloro-2-butenyl, 4,4,4-trifluoro-2-butenyl, 4-bromo-4,4-difluoro-2-butenyl, 3-bromo-3-butenyl, 3,4,4-trifluoro-3-butenyl, 3,4,4-tribromo-3-butenyl, 3-bromo-2-methyl-2-propenyl, 3,3-difluoro-2-methyl-2-propenyl, 3,3,3-trifluoro-2-methylpropenyl, 3-chloro-4,4,4-trifluoro-2-butenyl, 3,3,3-trifluoro-1-methyl-1-propenyl, 3,4,4-trifluoro-1,3-butadienyl, 3,4-dibromo-1-pentenyl, 4,4-difluoro-3-methyl-3-butenyl, 3,3,4,4,5,5,5-heptafluoro-1-pentenyl, 5,5-difluoro-4-pentenyl, 4,5,5-trifluoro-4-pentenyl, 3,4,4,4-tetrafluoro-3-trifluoromethyl-1-butenyl, 4,4,4-trifluoromethyl-3-methyl-2-butenyl, 3,5,5-trifluoro-2,4-pentadienyl, 4,4,5,5,6,6,6-heptafluoro-2-hexenyl, 3,4,4,5,5,5-hexafluoro-3-trifluoromethyl-1-pentenyl, 4,5,5,5-tetrafluoro-4-trifluoromethyl-2-pentenyl and 5-bromo-4,5,5-trifluoro-4-trifluoromethyl-2-pentenyl may be included, for example.

The $C_2$-$C_6$ haloalkynyl group represents, unless particularly limited, a straight-chained or branched alkynyl group having 2 to 6 carbon atoms substituted with 1 to 4 identical or different halogen atoms, and groups such as 3-chloro-2-propynyl, 3-bromo-2-propynyl, 3-iodo-2-propynyl, 3-chloro-1-propynyl and 5-chloro-4-pentynyl may be included, for example.

The amino-$C_1$-$C_6$ alkyl group represents, unless particularly limited, an alkyl group having 1 to 6 carbon atoms substituted with an amino group, in which the alkyl moiety has the same meaning as defined above, and groups such as 2-aminoethyl and 3-aminopropyl may be included, for example.

The mono($C_1$-$C_6$ alkyl)amino-$C_1$-$C_6$ alkyl group represents, unless particularly limited, a straight-chained or branched alkyl group having 1 to 6 carbon atoms substituted with an amino group which is mono-substituted with an alkyl group, in which the alkyl moiety has the same meaning as defined above, and groups such as 2-(methylamino)ethyl and 3-(methylamino)propyl may be included, for example.

The di($C_1$-$C_6$ alkyl)amino-$C_1$-$C_6$ alkyl group represents, unless particularly limited, a straight-chained or branched alkyl group having 1 to 6 carbon atoms substituted with an amino group which is di-substituted with alkyl groups, in which the alkyl moiety has the same meaning as defined above, and groups such as N,N-dimethylaminomethyl and N,N-dimethylaminoethyl may be included, for example.

The $C_1$-$C_6$ alkylthio-$C_1$-$C_6$ alkyl group represents, unless particularly limited, an alkyl group having 1 to 6 carbon atoms substituted with an alkylthio group having 1 to 6 carbon atoms, in which the alkyl moiety and the alkyl moiety of the alkylthio respectively have the same meanings as defined above, and groups such as methylthiomethyl and ethylthiomethyl may be included, for example.

The $C_1$-$C_6$ alkylsulfinyl-$C_1$-$C_6$ alkyl group represents, unless particularly limited, an alkyl group having 1 to 6 carbon atoms substituted with an alkylsulfinyl group having 1 to 6 carbon atoms, in which the alkyl moiety and the alkyl moiety of the alkylsulfinyl respectively have the same meanings as defined above, and groups such as methylsulfinylmethyl and ethylsulfinylmethyl may be included, for example.

The $C_1$-$C_6$ alkylsulfonyl-$C_1$-$C_6$ alkyl group represents, unless particularly limited, an alkyl group having 1 to 6 carbon atoms substituted with an alkylsulfonyl group having 1 to 6 carbon atoms, in which the alkyl moiety and the alkyl moiety of the alkylsulfonyl respectively have the same meanings as defined above, and groups such as methylsulfonylmethyl and ethylsulfonylmethyl may be included, for example.

The $C_1$-$C_6$ haloalkylthio-$C_1$-$C_6$ alkyl group represents, unless particularly limited, an alkyl group having 1 to 6 carbon atoms substituted with a (haloalkyl))-S-group having 1 to 6 carbon atoms, in which the alkyl moiety and the haloalkyl moiety respectively have the same meanings as defined above, and groups such as difluoromethylthiomethyl and trifluoromethylthiomethyl may be included, for example.

The $C_1$-$C_6$ haloalkylsulfinyl-$C_1$-$C_6$ alkyl group represents, unless particularly limited, an alkyl group having 1 to 6 carbon atoms substituted with a (haloalkyl)-SO— group having 1 to 6 carbon atoms, in which the alkyl moiety and the haloalkyl moiety respectively have the same meanings as defined above, and groups such as difluoromethylsulfinylmethyl and trifluoromethylsulfinylmethyl may be included, for example.

The $C_1$-$C_6$ haloalkylsulfonyl-$C_1$-$C_6$ alkyl group represents, unless particularly limited, an alkyl group having 1 to 6 carbon atoms substituted with a (haloalkyl)-$SO_2$— group having 1 to 6 carbon atoms, in which the alkyl moiety and the haloalkyl moiety respectively have the same meanings as defined above, and groups such as difluoromethylsulfonylmethyl and trifluoromethylsulfonylmethyl may be included, for example.

The phenyl-$C_1$-$C_6$ alkoxy-$C_1$-$C_6$ alkyl group represents, unless particularly limited, an alkyl group having 1 to 6 carbon atoms substituted with an alkoxy group having 1 to 6 carbon atoms which is substituted with a phenyl group, in which the alkyl moiety and the alkoxy moiety respectively have the same meanings as defined above, and groups such as benzyloxymethyl and benzyloxyethyl may be included, for example.

The $C_1$-$C_6$ alkoxy-$C_1$-$C_6$ alkoxy-$C_1$-$C_6$ alkyl group represents, unless particularly limited, an alkyl group having 1 to 6 carbon atoms substituted with an alkoxy group having 1 to 6 carbon atoms which is substituted with an alkoxy group having 1 to 6 carbon atoms, in which the alkyl moiety and the alkoxy moiety respectively have the same meanings as defined above, and groups such as 2-(2-methoxyethoxy)ethyl and 2-(2-ethoxyethoxy)ethyl may be included, for example.

The $C_3$-$C_8$ cycloalkyloxy-$C_1$-$C_6$ alkyl group represents, unless particularly limited, an alkyl group having 1 to 6 carbon atoms substituted with a (cycloalkyl)-O— group having 3 to 8 carbon atoms, in which the alkyl moiety and the cycloalkyl moiety respectively have the same meanings as defined above, and groups such as cyclopropyloxymethyl, cyclobutyloxymethyl, cyclopentyloxymethyl and cyclohexyloxymethyl may be included, for example.

The phenyloxy-$C_1$-$C_6$ alkyl group represents, unless particularly limited, an alkyl group having 1 to 6 carbon atoms substituted with a (phenyl)-O— group, in which the alkyl moiety has the same meanings as defined above, and groups such as phenoxymethyl, 2-phenoxyethyl and 3-phenoxypropyl may be included, for example.

The phenylthio-$C_1$-$C_6$ alkyl group represents, unless particularly limited, an alkyl group having 1 to 6 carbon atoms substituted with a (phenyl)-S-group, in which the alkyl moiety has the same meaning as defined above, and groups such as phenylthiomethyl, 2-phenylthioethyl and 3-phenylthiopropyl may be included, for example.

The $C_1$-$C_6$ haloalkoxy group represents, unless particularly limited, a straight-chained or branched alkyl-O— group having 1 to 6 carbon atoms substituted with 1 to 13, and preferably 1 to 5, identical or different halogen atoms, in which the haloalkyl moiety has the same meaning as defined above, and groups such as chloromethoxy, difluoromethoxy, chlorodifluoromethoxy, trifluoromethoxy and 2,2,2-trifluoroethoxy may be included, for example.

The $C_1$-$C_6$ haloalkoxy-$C_1$-$C_6$ alkyl group represents, unless particularly limited, an alkyl group having 1 to 6 carbon atoms substituted with a haloalkoxy group having 1 to 6 carbon atoms, in which the haloalkoxy moiety and the alkyl moiety respectively have the same meanings as defined above, and groups such as chloromethoxymethyl, difluoromethoxymethyl, chlorodifluoromethoxymethyl, trifluoromethoxymethyl and 2,2,2-trifluoroethoxymethyl may be included, for example.

The $C_1$-$C_6$ haloalkoxy-$C_1$-$C_6$ alkoxy group represents, unless particularly limited, an alkoxy group having 1 to 6 carbon atoms substituted with a haloalkoxy group having 1 to 6 carbon atoms, in which the haloalkoxy moiety and the alkyl moiety respectively have the same meanings as defined above, and groups such as chloromethoxymethoxy, difluoromethoxymethoxy, chlorodifluoromethoxymethoxy, trifluoromethoxymethoxy and 2,2,2-trifluoroethoxymethoxy may be included, for example.

The $C_1$-$C_6$ alkylthio-$C_1$-$C_6$ alkoxy-$C_1$-$C_6$ alkyl group represents, unless particularly limited, an alkyl group having 1 to 6 carbon atoms substituted with an alkoxy group having 1 to 6 carbon atoms which is substituted with an alkylthio group having 1 to 6 carbon atoms, in which the alkylthio moiety, the alkoxy moiety and the alkyl moiety respectively have the same meanings as defined above, and groups such as 2-methylthioethoxymethyl and 2-ethylthioethoxymethyl may be included, for example.

The $C_1$-$C_6$ alkylsulfinyl-$C_1$-$C_6$ alkoxy-$C_1$-$C_6$ alkyl group represents, unless particularly limited, an alkyl group having 1 to 6 carbon atoms substituted with an alkoxy group having 1 to 6 carbon atoms which is substituted with an alkylsulfinyl group having 1 to 6 carbon atoms, in which the alkylsulfinyl moiety, the alkoxy moiety and the alkyl moiety respectively have the same meanings as defined above, and groups such as 2-methylsulfinylethoxymethyl and 2-ethylsulfinylethoxymethyl may be included, for example.

The $C_1$-$C_6$ alkylsulfonyl-$C_1$-$C_6$ alkoxy-$C_1$-$C_6$ alkyl group represents, unless particularly limited, an alkyl group having 1 to 6 carbon atoms substituted with an alkoxy group having 1 to 6 carbon atoms which is substituted with an alkylsulfonyl group having 1 to 6 carbon atoms, in which the alkylsulfonyl moiety, the alkoxy moiety and the alkyl moiety respectively have the same meanings as defined above, and groups such as 2-methylsulfonylethoxymethyl and 2-ethylsulfonylethoxymethyl may be included, for example.

The cyano-$C_1$-$C_6$alkoxy-$C_1$-$C_6$ alkyl group represents, unless particularly limited, an alkyl group having 1 to 6 carbon atoms substituted with an alkoxy group having 1 to 6 carbon atoms which is substituted with a cyano group, in which the alkoxy moiety and the alkyl moiety respectively have the same meanings as defined above, and groups such as 2-cyanoethoxymethyl and 3-cyanopropoxymethyl may be included, for example.

The cyano-$C_1$-$C_6$ alkyl group represents, unless particularly limited, an alkyl group having 1 to 6 carbon atoms substituted with a cyano group, in which the alkyl moiety has the same meaning as defined above, and groups such as cyanomethyl and 2-cyanoethyl may be included, for example.

The $C_1$-$C_6$ alkylcarbonyloxy-$C_1$-$C_6$ alkyl group represents, unless particularly limited, an alkyl group having 1 to 6 carbon atoms substituted with an (alkyl)-C(=O)O— group having 1 to 6 carbon atoms, in which the alkyl moiety has the same meaning as defined above, and groups such as acetoxymethyl, propionyloxymethyl, isopropionyloxymethyl and pivaloyloxymethyl may be included, for example.

The $C_1$-$C_6$ acyl-$C_1$-$C_6$ alkyl group represents, unless particularly limited, an alkyl group having 1 to 6 carbon atoms substituted with an acyl group having 1 to 6 carbon atoms, in which the acyl moiety and the alkyl moiety respectively have the same meanings as defined above, and groups such as 2-oxopropyl, 3-oxopropyl and 2-oxobutyl may be included, for example.

The di($C_1$-$C_6$ alkoxy)-$C_1$-$C_6$ alkyl group represents, unless particularly limited, an alkyl group having 1 to 6 carbon atoms di-substituted with alkoxy groups each having 1 to 6 carbon atoms, in which the alkoxy moiety and the alkyl moiety respectively have the same meanings as defined above, and groups such as (2,2-dimethoxy)ethyl, (3,3-dimethoxy)propyl, (2,2-diethoxy)ethyl and (3,3-diethoxy)propyl may be included, for example.

The $C_1$-$C_6$ alkoxycarbonyl-$C_1$-$C_6$ alkyl group represents, unless particularly limited, an alkyl group having 1 to 6 carbon atoms substituted with an alkoxycarbonyl group having 1 to 6 carbon atoms, in which the alkoxy moiety and the alkyl moiety respectively have the same meanings as defined above, and groups such as 2-methoxy-2-oxoethyl, 2-ethoxy-2-oxoethyl and 2-tert-butoxy-2-oxoethyl may be included, for example.

The $C_1$-$C_6$ alkoxyimino-$C_1$-$C_6$ alkyl group represents, unless particularly limited, an alkyl group having 1 to 6 carbon atoms substituted with an (alkoxy)-N= group having 1 to 6 carbon atoms, in which the alkoxy moiety and the alkyl moiety respectively have the same meanings as defined above, and groups such as 2-methoxyiminoethyl and 3-methoxyiminopropyl may be included, for example.

The $C_6$-$C_{10}$ aryl group may be exemplified by groups such as phenyl and naphthyl.

The $C_6$-$C_{10}$ aryl-$C_1$-$C_6$ alkyl group represents, unless particularly limited, an alkyl group having 1 to 6 carbon atoms substituted with an aryl group having 6 to 10 carbon atoms, in which the aryl moiety and the alkyl moiety respectively have the same meanings as defined above, and groups such as benzyl, phenethyl, 3-phenylpropyl, naphthalen-1-ylmethyl and naphthalen-2-ylmethyl may be included, for example.

The $C_3$-$C_8$ halocycloalkyl group represents, unless particularly limited, a cycloalkyl group having 3 to 8 carbon atoms substituted with 1 to 5, and preferably 1 to 3, halogen atoms, in which the cycloalkyl moiety and the halogen atom respectively have the same meanings as defined above, and groups such as 2,2-difluorocyclopropyl and 2,2-dichlorocyclopropyl may be included, for example.

The nitro-$C_1$-$C_6$ alkyl group represents, unless particularly limited, an alkyl group having 1 to 6 carbon atoms substituted with a nitro group, in which the alkyl moiety has the same meaning as defined above, and groups such as nitromethyl and 2-nitroethyl may be included, for example.

The hydroxy-$C_1$-$C_6$ alkyl group represents, unless particularly limited, an alkyl group having 1 to 6 carbon atoms substituted with a hydroxyl group, in which the alkyl moiety has the same meaning as defined above, and groups such as 2-hydroxyethyl and 3-hydroxypropyl may be included, for example.

The $C_1$-$C_6$ acylamino group represents, unless particularly limited, an amino group substituted with an acyl group having 1 to 6 carbon atoms, in which the acyl moiety has the same meaning as defined above, and groups such as formamide, acetamide and propionamide may be included, for example.

The ($R^6R^7N$—C=O)—$C_1$-$C_6$ alkyl group represents, unless particularly limited, an alkyl group having 1 to 6 carbon atoms substituted with ($R^6R^7N$—C=O), in which the alkyl moiety has the same meaning as defined above, and groups such as N,N-dimethylaminocarbonylmethyl, N,N-dimethylaminocarbonylethyl and N-methyl-N-ethylaminocarbonylmethyl may be included, for example.

The $C_2$-$C_5$ alkylene chain may be exemplified, unless particularly limited, by groups such as ethylene, trimethylene, propylene, tetramethylene and pentamethylene.

The heterocyclic-oxy-$C_1$-$C_6$ alkyl group in which the heterocyclic moiety has 2 to 10 carbon atoms and 1 to 5 heteroatoms selected from an oxygen atom, a sulfur atom and a nitrogen atom represents, unless particularly limited, an alkyl group having 1 to 6 carbon atoms substituted with a (heterocyclic)-O-group, in which the alkyl moiety and the heterocyclic moiety having 2 to 10 carbon atoms and 1 to 5 heteroatoms selected from an oxygen atom, a sulfur atom and a nitrogen atom have the same meanings as defined above, and groups such as 2-(2-pyridyloxy)ethyl, 2-(2-pyrazinyloxy)ethyl, and 2-(2-thiazolyl)ethyl may be included, for example.

The $C_3$-$C_8$ cycloalkyl-$C_1$-$C_6$ alkoxy-$C_1$-$C_6$ alkyl group represents, unless particularly limited, an alkyl group having 1 to 6 carbon atoms substituted with an alkoxy group having 1 to 6 carbon atoms which is substituted with a cycloalkyl group having 3 to 8 carbon atoms, in which the alkyl moiety, the alkoxy moiety and the cycloalkyl moiety respectively have the same meanings as defined above, and groups such as cyclopropylmethyloxymethyl, cyclobutylmethyloxymethyl, cyclopentylmethyloxymethyl and cyclohexylmethyloxymethyl may be included, for example.

The phenylsulfinyl-$C_1$-$C_6$ alkyl group represents, unless particularly limited, an alkyl group having 1 to 6 carbon atoms substituted with a (phenyl)-SO-group, in which the alkyl moiety has the same meaning as defined above, and groups such as phenylsulfinylmethyl, 2-phenylsulfinylethyl, and 3-phenylsulfinylpropyl may be included, for example.

The phenylsulfonyl-$C_1$-$C_6$ alkyl group represents, unless particularly limited, an alkyl group having 1 to 6 carbon atoms substituted with a (phenyl)-$SO_2$-group, in which the alkyl moiety has the same meaning as defined above, and groups such as 2-phenylsulfonylethyl, 3-phenylsulfonylpropyl, and 4-phenylsulfonylbutyl may be included, for example.

The $C_1$-$C_6$ alkylidene group represents, unless particularly limited, a straight-chained or branched divalent alkyl group having 1 to 6 carbon atoms, and groups such as methylene, ethylidene, propylidene, and isopropylidene may be included, for example.

The $C_1$-$C_6$ alkylideneaminooxy-$C_1$-$C_6$ alkyl group represents, unless particularly limited, an alkyl group having 1 to 6 carbon atoms substituted with an (alkylidene)=N—O— having 1 to 6 carbon atoms, in which the alkylidene moiety and the alkyl moiety respectively have the same meanings as defined above, and groups such as methyleneaminooxymethyl, 2-(ethylideneaminooxy)ethyl, and 2-(isopropylideneaminooxy)ethyl may be included, for example.

The $C_3$-$C_8$ halocycloalkyl-$C_1$-$C_6$ alkyl group represents, unless particularly limited, an alkyl group having 1 to 6 carbon atoms substituted with a cycloalkyl group having 3 to 8 carbon atoms which is substituted with 1 to 5, preferably 1 to 3 halogen atoms, in which the cycloalkyl moiety, the alkyl moiety, and the halogen atom respectively have the same meanings as defined above, and groups such as 2,2-difluorocyclopropylmethyl, and 2,2-dichlorocyclopropylmethyl may be included, for example.

The alkali metal may be exemplified by sodium, potassium and the like.

The phrases "two adjacent $R^2$s may be joined with the respective carbon atoms to which they are directly bound, to form a 4- to 8-membered carbocyclic ring, or a 4- to 8-membered heterocyclic ring having 1 to 4 heteroatoms selected from an oxygen atom, a sulfur atom and a nitrogen atom," "two adjacent $R^{12}$s may be joined with the respective carbon atoms to which they are directly bound, to form a 4- to 8-membered carbocyclic ring, or a 4- to 8-membered heterocyclic ring having 1 to 4 heteroatoms selected from an oxygen atom, a sulfur atom and a nitrogen atom," and "two adjacent $R^{13}$s may be joined with the respective carbon atoms to which they are directly bound, to form a 4- to 8-membered carbocyclic ring, or a 4- to 8-membered heterocyclic ring having 1 to 4 heteroatoms selected from an oxygen atom, a sulfur atom and a nitrogen atom," may be exemplified by the following, unless particularly limited.

[Chemical Formula 5]

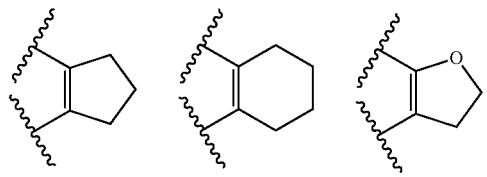

-continued

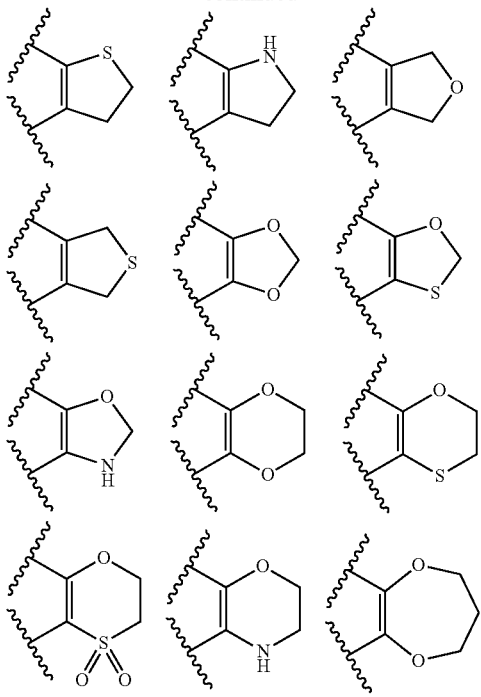

X$^1$ in the formula [I] of the present invention may be exemplified by an oxygen atom or a sulfur atom. A preferred X$^1$ includes an oxygen atom. With regard to the formula [I], X$^1$ is described in the form of carbonyl group; however, in the case where the substituent R$^1$ on the adjacent nitrogen atom is such as a hydrogen atom, X$^1$ is not in the carbonyl form, but may exist in the enol form, which is a tautomer of the carbonyl form.

X$^2$ in the formula [I] of the present invention represents =CH— or =N(O)$_m$— (provided that m represents an integer of 0 or 1). When X$^2$ is =CH—, the 6-membered ring containing X$^2$ turns to be a benzene ring which is fused with a pyrazine ring, to thus form a benzopyrazine ring. The benzene ring thus formed may be substituted with a substituent R$^2$ at the position of X$^2$, as is the case for the other carbon atoms on the benzene ring. In the present specification, this is expressed such that "the carbon atom may be substituted with R$^2$." Furthermore, when X$^2$ represents =N(O)$_m$—, that is, =N— or =N(O)—, the 6-membered ring containing X$^2$ turns to be a pyridine ring or a pyridine N-oxide ring which is fused with a pyrazine ring, to thus form a pyridopyrazine ring or an N-oxide ring thereof. Preferred X$^2$ in the formula [I] of the present invention includes =CH—, =C(R$^2$)—, or =N—.

R$^1$ in the formula [I] of the present invention may be exemplified by a hydrogen atom; a C$_1$-C$_{12}$ alkyl group; a C$_2$-C$_6$ alkenyl group; a C$_2$-C$_6$ alkynyl group; a C$_3$-C$_8$ cycloalkyl group; a C$_3$-C$_8$ cycloalkyl-C$_1$-C$_6$ alkyl group; a C$_1$-C$_6$ haloalkyl group; a C$_2$-C$_6$ haloalkenyl group; a C$_2$-C$_6$ haloalkynyl group; an amino-C$_1$-C$_6$ alkyl group; a nitro-C$_1$-C$_6$ alkyl group; a mono(C$_1$-C$_6$ alkyl)amino-C$_1$-C$_6$ alkyl group; a di(C$_1$-C$_6$ alkyl)amino-C$_1$-C$_6$ alkyl group; a C$_1$-C$_6$ alkylthio-C$_1$-C$_6$ alkyl group; a C$_1$-C$_6$ alkylsulfinyl-C$_1$-C$_6$ alkyl group; a C$_1$-C$_6$ alkylsulfonyl-C$_1$-C$_6$ alkyl group; a C$_1$-C$_6$ haloalkylthio-C$_1$-C$_6$ alkyl group; a C$_1$-C$_6$ haloalkylsulfinyl-C$_1$-C$_6$ alkyl group; a C$_1$-C$_6$ haloalkylsulfonyl-C$_1$-C$_6$ alkyl group; a C$_1$-C$_6$ alkoxy-C$_1$-C$_6$ alkyl group; a hydroxy-C$_1$-C$_6$ alkyl group; a phenyl-C$_1$-C$_6$ alkoxy-C$_1$-C$_6$ alkyl group (the phenyl moiety of the group may be substituted with one or two or more identical or different R$^4$s); a C$_1$-C$_6$ alkoxy-C$_1$-C$_6$ alkoxy-C$_1$-C$_6$ alkyl group; a C$_3$-C$_8$ cycloalkyloxy-C$_1$-C$_6$ alkyl group; a phenyloxy-C$_1$-C$_6$ alkyl group (the phenyl moiety of the group may be substituted with one or two or more identical or different R$^4$s); a phenylthio-C$_1$-C$_6$ alkyl group (the phenyl moiety of the group may be substituted with one or two or more identical or different R$^4$s); a C$_1$-C$_6$ haloalkoxy-C$_1$-C$_6$ alkyl group; a heterocyclic-C$_1$-C$_6$ alkoxy-C$_1$-C$_6$ alkyl group having 2 to 10 carbon atoms and 1 to 5 heteroatoms selected from an oxygen atom, a sulfur atom and a nitrogen atom (the heterocyclic moiety having 2 to 10 carbon atoms and 1 to 5 heteroatoms selected from an oxygen atom, a sulfur atom and a nitrogen atom in the group, may be substituted with one or two or more identical or different R$^5$s); a C$_1$-C$_6$ alkylthio-C$_1$-C$_6$ alkoxy-C$_1$-C$_6$ alkyl group; a C$_1$-C$_6$ alkylsulfinyl-C$_1$-C$_6$ alkoxy-C$_1$-C$_6$ alkyl group; a C$_1$-C$_6$ alkylsulfonyl-C$_1$-C$_6$ alkoxy-C$_1$-C$_6$ alkyl group; a cyano-C$_1$-C$_6$ alkoxy-C$_1$-C$_6$ alkyl group; a cyano-C$_1$-C$_6$ alkyl group; a C$_1$-C$_6$ alkylcarbonyloxy-C$_1$-C$_6$ alkyl group; a C$_1$-C$_6$ acyl-C$_1$-C$_6$ alkyl group; a di(C$_1$-C$_6$ alkoxy)-C$_1$-C$_6$ alkyl group; a C$_1$-C$_6$ alkoxycarbonyl-C$_1$-C$_6$ alkyl group; a C$_1$-C$_6$ alkoxyimino-C$_1$-C$_6$ alkyl group; a (R$^6$R$^7$N—C=O)—C$_1$-C$_6$ alkyl group; a C$_6$-C$_{10}$ aryl-C$_1$-C$_6$ alkyl group (the aryl moiety of the group may be substituted with one or two or more identical or different R$^8$s which will be described later); a heterocyclic-C$_1$-C$_6$ alkyl group in which the heterocyclic moiety has 2 to 10 carbon atoms and 1 to 5 heteroatoms selected from an oxygen atom, a sulfur atom and a nitrogen atom (the heterocyclic moiety having 2 to 10 carbon atoms and 1 to 5 heteroatoms selected from an oxygen atom, a sulfur atom and a nitrogen atom in the group, may be substituted with one or two or more identical or different R$^9$s which will be described later); a NR$^{10}$R$^{11}$ group; a C$_1$-C$_6$ alkoxy group; a C$_6$-C$_{10}$ aryl group (the group may be substituted with one or two or more identical or different R$^{12}$s which will be described later); or a heterocyclic group having 2 to 10 carbon atoms and 1 to 5 heteroatoms selected from an oxygen atom, a sulfur atom and a nitrogen atom (the group may be substituted with one or two or more identical or different R$^{13}$s which will be described later).

Preferred examples of R$^1$ include a hydrogen atom; a C$_1$-C$_{12}$ alkyl group; a C$_2$-C$_6$ alkenyl group; a C$_2$-C$_6$ alkynyl group; a C$_3$-C$_8$ cycloalkyl group; a C$_1$-C$_6$ haloalkyl group; a C$_2$-C$_6$ haloalkenyl group; a C$_1$-C$_6$ alkylthio-C$_1$-C$_6$ alkyl group; a C$_1$-C$_6$ alkylsulfonyl-C$_1$-C$_6$ alkyl group; a C$_1$-C$_6$ alkoxy-C$_1$-C$_6$ alkyl group; a C$_1$-C$_6$ alkoxy-C$_1$-C$_6$ alkoxy-C$_1$-C$_6$ alkyl group; a phenyloxy-C$_1$-C$_6$ alkyl group; a C$_1$-C$_6$ haloalkoxy-C$_1$-C$_6$ alkyl group; a tetrahydrofuran-C$_1$-C$_6$ alkoxy-C$_1$-C$_6$ alkyl group; a C$_1$-C$_6$ alkylsulfonyl-C$_1$-C$_6$ alkoxy-C$_1$-C$_6$ alkyl group; a cyano-C$_1$-C$_6$ alkoxy-C$_1$-C$_6$ alkyl group; a cyano-C$_1$-C$_6$ alkyl group; a C$_1$-C$_6$ alkylcarbonyloxy-C$_1$-C$_6$ alkyl group; a C$_1$-C$_6$ acyl-C$_1$-C$_6$ alkyl group; a C$_1$-C$_6$ alkoxycarbonyl-C$_1$-C$_6$ alkyl group; a (R$^6$R$^7$N—C=O)—C$_1$-C$_6$ alkyl group; a C$_6$-C$_{10}$ aryl-C$_1$-C$_6$ alkyl group (the aryl moiety of the group may be substituted with one or two or more identical or different R$^8$s which will be described later); a heterocyclic-C$_1$-C$_6$ alkyl group (the group may be substituted with one or two or more identical or different R$^9$s which will be described later); a NR$^{10}$R$^{11}$ group; a C$_6$-C$_{10}$ aryl group (the group may be substituted with one or two or more identical or different R$^{12}$s which will be described later); a heterocyclic group (the group may be substituted with one or two or more identical or different R$^{13}$s which will be described later); and the like. More preferred examples of R$^1$ include a C$_1$-C$_{12}$ alkyl group, a C$_2$-C$_6$ alkenyl group, a C$_2$-C$_6$ alkynyl group, a C$_3$-C$_8$ cycloalkyl group, a C$_1$-C$_6$ haloalkyl group, a C$_2$-C$_6$ haloalkenyl group, a C$_1$-C$_6$ alkylthio-C$_1$-C$_6$ alkyl group, a $C_1$-$C_6$ alkylsulfonyl-$C_1$-$C_6$ alkyl group, a $C_1$-$C_6$ alkoxy-$C_1$-$C_6$ alkyl group, a $C_1$-$C_6$ alkoxy-$C_1$-$C_6$ alkoxy-$C_1$-$C_6$ alkyl group, a $C_1$-$C_6$ haloalkoxy-$C_1$-$C_6$ alkyl group, a tetrahydrofuran-$C_1$-$C_6$ alkoxy-$C_1$-$C_6$ alkyl group, a cyano-$C_1$-$C_6$ alkyl group, a $C_1$-$C_6$ alkoxycarbonyl-$C_1$-$C_6$ alkyl group, a $C_6$-$C_{10}$ aryl-$C_1$-$C_6$ alkyl group (the aryl moiety of the group may be substituted with one or two or more identical or different $R^8$s which will be described later), a heterocyclic-$C_1$-$C_6$ alkyl group (the group may be substituted with one or two or more identical or different $R^9$s which will be described later), a $C_6$-$C_{10}$ aryl group (the group may be substituted with one or two or more identical or different $R^{12}$s which will be described later), a heterocyclic group (the group may be substituted with one or two or more identical or different $R^{13}$s which will be described later); and the like.

$R^2$ in the formula [I] of the present invention may be exemplified by a halogen atom; a hydroxyl group; a nitro group; a cyano group; a $C_1$-$C_6$ alkyl group; a $C_3$-$C_8$ cycloalkyl group; a $C_3$-$C_8$ cycloalkyl-$C_1$-$C_6$ alkyl group; a $C_2$-$C_6$ alkenyl group; a $C_2$-$C_6$ alkynyl group; a $C_1$-$C_6$ haloalkyl group; a $C_1$-$C_8$ halocycloalkyl group; a $C_1$-$C_6$ alkoxy group; a $C_3$-$C_8$ cycloalkyloxy group; a $C_2$-$C_6$ alkenyloxy group; a $C_2$-$C_6$ alkynyloxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; an amino group; a mono($C_1$-$C_6$ alkyl)amino group; a di($C_1$-$C_6$ alkyl)amino group; a $C_1$-$C_6$ alkoxy-$C_1$-$C_6$ alkyl group; a $C_1$-$C_6$ acyl group; a $C_1$-$C_6$ alkoxyimino-$C_1$-$C_6$ alkyl group; a carboxyl group; a $C_1$-$C_6$ alkoxycarbonyl group; a mono($C_1$-$C_6$ alkyl)aminocarbonyl group; a di($C_1$-$C_6$ alkyl)aminocarbonyl group; a heterocyclic-$C_1$-$C_6$ alkyl group in which the heterocyclic moiety has 2 to 10 carbon atoms and 1 to 5 heteroatoms selected from an oxygen atom, a sulfur atom and a nitrogen atom; and the like.

Preferred examples of $R^2$ include a halogen atom; a nitro group; a $C_1$-$C_6$ alkyl group; a $C_1$-$C_6$ haloalkyl group; a $C_1$-$C_6$ alkoxy group; a $C_1$-$C_6$ alkylthio group; a $C_1$-$C_6$ alkoxy-$C_1$-$C_6$ alkyl group; a $C_1$-$C_6$ alkylsulfonyl group; and the like.

More preferred examples of $R^2$ include a halogen atom; a $C_1$-$C_6$ alkyl group; a $C_1$-$C_6$ haloalkyl group; a $C_1$-$C_6$ alkoxy group; a $C_1$-$C_6$ alkylthio group; a $C_1$-$C_6$ alkylsulfonyl group; and the like, and even more preferably, a halogen atom; a $C_1$-$C_6$ alkyl group; a $C_1$-$C_6$ haloalkyl group; and a $C_1$-$C_6$ alkoxy group.

n in the formula [I] of the present invention is an integer from 0 to 4 (provided that when $X^2$ is $N(O)_m$, an integer from 0 to 3), preferably 0 to 2, and more preferably 0 to 1.

$R^3$ in the formula [I] of the present invention may be exemplified by a hydroxyl group; $O^-M^+$ ($M^+$ represents an alkali metal cation or an ammonium cation); an amino group; a halogen atom; a $C_1$-$C_6$ alkylsulfonyloxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; a $C_2$-$C_6$ alkenylthio group; a $C_2$-$C_6$ alkenylsulfinyl group; a $C_2$-$C_6$ alkenylsulfonyl group; a $C_2$-$C_6$ alkynylthio group; a $C_2$-$C_6$ alkynylsulfinyl group; a $C_2$-$C_6$ alkynylsulfonyl group; a $C_1$-$C_6$ alkylcarbonyloxy group; a $C_2$-$C_6$ alkenylcarbonyloxy group; a $C_2$-$C_6$ alkynylcarbonyloxy group; a phenoxy group (the group may be substituted with one or two or more identical or different $R^{14}$s); a phenylthio group (the group may be substituted with one or two or more different $R^{14}$s); a phenylsulfinyl group (the group may be substituted with one or two or more different $R^{14}$s); a phenylsulfonyl group (the group may be substituted with one or two or more different $R^{14}$s); a phenylsulfonyloxy group (the group may be substituted with one or two or more different $R^{14}$s); a phenylcarbonyloxy group (the group may be substituted with one or two or more different $R^{14}$s); a 1,2,4-triazol-1-yl group; a 1,2,3-triazol-1-yl group; a 1,2,3-triazol-2-yl group; an imidazol-1-yl group; a pyrazol-1-yl group; a tetrazol-1-yl group; a tetrazol-2-yl group; and the like. A preferred example of $R^3$ includes a hydroxyl group, and derivatives such as salts, ethers and esters of these groups may also be employed.

A more preferred example of $R^3$ include a hydroxyl group.

$R^8$ in the formula [I] of the present invention may be exemplified by a halogen atom; a nitro group; a cyano group; a $C_1$-$C_6$ alkyl group; a $C_2$-$C_6$ alkenyl group; a $C_2$-$C_6$ alkynyl group; a $C_3$-$C_8$ cycloalkyl group; a $C_1$-$C_6$ haloalkyl group; a $C_1$-$C_6$ alkoxy group; a $C_2$-$C_6$ alkenyloxy group; a $C_2$-$C_6$ alkynyloxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; a $C_1$-$C_6$ alkoxycarbonyl group; a $C_1$-$C_6$ acyl group; or a $C_1$-$C_6$ alkoxy-$C_1$-$C_6$ alkyl group. Preferred examples of $R^8$ include a halogen atom; a $C_1$-$C_6$ haloalkyl group; a $C_1$-$C_6$ alkoxy group; a $C_1$-$C_6$ haloalkoxy group; and the like.

$R^9$ in the formula [I] of the present invention may be exemplified by an oxo group; a halogen atom; a nitro group; a cyano group; a $C_1$-$C_6$ alkyl group; a $C_2$-$C_6$ alkenyl group; a $C_2$-$C_6$ alkynyl group; a $C_3$-$C_8$ cycloalkyl group; a $C_1$-$C_6$ haloalkyl group; a $C_1$-$C_6$ alkoxy group; a $C_2$-$C_6$ alkenyloxy group; a $C_2$-$C_6$ alkynyloxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; a $C_1$-$C_6$ alkoxycarbonyl group; a $C_1$-$C_6$ acyl group; or a $C_1$-$C_6$ alkoxy-$C_1$-$C_6$ alkyl group.

Preferred examples of $R^9$ include a $C_1$-$C_6$ alkyl group; a halogen atom; a $C_1$-$C_6$ haloalkyl group and the like.

$R^{12}$ in the formula [I] of the present invention may be exemplified by a halogen atom; a hydroxyl group; a nitro group; a cyano group; a $C_1$-$C_6$ alkyl group; a $C_3$-$C_8$ cycloalkyl group; a $C_3$-$C_8$ cycloalkyl-$C_1$-$C_6$ alkyl group; a $C_2$-$C_6$ alkenyl group; a $C_2$-$C_6$ alkynyl group; a $C_1$-$C_6$ haloalkyl group; a $C_1$-$C_6$ alkoxy group; a $C_3$-$C_8$ cycloalkyloxy group; a $C_2$-$C_6$ alkenyloxy group; a $C_2$-$C_6$ alkynyloxy group; a $C_1$-$C_6$ alkylcarbonyloxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; an amino group; a $C_1$-$C_6$ acylamino group; a mono($C_1$-$C_6$ alkyl)amino group; a di($C_1$-$C_6$ alkyl)amino group; a $C_1$-$C_6$ alkoxy-$C_1$-$C_6$ alkyl group; a $C_1$-$C_6$ alkoxy-$C_1$-$C_6$ alkoxy group; a $C_3$-$C_8$ cycloalkyl-$C_1$-$C_6$ alkyloxy group; a $C_1$-$C_6$ haloalkoxy-$C_1$-$C_6$ alkoxy group; a cyano-$C_1$-$C_6$ alkoxy group; a $C_1$-$C_6$ acyl group; a $C_1$-$C_6$ alkoxyimino-$C_1$-$C_6$ alkyl group; a carboxyl group; a $C_1$-$C_6$ alkoxycarbonyl group; a carbamoyl group; a mono($C_1$-$C_6$ alkyl)aminocarbonyl group; a di($C_1$-$C_6$ alkyl)aminocarbonyl group; a heterocyclic group having 2 to 10 carbon atoms and 1 to 5 heteroatoms selected from an oxygen atom, a sulfur atom and a nitrogen atom (the heterocyclic moiety of the group may be substituted with one or two or more identical or different $R^{14}$s which will be described later); a heterocyclic-$C_1$-$C_6$ alkoxy group in which the heterocyclic moiety has 2 to 10 carbon atoms and 1 to 5 heteroatoms selected from an oxygen atom, a sulfur atom and a nitrogen atom (the heterocyclic moiety having 2 to 10 carbon atoms and 1 to 5 heteroatoms selected from an oxygen atom, a sulfur atom and a nitrogen atom, may be substituted with one or two or more identical or different $R^{14}$s which will be described later); and the like.

Preferred examples of $R^{12}$ include a halogen atom; a hydroxyl group; a nitro group; a cyano group; a $C_1$-$C_6$ alkyl group; a $C_3$-$C_8$ cycloalkyl group; a $C_1$-$C_6$ haloalkyl group; a $C_1$-$C_6$ alkoxy group; a $C_2$-$C_6$ alkenyloxy group; a $C_2$-$C_6$ alkynyloxy group; a $C_1$-$C_6$ haloalkoxy group; a $C_1$-$C_6$ alkylthio group; a $C_1$-$C_6$ alkylsulfonyl group; a $C_1$-$C_6$ haloalkylthio group; a $C_1$-$C_6$ alkoxy-$C_1$-$C_6$ alkyl group; a $C_3$-$C_8$ cycloalkyl-$C_1$-$C_6$ alkyloxy group; a $C_1$-$C_6$ haloalkoxy-$C_1$-$C_6$ alkoxy group; a cyano-$C_1$-$C_6$ alkoxy group; a $C_1$-$C_6$ acyl group; a $C_1$-$C_6$ alkoxycarbonyl group; a di($C_1$-$C_6$ alkyl) amino group; a heterocyclic-$C_1$-$C_6$ alkoxy group; and those shown below.

[Chemical Formula 6]

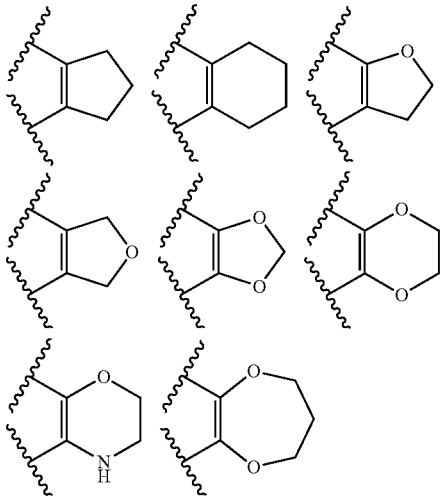

More preferred examples of $R^{12}$ include a halogen atom; a $C_1$-$C_6$ alkyl group; a $C_1$-$C_6$ haloalkyl group; a $C_1$-$C_6$ alkoxy group; a $C_2$-$C_6$ alkenyloxy group; a $C_2$-$C_6$ alkynyloxy group; a $C_1$-$C_6$ haloalkoxy group; a $C_1$-$C_6$ acyl group; and those shown below.

[Chemical Formula 7]

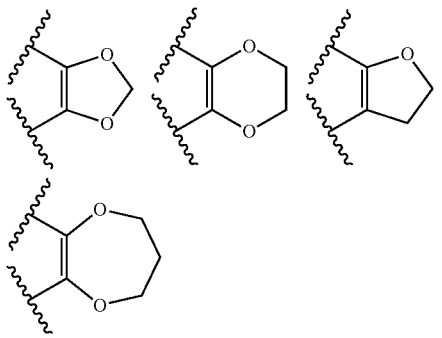

More preferred examples thereof include a halogen atom; a $C_1$-$C_6$ alkyl group; a $C_1$-$C_6$ haloalkyl group; a $C_1$-$C_6$ alkoxy group; a $C_1$-$C_6$ haloalkoxy group; and those shown below.

[Chemical Formula 8]

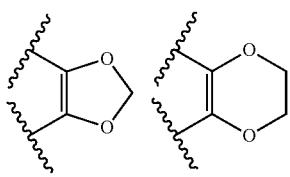

$A^1$ in the formula [I] of the present invention represents —C($R^{15}R^{16}$)

$A^2$ in the formula [I] of the present invention represents —C($R^{17}R^{18}$)— or C=O.

$A^3$ in the formula [I] of the present invention represents —C($R^{19}R^{20}$)

That is, -$A^1$-$A^2$-$A^3$- in the formula [I] of the present invention represents:
—C($R^{15}R^{16}$)—C($R^{17}R^{18}$)—C)($R^{19}R^{20}$)— or
—C($R^{15}R^{16}$)—C(=O)—C)($R^{19}R^{20}$)—,
and they form a 6-membered carbocyclic ring together with adjacent carbon atoms.

$R^{15}$, $R^{16}$, $R^{17}$, $R^{18}$, $R^{19}$ and $R^{20}$ used herein each independently include a hydrogen atom; or a $C_1$-$C_6$ alkyl group. Furthermore, $R^{15}$ and $R^{20}$ may be joined with adjacent carbon atoms to form a 5- to 10-membered, and preferably 5- to 8-membered, carbocyclic ring. In other words, $R^{15}$ and $R^{20}$ may be joined to form a divalent straight-chained or branched $C_2$-$C_5$ alkylene chain. A preferred alkylene group may be exemplified by an ethylene group.

Specific examples of the heterocyclic group as indicated in the "heterocyclic group having 2 to 10 carbon atoms and 1 to 5 heteroatoms arbitrarily selected from an oxygen atom, a sulfur atom and a nitrogen atom," "heterocyclic-$C_1$-$C_6$ alkoxy-$C_1$-$C_6$ alkyl group in which the heterocyclic moiety has 2 to 10 carbon atoms and 1 to 5 heteroatoms selected from an oxygen atom, a sulfur atom and a nitrogen atom," "heterocyclic-$C_1$-$C_6$ alkyl group in which the heterocyclic moiety has 2 to 10 carbon atoms and 1 to 5 heteroatoms selected from an oxygen atom, a sulfur atom and a nitrogen atom," or "heterocyclic-$C_1$-$C_6$ alkoxy group in which the heterocyclic moiety has 2 to 10 carbon atoms and 1 to 5 heteroatoms arbitrarily selected from an oxygen atom, a sulfur atom and a nitrogen atom," include tetrahydrofuran, tetrahydrothiophene, tetrahydrothiophene dioxide, tetrahydrothiopyrane, tetrahydrothiopyranedioxide, 4,5-dihydroisoxazole, thiophene, pyrazole, oxazole, isoxazole, thiazole, isothiazole, 1,2,4-triazole, 1,2,4-oxadiazole, 1,3,4-thiadiazole, pyridine, pyridazine, pyrimidine, pyrazine, 2,3-dihydrobenzofuran, 1,3-benzodioxole, benzo-1,4-dioxane, benzofuran, indole and the like.

A group of preferred examples of the heterocyclic ring include 4,5-dihydroisoxazole, thiophene, pyrazole, oxazole, isoxazole, thiazole, isothiazole, pyridine, pyrazine, 1,3-benzodioxole, and benzo-1,4-dioxane. More preferred examples of the heterocyclic ring include thiophene, isoxazole, pyridine, 1,3-benzodioxole, benzo-1,4-dioxane and the like.

The heterocyclic group formed from the heterocyclic ring shown in the formula [I] of the present invention can be made into a radical being attached at any position of a selected heterocyclic ring. Even in the case where the selected heterocyclic ring is a ring fused with a benzene ring, the position at which the radical is formed is not limited to the heterocyclic moiety, and a position on the benzene ring can also be selected.

Specific preferred examples of the compound represented by formula [I] of the present invention will be shown in the following Table 1 to Table 45. However, the compound of the present invention is not intended to be limited to these compounds. Additionally, compound numbers will be referred in the following descriptions.

The following notations in the tables in the present specification represent the respective corresponding groups as indicated below. For example, Me represents a methyl group,
Et represents an ethyl group,
n-Pr represents an n-propyl group,
i-Pr represents an isopropyl group,
c-Pr represents a cyclopropyl group,
n-Bu represents an n-butyl group,
s-Bu represents a sec-butyl group, i-Bu represents an isobutyl group,
t-Bu represents a tert-butyl group,
c-Bu represents a cyclobutyl group,
n-Pen represents an n-pentyl group,
c-Pen represents a cyclopentyl group,
n-Hex represents an n-hexyl group,
Ph represents a phenyl group,
Bn represents a benzyl group,
"–" for $R^2$ and $R^{12}$ implies that they are unsubstituted,
(4-Cl)Bn represents a 4-chlorobenzyl group,
3,4-($CH_2CH_2CH_2CH_2$)— represents the following chemical structure in which the 3-position and the 4-position are bound by the butylene group to form a ring:

[Chemical Formula 9]

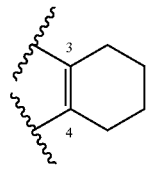

and 3,4-($OCH_2CH_2O$)— represents the following chemical structure in which the 3-position and the 4-position are similarly bound by the ethylenedioxy group to form a ring:

[Chemical Formula 10]

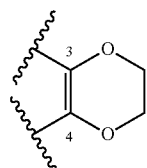

Furthermore, with regard to A in the tables, A-1, A-2, A-3, A-4, A-5, A-6 and A-7 respectively represent the following groups.

[Chemical Formula 11]

A-1

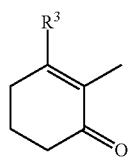

A-2

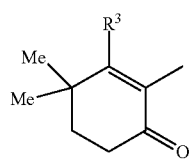

A-3

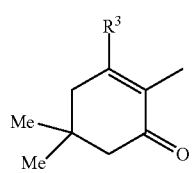

A-4

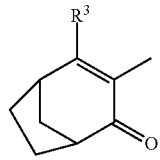

A-5

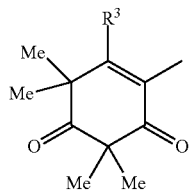

A-6

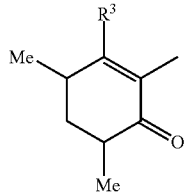

A-7

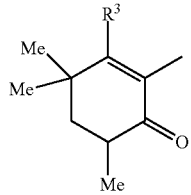

TABLE 1

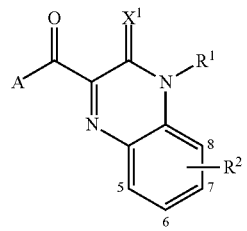

| Compound No. | A | $X^1$ | $R^1$ | $R^2$ | $R^3$ |
|---|---|---|---|---|---|
| I-1 | A-1 | O | H | — | OH |
| I-2 | A-1 | O | Me | — | OH |
| I-3 | A-2 | O | Me | — | OH |
| I-4 | A-3 | O | Me | — | OH |
| I-5 | A-4 | O | Me | — | OH |
| I-6 | A-5 | O | Me | — | OH |
| I-7 | A-1 | O | Et | — | OH |
| I-8 | A-2 | O | Et | — | OH |
| I-9 | A-3 | O | Et | — | OH |
| I-10 | A-4 | O | Et | — | OH |
| I-11 | A-5 | O | Et | — | OH |
| I-12 | A-1 | O | n-Pr | — | OH |
| I-13 | A-1 | O | i-Pr | — | OH |
| I-14 | A-1 | O | c-Pr | — | OH |
| I-15 | A-1 | O | n-Bu | — | OH |
| I-16 | A-1 | O | s-Bu | — | OH |
| I-17 | A-1 | O | i-Bu | — | OH |
| I-18 | A-1 | O | t-Bu | — | OH |
| I-19 | A-1 | O | c-Bu | — | OH |
| I-20 | A-1 | O | n-Pen | — | OH |
| I-21 | A-1 | O | c-Pen | — | OH |
| I-22 | A-1 | O | n-Hex | — | OH |
| I-23 | A-1 | O | c-Hex | — | OH |

TABLE 1-continued

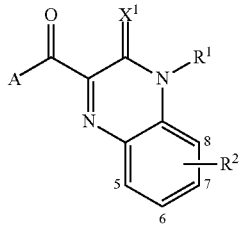

| Compound No. | A | X¹ | R¹ | R² | R³ |
|---|---|---|---|---|---|
| I-24 | A-1 | O | n-$C_7H_{15}$ | — | OH |
| I-25 | A-1 | O | n-$C_8H_{17}$ | — | OH |
| I-26 | A-1 | O | n-$C_9H_{19}$ | — | OH |
| I-27 | A-1 | O | n-$C_{10}H_{21}$ | — | OH |
| I-28 | A-1 | O | n-$C_{11}H_{23}$ | — | OH |
| I-29 | A-1 | O | n-$C_{12}H_{25}$ | — | OH |
| I-30 | A-1 | O | $CH_2CH=CH_2$ | — | OH |
| I-31 | A-2 | O | $CH_2CH=CH_2$ | — | OH |
| I-32 | A-3 | O | $CH_2CH=CH_2$ | — | OH |
| I-33 | A-4 | O | $CH_2CH=CH_2$ | — | OH |

TABLE 2

| Compound No. | A | X¹ | R¹ | R² | R³ |
|---|---|---|---|---|---|
| I-34 | A-5 | O | $CH_2CH=CH_2$ | — | OH |
| I-35 | A-1 | O | $CH_2C\equiv CH$ | — | OH |
| I-36 | A-2 | O | $CH_2C\equiv CH$ | — | OH |
| I-37 | A-3 | O | $CH_2C\equiv CH$ | — | OH |
| I-38 | A-4 | O | $CH_2C\equiv CH$ | — | OH |
| I-39 | A-5 | O | $CH_2C\equiv CH$ | — | OH |
| I-40 | A-1 | O | $CH_2CF_3$ | — | OH |
| I-41 | A-2 | O | $CH_2CF_3$ | — | OH |
| I-42 | A-3 | O | $CH_2CF_3$ | — | OH |
| I-43 | A-4 | O | $CH_2CF_3$ | — | OH |
| I-44 | A-5 | O | $CH_2CF_3$ | — | OH |
| I-45 | A-1 | O | $CH_2CH_2F$ | — | OH |
| I-46 | A-1 | O | $CH_2CH_2Cl$ | — | OH |
| I-47 | A-1 | O | $CH_2CH_2CF_3$ | — | OH |
| I-48 | A-1 | O | $CH_2CH=CCl_2$ | — | OH |
| I-49 | A-1 | O | $CH_2OMe$ | — | OH |
| I-50 | A-1 | O | $CH_2OEt$ | — | OH |
| I-51 | A-2 | O | $CH_2OEt$ | — | OH |
| I-52 | A-3 | O | $CH_2OEt$ | — | OH |
| I-53 | A-4 | O | $CH_2OEt$ | — | OH |
| I-54 | A-5 | O | $CH_2OEt$ | — | OH |
| I-55 | A-1 | O | CH(Me)OMe | — | OH |
| I-56 | A-1 | O | CH(Me)OEt | — | OH |
| I-57 | A-1 | O | $CH_2OPh$ | — | OH |
| I-58 | A-1 | O | $CH_2OCH_2CH_2OMe$ | — | OH |
| I-59 | A-1 | O | $CH_2OCH_2CF_3$ | — | OH |
| I-60 | A-2 | O | $CH_2OCH_2CF_3$ | — | OH |
| I-61 | A-3 | O | $CH_2OCH_2CF_3$ | — | OH |
| I-62 | A-4 | O | $CH_2OCH_2CF_3$ | — | OH |
| I-63 | A-5 | O | $CH_2OCH_2CF_3$ | — | OH |
| I-64 | A-1 | O | CH(Me)$OCH_2CF_3$ | — | OH |
| I-65 | A-1 | O | $CH_2OCH_2$-(tetrahydrofuran-2-yl) | — | OH |
| I-66 | A-1 | O | CH(Me)$OCH_2$-(tetrahydrofuran-2-yl) | — | OH |
| I-67 | A-1 | O | $CH_2OCH_2CH_2SO_2Me$ | — | OH |
| I-68 | A-1 | O | $CH_2OCH_2CH_2CN$ | — | OH |
| I-69 | A-1 | O | $CH_2OC(=O)$t-Bu | — | OH |
| I-70 | A-1 | O | $CH_2SMe$ | — | OH |

TABLE 3

| Compound No. | A | X¹ | R¹ | R² | R³ |
|---|---|---|---|---|---|
| I-71 | A-4 | O | $CH_2SMe$ | — | OH |
| I-72 | A-1 | O | $CH_2SEt$ | — | OH |
| I-73 | A-1 | O | $CH_2S$-n-Pr | — | OH |
| I-74 | A-1 | O | CH(Me)SMe | — | OH |
| I-75 | A-1 | O | CH(Me)SEt | — | OH |
| I-76 | A-1 | O | CH(Me)S-n-Pr | — | OH |
| I-77 | A-1 | O | $CH_2SOMe$ | — | OH |
| I-78 | A-1 | O | $CH_2SOEt$ | — | OH |
| I-79 | A-1 | O | $CH_2SO$-n-Pr | — | OH |
| I-80 | A-1 | O | $CH_2SO_2Me$ | — | OH |
| I-81 | A-4 | O | $CH_2SO_2Me$ | — | OH |
| I-82 | A-1 | O | $CH_2SO_2Et$ | — | OH |
| I-83 | A-1 | O | $CH_2SO_2$n-Pr | — | OH |
| I-84 | A-1 | O | CH(Me)$SO_2Me$ | — | OH |
| I-85 | A-1 | O | CH(Me)$SO_2Et$ | — | OH |
| I-86 | A-1 | O | CH(Me)$SO_2$-n-Pr | — | OH |
| I-87 | A-1 | O | $CH_2CH_2OH$ | — | OH |
| I-88 | A-1 | O | $CH_2CH_2OMe$ | — | OH |
| I-89 | A-1 | O | $CH_2CH_2OEt$ | — | OH |
| I-90 | A-1 | O | CH(Me)$CH_2OMe$ | — | OH |
| I-91 | A-1 | O | $CH_2CH_2SMe$ | — | OH |
| I-92 | A-1 | O | $CH_2CH_2SO_2Me$ | — | OH |
| I-93 | A-1 | O | $CH_2CH_2CH_2OMe$ | — | OH |
| I-94 | A-1 | O | $CH_2C(=O)Me$ | — | OH |
| I-95 | A-1 | O | $CH_2C(=O)OMe$ | — | OH |
| I-96 | A-1 | O | $CH_2C(=O)OEt$ | — | OH |
| I-97 | A-1 | O | $CH_2C(=O)O$-n-Pr | — | OH |
| I-98 | A-1 | O | $CH_2C(=O)O$-i-Pr | — | OH |
| I-99 | A-1 | O | $CH_2C(=O)O$-t-Bu | — | OH |
| I-100 | A-1 | O | $CH_2C(=O)NMe_2$ | — | OH |
| I-101 | A-1 | O | $CH_2C(=O)$-morpholin-4-yl | — | OH |
| I-102 | A-1 | O | $CH_2CN$ | — | OH |
| I-103 | A-1 | O | $CH_2CH_2CN$ | — | OH |
| I-104 | A-1 | O | CH(Me)$CH_2CN$ | — | OH |
| I-105 | A-1 | O | $CH_2CH_2CH_2CN$ | — | OH |
| I-106 | A-1 | O | $CH_2CH_2NO_2$ | — | OH |
| I-107 | A-1 | O | Bn | — | OH |
| I-108 | A-1 | O | (2-F)Bn | — | OH |

TABLE 4

| Compound No. | A | X¹ | R¹ | R² | R³ |
|---|---|---|---|---|---|
| I-109 | A-1 | O | (3-F)Bn | — | OH |
| I-110 | A-1 | O | (4-F)Bn | — | OH |
| I-111 | A-1 | O | (2-Cl)Bn | — | OH |
| I-112 | A-1 | O | (3-Cl)Bn | — | OH |
| I-113 | A-1 | O | (4-Cl)Bn | — | OH |
| I-114 | A-1 | O | (2-Me)Bn | — | OH |
| I-115 | A-1 | O | (3-Me)Bn | — | OH |
| I-116 | A-1 | O | (4-Me)Bn | — | OH |
| I-117 | A-1 | O | (2-$CF_3$)Bn | — | OH |
| I-118 | A-1 | O | (3-$CF_3$)Bn | — | OH |
| I-119 | A-1 | O | (4-$CF_3$)Bn | — | OH |
| I-120 | A-1 | O | (2-OMe)Bn | — | OH |
| I-121 | A-2 | O | (2-OMe)Bn | — | OH |
| I-122 | A-3 | O | (2-OMe)Bn | — | OH |
| I-123 | A-4 | O | (2-OMe)Bn | — | OH |
| I-124 | A-5 | O | (2-OMe)Bn | — | OH |
| I-125 | A-1 | O | (3-OMe)Bn | — | OH |
| I-126 | A-1 | O | (4-OMe)Bn | — | OH |
| I-127 | A-1 | O | (2,4-$(OMe)_2$)Bn | — | OH |
| I-128 | A-1 | O | (2,6-$(OMe)_2$)Bn | — | OH |
| I-129 | A-1 | O | (3,5-$(OMe)_2$)Bn | — | OH |
| I-130 | A-1 | O | CH(Me)Ph | — | OH |
| I-131 | A-1 | O | 3-methylisoxazolin-5-yl | — | OH |

TABLE 4-continued
| Compound No. | A | X¹ | R¹ | R² | R³ |
|---|---|---|---|---|---|
| I-132 | A-2 | O | 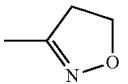 | — | OH |
| I-133 | A-3 | O | 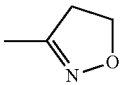 | — | OH |
| I-134 | A-4 | O | 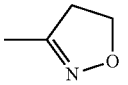 | — | OH |
| I-135 | A-5 | O | 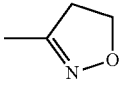 | — | OH |
| I-136 | A-1 | O | 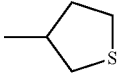 | — | OH |
| I-137 | A-1 | O | 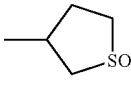 | — | OH |
| I-138 | A-1 | O | 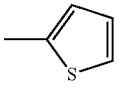 | — | OH |
TABLE 5
| Compound No. | A | X¹ | R¹ | R² | R³ |
|---|---|---|---|---|---|
| I-139 | A-1 | O | 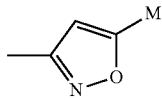 | — | OH |
| I-140 | A-2 | O | 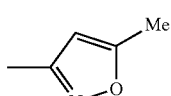 | — | OH |
| I-141 | A-3 | O | 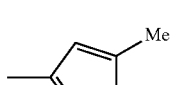 | — | OH |
| I-142 | A-4 | O |  | — | OH |
| I-143 | A-5 | O | 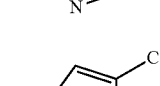 | — | OH |
| I-144 | A-1 | O | 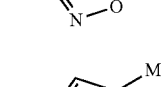 | — | OH |
| I-145 | A-1 | O | 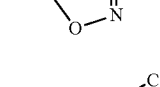 | — | OH |
TABLE 5-continued
| Compound No. | A | X¹ | R¹ | R² | R³ |
|---|---|---|---|---|---|
| I-146 | A-2 | O | 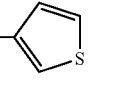 | — | OH |
| I-147 | A-3 | O | 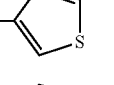 | — | OH |
| I-148 | A-4 | O | 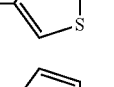 | — | OH |
| I-149 | A-5 | O | 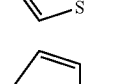 | — | OH |
| I-150 | A-1 | O | 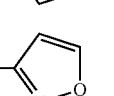 | — | OH |
| I-151 | A-1 | O | 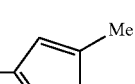 | — | OH |
| I-152 | A-1 | O |  | — | OH |
| I-153 | A-1 | O | 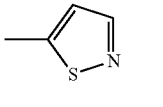 | — | OH |
| I-154 | A-1 | O | 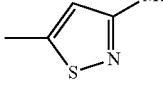 | — | OH |
TABLE 6
| Compound No. | A | X¹ | R¹ | R² | R³ |
|---|---|---|---|---|---|
| I-155 | A-1 | O | 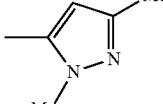 | — | OH |
| I-156 | A-1 | O |  | — | OH |
| I-157 | A-1 | O |  | — | OH |

TABLE 6-continued
| Compound No. | A | X¹ | R¹ | R² | R³ |
|---|---|---|---|---|---|
| I-158 | A-1 | O | 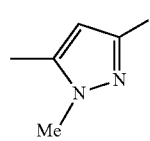 | — | OH |
| I-159 | A-1 | O | 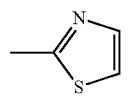 | — | OH |
| I-160 | A-1 | O | 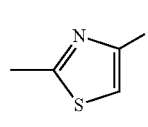 | — | OH |
| I-161 | A-1 | O | 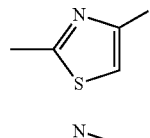 | — | OH |
| I-162 | A-1 | O | 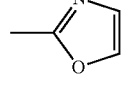 | — | OH |
| I-163 | A-1 | O | 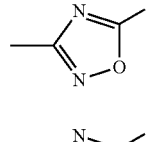 | — | OH |
| I-164 | A-1 | O | 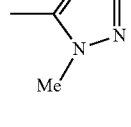 | — | OH |
| I-165 | A-1 | O | 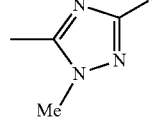 | — | OH |
| I-166 | A-1 | O | 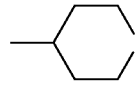 | — | OH |
| I-167 | A-1 | O | 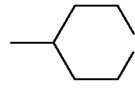 | — | OH |
| I-168 | A-1 | O | 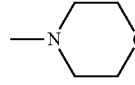 | — | OH |
TABLE 7
| Compound No. | A | X¹ | R¹ | R² | R³ |
|---|---|---|---|---|---|
| I-169 | A-1 | O | 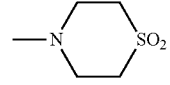 | — | OH |
| I-170 | A-1 | O | 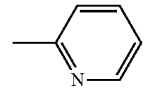 | — | OH |
| I-171 | A-1 | O | 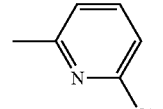 | — | OH |
| I-172 | A-1 | O | 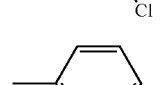 | — | OH |
| I-173 | A-1 | O | 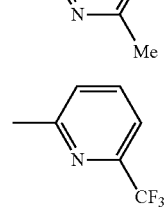 | — | OH |
| I-174 | A-1 | O | 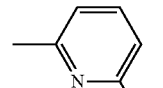 | — | OH |
| I-175 | A-1 | O | 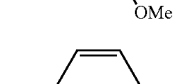 | — | OH |
| I-176 | A-1 | O | 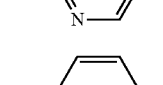 | — | OH |
| I-177 | A-1 | O | 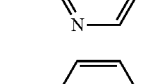 | — | OH |
| I-178 | A-1 | O | 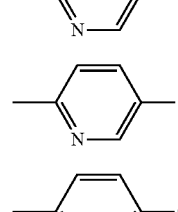 | — | OH |
| I-179 | A-1 | O | 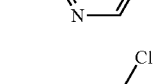 | — | OH |
| I-180 | A-1 | O | 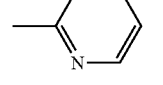 | — | OH |
| I-181 | A-1 | O | 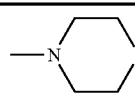 | — | OH |
| I-182 | A-1 | O | 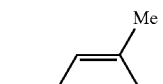 | — | OH |

TABLE 8
| Compound No. | A | X¹ | R¹ | R² | R³ |
|---|---|---|---|---|---|
| I-183 | A-1 | O | 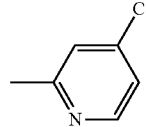 | — | OH |
| I-184 | A-1 | O | 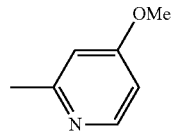 | — | OH |
| I-185 | A-1 | O | 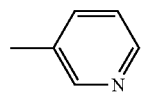 | — | OH |
| I-186 | A-1 | O | 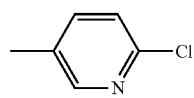 | — | OH |
| I-187 | A-1 | O | 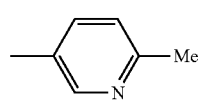 | — | OH |
| I-188 | A-1 | O |  | — | OH |
| I-189 | A-1 | O | 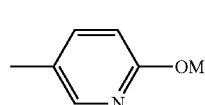 | — | OH |
| I-190 | A-2 | O | 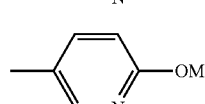 | — | OH |
| I-191 | A-3 | O | 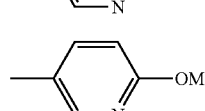 | — | OH |
| I-192 | A-4 | O | 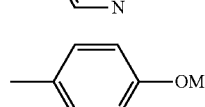 | — | OH |
| I-193 | A-5 | O | 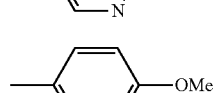 | — | OH |
| I-194 | A-1 | O | 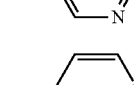 | — | OH |
| I-195 | A-1 | O | 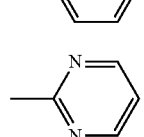 | — | OH |
| I-196 | A-1 | O | 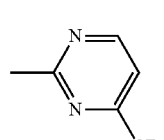 | — | OH |
TABLE 8-continued
| Compound No. | A | X¹ | R¹ | R² | R³ |
|---|---|---|---|---|---|
| I-197 | A-1 | O | 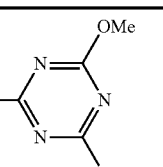 | — | OH |
TABLE 9
| Compound No. | A | X¹ | R¹ | R² | R³ |
|---|---|---|---|---|---|
| I-198 | A-1 | O | 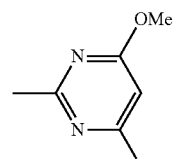 | — | OH |
| I-199 | A-1 | O | 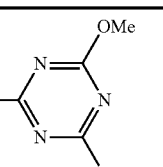 | — | OH |
| I-200 | A-1 | O | 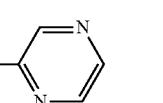 | — | OH |
| I-201 | A-1 | O | 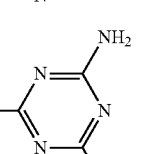 | — | OH |
| I-202 | A-1 | O | 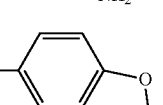 | — | OH |
| I-203 | A-2 | O | 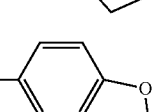 | — | OH |
| I-204 | A-3 | O | 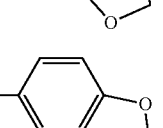 | — | OH |
| I-205 | A-4 | O | 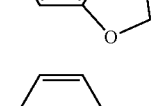 | — | OH |
| I-206 | A-5 | O | 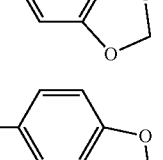 | — | OH |

TABLE 9-continued

| Compound No. | A | X¹ | R¹ | R² | R³ |
|---|---|---|---|---|---|
| I-207 | A-1 | O | (5-methyl-2,2-difluoro-1,3-benzodioxole) | — | OH |
| I-208 | A-1 | O | (5-methyl-2,2-dimethyl-1,3-benzodioxole) | — | OH |

TABLE 10

| Compound No. | A | X¹ | R¹ | R² | R³ |
|---|---|---|---|---|---|
| I-209 | A-1 | O | (6-methyl-2,3-dihydro-1,4-benzodioxine) | — | OH |
| I-210 | A-1 | O | (6-methyl-2,2,3,3-tetrafluoro-2,3-dihydro-1,4-benzodioxine) | — | OH |
| I-211 | A-1 | O | CH₂-(tetrahydrofuran-2-yl) | — | OH |
| I-212 | A-1 | O | CH₂-(3-methyl-4,5-dihydroisoxazol-5-yl) | — | OH |
| I-213 | A-1 | O | CH₂-(3-methylisoxazol-5-yl) | — | OH |
| I-214 | A-1 | O | NH₂ | — | OH |
| I-215 | A-1 | O | NHMe | — | OH |
| I-216 | A-1 | O | NMe₂ | — | OH |
| I-217 | A-1 | O | OMe | — | OH |
| I-218 | A-1 | O | OEt | — | OH |
| I-219 | A-1 | O | Me | 5-F | OH |
| I-220 | A-1 | O | Me | 6-F | OH |
| I-221 | A-1 | O | Me | 7-F | OH |
| I-222 | A-1 | O | Me | 8-F | OH |
| I-223 | A-1 | O | Me | 5-Cl | OH |
| I-224 | A-1 | O | CH₂CH₂OMe | 5-Cl | OH |
| I-225 | A-1 | O | Me | 6-Cl | OH |
| I-226 | A-1 | O | CH₂CH₂OMe | 6-Cl | OH |
| I-227 | A-1 | O | Me | 7-Cl | OH |
| I-228 | A-1 | O | CH₂CH₂OMe | 7-Cl | OH |
| I-229 | A-1 | O | Me | 8-Cl | OH |
| I-230 | A-1 | O | CH₂CH₂OMe | 8-Cl | OH |
| I-232 | A-1 | O | Me | 7-Me | OH |
| I-233 | A-1 | O | Me | 6-CF₃ | OH |
| I-234 | A-1 | O | Me | 7-CF₃ | OH |
| I-235 | A-1 | O | Me | 6-OH | OH |
| I-236 | A-1 | O | Me | 7-OH | OH |

TABLE 11

| Compound No. | A | X¹ | R¹ | R² | R³ |
|---|---|---|---|---|---|
| I-237 | A-1 | O | Me | 6-OMe | OH |
| I-238 | A-1 | O | Me | 7-OMe | OH |
| I-239 | A-1 | O | Me | 6-OCF₂ | OH |
| I-240 | A-1 | O | Me | 7-OCF₃ | OH |
| I-241 | A-1 | O | Me | 5-SMe | OH |
| I-242 | A-1 | O | Me | 6-SMe | OH |
| I-243 | A-1 | O | Me | 7-SMe | OH |
| I-244 | A-1 | O | Me | 8-SMe | OH |
| I-245 | A-1 | O | Me | 5-SO₂Me | OH |
| I-246 | A-1 | O | Me | 6-SO₂Me | OH |
| I-247 | A-1 | O | Me | 7-SO₂Me | OH |
| I-248 | A-1 | O | Me | 8-SO₂Me | OH |
| I-249 | A-1 | O | Me | 6-NO₂ | OH |
| I-250 | A-1 | O | Me | 7-NO₂ | OH |
| I-251 | A-1 | O | Me | 6-NH₂ | OH |
| I-252 | A-1 | O | Me | 7-NH₂ | OH |
| I-253 | A-1 | O | Me | 7-CN | OH |
| I-254 | A-1 | O | Me | 6,7-Cl₂ | OH |
| I-255 | A-1 | O | Me | 6,7-Me₂ | OH |
| I-256 | A-1 | S | Me | — | OH |
| I-257 | A-4 | O | Me | — | S(n-Hex) |
| I-258 | A-4 | O | Me | — | SO(n-Hex) |
| I-259 | A-4 | O | Me | — | SO₂(n-Hex) |
| I-260 | A-4 | O | Me | — | SPh |
| I-261 | A-4 | O | Me | — | SOPh |
| I-262 | A-4 | O | Me | — | SO₂Ph |
| I-263 | A-1 | O | (1-methylnaphthalene) | — | OH |
| I-264 | A-1 | O | (2-methylnaphthalene) | — | OH |
| I-265 | A-1 | O | (3-methyl-5-t-Bu-isoxazole) | — | OH |

TABLE 12

| Compound No. | A | X¹ | R¹ | R² | R³ |
|---|---|---|---|---|---|
| I-266 | A-1 | O | (1,3,5-trimethylpyrazole) | — | OH |
| I-267 | A-1 | O | (3-methyl-5-CF₃-1-methylpyrazole) | — | OH |
| I-268 | A-1 | O | (2-methyl-4-CF₃-oxazole) | — | OH |

TABLE 12-continued

| Compound No. | A | X¹ | R¹ | R² | R³ |
|---|---|---|---|---|---|
| I-269 | A-1 | O | 2-methyl-1,3,4-thiadiazol-5-yl | — | OH |
| I-270 | A-1 | O | 2,5-dimethyl-1,3,4-thiadiazol-yl | — | OH |
| I-271 | A-1 | O | 5-bromo-2-methylpyridinyl | — | OH |
| I-272 | A-1 | O | 2,3-dimethylpyridinyl | — | OH |
| I-273 | A-1 | O | 6-chloro-3-methylpyridazinyl | — | OH |
| I-274 | A-1 | O | 2-(NHEt)-4-methyl-6-(NHi-Pr)-1,3,5-triazinyl | — | OH |
| I-275 | A-1 | O | 4-methyl-6-methyl-3-oxo-3,4-dihydro-2H-benzo[b][1,4]oxazin-6-yl | — | OH |
| I-276 | A-1 | O | 1-methyl-5-methyl-1H-indol-5-yl | — | OH |

TABLE 13

| Compound No. | A | X¹ | R¹ | R² | R³ |
|---|---|---|---|---|---|
| I-277 | A-1 | O | benzofuran-5-yl-methyl | — | OH |
| I-278 | A-1 | O | N(Me)C(=O)Ot-Bu | — | OH |
| I-279 | A-1 | O | 2-OMe-5-methylpyridinyl | 5-F | OH |
| I-280 | A-1 | O | Bn | 6-F | OH |
| I-281 | A-1 | O | 3-methyl-5-methylisoxazolyl | 6-F | OH |
| I-282 | A-1 | O | Me | 5-CH₂OMe | OH |
| I-283 | A-1 | O | 2-OMe-5-methylpyridinyl | 5,7-F₂ | OH |
| I-284 | A-1 | O | 2-methyl-5-methylpyridinyl | 7-Cl | OH |
| I-285 | A-1 | O | CH₂-c-Pr | — | OH |
| I-286 | A-1 | O | CH₂-c-Bu | — | OH |
| I-287 | A-1 | O | CH₂c-Pen | — | OH |
| I-288 | A-1 | O | CH₂O-c-Pen | — | OH |
| I-289 | A-1 | O | CH₂CH₂NH₂ | — | OH |
| I-290 | A-1 | O | CH₂CH₂NHEt | — | OH |
| I-291 | A-1 | O | CH₂CH₂NMe₂ | — | OH |
| I-292 | A-1 | O | CH₂CH₂NEt₂ | — | OH |
| I-293 | A-1 | O | CH₂CH₂CHO | — | OH |
| I-294 | A-1 | O | CH₂-(2,2-difluorocyclopropyl) | — | OH |
| I-295 | A-1 | O | CH₂-(2,2-dichlorocyclopropyl) | — | OH |
| I-296 | A-1 | O | CH₂OCH₂-c-Pr | — | OH |
| I-297 | A-1 | O | CH₂SPh | — | OH |
| I-298 | A-1 | O | CH₂CH₂O-(2-pyridyl) | — | OH |

TABLE 14

| Compound No. | A | X¹ | R¹ | R² | R³ |
|---|---|---|---|---|---|
| I-299 | A-1 | O | CH₂SCH₂CF₃ | — | OH |
| I-300 | A-1 | O | CH₂SOCH₂CF₃ | — | OH |
| I-301 | A-1 | O | CH₂SO₂CH₂CF₃ | — | OH |
| I-302 | A-1 | O | CH₂OCH₂Ph | — | OH |
| I-303 | A-1 | O | CH₂SOPh | — | OH |
| I-304 | A-1 | O | CH₂SO₂Ph | — | OH |
| I-305 | A-1 | O | CH₂OCH₂CH₂SMe | — | OH |
| I-306 | A-1 | O | CH₂OCH₃CH₂SOMe | — | OH |
| I-307 | A-1 | O | CH₂CH₂CH(OEt)₂ | — | OH |
| I-308 | A-1 | O | CH₂C(Me)=NOMe | — | OH |
| I-309 | A-1 | O | CH₂CH₂ON=CMe₂ | — | OH |
| I-310 | A-1 | O | Me | 7-CH=CMe₂ | OH |
| I-311 | A-1 | O | Me | 7-C≡CMe | OH |
| I-312 | A-1 | O | Me | 7-CH₂-c-Pr | OH |
| I-313 | A-1 | O | Me | 7-C(Me)=CF₂ | OH |
| I-314 | A-1 | O | Me | 7-(2,2-difluorocyclopropyl) | OH |
| I-315 | A-1 | O | Me | 7-O-c-Pr | OH |

TABLE 14-continued

| Compound No. | A | $X^1$ | $R^1$ | $R^2$ | $R^3$ |
|---|---|---|---|---|---|
| I-316 | A-1 | O | Me | 7-CH$_2$-(2,2-difluorocyclopropyl) | OH |
| I-317 | A-1 | O | Me | 7-OCH$_2$c-Pr | OH |
| I-318 | A-1 | O | Me | 7-OCH$_2$OMe | OH |
| I-319 | A-1 | O | Me | 7-OC(=O)Me | OH |
| I-320 | A-1 | O | Me | 7-SOMe | OH |
| I-321 | A-1 | O | Me | 7-SCF$_3$ | OH |
| I-322 | A-1 | O | Me | 7-SOCH$_2$CF$_3$ | OH |
| I-323 | A-1 | O | Me | 7-SO$_2$CH$_2$CF$_3$ | OH |
| I-324 | A-1 | O | Me | 7-NMe$_2$ | OH |
| I-325 | A-1 | O | Me | 7-NHC(=O)Me | OH |
| I-326 | A-1 | O | Me | 7-CH$_2$OH | OH |
| I-327 | A-1 | O | Me | 7-CH(OEt)$_2$ | OH |
| I-328 | A-1 | O | Me | 7-CH$_2$SMe | OH |
| I-329 | A-1 | O | Me | 7-CH$_2$SOMe | OH |
| I-330 | A-1 | O | Me | 7-CH$_2$SO$_2$Me | OH |
| I-331 | A-1 | O | Me | 7-CH$_2$SCHF$_2$ | OH |
| I-332 | A-1 | O | Me | 7-CH$_2$SOCHF$_2$ | OH |
| I-333 | A-1 | O | Me | 7-CH$_2$SO$_2$CHF$_2$ | OH |

TABLE 15

| Compound No. | A | $X^1$ | $R^1$ | $R^2$ | $R^3$ |
|---|---|---|---|---|---|
| I-334 | A-1 | O | Me | 7-CH$_2$CN | OH |
| I-335 | A-1 | O | Me | 7-C(Me)=NOMe | OH |
| I-336 | A-1 | O | Me | 7-C(=O)NH$_2$ | OH |
| I-337 | A-1 | O | Me | 7-(pyrazol-1-yl) | OH |
| I-338 | A-1 | O | CH$_2$OCH$_2$Ph(2-F) | — | OH |
| I-339 | A-1 | O | CH$_2$OCH$_2$Ph(2-Cl) | — | |
| I-340 | A-1 | O | CH$_2$OCH$_2$Ph(2-NO$_2$) | — | OH |
| I-341 | A-1 | O | CH$_2$OCH$_2$Ph(2-CN) | — | OH |
| I-342 | A-1 | O | CH$_2$OCH$_2$Ph(2-Me) | — | OH |
| I-343 | A-1 | O | CH$_2$OCH$_2$Ph(2-CF$_3$) | — | OH |
| I-344 | A-1 | O | CH$_2$OCH$_2$Ph(2-OMe) | — | OH |
| I-345 | A-1 | O | CH$_2$OCH$_2$Ph(2-OCF$_3$) | — | OH |
| I-346 | A-1 | O | CH$_2$OCH$_2$Ph(2-SMe) | — | OH |
| I-347 | A-1 | O | CH$_2$OCH$_2$Ph(2-SO$_2$Me) | — | OH |
| I-348 | A-1 | O | CH$_2$OCH$_2$Ph(2-SCF$_3$) | — | OH |
| I-349 | A-1 | O | CH$_2$OCH$_2$Ph(2-CO$_2$Me) | — | OH |
| I-350 | A-1 | O | CH$_2$OCH$_2$Ph(2-COMe) | — | OH |
| I-351 | A-1 | O | (2-NO$_2$)Bn | — | OH |
| I-352 | A-1 | O | (2-CN)Bn | — | OH |
| I-353 | A-1 | O | (3-SMe)Bn | — | OH |
| I-354 | A-1 | O | (3-SO$_2$Me)Bn | — | OH |
| I-355 | A-1 | O | (3-SCF$_3$)Bn | — | OH |
| I-356 | A-1 | O | (3-CO$_2$Me)Bn | — | OH |
| I-157 | A-1 | O | (3-COMe)Bn | — | OH |
| I-358 | A-1 | O | (3-OMe)Bn | — | OH |
| I-359 | A-1 | O | 6-methyl-3-nitropyridin-2-yl | — | OH |
| I-360 | A-1 | O | 6-methyl-5-cyanopyridin-2-yl | — | OH |
| I-361 | A-1 | O | 6-methyl-5-cyclopropylpyridin-3-yl | — | OH |
| I-362 | A-1 | O | 5-methyl-2-(methylthio)pyridin-2-yl | — | OH |

TABLE 16

| Compound No. | A | $X^1$ | $R^1$ | $R^2$ | $R^3$ |
|---|---|---|---|---|---|
| I-363 | A-1 | O | Et | 5-Cl | OH |
| I-364 | A-1 | O | n-Bu | 5-Cl | OH |
| I-365 | A-1 | O | 6-methyl-5-methylpyridin-3-yl | 5-F | OH |
| I-366 | A-1 | O | 6-methyl-5-methylpyridin-3-yl | 5-Cl | OH |
| I-367 | A-1 | O | 6-methyl-5-methylpyridin-3-yl | 5-Me | OH |
| I-368 | A-1 | O | 6-methyl-5-methylpyridin-3-yl | 7-Me | OH |
| I-369 | A-1 | O | 6-methyl-5-methylpyridin-3-yl | 7-CF$_3$ | OH |
| I-370 | A-1 | O | 6-methyl-5-methylpyridin-3-yl | 7-OMe | OH |
| I-371 | A-1 | O | 2,6-dimethylpyridin-3-yl | 6-F | OH |
| I-372 | A-1 | O | 2,6-dimethylpyridin-3-yl | 6-CF$_3$ | OH |
| I-373 | A-1 | O | 5-methyl-2-methylpyrazin-2-yl | — | OH |
| I-374 | A-1 | O | 5-methyl-2-methylpyrazin-2-yl | 5-F | OH |

TABLE 16-continued

| Compound No. | A | X¹ | R¹ | R² | R³ |
|---|---|---|---|---|---|
| I-375 | A-1 | O | 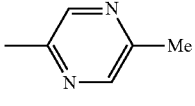 2,5-dimethylpyrazinyl | 5-Cl | OH |
| I-376 | A-1 | O | 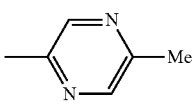 2,5-dimethylpyrazinyl | 5-Me | OH |

TABLE 17

| Compound No. | A | X¹ | R¹ | R² | R³ |
|---|---|---|---|---|---|
| I-377 | A-1 | O | 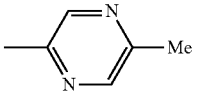 | 7-Me | OH |
| I-378 | A-1 | O | 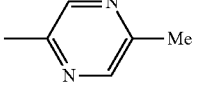 | 7-OMe | OH |
| I-379 | A-1 | O | 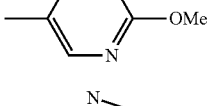 | 5-Cl | OH |
| I-380 | A-1 | O | 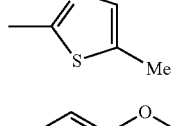 | — | OH |
| I-381 | A-1 | O | 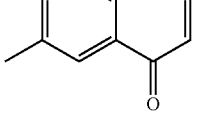 | — | OH |
| I-382 | A-1 | O | 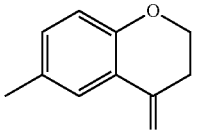 | — | OH |
| I-383 | A-1 | O | 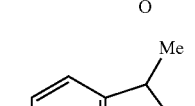 | — | OH |
| I-384 | A-1 | O | 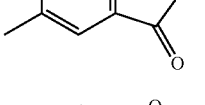 | — | OH |
| I-385 | A-1 | O | 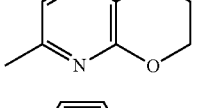 | 5-Me | OH |

TABLE 17-continued

| Compound No. | A | X¹ | R¹ | R² | R³ |
|---|---|---|---|---|---|
| I-386 | A-1 | O | 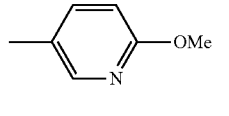 | 5-Br | OH |
| I-387 | A-1 | O | 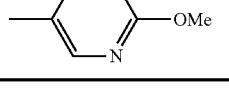 | 7-Me | OH |

TABLE 18

| Compound No. | A | X¹ | R¹ | R² | R³ |
|---|---|---|---|---|---|
| I-388 | A-1 | O | 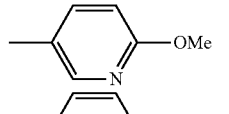 | 7-OMe | OH |
| I-389 | A-1 | O | 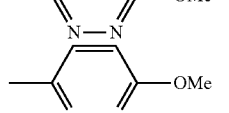 | — | OH |
| I-390 | A-1 | O | 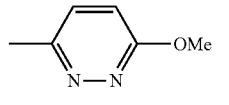 | 5-F | OH |
| I-391 | A-1 | O | 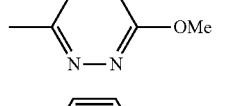 | 5-Cl | OH |
| I-392 | A-1 | O | 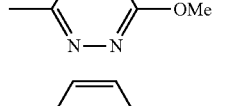 | 5-Me | OH |
| I-393 | A-1 | O | 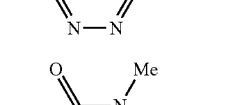 | 7-Me | OH |
| I-394 | A-1 | O | 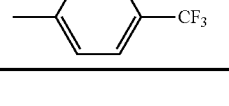 | 7-OMe | OH |
| I-395 | A-1 | O | 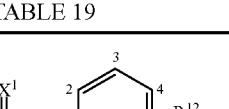 | — | OH |

TABLE 19

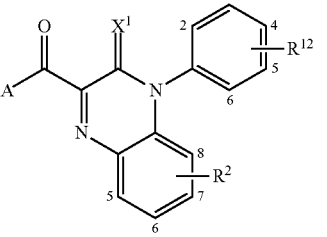

| Compound No. | A | X¹ | R¹² | R² | R³ |
|---|---|---|---|---|---|
| II-1 | A-1 | O | — | — | OH |
| II-2 | A-2 | O | — | — | OH |

TABLE 19-continued

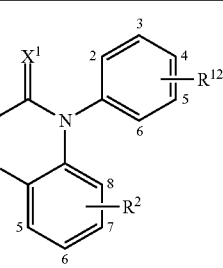

| Compound No. | A | X¹ | R¹² | R² | R³ |
|---|---|---|---|---|---|
| II-3 | A-3 | O | — | — | OH |
| II-4 | A-4 | O | — | — | OH |
| II-5 | A-5 | O | — | — | OH |
| II-6 | A-1 | O | 2-F | — | OH |
| II-7 | A-1 | O | 3-F | — | OH |
| II-8 | A-1 | O | 4-F | — | OH |
| II-9 | A-1 | O | 2-Cl | — | OH |
| II-10 | A-4 | O | 2-Cl | — | OH |
| II-11 | A-1 | O | 3-Cl | — | OH |
| II-12 | A-4 | O | 3-Cl | — | OH |
| II-13 | A-1 | O | 4-Cl | — | OH |
| II-14 | A-4 | O | 4-Cl | — | OH |
| II-15 | A-5 | O | 4-Cl | — | OH |
| II-16 | A-1 | O | 2-Br | — | OH |
| II-17 | A-1 | O | 3-Br | — | OH |
| II-18 | A-1 | O | 4-Br | — | OH |
| II-19 | A-1 | O | 2-Me | — | OH |
| II-20 | A-1 | O | 3-Me | — | OH |
| II-21 | A-1 | O | 4-Me | — | OH |
| II-22 | A-1 | O | 2-Et | — | OH |
| II-23 | A-1 | O | 3-Et | — | OH |
| II-24 | A-1 | O | 4-Et | — | OH |
| II-25 | A-1 | O | 2-n-Pr | — | OH |
| II-26 | A-1 | O | 3-n-Pr | — | OH |
| II-27 | A-1 | O | 4-n-Pr | — | OH |
| II-28 | A-1 | O | 2-i-Pr | — | OH |
| II-29 | A-1 | O | 3-i-Pr | — | OH |
| II-30 | A-1 | O | 4-i-Pr | — | OH |
| II-31 | A-1 | O | 2-c-Pr | — | OH |
| II-32 | A-1 | O | 3-c-Pr | — | OH |
| II-33 | A-1 | O | 4-c-Pr | — | OH |

TABLE 20

| Compound No. | A | X¹ | R¹² | R² | R³ |
|---|---|---|---|---|---|
| II-34 | A-1 | O | 2-CF₃ | — | OH |
| II-35 | A-2 | O | 2-CF₃ | — | OH |
| II-36 | A-3 | O | 2-CF₃ | — | OH |
| II-37 | A-4 | O | 2-CF₃ | — | OH |
| II-38 | A-5 | O | 2-CF₃ | — | OH |
| II-39 | A-1 | O | 3-CF₃ | — | OH |
| II-40 | A-2 | O | 3-CF₃ | — | OH |
| II-41 | A-3 | O | 3-CF₃ | — | OH |
| II-42 | A-4 | O | 3-CF₃ | — | OH |
| II-43 | A-5 | O | 3-CF₃ | — | OH |
| II-44 | A-1 | O | 4-CF₃ | — | OH |
| II-45 | A-2 | O | 4-CF₃ | — | OH |
| II-46 | A-3 | O | 4-CF₃ | — | OH |
| II-47 | A-4 | O | 4-CF₃ | — | OH |
| II-48 | A-5 | O | 4-CF₃ | — | OH |
| II-49 | A-1 | O | 2-OH | — | OH |
| II-50 | A-1 | O | 3-OH | — | OH |
| II-51 | A-1 | O | 4-OH | — | OH |
| II-52 | A-1 | O | 2-OMe | — | OH |
| II-53 | A-2 | O | 2-OMe | — | OH |
| II-54 | A-3 | O | 2-OMe | — | OH |
| II-55 | A-4 | O | 2-OMe | — | OH |
| II-56 | A-5 | O | 2-OMe | — | OH |
| II-57 | A-1 | O | 3-OMe | — | OH |
| II-58 | A-2 | O | 3-OMe | — | OH |
| II-59 | A-3 | O | 3-OMe | — | OH |

TABLE 20-continued

| Compound No. | A | X¹ | R¹² | R² | R³ |
|---|---|---|---|---|---|
| II-60 | A-4 | O | 3-OMe | — | OH |
| II-61 | A-5 | O | 3-OMe | — | OH |
| II-62 | A-1 | O | 4-OMe | — | OH |
| II-63 | A-2 | O | 4-OMe | — | OH |
| II-64 | A-3 | O | 4-OMe | — | OH |
| II-65 | A-4 | O | 4-OMe | — | OH |
| II-66 | A-5 | O | 4-OMe | — | OH |
| II-67 | A-1 | O | 2-OEt | — | OH |
| II-68 | A-1 | O | 3-OEt | — | OH |
| II-69 | A-1 | O | 4-OEt | — | OH |
| II-70 | A-1 | O | 2-O—n-Pr | — | OH |
| II-71 | A-1 | O | 3-O—n-Pr | — | OH |
| II-72 | A-1 | O | 4-O—n-Pr | — | OH |

TABLE 21

| Compound No. | A | X¹ | R¹² | R² | R³ |
|---|---|---|---|---|---|
| II-73 | A-1 | O | 2-O—i-Pr | — | OH |
| II-74 | A-1 | O | 3-O—i-Pr | — | OH |
| II-75 | A-1 | O | 4-O—i-Pr | — | OH |
| II-76 | A-1 | O | 2-O—c-Pr | — | OH |
| II-77 | A-1 | O | 3-O—c-Pr | — | OH |
| II-78 | A-1 | O | 4-O—c-Pr | — | OH |
| II-79 | A-1 | O | 2-OCH₂CH=CH₂ | — | OH |
| II-80 | A-1 | O | 3-OCH₂CH=CH₂ | — | OH |
| II-81 | A-1 | O | 4-OCH₂CH=CH₂ | — | OH |
| II-82 | A-1 | O | 2-OCH₂C≡CH | — | OH |
| II-83 | A-1 | O | 3-OCH₂C≡CH | — | OH |
| II-84 | A-1 | O | 4-OCH₂C≡CH | — | OH |
| II-85 | A-1 | O | 2-OCHF₂ | — | OH |
| II-86 | A-2 | O | 2-OCHF₂ | — | OH |
| II-87 | A-3 | O | 2-OCHF₂ | — | OH |
| II-88 | A-4 | O | 2-OCHF₂ | — | OH |
| II-89 | A-5 | O | 2-OCHF₂ | — | OH |
| II-90 | A-1 | O | 3-OCHF₂ | — | OH |
| II-91 | A-2 | O | 3-OCHF₂ | — | OH |
| II-92 | A-3 | O | 3-OCHF₂ | — | OH |
| II-93 | A-4 | O | 3-OCHF₂ | — | OH |
| II-94 | A-5 | O | 3-OCHF₂ | — | OH |
| II-95 | A-1 | O | 4-OCHF₂ | — | OH |
| II-96 | A-2 | O | 4-OCHF₂ | — | OH |
| II-97 | A-3 | O | 4-OCHF₂ | — | OH |
| II-98 | A-4 | O | 4-OCHF₂ | — | OH |
| II-99 | A-5 | O | 4-OCHF₂ | — | OH |
| II-100 | A-1 | O | 2-OCF₃ | — | OH |
| II-101 | A-1 | O | 3-OCF₃ | — | OH |
| II-102 | A-2 | O | 3-OCF₃ | — | OH |
| II-103 | A-3 | O | 3-OCF₃ | — | OH |
| II-104 | A-4 | O | 3-OCF₃ | — | OH |
| II-105 | A-5 | O | 3-OCF₃ | — | OH |
| II-106 | A-1 | O | 4-OCF₃ | — | OH |
| II-107 | A-2 | O | 4-OCF₃ | — | OH |
| II-108 | A-3 | O | 4-OCF₃ | — | OH |
| II-109 | A-4 | O | 4-OCF₃ | — | OH |
| II-110 | A-5 | O | 4-OCF₃ | — | OH |
| II-111 | A-1 | O | 2-OCH₂CH₂OMe | — | OH |

TABLE 22

| Compound No. | A | X¹ | R¹² | R² | R³ |
|---|---|---|---|---|---|
| II-112 | A-1 | O | 3-OCH₂CH₂OMe | — | OH |
| II-113 | A-1 | O | 4-OCH₂CH₂OMe | — | OH |
| II-114 | A-1 | O | 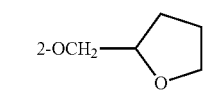 | — | OH |

TABLE 22-continued

| Compound No. | A | $X^1$ | $R^{12}$ | $R^2$ | $R^3$ |
|---|---|---|---|---|---|
| II-115 | A-1 | O | 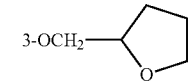 3-OCH$_2$— (tetrahydrofuran) | — | OH |
| II-116 | A-1 | O | 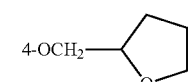 4-OCH$_2$— (tetrahydrofuran) | — | OH |
| II-117 | A-1 | O | 2-OC(=O)Me | — | OH |
| II-118 | A-1 | O | 3-OC(=O)Me | — | OH |
| II-119 | A-1 | O | 3-OC(=O)Me | — | OH |
| II-120 | A-1 | O | 2-SMe | — | OH |
| II-121 | A-1 | O | 3-SMe | — | OH |
| II-122 | A-1 | O | 4-SMe | — | OH |
| II-123 | A-1 | O | 2-SO$_2$Me | — | OH |
| II-124 | A-1 | O | 3-SO$_2$Me | — | OH |
| II-125 | A-1 | O | 4-SO$_2$Me | — | OH |
| II-126 | A-1 | O | 2-SCF$_3$ | — | OH |
| II-127 | A-1 | O | 3-SCF$_3$ | — | OH |
| II-128 | A-1 | O | 4-SCF$_3$ | — | OH |
| II-129 | A-1 | O | 2-NO$_2$ | — | OH |
| II-130 | A-1 | O | 3-NO$_2$ | — | OH |
| II-131 | A-1 | O | 4-NO$_2$ | — | OH |
| II-132 | A-1 | O | 2-NH$_2$ | — | OH |
| II-133 | A-1 | O | 3-NH$_2$ | — | OH |
| II-134 | A-1 | O | 4-NH$_2$ | — | OH |
| II-135 | A-1 | O | 2-CN | — | OH |
| II-136 | A-1 | O | 3-CN | — | OH |
| II-137 | A-1 | O | 4-CN | — | OH |
| II-138 | A-1 | O | 2-C(=O)Me | — | OH |
| II-139 | A-1 | O | 3-C(=O)Me | — | OH |
| II-140 | A-1 | O | 4-C(=O)Me | — | OH |
| II-141 | A-1 | O | 2-C(=O)OH | — | OH |
| II-142 | A-1 | O | 3-C(=O)OH | — | OH |
| II-143 | A-1 | O | 4-C(=O)OH | — | OH |
| II-144 | A-1 | O | 2-C(=O)OMe | — | OH |
| II-145 | A-1 | O | 3-C(=O)OMe | — | OH |
| II-146 | A-1 | O | 4-C(=O)OMe | — | OH |

TABLE 23

| Compound No. | A | $X^1$ | $R^{12}$ | $R^2$ | $R^3$ |
|---|---|---|---|---|---|
| II-147 | A-1 | O | 2-CH$_2$OMe | — | OH |
| II-148 | A-1 | O | 3-CH$_2$OMe | — | OH |
| II-149 | A-1 | O | 4-CH$_2$OMe | — | OH |
| II-150 | A-1 | O | 2,3-F$_2$ | — | OH |
| II-151 | A-1 | O | 2,4-F$_2$ | — | OH |
| II-152 | A-1 | O | 2,5-F$_2$ | — | OH |
| II-153 | A-1 | O | 2,6-F$_2$ | — | OH |
| II-154 | A-1 | O | 3,4-F$_2$ | — | OH |
| II-155 | A-1 | O | 3,5-F$_2$ | — | OH |
| II-156 | A-1 | O | 2,3-Cl$_2$ | — | OH |
| II-157 | A-1 | O | 2,4-Cl$_2$ | — | OH |
| II-158 | A-1 | O | 2,5-Cl$_2$ | — | OH |
| II-159 | A-1 | O | 2,6-Cl$_2$ | — | OH |
| II-160 | A-1 | O | 3,4-Cl$_2$ | — | OH |
| II-161 | A-1 | O | 3,5-Cl$_2$ | — | OH |
| II-162 | A-1 | O | 2-F, 3-OMe | — | OH |
| II-163 | A-1 | O | 2-Cl, 3-OMe | — | OH |
| II-164 | A-1 | O | 2-Me, 3-OMe | — | OH |
| II-165 | A-1 | O | 2,3-(OMe)$_2$ | — | OH |
| II-166 | A-1 | O | 3-OMe, 4-F | — | OH |
| II-167 | A-1 | O | 3-OMe, 4-Cl | — | OH |
| II-168 | A-1 | O | 3-OMe, 4-Me | — | OH |
| II-169 | A-1 | O | 3,4-(OMe)$_2$ | — | OH |
| II-170 | A-1 | O | 3-OMe, 5-F | — | OH |
| II-171 | A-1 | O | 3-OMe, 5-Cl | — | OH |
| II-172 | A-1 | O | 3-OMe, 5-Me | — | OH |
| II-173 | A-1 | O | 3,5-(OMe)$_2$ | — | OH |
| II-174 | A-1 | O | 2-F, 4-OMe | — | OH |
| II-175 | A-1 | O | 2-Cl, 4-OMe | — | OH |
| II-176 | A-1 | O | 2-Me, 4-OMe | — | OH |

TABLE 23-continued

| Compound No. | A | $X^1$ | $R^{12}$ | $R^2$ | $R^3$ |
|---|---|---|---|---|---|
| II-177 | A-1 | O | 2,4-(OMe)$_2$ | — | OH |
| II-178 | A-1 | O | 3-F, 4-OMe | — | OH |
| II-179 | A-1 | O | 3-Cl, 4-OMe | — | OH |
| II-180 | A-1 | O | 3-Me, 4-OMe | — | OH |
| II-181 | A-1 | O | 2-F, 5-OMe | — | OH |
| II-182 | A-1 | O | 2-Cl, 5-OMe | — | OH |
| II-183 | A-1 | O | 2-Me, 5-OMe | — | OH |
| II-184 | A-1 | O | 2,5-(OMe)$_2$ | — | OH |
| II-185 | A-1 | O | 3,4,5-(OMe)$_3$ | — | OH |

TABLE 24

| Compound No. | A | $X^1$ | $R^{12}$ | $R^2$ | $R^3$ |
|---|---|---|---|---|---|
| II-186 | A-1 | O | 4-OMe | 5-F | OH |
| II-187 | A-1 | O | 4-OMe | 6-F | OH |
| II-188 | A-1 | O | 4-OMe | 7-F | OH |
| II-189 | A-1 | O | 4-OMe | 8-F | OH |
| II-190 | A-1 | O | — | 5-Cl | OH |
| II-191 | A-1 | O | — | 6-Cl | OH |
| II-192 | A-1 | O | — | 7-Cl | OH |
| II-193 | A-1 | O | — | 8-Cl | OH |
| II-194 | A-1 | O | 4-OMe | 5-Cl | OH |
| II-195 | A-1 | O | 4-OMe | 6-Cl | OH |
| II-196 | A-1 | O | 4-OMe | 7-Cl | OH |
| II-197 | A-1 | O | 4-OMe | 8-Cl | OH |
| II-198 | A-1 | S | — | — | OH |
| II-199 | A-4 | O | — | — | S(n-Hex) |
| II-200 | A-4 | O | — | — | SO(n-Hex) |
| II-201 | A-4 | O | — | — | SO$_2$(n-Hex) |
| II-202 | A-4 | O | — | — | SPh |
| II-203 | A-4 | O | — | — | SOPh |
| II-204 | A-4 | O | — | — | SO$_2$Ph |
| II-205 | A-1 | O | 4-OCH$_2$CN | — | OH |
| II-206 | A-1 | O | 3-OCH$_2$-c-Pr | — | OH |
| II-207 | A-1 | O | 3-OCH$_2$CF$_3$ | — | OH |
| II-208 | A-1 | O | 4-OCH$_2$-c-Pr | — | OH |
| II-209 | A-1 | O | 4-OCH$_2$CF$_3$ | — | OH |
| II-210 | A-1 | O | 4-NMe$_2$ | — | OH |
| II-211 | A-1 | O | 3,4-Me$_2$ | — | OH |
| II-212 | A-1 | O | 2-F, 4-Me | — | OH |
| II-213 | A-1 | O | 3-F, 4-Me | — | OH |
| II-214 | A-1 | O | 3-Me, 4-F | — | OH |
| II-215 | A-1 | O | 2-Cl, 4-Me | — | OH |
| II-216 | A-1 | O | 3-Cl, 4-Me | — | OH |
| II-217 | A-1 | O | 3-OEt, 4-OMe | — | OH |
| II-218 | A-1 | O | 2,3,4-(OMe)$_3$ | — | OH |
| II-219 | A-1 | O | 2,5-F$_2$, 4-OMe | — | OH |
| II-220 | A-1 | O | 3,5-F$_2$, 4-OMe | — | OH |
| II-221 | A-1 | O | 3,5-Cl$_2$, 4-OMe | — | OH |
| II-222 | A-1 | O | 3,4-(CH$_2$CH$_2$CH$_2$)— | — | OH |
| II-223 | A-1 | O | 3,4-(CH$_2$CH$_2$CH$_2$CH$_2$)— | — | OH |

TABLE 25

| Compound No. | A | $X^1$ | $R^{12}$ | $R^2$ | $R^3$ |
|---|---|---|---|---|---|
| II-224 | A-1 | O | 3,4-(CH$_2$OCH$_2$)— | — | OH |
| II-225 | A-1 | O | 3,4-(CH$_2$O)— | 7-F | OH |
| II-226 | A-1 | O | 2,3-(OCH$_2$CH$_2$O)— | — | OH |
| II-227 | A-2 | O | 3,4-(OCH$_2$CH$_2$O)— | — | OH |
| II-228 | A-3 | O | 3,4-(OCH$_2$CH$_2$O)— | — | OH |
| II-229 | A-6 | O | 3,4-(OCH$_2$CH$_2$O)— | — | OH |
| II-230 | A-7 | O | 3,4-(OCH$_2$CH$_2$O)— | — | OH |
| II-231 | A-1 | O | 3,4-(OCH$_2$CH(Me)O)— | — | OH |
| II-232 | A-1 | O | 3,4-(OCH$_2$CH$_2$CH$_2$O)— | — | OH |
| II-233 | A-1 | O | — | 5-F | OH |
| II-234 | A-1 | O | 3,4,5-(OMe)$_3$ | 5-F | OH |
| II-235 | A-1 | O | 3,5-F$_2$, 4-OMe | 5-F | OH |
| II-236 | A-1 | O | 3,4-(OCH$_2$CH$_2$O)— | 5-F | OH |
| II-237 | A-1 | O | — | 6-F | OH |
| II-238 | A-1 | O | 3,4,5-(OMe)$_3$ | 6-F | OH |

TABLE 25-continued

| Compound No. | A | X¹ | R¹² | R² | R³ |
|---|---|---|---|---|---|
| II-239 | A-1 | O | 3,4-(OCH$_2$O)— | 6-F | OH |
| II-240 | A-1 | O | 3,4-(OCH$_2$CH$_2$O)— | 6-F | OH |
| II-241 | A-1 | O | — | 7-F | OH |
| II-242 | A-1 | O | 3,4-(OCH$_2$CH$_2$O)— | 7-F | OH |
| II-243 | A-1 | O | — | 8-F | OH |
| II-244 | A-1 | O | — | 5-Me | OH |
| II-245 | A-1 | O | 4-OMe | 5-Me | OH |
| II-246 | A-1 | O | — | 6-Me | OH |
| II-247 | A-1 | O | 4-OMe | 7-Me | OH |
| II-248 | A-1 | O | 3,5-F$_2$, 4-OMe | 7-Me | OH |
| II-249 | A-1 | O | — | 6-CF$_3$ | OH |
| II-250 | A-1 | O | — | 6-OMe | OH |
| II-251 | A-1 | O | 4-OMe | 6-OMe | OH |
| II-252 | A-1 | O | — | 7-OMe | OH |
| II-253 | A-1 | O | 4-OMe | 7-OMe | OH |
| II-254 | A-1 | O | 2,5-F$_2$, 4-OMe | 7-OMe | OH |
| II-255 | A-1 | O | 3,5-F$_2$, 4-OMe | 7-OMe | OH |
| II-256 | A-1 | O | — | 8-OMe | OH |
| II-257 | A-1 | O | 4-OMe | 8-OMe | OH |
| II-258 | A-1 | O | 4-OMe | 5,6-F$_2$ | OH |
| II-259 | A-1 | O | 4-OMe | 5,7-F$_2$ | OH |
| II-260 | A-1 | O | — | 6,7-F$_2$ | OH |
| II-261 | A-1 | O | — | 6,8-F$_2$ | OH |

TABLE 26

| Compound No. | A | X¹ | R¹² | R² | R³ |
|---|---|---|---|---|---|
| II-262 | A-1 | O | 4-OMe | 5,7-Cl$_2$ | OH |
| II-263 | A-1 | O | 4-OMe | 6-F, 7-OMe | OH |
| II-264 | A-1 | O | — | 7-c-Pr | OH |
| II-265 | A-1 | O | — | 7-OCH$_2$CH=CH$_2$ | OH |
| II-266 | A-1 | O | — | 7-OCH$_2$C≡CH | OH |
| II-267 | A-1 | O | — | 7-NHMe | OH |
| II-268 | A-1 | O | — | 7-C(=O)H | OH |
| II-269 | A-1 | O | — | 6-C(=O)Me | OH |
| II-270 | A-1 | O | — | 7-C(=O)OH | OH |
| II-271 | A-1 | O | — | 7-C(=O)OMe | OH |
| II-272 | A-1 | O | — | 7-C(=O)OEt | OH |
| II-273 | A-1 | O | — | 7-C(=O)NHNe | OH |
| II-274 | A-1 | O | — | 7-C(=O)NMe$_2$ | OH |
| II-275 | A-1 | O | — | 6,7-(OCH$_2$CH$_2$O)— | OH |
| II-276 | A-1 | O | — | 6,7-(OCH$_2$O)— | OH |
| II-277 | A-1 | O | 4-OMe | 6,7-(OCH$_2$CH$_2$O)— | OH |
| II-278 | A-1 | O | 4-OMe | 6,7-(OCH$_2$O)— | OH |
| II-279 | A-1 | O | 2-CONHMe | — | OH |
| II-280 | A-1 | O | 2-CONMe$_2$ | — | OH |
| II-281 | A-1 | O | 2-NHCOMe | — | OH |
| II-282 | A-1 | O | 4-CH$_2$-c-Pr | — | OH |
| II-283 | A-1 | O | 4-CH=CH$_2$ | — | OH |
| II-284 | A-1 | O | 4-C≡CMe | — | OH |
| II-285 | A-1 | O | 3-CH=CF$_2$ | — | OH |
| II-286 | A-1 | O | 3-(2,2-difluorocyclopropyl) | — | OH |
| II-287 | A-1 | O | 4-CH$_2$-(2,2-difluorocyclopropyl) | — | OH |
| II-288 | A-1 | O | 4-CH$_2$OH | — | OH |
| II-289 | A-1 | O | 4-CH$_2$SMe | — | OH |
| II-290 | A-1 | O | 4-CH$_2$SOMe | — | OH |
| II-291 | A-1 | O | 4-CH$_2$SO$_2$Me | — | OH |
| II-292 | A-1 | O | 4-CH$_2$SCHF$_2$ | — | OH |
| II-293 | A-1 | O | 4-CH$_2$SOCHF$_2$ | — | OH |
| II-294 | A-1 | O | 4-CH$_2$SO$_2$CHF$_2$ | — | OH |
| II-295 | A-1 | O | 4-CH$_2$CN | — | OH |

TABLE 27

| Compound No. | A | X¹ | R¹² | R² | R³ |
|---|---|---|---|---|---|
| II-296 | A-1 | O | 4-NHMe | — | OH |
| II-297 | A-1 | O | 4-OCH$_2$OCH$_2$CF$_3$ | — | OH |
| II-298 | A-1 | O | 4-C(Me)=NOMe | — | OH |
| II-299 | A-1 | O | 2-CONH$_2$ | — | OH |
| II-300 | A-1 | O | 4-(pyrazol-1-yl) | — | OH |
| II-301 | A-1 | O | 3-F, 4-OMe | 5-Cl | OH |
| II-302 | A-1 | O | 4-OMe | 5,6,8-F$_3$, 7-OMe | OH |
| II-303 | A-1 | O | — | 7-CF$_3$ | OH |
| II-304 | A-1 | O | 4-F | 7-OMe | OH |
| II-305 | A-1 | O | 4-OCHF$_2$ | 7-OMe | OH |
| II-306 | A-1 | O | 4-Me | 7-OMe | OH |
| II-307 | A-1 | O | 4-OMe | 5-Br | OH |
| II-308 | A-1 | O | 4-OMe | 5-CN | OH |
| II-309 | A-1 | O | 4-OMe | 5-CF$_3$ | OH |
| II-310 | A-1 | O | 2,3,5,6-F$_4$, 4-OMe | — | OH |
| II-311 | A-1 | O | 4-Me | 5-Cl | OH |
| II-312 | A-1 | O | 3-F, 4-Me | 5-Cl | OH |
| II-313 | A-1 | O | 2-F, 4-OMe | 5-Cl | OH |
| II-314 | A-1 | O | 3-F | 6-F | OH |
| II-315 | A-1 | O | 3-Me | 6-F | OH |
| II-316 | A-1 | O | 3-F, 4-OMe | 5-Me | OH |
| II-317 | A-1 | O | 4-F | 5-F | OH |
| II-318 | A-1 | O | 4-F | 5-Cl | OH |
| II-319 | A-1 | O | 4-F | 5-Me | OH |
| II-320 | A-1 | O | 4-OCHF$_2$ | 5-F | OH |
| II-321 | A-1 | O | 4-OCHF$_2$ | 5-Cl | OH |
| II-322 | A-1 | O | 4-OCHF$_2$ | 5-Me | OH |
| II-323 | A-1 | O | 3-F, 4-OEt | — | OH |

TABLE 28

| Compound No. | A | X¹ | R¹ | R² | R³ |
|---|---|---|---|---|---|
| III-1 | A-1 | O | H | — | OH |
| III-2 | A-1 | O | Me | — | OH |
| III-3 | A-2 | O | Me | — | OH |
| III-4 | A-3 | O | Me | — | OH |
| III-5 | A-4 | O | Me | — | OH |
| III-6 | A-5 | O | Me | — | OH |
| III-7 | A-1 | O | Et | — | OH |
| III-8 | A-2 | O | Et | — | OH |
| III-9 | A-3 | O | Et | — | OH |
| III-10 | A-4 | O | Et | — | OH |
| III-11 | A-5 | O | Et | — | OH |
| III-12 | A-1 | O | n-Pr | — | OH |
| III-13 | A-1 | O | i-Pr | — | OH |
| III-14 | A-1 | O | c-Pr | — | OH |
| III-15 | A-1 | O | n-Bu | — | OH |
| III-16 | A-1 | O | s-Bu | — | OH |
| III-17 | A-1 | O | i-Bu | — | OH |
| III-18 | A-1 | O | t-Bu | — | OH |
| III-19 | A-1 | O | c-Bu | — | OH |
| III-20 | A-1 | O | n-Pen | — | OH |
| III-21 | A-1 | O | c-Pen | — | OH |
| III-22 | A-1 | O | n-Hex | — | OH |
| III-23 | A-1 | O | c-Hex | — | OH |
| III-24 | A-1 | O | n-C$_7$H$_{15}$ | — | OH |
| III-25 | A-1 | O | n-C$_8$H$_{17}$ | — | OH |

TABLE 28-continued

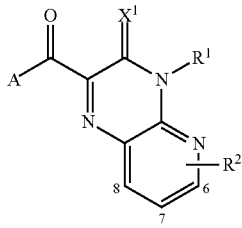

| Compound No. | A | X¹ | R¹ | R² | R³ |
|---|---|---|---|---|---|
| III-26 | A-1 | O | n-C₉H₁₉ | — | OH |
| III-27 | A-1 | O | n-C₁₀H₂₁ | — | OH |
| III-28 | A-1 | O | n-C₁₁H₂₃ | — | OH |
| III-29 | A-1 | O | n-C₁₂H₂₅ | — | OH |
| III-30 | A-1 | O | CH₂CH=CH₂ | — | OH |
| III-31 | A-2 | O | CH₂CH=CH₂ | — | OH |
| III-32 | A-3 | O | CH₂CH=CH₂ | — | OH |
| III-33 | A-4 | O | CH₂CH=CH₂ | — | OH |
| III-34 | A-5 | O | CH₂CH=CH₂ | — | OH |
| III-35 | A-1 | O | CH₂C≡CH | — | OH |

TABLE 29

| Compound No. | A | X¹ | R¹ | R² | R³ |
|---|---|---|---|---|---|
| III-36 | A-2 | O | CH₂C≡CH | — | OH |
| III-37 | A-3 | O | CH₂C≡CH | — | OH |
| III-38 | A-4 | O | CH₂C≡CH | — | OH |
| III-39 | A-5 | O | CH₂C≡CH | — | OH |
| III-40 | A-1 | O | CH₂CF₃ | — | OH |
| III-41 | A-2 | O | CH₂CF₃ | — | OH |
| III-42 | A-3 | O | CH₂CF₃ | — | OH |
| III-43 | A-4 | O | CH₂CF₃ | — | OH |
| III-44 | A-5 | O | CH₂CF₃ | — | OH |
| III-45 | A-1 | O | CH₂CH₂F | — | OH |
| III-46 | A-1 | O | CH₂CH₂Cl | — | OH |
| III-47 | A-1 | O | CH₂CH₂CF₃ | — | OH |
| III-48 | A-1 | O | CH₂CH=CCl₂ | — | OH |
| III-49 | A-1 | O | CH₂OMe | — | OH |
| III-50 | A-1 | O | CH₂OEt | — | OH |
| III-51 | A-2 | O | CH₂OEt | — | OH |
| III-52 | A-3 | O | CH₂OEt | — | OH |
| III-53 | A-4 | O | CH₂OEt | — | OH |
| III-54 | A-5 | O | CH₂OEt | — | OH |
| III-55 | A-1 | O | CH(Me)OMe | — | OH |
| III-56 | A-1 | O | CH(Me)OEt | — | OH |
| III-57 | A-1 | O | CH₂OPh | — | OH |
| III-58 | A-1 | O | CH₂OCH₂CH₂OMe | — | OH |
| III-59 | A-1 | O | CH₂OCH₂CF₃ | — | OH |
| III-60 | A-2 | O | CH₂OCH₂CF₃ | — | OH |
| III-61 | A-3 | O | CH₂OCH₂CF₃ | — | OH |
| III-62 | A-4 | O | CH₂OCH₂CF₃ | — | OH |
| III-63 | A-5 | O | CH₂OCH₂CF₃ | — | OH |
| III-64 | A-1 | O | CH(Me)OCH₂CF₃ | — | OH |
| III-65 | A-1 | O | CH₂OCH₂-(tetrahydrofuran-2-yl) | — | OH |
| III-66 | A-1 | O | CH(Me)OCH₂-(tetrahydrofuran-2-yl) | — | OH |
| III-67 | A-1 | O | CH₂OCH₂CH₂SO₂Me | — | OH |
| III-68 | A-1 | O | CH₂OCH₂CH₂CN | — | OH |
| III-69 | A-1 | O | CH₂OC(=O)t-Bu | — | OH |
| III-70 | A-1 | O | CH₂SMe | — | OH |
| III-71 | A-4 | O | CH₂SMe | — | OH |
| III-72 | A-1 | O | CH₂SEt | — | OH |

TABLE 30

| Compound No. | A | X¹ | R¹ | R² | R³ |
|---|---|---|---|---|---|
| III-73 | A-1 | O | CH₂S-n-Pr | — | OH |
| III-74 | A-1 | O | CH(Me)SMe | — | OH |
| III-75 | A-1 | O | CH(Me)SEt | — | OH |
| III-76 | A-1 | O | CH(Me)S-n-Pr | — | OH |
| III-77 | A-1 | O | CH₂SOMe | — | OH |
| III-78 | A-1 | O | CH₂SOEt | — | OH |
| III-79 | A-1 | O | CH₂SO-n-Pr | — | OH |
| III-80 | A-1 | O | CH₂SO₂Me | — | OH |
| III-81 | A-4 | O | CH₂SO₂Me | — | OH |
| III-82 | A-1 | O | CH₂SO₂Et | — | OH |
| III-83 | A-1 | O | CH₂SO₂-n-Pr | — | OH |
| III-84 | A-1 | O | CH(Me)SO₂Me | — | OH |
| III-85 | A-1 | O | CH(Me)SO₂Et | — | OH |
| III-86 | A-1 | O | CH(Me)SO₂-n-Pr | — | OH |
| III-87 | A-1 | O | CH₂CH₂OH | — | OH |
| III-88 | A-1 | O | CH₂CH₂OMe | — | OH |
| III-89 | A-1 | O | CH₂CH₂OEt | — | OH |
| III-90 | A-1 | O | CH(Me)CH₂OMe | — | OH |
| III-91 | A-1 | O | CH₂CH₂SMe | | OH |
| III-92 | A-1 | O | CH₂CH₂SO₂Me | — | OH |
| III-93 | A-1 | O | CH₂CH₂CH₂OMe | — | OH |
| III-94 | A-1 | O | CH₂C(=O)Me | — | OH |
| III-95 | A-1 | O | CH₂C(=O)OMe | — | OH |
| III-96 | A-1 | O | CH₂C(=O)OEt | — | OH |
| III-97 | A-1 | O | CH₂C(=O)On-Pr | — | OH |
| III-98 | A-1 | O | CH₂C(=O)Oi-Pr | — | OH |
| III-99 | A-1 | O | CH₂C(=O)Ot-Bu | — | OH |
| III-100 | A-1 | O | CH₂C(=O)NMe₂ | — | OH |
| III-101 | A-1 | O | CH₂C(=O)-morpholino | — | OH |
| III-102 | A-1 | O | CH₂CN | — | OH |
| III-103 | A-1 | O | CH₂CH₂CN | — | OH |
| III-104 | A-1 | O | CH(Me)CH₂CN | — | OH |
| III-105 | A-1 | O | CH₂CH₂CH2CN | — | OH |
| III-106 | A-1 | O | CH₂CH₂NO₂ | — | OH |
| III-107 | A-1 | O | Bn | — | OH |
| III-108 | A-1 | O | (2-F)Bn | — | OH |
| III-109 | A-1 | O | (3-F)Bn | — | OH |
| III-110 | A-1 | O | (4-F)Bn | — | OH |
| III-111 | A-1 | O | (2-Cl)Bn | — | OH |

TABLE 31

| Compound No. | A | X¹ | R¹ | R² | R³ |
|---|---|---|---|---|---|
| III-112 | A-1 | O | (3-Cl)Bn | — | OH |
| III-113 | A-1 | O | (4-Cl)Bn | — | OH |
| III-114 | A-1 | O | (2-Me)Bn | — | OH |
| III-115 | A-1 | O | (3-Me)Bn | — | OH |
| III-116 | A-1 | O | (4-Me)Bn | — | OH |
| III-117 | A-1 | O | (2-CF₃)Bn | — | OH |
| III-118 | A-1 | O | (3-CF₃)Bn | — | OH |
| III-119 | A-1 | O | (4-CF₃)Bn | — | OH |
| III-120 | A-1 | O | (2-OMe)Bn | — | OH |
| III-121 | A-2 | O | (2-OMe)Bn | — | OH |
| III-122 | A-3 | O | (2-OMe)Bn | — | OH |
| III-123 | A-4 | O | (2-OMe)Bn | — | OH |
| III-124 | A-5 | O | (2-OMe)Bn | — | OH |
| III-125 | A-1 | O | (3-OMe)Bn | — | OH |
| III-126 | A-1 | O | (4-OMe)Bn | — | OH |
| III-127 | A-1 | O | (2,4-(OMe)₂)Bn | — | OH |
| III-128 | A-1 | O | (2,6-(OMe)₂)Bn | — | OH |
| III-129 | A-1 | O | (3,5-(OMe)₂)Bn | — | OH |
| III-130 | A-1 | O | CH(Me)Ph | — | OH |
| III-131 | A-1 | O | 3-methyl-4,5-dihydroisoxazol-5-yl | | OH |

TABLE 31-continued
| Compound No. | A | X¹ | R¹ | R² | R³ |
|---|---|---|---|---|---|
| III-132 | A-2 | O | 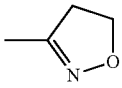 | — | OH |
| III-133 | A-3 | O | 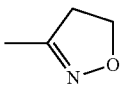 | — | OH |
| III-134 | A-4 | O | 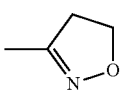 | — | OH |
| III-135 | A-5 | O | 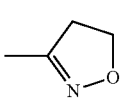 | — | OH |
| III-136 | A-1 | O | 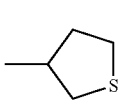 | — | OH |
| III-137 | A-1 | O | 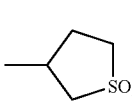 | — | OH |
| III-138 | A-1 | O | 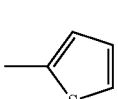 | — | OH |
| III-139 | A-1 | O | 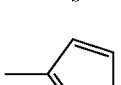 | — | OH |
| III-140 | A-2 | O | 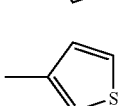 | — | OH |
TABLE 32
| Compound No. | A | X¹ | R¹ | R² | R³ |
|---|---|---|---|---|---|
| III-141 | A-3 | O | 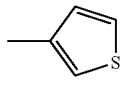 | — | OH |
| III-142 | A-4 | | 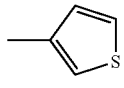 | — | OH |
| III-143 | A-5 | | 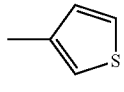 | — | OH |
| III-144 | A-1 | | 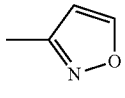 | — | OH |
| III-145 | A-1 | | 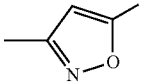 | — | OH |
| III-146 | A-2 | | 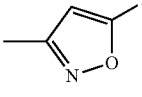 | — | OH |
| III-147 | A-3 | | 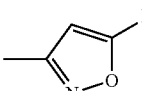 | — | OH |
| III-148 | A-4 | | 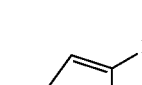 | — | OH |
| III-149 | A-5 | | 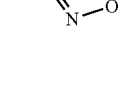 | — | OH |
| III-150 | A-1 | | 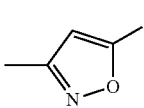 | — | OH |
| III-151 | A-1 | |  | — | OH |
| III-152 | A-1 | | 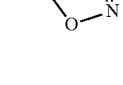 | — | OH |
| III-153 | A-1 | | 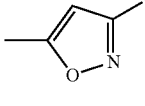 | — | OH |
| III-154 | A-1 | | 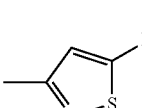 | — | OH |
| III-155 | A-1 | | 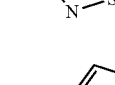 | — | OH |
| III-156 | A-1 | | 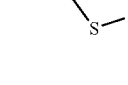 | — | OH |
| III-157 | A-1 | | 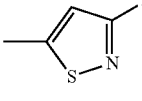 | — | OH |

TABLE 33
| Compound No. | A | X¹ | R¹ | R² | R³ |
|---|---|---|---|---|---|
| III-158 | A-1 | O | 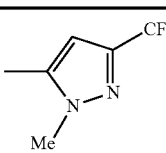 | — | OH |
| III-159 | A-1 | O | 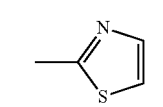 | — | OH |
| III-160 | A-1 | O | 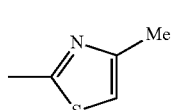 | — | OH |
| III-161 | A-1 | O | 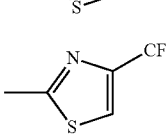 | — | OH |
| III-162 | A-1 | O | 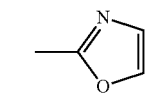 | — | OH |
| III-163 | A-1 | O | 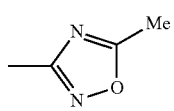 | — | OH |
| III-164 | A-1 | O | 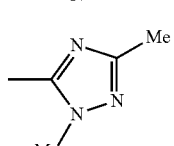 | — | OH |
| III-165 | A-1 | O | 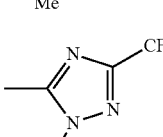 | — | OH |
| III-166 | A-1 | O | 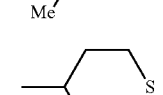 | — | OH |
| III-167 | A-1 | O | 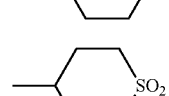 | — | OH |
| III-168 | A-1 | O | 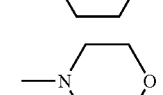 | — | OH |
| III-169 | A-1 | O | 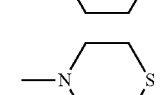 | — | OH |
| III-170 | A-1 | O | 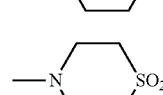 | — | OH |
| III-171 | A-1 | O | 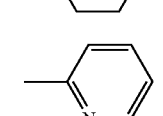 | — | OH |
TABLE 33-continued
| Compound No. | A | X¹ | R¹ | R² | R³ |
|---|---|---|---|---|---|
| III-172 | A-1 | O | 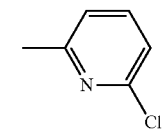 | — | OH |
| III-173 | A-1 | O | 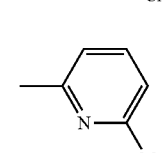 | — | OH |
TABLE 34
| Compound No. | A | X¹ | R¹ | R² | R³ |
|---|---|---|---|---|---|
| III-174 | A-1 | O | 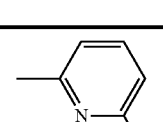 | — | OH |
| III-175 | A-1 | O | 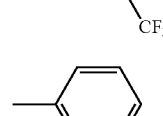 | — | OH |
| III-176 | A-1 | O | 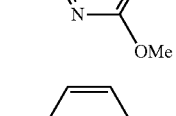 | — | OH |
| III-177 | A-1 | O | 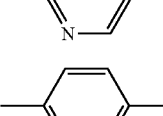 | — | OH |
| III-178 | A-1 | O | 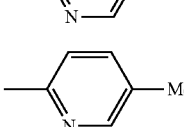 | — | OH |
| III-179 | A-1 | O | 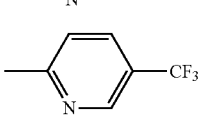 | — | OH |
| III-180 | A-1 | O | 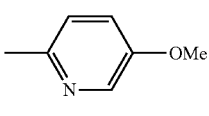 | — | OH |
| III-181 | A-1 | O | 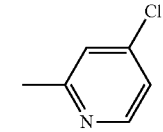 | — | OH |
| III-182 | A-1 | O | 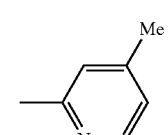 | — | OH |

TABLE 34-continued

| Compound No. | A | X¹ | R¹ | R² | R³ |
|---|---|---|---|---|---|
| III-183 | A-1 | O | 2-methyl-4-trifluoromethylpyridin-5-yl | — | OH |
| III-184 | A-1 | O | 2-methyl-4-methoxypyridin-5-yl | — | OH |
| III-185 | A-1 | O | pyridin-3-yl | — | OH |
| III-186 | A-1 | O | 6-chloropyridin-3-yl | — | OH |
| III-187 | A-1 | O | 6-methylpyridin-3-yl | — | OH |
| III-188 | A-1 | O | 6-trifluoromethylpyridin-3-yl | — | OH |
| III-189 | A-1 | O | 6-methoxypyridin-3-yl | — | OH |
| III-190 | A-2 | O | 6-methoxypyridin-3-yl | — | OH |

TABLE 35

| Compound No. | A | X¹ | R¹ | R² | R³ |
|---|---|---|---|---|---|
| III-191 | A-3 | O | 6-methoxypyridin-3-yl | — | OH |
| III-192 | A-4 | O | 6-methoxypyridin-3-yl | — | OH |
| III-193 | A-5 | O | 6-methoxypyridin-3-yl | — | OH |
| III-194 | A-1 | O | pyridin-4-yl | — | OH |
| III-195 | A-1 | O | 2-methylpyrimidin-5-yl | — | OH |
| III-196 | A-1 | O | 2-methyl-4-trifluoromethylpyrimidin-5-yl | — | OH |
| III-197 | A-1 | O | 2-methyl-4,6-dimethoxypyrimidin-5-yl | — | OH |
| III-198 | A-1 | O | 2-methyl-4,6-dimethoxy-1,3,5-triazin-5-yl | — | OH |
| III-199 | A-1 | O | pyrazinyl | — | OH |
| III-200 | A-1 | O | 2,4-diamino-6-methyl-1,3,5-triazin-5-yl | — | OH |
| III-201 | A-1 | O | 2,3-dihydrobenzofuran-5-yl | — | OH |
| III-202 | A-1 | O | benzo[1,3]dioxol-5-yl | — | OH |
| III-203 | A-2 | O | benzo[1,3]dioxol-5-yl | — | OH |
| III-204 | A-3 | O | benzo[1,3]dioxol-5-yl | — | OH |
| III-205 | A-4 | O | benzo[1,3]dioxol-5-yl | — | OH |

TABLE 36

| Compound No. | A | X¹ | R¹ | R² | R³ |
|---|---|---|---|---|---|
| III-206 | A-5 | O | 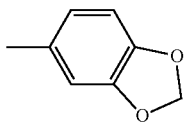 | — | OH |
| III-207 | A-1 | O | 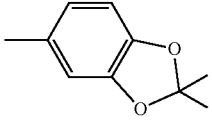 | — | OH |
| III-208 | A-1 | O | 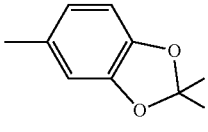 | — | OH |
| III-209 | A-1 | O | 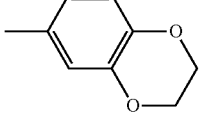 | — | OH |
| III-210 | A-1 | O | 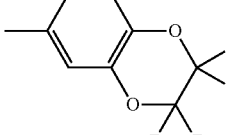 | — | OH |
| III-211 | A-1 | O | 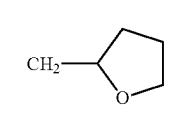 | — | OH |
| III-212 | A-1 | O | 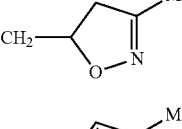 | — | OH |
| III-213 | A-1 | O | 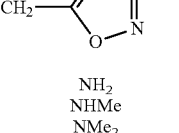 | — | OH |
| III-214 | A-1 | O | NH₂ | — | OH |
| III-215 | A-1 | O | NHMe | — | OH |
| III-216 | A-1 | O | NMe₂ | — | OH |
| III-217 | A-1 | O | OMe | — | OH |
| III-218 | A-1 | O | OEt | — | OH |
| III-219 | A-1 | O | Me | 6-F | OH |
| III-220 | A-1 | O | Me | 6-Cl | OH |
| III-221 | A-1 | O | Me | 6-OMe | OH |
| III-222 | A-1 | S | Me | — | OH |
| III-223 | A-4 | O | Me | — | S(n-Hex) |
| III-224 | A-4 | O | Me | — | SO(n-Hex) |
| III-225 | A-4 | O | Me | — | SO₂(n-Hex) |
| III-226 | A-4 | O | Me | — | SPh |
| III-227 | A-4 | O | Me | — | SOPh |
| III-228 | A-4 | O | Me | — | SO₂Ph |
| III-229 | A-1 | O | CH₂CH₂CH=CH₂ | — | OH |
| III-230 | A-1 | O | CH₂CH₂CH=C(Me)₂ | — | OH |
| III-231 | A-1 | O | CH₂CH₂C≡CH | — | OH |
| III-232 | A-1 | O | CH₂CH₂C(Me)=CF₂ | — | OH |
| III-233 | A-1 | O | CH(Me)C(=O)Ot-Bu | — | OH |

TABLE 37

| Compound No. | A | X¹ | R¹ | R² | R³ |
|---|---|---|---|---|---|
| III-234 | A-1 | O | (2-OCHF₂)Bn | — | OH |
| III-235 | A-1 | O | CH₂CH₂Ph | — | OH |
| III-236 | A-1 | O | 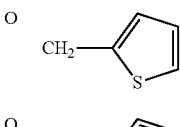 | — | OH |
| III-237 | A-1 | O | 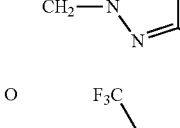 | — | OH |
| III-238 | A-1 | O | 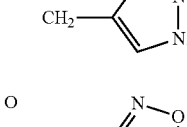 | — | OH |
| III-239 | A-1 | O | 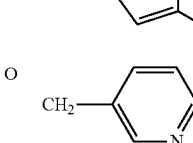 | — | OH |
| III-240 | A-1 | O | 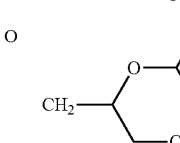 | — | OH |
| III-241 | A-1 | O | 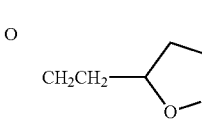 | — | OH |
| III-242 | A-1 | O | 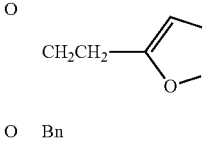 | — | OH |
| III-243 | A-1 | O | 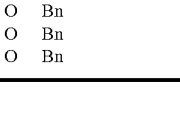 | — | OH |
| III-244 | A-1 | O | Bn | 8-Me | OH |
| III-245 | A-1 | O | Bn | 7-Me | OH |
| III-246 | A-1 | O | Bn | 6-Me | OH |
| III-247 | A-1 | O | Bn | 6-OMe | OH |

TABLE 38

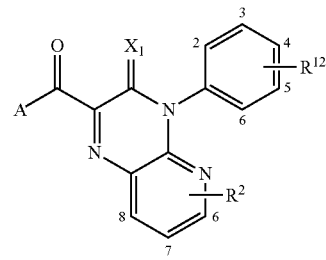

| Compound No. | A | X¹ | R¹² | R² | R³ |
|---|---|---|---|---|---|
| IV-1 | A-1 | O | — | — | OH |
| IV-2 | A-2 | O | — | — | OH |
| IV-3 | A-3 | O | — | — | OH |

TABLE 38-continued

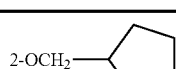

| Compound No. | A | X¹ | R¹² | R² | R³ |
|---|---|---|---|---|---|
| IV-4 | A-4 | O | — | — | OH |
| IV-5 | A-5 | O | — | — | OH |
| IV-6 | A-1 | O | 2-F | — | OH |
| IV-7 | A-1 | O | 3-F | — | OH |
| IV-8 | A-1 | O | 4-F | — | OH |
| IV-9 | A-1 | O | 2-Cl | — | OH |
| IV-10 | A-4 | O | 2-Cl | — | OH |
| IV-11 | A-1 | O | 3-Cl | — | OH |
| IV-12 | A-4 | O | 3-Cl | — | OH |
| IV-13 | A-1 | O | 4-Cl | — | OH |
| IV-14 | A-4 | O | 4-Cl | — | OH |
| IV-15 | A-5 | O | 4-Cl | — | OH |
| IV-16 | A-1 | O | 2-Br | — | OH |
| IV-17 | A-1 | O | 3-Br | — | OH |
| IV-18 | A-1 | O | 4-Br | — | OH |
| IV-19 | A-1 | O | 2-Me | — | OH |
| IV-20 | A-1 | O | 3-Me | — | OH |
| IV-21 | A-1 | O | 4-Me | — | OH |
| IV-22 | A-1 | O | 2-Et | — | OH |
| IV-23 | A-1 | O | 3-Et | — | OH |
| IV-24 | A-1 | O | 4-Et | — | OH |
| IV-25 | A-1 | O | 2-n-Pr | — | OH |
| IV-26 | A-1 | O | 3-n-Pr | — | OH |
| IV-27 | A-1 | O | 4-n-Pr | — | OH |
| IV-28 | A-1 | O | 2-i-Pr | — | OH |
| IV-29 | A-1 | O | 3-i-Pr | — | OH |
| IV-30 | A-1 | O | 4-i-Pr | — | OH |
| IV-31 | A-1 | O | 2-c-Pr | — | OH |
| IV-32 | A-1 | O | 3-c-Pr | — | OH |
| IV-33 | A-1 | O | 4-c-Pr | — | OH |
| IV-34 | A-1 | O | 2-CF₃ | — | OH |

TABLE 39

| Compound No. | A | X¹ | R¹² | R² | R³ |
|---|---|---|---|---|---|
| IV-35 | A-2 | O | 2-CF₃ | — | OH |
| IV-36 | A-3 | O | 2-CF₃ | — | OH |
| IV-37 | A-4 | O | 2-CF₃ | — | OH |
| IV-38 | A-5 | O | 2-CF₃ | — | OH |
| IV-39 | A-1 | O | 3-CF₃ | — | OH |
| IV-40 | A-2 | O | 3-CF₃ | — | OH |
| IV-41 | A-3 | O | 3-CF₃ | — | OH |
| IV-42 | A-4 | O | 3-CF₃ | — | OH |
| IV-43 | A-5 | O | 3-CF₃ | — | OH |
| IV-44 | A-1 | O | 4-CF₃ | — | OH |
| IV-45 | A-2 | O | 4-CF₃ | — | OH |
| IV-46 | A-3 | O | 4-CF₃ | — | OH |
| IV-47 | A-4 | O | 4-CF₃ | — | OH |
| IV-48 | A-5 | O | 4-CF₃ | — | OH |
| IV-49 | A-1 | O | 2-OH | — | OH |
| IV-50 | A-1 | O | 3-OH | — | OH |
| IV-51 | A-1 | O | 4-OH | — | OH |
| IV-52 | A-1 | O | 2-OMe | — | OH |
| IV-53 | A-2 | O | 2-OMe | — | OH |
| IV-54 | A-3 | O | 2-OMe | — | OH |
| IV-55 | A-4 | O | 2-OMe | — | OH |
| IV-56 | A-5 | O | 2-OMe | — | OH |
| IV-57 | A-1 | O | 3-OMe | — | OH |
| IV-58 | A-2 | O | 3-OMe | — | OH |
| IV-59 | A-3 | O | 3-OMe | — | OH |
| IV-60 | A-4 | O | 3-OMe | — | OH |

TABLE 39-continued

| Compound No. | A | X¹ | R¹² | R² | R³ |
|---|---|---|---|---|---|
| IV-61 | A-5 | O | 3-OMe | — | OH |
| IV-62 | A-1 | O | 4-OMe | — | OH |
| IV-63 | A-2 | O | 4-OMe | — | OH |
| IV-64 | A-3 | O | 4-OMe | — | OH |
| IV-65 | A-4 | O | 4-OMe | — | OH |
| IV-66 | A-5 | O | 4-OMe | — | OH |
| IV-67 | A-1 | O | 2-OEt | — | OH |
| IV-68 | A-1 | O | 3-OEt | — | OH |
| IV-69 | A-1 | O | 4-OEt | — | OH |
| IV-70 | A-1 | O | 2-O—n-Pr | — | OH |
| IV-71 | A-1 | O | 3-O—n-Pr | — | OH |
| IV-72 | A-1 | O | 4-O—n-Pr | — | OH |
| IV-73 | A-1 | O | 2-O—i-Pr | — | OH |
| IV-74 | A-1 | O | 3-O—i-Pr | — | OH |
| IV-75 | A-1 | O | 4-O—i-Pr | — | OH |

TABLE 40

| Compound No. | A | X¹ | R¹² | R² | R³ |
|---|---|---|---|---|---|
| IV-76 | A-1 | O | 2-O—c-Pr | — | OH |
| IV-77 | A-1 | O | 3-O—c-Pr | — | OH |
| IV-78 | A-1 | O | 4-O—c-Pr | — | OH |
| IV-79 | A-1 | O | 2-OCH₂CH=CH₂ | — | OH |
| IV-80 | A-1 | O | 3-OCH₂CH=CH₂ | — | OH |
| IV-81 | A-1 | O | 4-OCH₂CH=CH₂ | — | OH |
| IV-82 | A-1 | O | 2-OCH₂C≡CH | — | OH |
| IV-83 | A-1 | O | 3-OCH₂C≡CH | — | OH |
| IV-84 | A-1 | O | 4-OCH₂C≡CH | — | OH |
| IV-85 | A-1 | O | 2-OCHF₂ | — | OH |
| IV-86 | A-2 | O | 2-OCHF₂ | — | OH |
| IV-87 | A-3 | O | 2-OCHF₂ | — | OH |
| IV-88 | A-4 | O | 2-OCHF₂ | — | OH |
| IV-89 | A-5 | O | 2-OCHF₂ | — | OH |
| IV-90 | A-1 | O | 3-OCHF₂ | — | OH |
| IV-91 | A-2 | O | 3-OCHF₂ | — | OH |
| IV-92 | A-3 | O | 3-OCHF₂ | — | OH |
| IV-93 | A-4 | O | 3-OCHF₂ | — | OH |
| IV-94 | A-5 | O | 3-OCHF₂ | — | OH |
| IV-95 | A-1 | O | 4-OCHF₂ | — | OH |
| IV-96 | A-2 | O | 4-OCHF₂ | — | OH |
| IV-97 | A-3 | O | 4-OCHF₂ | — | OH |
| IV-98 | A-4 | O | 4-OCHF₂ | — | OH |
| IV-99 | A-5 | O | 4-OCHF₂ | — | OH |
| IV-100 | A-1 | O | 2-OCF₃ | — | OH |
| IV-101 | A-1 | O | 3-OCF₃ | — | OH |
| IV-102 | A-2 | O | 3-OCF₃ | — | OH |
| IV-103 | A-3 | O | 3-OCF₃ | — | OH |
| IV-104 | A-4 | O | 3-OCF₃ | — | OH |
| IV-105 | A-5 | O | 3-OCF₃ | — | OH |
| IV-106 | A-1 | O | 4-OCF₃ | — | OH |
| IV-107 | A-2 | O | 4-OCF₃ | — | OH |
| IV-108 | A-3 | O | 4-OCF₃ | — | OH |
| IV-109 | A-4 | O | 4-OCF₃ | — | OH |
| IV-110 | A-5 | O | 4-OCF₃ | — | OH |
| IV-111 | A-1 | O | 2-OCH₂CH₂OMe | — | OH |
| IV-112 | A-1 | O | 3-OCH₂CH₂OMe | — | OH |
| IV-113 | A-1 | O | 4-OCH₂CH₂OMe | — | OH |

TABLE 41

| Compound No. | A | X¹ | R¹² | R² | R³ |
|---|---|---|---|---|---|
| IV-114 | A-1 | O | 2-OCH₂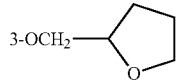 | — | OH |
| IV-115 | A-1 | O | 3-OCH₂ | — | OH |

TABLE 41-continued

| Compound No. | A | X¹ | R¹² | R² | R³ |
|---|---|---|---|---|---|
| IV-116 | A-1 | O | 4-OCH₂-(tetrahydrofuran-2-yl) | — | OH |
| IV-117 | A-1 | O | 2-OC(=O)Me | — | OH |
| IV-118 | A-1 | O | 3-OC(=O)Me | — | OH |
| IV-119 | A-1 | O | 3-OC(=O)Me | — | OH |
| IV-120 | A-1 | O | 2-SMe | — | OH |
| IV-121 | A-1 | O | 3-SMe | — | OH |
| IV-122 | A-1 | O | 4-SMe | — | OH |
| IV-123 | A-1 | O | 2-SO₂Me | — | OH |
| IV-124 | A-1 | O | 3-SO₂Me | — | OH |
| IV-125 | A-1 | O | 4-SO₂Me | — | OH |
| IV-126 | A-1 | O | 2-SCF₃ | — | OH |
| IV-127 | A-1 | O | 3-SCF₃ | — | OH |
| IV-128 | A-1 | O | 4-SCF₃ | — | OH |
| IV-129 | A-1 | O | 2-NO₂ | — | OH |
| IV-130 | A-1 | O | 3-NO₂ | — | OH |
| IV-131 | A-1 | O | 4-NO₂ | — | OH |
| IV-132 | A-1 | O | 2-NH₂ | — | OH |
| IV-133 | A-1 | O | 3-NH₂ | — | OH |
| IV-134 | A-1 | O | 4-NH₂ | — | OH |
| IV-135 | A-1 | O | 2-CN | — | OH |
| IV-136 | A-1 | O | 3-CN | — | OH |
| IV-137 | A-1 | O | 4-CN | — | OH |
| IV-138 | A-1 | O | 2-C(=O)Me | — | OH |
| IV-139 | A-1 | O | 3-C(=O)Me | — | OH |
| IV-140 | A-1 | O | 4-C(=O)Me | — | OH |
| IV-141 | A-1 | O | 2-C(=O)OH | — | OH |
| IV-142 | A-1 | O | 3-C(=O)OH | — | OH |
| IV-143 | A-1 | O | 4-C(=O)OH | — | OH |
| IV-144 | A-1 | O | 2-C(=O)OMe | — | OH |
| IV-145 | A-1 | O | 3-C(=O)OMe | — | OH |
| IV-146 | A-1 | O | 4-C(=O)OMe | — | OH |
| IV-147 | A-1 | O | 2-CH₂OMe | — | OH |
| IV-148 | A-1 | O | 3-CH₂OMe | — | OH |

TABLE 42

| Compound No. | A | X¹ | R¹² | R² | R³ |
|---|---|---|---|---|---|
| IV-149 | A-1 | O | 4-CH₂OMe | — | OH |
| IV-150 | A-1 | O | 2,3-F₂ | — | OH |
| IV-151 | A-1 | O | 2,4-F₂ | — | OH |
| IV-152 | A-1 | O | 2,5-F₂ | — | OH |
| IV-153 | A-1 | O | 2,6-F₂ | — | OH |
| IV-154 | A-1 | O | 3,4-F₂ | — | OH |
| IV-155 | A-1 | O | 3,5-F₂ | — | OH |
| IV-156 | A-1 | O | 2,3-Cl₂ | — | OH |
| IV-157 | A-1 | O | 2,4-Cl₂ | — | OH |
| IV-158 | A-1 | O | 2,5-Cl₂ | — | OH |
| IV-159 | A-1 | O | 2,6-Cl₂ | — | OH |
| IV-160 | A-1 | O | 3,4-Cl₂ | — | OH |
| IV-161 | A-1 | O | 3,5-Cl₂ | — | OH |
| IV-162 | A-1 | O | 2-F, 3-OMe | — | OH |
| IV-163 | A-1 | O | 2-Cl, 3-OMe | — | OH |
| IV-164 | A-1 | O | 2-Me, 3-OMe | — | OH |
| IV-165 | A-1 | O | 2,3-(OMe)₂ | — | OH |
| IV-166 | A-1 | O | 3-OMe, 4-F | — | OH |
| IV-167 | A-1 | O | 3-OMe, 4-Cl | — | OH |
| IV-168 | A-1 | O | 3-OMe, 4-Me | — | OH |
| IV-169 | A-1 | O | 3,4-(OMe)₂ | — | OH |
| IV-170 | A-1 | O | 3-OMe, 5-F | — | OH |
| IV-171 | A-1 | O | 3-OMe, 5-Cl | — | OH |
| IV-172 | A-1 | O | 3-OMe, 5-Me | — | OH |
| IV-173 | A-1 | O | 3,5-(OMe)₂ | — | OH |
| IV-174 | A-1 | O | 2-F, 4-OMe | — | OH |
| IV-175 | A-1 | O | 2-Cl, 4-OMe | — | OH |
| IV-176 | A-1 | O | 2-Me, 4-OMe | — | OH |
| IV-177 | A-1 | O | 2,4-(OMe)₂ | — | OH |
| IV-178 | A-1 | O | 3-F, 4-OMe | — | OH |
| IV-179 | A-1 | O | 3-Cl, 4-OMe | — | OH |
| IV-180 | A-1 | O | 3-Me, 4-OMe | — | OH |
| IV-181 | A-1 | O | 2-F, 5-OMe | — | OH |

TABLE 42-continued

| Compound No. | A | X¹ | R¹² | R² | R³ |
|---|---|---|---|---|---|
| IV-182 | A-1 | O | 2-Cl, 5-OMe | — | OH |
| IV-183 | A-1 | O | 2-Me, 5-OMe | — | OH |
| IV-184 | A-1 | O | 2,5-(OMe)₂ | — | OH |
| IV-185 | A-1 | O | 3,4,5-(OMe)₃ | — | OH |
| IV-186 | A-1 | O | — | 6-F | OH |
| IV-187 | A-1 | O | 4-OMe | 6-F | OH |

TABLE 43

| Compound No. | A | X¹ | R¹² | R² | R³ |
|---|---|---|---|---|---|
| IV-188 | A-1 | O | — | 6-Cl | OH |
| IV-189 | A-1 | O | 4-OMe | 6-Cl | OH |
| IV-190 | A-1 | O | — | 6-OMe | OH |
| IV-191 | A-1 | O | 4-OMe | 6-OMe | OH |
| IV-192 | A-1 | S | — | — | OH |
| IV-193 | A-1 | S | 4-OMe | — | OH |
| IV-194 | A-4 | O | — | — | S(n-Hex) |
| IV-195 | A-4 | O | — | — | SO(n-Hex) |
| IV-196 | A-4 | O | — | — | SO₂(n-Hex) |
| IV-197 | A-4 | O | — | — | SPh |
| IV-198 | A-4 | O | — | — | SOPh |
| IV-199 | A-4 | O | — | — | SO₂Ph |
| IV-200 | A-1 | O | 2-F, 5-CF₃ | — | OH |
| IV-201 | A-1 | O | 3-CF₃, 4-F | — | OH |
| IV-202 | A-1 | O | 2-F, 3-CF₃ | — | OH |
| IV-203 | A-1 | O | 3-F, 5-CF₃ | — | OH |
| IV-204 | A-1 | O | 2,3-(Me)₂ | — | OH |
| IV-205 | A-1 | O | 2,4-(Me)₂ | — | OH |
| IV-206 | A-1 | O | 2,5-(Me)₂ | — | OH |
| IV-207 | A-1 | O | 2,6-(Me)₂ | — | OH |
| IV-208 | A-1 | O | 3,4-(Me)₂ | — | OH |
| IV-209 | A-1 | O | 3,5-(Me)₂ | — | OH |
| IV-210 | A-1 | O | 3,5-(CF₃)₂ | — | OH |
| IV-211 | A-1 | O | 2,6-(OMe)₂ | — | OH |
| IV-212 | A-1 | O | 2-F, 3-Cl | — | OH |
| IV-213 | A-1 | O | 2-F, 4-Cl | — | OH |
| IV-214 | A-1 | O | 2-F, 5-Cl | — | OH |
| IV-215 | A-1 | O | 3-F, 4-Cl | — | OH |
| IV-216 | A-1 | O | 4-F, 2-Cl | — | OH |
| IV-217 | A-1 | O | 4-F, 3-Cl | — | OH |
| IV-218 | A-1 | O | 2-F, 3-Me | — | OH |
| IV-219 | A-1 | O | 2-F, 4-Me | — | OH |
| IV-220 | A-1 | O | 2-F, 5-Me | — | OH |
| IV-221 | A-1 | O | 3-F, 2-Me | — | OH |
| IV-222 | A-1 | O | 3-F, 4-Me | — | OH |
| IV-223 | A-4 | O | 3-F, 4-Me | — | OH |
| IV-224 | A-1 | O | 3-F, 5-Me | — | OH |
| IV-225 | A-1 | O | 4-F, 2-Me | — | OH |
| IV-226 | A-1 | O | 4-F, 3-Me | — | OH |

TABLE 44

| Compound No. | A | X¹ | R¹² | R² | R³ |
|---|---|---|---|---|---|
| IV-227 | A-1 | O | 5-F, 2-Me | — | OH |
| IV-228 | A-1 | O | 2-F, 4-CF₃ | — | OH |
| IV-229 | A-1 | O | 3-F, 4-CF₃ | — | OH |
| IV-230 | A-1 | O | 4-F, 2-CF₃ | — | OH |
| IV-231 | A-1 | O | 3-F, 2-OMe | — | OH |
| IV-232 | A-1 | O | 4-F, 2-OMe | — | OH |
| IV-233 | A-1 | O | 5-F, 2-OMe | — | OH |
| IV-234 | A-1 | O | 2-F, 4-OCHF₂ | — | OH |
| IV-235 | A-1 | O | 3-F, 4-OCHF₂ | — | OH |
| IV-236 | A-1 | O | 4-F, 2-OCHF₂ | — | OH |
| IV-237 | A-1 | O | 4-F, 3-CN | — | OH |
| IV-238 | A-1 | O | 2-Cl, 4-Me | — | OH |
| IV-239 | A-1 | O | 3-Cl, 4-Me | — | OH |
| IV-240 | A-1 | O | 3-Cl, 4-OCHF₂ | — | OH |
| IV-241 | A-1 | O | 4-Me, 3-CF₃ | — | OH |
| IV-242 | A-1 | O | 4-Me, 2-OMe | — | OH |
| IV-243 | A-1 | O | 3-Me, 4-CN | — | OH |
| IV-244 | A-1 | O | 4-Me, 3-CN | — | OH |

TABLE 44-continued

| Compound No. | A | X$^1$ | R$^{12}$ | R$^2$ | R$^3$ |
|---|---|---|---|---|---|
| IV-245 | A-1 | O | 2,3,4-F$_3$ | — | OH |
| IV-246 | A-1 | O | 2,3,5-F$_3$ | — | OH |
| IV-247 | A-1 | O | 2,4,5-F$_3$ | — | OH |
| IV-248 | A-1 | O | 3,4,5-F$_3$ | — | OH |
| IV-249 | A-1 | O | 2,3-F$_2$, 4-Me | — | OH |
| IV-250 | A-1 | O | 2,6-F$_2$, 4-OMe | — | OH |
| IV-251 | A-1 | O | 3,5-F$_2$, 4-OMe | — | OH |
| IV-252 | A-1 | O | 4-F, 2-Cl, 5-Me | — | OH |
| IV-253 | A-1 | O | — | 7-Cl | OH |
| IV-254 | A-1 | O | — | 6-Me | OH |
| IV-255 | A-1 | O | — | 7-Me | OH |
| IV-256 | A-1 | O | — | 8-Me | OH |
| IV-257 | A-1 | O | 3-Me | 8-Me | OH |
| IV-258 | A-1 | O | 3-CF$_3$ | 8-Me | OH |
| IV-259 | A-1 | O | 4-OMe | 8-Me | OH |
| IV-260 | A-1 | O | 3-F, 4-Me | 8-Me | OH |
| IV-261 | A-4 | O | 3-F, 4-Me | 8-Me | OH |
| IV-262 | A-1 | O | 3-F, 4-OMe | 8-Me | OH |
| IV-263 | A-1 | O | — | 8-OMe | OH |
| IV-264 | A-1 | O | 3-CF$_3$ | 8-OMe | OH |

TABLE 45

| Compound No. | A | X$^1$ | R$^{12}$ | R$^2$ | R$^3$ |
|---|---|---|---|---|---|
| IV-265 | A-1 | O | 3-F, 4-Me | 8-Cl | OH |
| IV-266 | A-1 | O | 3-F, 4-Me | 6-F | OH |
| IV-267 | A-1 | O | 3-F, 4-Me | 6-Cl | OH |
| IV-268 | A-1 | O | 3-F, 4-Me | 7-Me | OH |
| IV-269 | A-1 | O | 3-F, 4-Me | 6-Me | OH |
| IV-270 | A-1 | O | — | 8-Cl | OH |
| IV-271 | A-1 | O | 3-F, 4-Me | 6-OMe | OH |
| IV-272 | A-1 | O | 3-F, 4-Me | 6-OMe | OH |
| IV-273 | A-1 | O | 4-OMe | 8-Cl | OH |
| IV-274 | A-1 | O | 4-OMe | 6,8-Me$_2$ | OH |
| IV-275 | A-1 | O | 3-F, 4-OMe | 6,8-Me$_2$ | OH |
| IV-276 | A-1 | O | 3,4-(OCH$_2$O)— | 8-Me | OH |
| IV-277 | A-1 | O | 3,4-(OCH$_2$CH$_2$O)— | 8-Me | OH |
| IV-278 | A-1 | O | 3,4-(OCH$_2$O)— | 6,8-Me$_2$ | OH |
| IV-279 | A-1 | O | 3,4-(OCH$_2$CH$_2$O)— | 6,8-Me$_2$ | OH |
| IV-280 | A-1 | O | 4-OMe | 6-Cl, 8-Me | OH |
| IV-281 | A-1 | O | 3-F, 4-OMe | 6-Cl, 8-Me | OH |
| IV-282 | A-1 | O | 3,4-(OCH$_2$O)— | 6-Cl, 8-Me | OH |
| IV-283 | A-1 | O | 3,4-(OCH$_2$CH$_2$O)— | 6-Cl, 8-Me | OH |
| IV-284 | A-1 | O | — | 6-SMe | OH |
| IV-285 | A-1 | O | 3,4-(OCH$_2$CH$_2$O)— | 6-OMe | OH |
| IV-286 | A-1 | O | 3-F, 4-OEt | — | OH |
| IV-287 | A-1 | O | 3,4-(OCH$_2$O)— | 8-Cl | OH |

Specific preferred examples of the compound represented by formula [J2] which is a production intermediate of the present invention will be shown in the following Table 46 to Table 81. However, the compound is not intended to be limited to these compounds as in the case of the compound of the present invention. Additionally, compound numbers will be referred in the following descriptions, and the notations in the tables have the same meanings as mentioned above.

TABLE 46

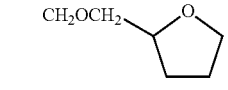

| Compound No. | X$^1$ | R$^1$ | R$^2$ |
|---|---|---|---|
| V-1 | O | H | — |
| V-2 | O | Me | — |
| V-3 | O | Et | — |
| V-4 | O | n-Pr | — |
| V-5 | O | i-Pr | — |
| V-6 | O | c-Pr | — |
| V-7 | O | n-Bu | — |
| V-8 | O | s-Bu | — |
| V-9 | O | i-Bu | — |
| V-10 | O | t-Bu | — |
| V-11 | O | c-Bu | — |
| V-12 | O | n-Pen | — |
| V-13 | O | c-Pen | — |
| V-14 | O | n-Hex | — |
| V-15 | O | c-Hex | — |
| V-16 | O | n-C$_7$H$_{15}$ | — |
| V-17 | O | n-C$_8$H$_{17}$ | — |
| V-18 | O | n-C$_9$H$_{19}$ | — |
| V-19 | O | n-C$_{10}$H$_{21}$ | — |
| V-20 | O | n-C$_{11}$H$_{23}$ | — |
| V-21 | O | n-C$_{12}$H$_{35}$ | — |
| V-22 | O | CH$_2$CH=CH$_2$ | — |
| V-23 | O | CH$_2$C≡CH | — |
| V-24 | O | CH$_2$CF$_3$ | — |
| V-25 | O | CH$_2$CH$_2$F | — |
| V-26 | O | CH$_2$CH$_2$Cl | — |
| V-27 | O | CH$_2$CH$_2$CF$_3$ | — |
| V-28 | O | CH$_2$CH=CCl$_2$ | — |
| V-29 | O | CH$_2$OMe | — |
| V-30 | O | CH$_2$OEt | — |
| V-31 | O | CH(Me)OMe | — |
| V-32 | O | CH(Me)OEt | — |
| V-33 | O | CH$_2$OPh | — |
| V-34 | O | CH$_3$OCH$_2$CH$_2$OMe | — |

TABLE 47

| Compound No. | X$^1$ | R$^1$ | R$^2$ |
|---|---|---|---|
| V-35 | O | CH$_2$OCH$_2$CF$_3$ | — |
| V-36 | O | CH(Me)OCH$_2$CF$_3$ | — |
| V-37 | O | CH$_2$OCH$_2$-(tetrahydrofuran-2-yl) | — |
| V-38 | O | CH(Me)OCH$_2$-(tetrahydrofuran-2-yl) | — |
| V-39 | O | CH$_2$OCH$_2$CH$_2$SO$_2$Me | — |
| V-40 | O | CH$_2$OCH$_2$CH$_2$CN | — |
| V-41 | O | CH$_2$OC(=O)t-Bu | — |
| V-42 | O | CH$_2$SMe | — |
| V-43 | O | CH$_2$SEt | — |
| V-44 | O | CH$_2$S—n-Pr | — |
| V-45 | O | CH(Me)SMe | — |
| V-46 | O | CH(Me)SEt | — |
| V-47 | O | CH(Me)S—n-Pr | — |
| V-48 | O | CH$_2$SOMe | — |
| V-49 | O | CH$_2$SOEt | — |
| V-50 | O | CH$_2$SO—n-Pr | — |

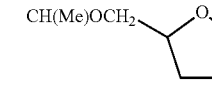

TABLE 47-continued

| Compound No. | X¹ | R¹ | R² |
|---|---|---|---|
| V-51 | O | CH₂SO₂Me | — |
| V-52 | O | CH₂SO₂Et | — |
| V-53 | O | CH₂SO₂n-Pr | — |
| V-54 | O | CH(Me)SO₂Me | — |
| V-55 | O | CH(Me)SO₂Et | — |
| V-56 | O | CH(Me)SO₂—n-Pr | — |
| V-57 | O | CH₂CH₂OH | — |
| V-58 | O | CH₂CH₂OMe | — |
| V-59 | O | CH₂CH₂OEt | — |
| V-60 | O | CH(Me)CH₂OMe | — |
| V-61 | O | CH₂CH₂SMe | — |
| V-62 | O | CH₂CH₂SO₂Me | — |
| V-63 | O | CH₂CH₂CH₂OMe | — |
| V-64 | O | CH₂C(=O)Me | — |
| V-65 | O | CH₂C(=O)OMe | — |
| V-66 | O | CH₂C(=O)OEt | — |
| V-67 | O | CH₂C(=O)O—n-Pr | — |
| V-68 | O | CH₂C(=O)O—i-Pr | — |
| V-69 | O | CH₂C(=O)O—t-Bu | — |
| V-70 | O | CH₂C(=O)NMe₂ | — |

TABLE 48

| Compound No. | X¹ | R¹ | R² |
|---|---|---|---|
| V-71 | O | CH₂C(=O)—N(morpholino) | — |
| V-72 | O | CH₂CN | — |
| V-73 | O | CH₂CH₂CN | — |
| V-74 | O | CH(Me)CH₂CN | — |
| V-75 | O | CH₂CH₂CH₂CN | — |
| V-76 | O | CH₂CH₂NO₂ | — |
| V-77 | O | Bn | — |
| V-78 | O | (2-F)Bn | — |
| V-79 | O | (3-F)Bn | — |
| V-80 | O | (4-F)Bn | — |
| V-81 | O | (2-Cl)Bn | — |
| V-82 | O | (3-Cl)Bn | — |
| V-83 | O | (4-Cl)Bn | — |
| V-84 | O | (2-Me)Bn | — |
| V-85 | O | (3-Me)Bn | — |
| V-86 | O | (4-Me)Bn | — |
| V-87 | O | (2-CF₃)Bn | — |
| V-88 | O | (3-CF₃)Bn | — |
| V-89 | O | (4-CF₃)Bn | — |
| V-90 | O | (2-OMe)Bn | — |
| V-91 | O | (3-OMe)Bn | — |
| V-92 | O | (4-OMe)Bn | — |
| V-93 | O | (2,4-(OMe)₂)Bn | — |
| V-94 | O | (2,6-(OMe)₂)Bn | — |
| V-95 | O | (3,5-(OMe)₂)Bn | — |
| V-96 | O | CH(Me)Ph | — |
| V-97 | O | 3-methyl-4,5-dihydroisoxazol-5-yl | — |
| V-98 | O | tetrahydrothiophen-3-yl | — |
| V-99 | O | tetrahydrothiophene-3-yl 1,1-dioxide | — |
| V-100 | O | thiophen-2-yl | — |

TABLE 49

| Compound No. | X¹ | R¹ | R² |
|---|---|---|---|
| V-101 | O | thiophen-3-yl | — |
| V-102 | O | isoxazol-3-yl | — |
| V-103 | O | 5-Me-isoxazol-3-yl | — |
| V-104 | O | 5-CF₃-isoxazol-3-yl | — |
| V-105 | O | 3-Me-isoxazol-5-yl | — |
| V-106 | O | 3-CF₃-isoxazol-5-yl | — |
| V-107 | O | isothiazol-3-yl | — |
| V-108 | O | 5-Me-isothiazol-3-yl | — |
| V-109 | O | isothiazol-5-yl | — |
| V-110 | O | 3-Me-isothiazol-5-yl | — |
| V-111 | O | 1,3-diMe-pyrazol-5-yl | — |
| V-112 | O | 1-Me-3-CF₃-pyrazol-5-yl | — |

TABLE 50

| Compound No. | X¹ | R¹ | R² |
|---|---|---|---|
| V-113 | O | 2-thiazolyl (methyl-substituted) | — |
| V-114 | O | 2-methyl-4-Me-thiazolyl | — |
| V-115 | O | 2-methyl-4-CF₃-thiazolyl | — |
| V-116 | O | 2-methyl-oxazolyl | — |
| V-117 | O | 3-methyl-5-Me-1,2,4-oxadiazolyl | — |
| V-118 | O | 1,3-dimethyl-5-Me-1,2,4-triazolyl | — |
| V-119 | O | 1,5-dimethyl-3-CF₃-1,2,4-triazolyl | — |
| V-120 | O | 4-tetrahydrothiopyranyl | — |
| V-121 | O | 4-(tetrahydrothiopyranyl-SO₂) | — |
| V-122 | O | morpholinyl | — |
| V-123 | O | thiomorpholinyl | — |
| V-124 | O | thiomorpholinyl-SO₂ | — |
| V-125 | O | 2-pyridyl | — |
| V-126 | O | 6-chloro-2-pyridyl | — |

TABLE 51

| Compound No. | X¹ | R¹ | R² |
|---|---|---|---|
| V-127 | O | 2,6-dimethylpyridyl | — |
| V-128 | O | 2-methyl-6-CF₃-pyridyl | — |
| V-129 | O | 2-methyl-6-OMe-pyridyl | — |
| V-130 | O | 2-methyl-5-F-pyridyl | — |
| V-131 | O | 2-methyl-5-Cl-pyridyl | — |
| V-132 | O | 2,5-dimethylpyridyl | — |
| V-133 | O | 2-methyl-5-CF₃-pyridyl | — |
| V-134 | O | 2-methyl-5-OMe-pyridyl | — |
| V-135 | O | 2-methyl-4-Cl-pyridyl | — |
| V-136 | O | 2,4-dimethylpyridyl | — |
| V-137 | O | 2-methyl-4-CF₃-pyridyl | — |
| V-138 | O | 2-methyl-4-OMe-pyridyl | — |

TABLE 51-continued

| Compound No. | X¹ | R¹ | R² |
|---|---|---|---|
| V-139 | O | 3-pyridyl | — |

TABLE 52

| Compound No. | X¹ | R¹ | R² |
|---|---|---|---|
| V-140 | O | 6-Cl-pyridin-3-yl | — |
| V-141 | O | 6-Me-pyridin-3-yl | — |
| V-142 | O | 6-CF₃-pyridin-3-yl | — |
| V-143 | O | 6-OMe-pyridin-3-yl | — |
| V-144 | O | 6-OMe-pyridin-3-yl | — |
| V-145 | O | 6-OMe-pyridin-3-yl | — |
| V-146 | O | 6-OMe-pyridin-3-yl | — |
| V-147 | O | 4-pyridyl | — |
| V-148 | O | pyrimidin-2-yl | — |
| V-149 | O | 4-CF₃-pyrimidin-2-yl | — |
| V-150 | O | 4,6-diOMe-pyrimidin-2-yl | — |

TABLE 52-continued

| Compound No. | X¹ | R¹ | R² |
|---|---|---|---|
| V-151 | O | 4,6-diOMe-1,3,5-triazin-2-yl | — |

TABLE 53

| Compound No. | X¹ | R¹ | R² |
|---|---|---|---|
| V-152 | O | pyrazin-2-yl | — |
| V-153 | O | 4,6-diNH₂-1,3,5-triazin-2-yl | — |
| V-154 | O | 2,3-dihydrobenzofuran-5-yl | — |
| V-155 | O | 1,3-benzodioxol-5-yl | — |
| V-156 | O | 2,2-difluoro-1,3-benzodioxol-5-yl | — |
| V-157 | O | 2,2-dimethyl-1,3-benzodioxol-5-yl | — |
| V-158 | O | 2,3-dihydro-1,4-benzodioxin-6-yl | — |
| V-159 | O | 2,2,3,3-tetrafluoro-2,3-dihydro-1,4-benzodioxin-6-yl | — |
| V-160 | O | (tetrahydrofuran-2-yl)methyl | — |

TABLE 53-continued

| Compound No. | X¹ | R¹ | R² |
|---|---|---|---|
| V-161 | O | 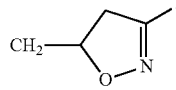 | — |
| V-162 | O | 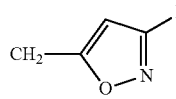 | — |
| V-163 | O | NH₂ | — |

TABLE 54

| Compound No. | X¹ | R¹ | R² |
|---|---|---|---|
| V-164 | O | NHMe | — |
| V-165 | O | NMe₂ | — |
| V-166 | O | OMe | — |
| V-167 | O | OEt | — |
| V-168 | O | Me | 5-F |
| V-169 | O | Me | 6-F |
| V-170 | O | Me | 7-F |
| V-171 | O | Me | 8-F |
| V-172 | O | Me | 5-Cl |
| V-173 | O | CH₂CH₂OMe | 5-Cl |
| V-174 | O | Me | 6-Cl |
| V-175 | O | CH₂CH₂OMe | 6-Cl |
| V-176 | O | Me | 7-Cl |
| V-177 | O | CH₂CH₂OMe | 7-Cl |
| V-178 | O | Me | 8-Cl |
| V-179 | O | CH₂CH₂OMe | 8-Cl |
| V-180 | O | Me | 7-Me |
| V-181 | O | Me | 6-CF₃ |
| V-182 | O | Me | 7-CF₃ |
| V-183 | O | Me | 6-OH |
| V-184 | O | Me | 7-OH |
| V-185 | O | Me | 6-OMe |
| V-186 | O | Me | 7-OMe |
| V-187 | O | Me | 6-OCF₃ |
| V-188 | O | Me | 7-OCF₃ |
| V-189 | O | Me | 5-SMe |
| V-190 | O | Me | 6-SMe |
| V-191 | O | Me | 7-SMe |
| V-192 | O | Me | 8-SMe |
| V-193 | O | Me | 5-SO₂Me |
| V-194 | O | Me | 6-SO₂Me |
| V-195 | O | Me | 7-SO₂Me |
| V-196 | O | Me | 8-SO₂Me |
| V-197 | O | Me | 6-NO₂ |
| V-198 | O | Me | 7-NO₂ |
| V-199 | O | Me | 6-NH₂ |
| V-200 | O | Me | 7-NH₂ |

TABLE 55

| Compound No. | X¹ | R¹ | R² |
|---|---|---|---|
| V-201 | O | Me | 7-CN |
| V-202 | O | Me | 6,7-Cl₂ |
| V-203 | O | Me | 6,7-Me₂ |
| V-204 | S | Me | — |
| V-205 | O | 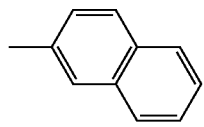 | — |

TABLE 55-continued

| Compound No. | X¹ | R¹ | R² |
|---|---|---|---|
| V-206 | O | 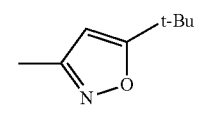 | — |
| V-207 | O | 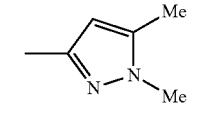 | — |
| V-208 | O | 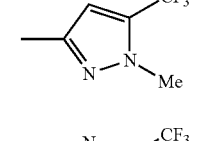 | — |
| V-209 | O | 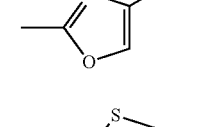 | — |
| V-210 | O | 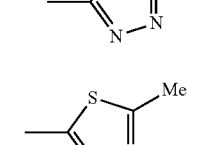 | — |
| V-211 | O | 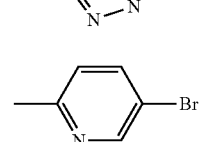 | — |
| V-212 | O | 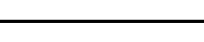 | — |
| V-213 | O | 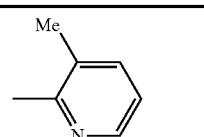 | — |

TABLE 56

| Compound No. | X¹ | R¹ | R² |
|---|---|---|---|
| V-214 | O | 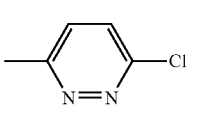 | — |
| V-215 | O | 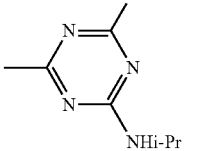 | — |
| V-216 | O | 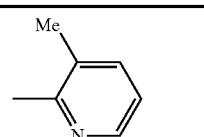 | — |

TABLE 56-continued

| Compound No. | X¹ | R¹ | R² |
|---|---|---|---|
| V-217 | O | 6-methyl-4-methyl-benzo[1,4]oxazin-3(4H)-one | — |
| V-218 | O | 5-methyl-1-methyl-indole | — |
| V-219 | O | 5-methyl-benzofuran | — |
| V-220 | O | N(Me)C(=O)Ot-Bu | — |
| V-221 | O | 5-methyl-2-methoxy-pyridine | 5-F |
| V-222 | O | Bn | 6-F |
| V-223 | O | 3-methyl-5-methyl-isoxazole | 6-F |
| V-224 | O | Me | 5-CH$_2$OMe |
| V-225 | O | 5-methyl-2-methoxy-pyridine | 5,7-F$_2$ |
| V-226 | O | 2-methyl-5-methyl-pyridine | 7-Cl |
| V-227 | O | CH$_2$—c-Pr | — |
| V-228 | O | CH$_2$—c-Bu | — |
| V-229 | O | CH$_2$-c-Pen | — |
| V-230 | O | CH$_2$O—c-Pen | — |

TABLE 57

| Compound No. | X¹ | R¹ | R² |
|---|---|---|---|
| V-231 | O | CH$_2$CH$_2$NH$_2$ | — |
| V-232 | O | CH$_2$CH$_2$NHEt | — |
| V-233 | O | CH$_2$CH$_2$NMe$_2$ | — |
| V-234 | O | CH$_2$CH$_2$NEt$_2$ | — |
| V-235 | O | CH$_2$CH$_2$CHO | — |
| V-236 | O | CH$_2$-(2,2-difluorocyclopropyl) | — |
| V-237 | O | CH$_2$-(2,2-dichlorocyclopropyl) | — |

TABLE 57-continued

| Compound No. | X¹ | R¹ | R² |
|---|---|---|---|
| V-238 | O | CH$_2$OCH$_2$—c-Pr | — |
| V-239 | O | CH$_2$SPh | — |
| V-240 | O | CH$_2$CH$_2$O-(2-pyridyl) | — |
| V-241 | O | CH$_2$SCH$_2$CF$_3$ | — |
| V-242 | O | CH$_2$SOCH$_2$CF$_3$ | — |
| V-243 | O | CH$_2$SO$_2$CH$_2$CF$_3$ | — |
| V-244 | O | CH$_2$OCH$_2$Ph | — |
| V-245 | O | CH$_2$SOPh | — |
| V-246 | O | CH$_2$SO$_2$Ph | — |
| V-247 | O | CH$_2$OCH$_2$CH$_2$SMe | — |
| V-248 | O | CH$_2$OCH$_2$CH$_2$SOMe | — |
| V-249 | O | CH$_2$CH$_2$CH(OEt)$_2$ | — |
| V-250 | O | CH$_2$C(Me)=NOMe | — |
| V-251 | O | CH$_2$CH$_2$ON=CMe$_2$ | — |
| V-252 | O | Me | 7-CH=CMe$_2$ |
| V-253 | O | Me | 7-C≡CMe |
| V-254 | O | Me | 7-CH$_2$—c-Pr |
| V-255 | O | Me | 7-C(Me)=CF$_3$ |
| V-256 | O | Me | 7-(2,2-difluorocyclopropyl) |
| V-257 | O | Me | 7-O—c-Pr |

TABLE 58

| Compound No. | X¹ | R¹ | R² |
|---|---|---|---|
| V-258 | O | Me | 7-CH$_2$-(2,2-difluorocyclopropyl) |
| V-259 | O | Me | 7-OCH$_2$—c-Pr |
| V-260 | O | Me | 7-OCH$_2$OMe |
| V-261 | O | Me | 7-OC(=O)Me |
| V-262 | O | Me | 7-SOMe |
| V-263 | O | Me | 7-SCF$_3$ |
| V-264 | O | Me | 7-SOCH$_2$CF$_3$ |
| V-265 | O | Me | 7-SO$_2$CH$_2$CF$_3$ |
| V-266 | O | Me | 7-NMe$_2$ |
| V-267 | O | Me | 7-NHC(=O)Me |
| V-268 | O | Me | 7-CH$_2$OH |
| V-269 | O | Me | 7-CH(OEt)$_2$ |
| V-270 | O | Me | 7-CH$_2$SMe |
| V-271 | O | Me | 7-CH$_2$SOMe |
| V-272 | O | Me | 7-CH$_2$SO$_2$Me |
| V-273 | O | Me | 7-CH$_2$SCHF$_2$ |
| V-274 | O | Me | 7-CH$_2$SOCHF$_2$ |
| V-275 | O | Me | 7-CH$_2$SO$_2$CHF$_2$ |
| V-276 | O | Me | 7-CH$_2$CN |
| V-277 | O | Me | 7-C(Me)=NOMe |
| V-278 | O | Me | 7-C(=O)NH$_2$ |
| V-279 | O | Me | 7-(1-pyrazolyl) |
| V-280 | O | CH$_2$OCH$_2$Ph(2-F) | — |
| V-281 | O | CH$_2$OCH$_2$Ph(2-Cl) | — |
| V-282 | O | CH$_2$OCH$_2$Ph(2-NO$_2$) | — |
| V-283 | O | CH$_2$OCH$_2$Ph(2-CN) | — |
| V-284 | O | CH$_2$OCH$_2$Ph(2-Me) | — |
| V-285 | O | CH$_2$OCH$_2$Ph(2-CF$_3$) | — |
| V-286 | O | CH$_2$OCH$_2$Ph(2-OMe) | — |

TABLE 58-continued

| Compound No. | X¹ | R¹ | R² |
|---|---|---|---|
| V-287 | O | CH₂OCH₂Ph(2-OCF₃) | — |
| V-288 | O | CH₂OCH₂Ph(2-SMe) | — |
| V-289 | O | CH₂OCH₂Ph(2-SO₂Me) | — |
| V-290 | O | CH₂OCH₂Ph(2-SCF₃) | — |
| V-291 | O | CH₂OCH₂Ph(2-CO₂Me) | — |
| V-292 | O | CH₂OCH₂Ph(2-COMe) | — |
| V-293 | O | (2-NO₂)Bn | — |
| V-294 | O | (2-CN)Bn | — |
| V-295 | O | (3-SMe)Bn | — |

TABLE 59

| Compound No. | X¹ | R¹ | R² |
|---|---|---|---|
| V-296 | O | (3-SO₂Me)Bn | — |
| V-297 | O | (3-SCF₃)Bn | — |
| V-298 | O | (3-CO₂Me)Bn | — |
| V-299 | O | (3-COMe)Bn | — |
| V-300 | O | (3-OMe)Bn | — |
| V-301 | O | 5-NO₂-pyridin-2-yl-methyl | — |
| V-302 | O | 5-CN-pyridin-2-yl-methyl | — |
| V-303 | O | 5-cyclopropyl-pyridin-2-yl-methyl | — |
| V-304 | O | 6-SMe-pyridin-3-yl-methyl | — |
| V-305 | O | Et | 5-Cl |
| V-306 | O | n-Bu | 5-Cl |
| V-307 | O | 5-Me-pyridin-2-yl-methyl | 7-Me |
| V-308 | O | 6-Me-pyridin-2-yl-methyl | 6-CF₃ |
| V-309 | O | 5-Me-pyrazin-2-yl-methyl | — |
| V-310 | O | 6-OMe-pyridin-3-yl-methyl | 5-Cl |
| V-311 | O | 6-Me-pyridin-2-yl-methyl | 6-F |
| V-312 | O | 2-Me-5-Me-thiazol-? | — |
| V-313 | O | NHC(=O)O—t-Bu | — |
| V-314 | O | N(Me)C(=O)O—t-Bu | — |
| V-315 | O | 5-Me-pyridin-2-yl-methyl | 5-F |
| V-316 | O | 5-Me-pyridin-2-yl-methyl | 5-Cl |
| V-317 | O | 5-Me-pyridin-2-yl-methyl | 5-Me |
| V-318 | O | 6-OMe-pyridin-3-yl-methyl | 5-Me |
| V-319 | O | 1-Me-3-Me-6-CF₃-2-oxo-pyridin-? | — |

TABLE 60

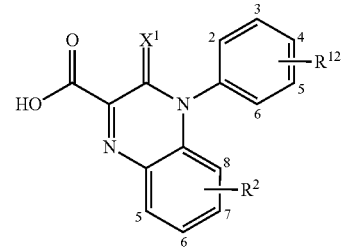

| Compound No. | X¹ | R¹² | R² |
|---|---|---|---|
| VI-1 | O | — | — |
| VI-2 | O | 2-F | — |
| VI-3 | O | 3-F | — |
| VI-4 | O | 4-F | — |
| VI-5 | O | 2-Cl | — |
| VI-6 | O | 3-Cl | — |
| VI-7 | O | 4-Cl | — |
| VI-8 | O | 2-Br | — |
| VI-9 | O | 3-Br | — |
| VI-10 | O | 4-Br | — |
| VI-11 | O | 2-Me | — |
| VI-12 | O | 3-Me | — |
| VI-13 | O | 4-Me | — |
| VI-14 | O | 2-Et | — |
| VI-15 | O | 3-Et | — |
| VI-16 | O | 4-Et | — |
| VI-17 | O | 2-n-Pr | — |
| VI-18 | O | 3-n-Pr | — |
| VI-19 | O | 4-n-Pr | — |
| VI-20 | O | 2-i-Pr | — |
| VI-21 | O | 3-i-Pr | — |
| VI-22 | O | 4-i-Pr | — |

TABLE 60-continued

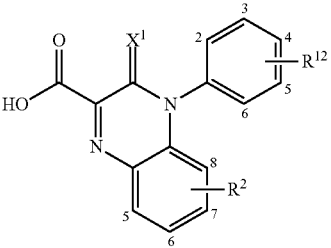

| Compound No. | X¹ | R¹² | R² |
|---|---|---|---|
| VI-23 | O | 2-c-Pr | — |
| VI-24 | O | 3-c-Pr | — |
| VI-25 | O | 4-c-Pr | — |
| VI-26 | O | 2-CF₃ | — |
| VI-27 | O | 3-CF₃ | — |
| VI-28 | O | 4-CF₃ | — |
| VI-29 | O | 2-OH | — |
| VI-30 | O | 3-OH | — |
| VI-31 | O | 4-OH | — |
| VI-32 | O | 2-OMe | — |
| VI-33 | O | 3-OMe | — |
| VI-34 | O | 4-OMe | — |
| VI-35 | O | 2-OEt | — |
| VI-36 | O | 3-OEt | — |

TABLE 61

| Compound No. | X¹ | R¹² | R² |
|---|---|---|---|
| VI-37 | O | 4-OEt | — |
| VI-38 | O | 2-O—n-Pr | — |
| VI-39 | O | 3-O—n-Pr | — |
| VI-40 | O | 4-O—n-Pr | — |
| VI-41 | O | 2-O—i-Pr | — |
| VI-42 | O | 3-O—i-Pr | — |
| VI-43 | O | 4-O—i-Pr | — |
| VI-44 | O | 2-O—c-Pr | — |
| VI-45 | O | 3-O—c-Pr | — |
| VI-46 | O | 4-O—c-Pr | — |
| VI-47 | O | 2-OCH₂CH=CH₂ | — |
| VI-48 | O | 3-OCH₂CH=CH₂ | — |
| VI-49 | O | 4-OCH₂CH=CH₂ | — |
| VI-50 | O | 2-OCH₂C≡CH | — |
| VI-51 | O | 3-OCH₂C≡CH | — |
| VI-52 | O | 4-OCH₂C≡CH | — |
| VI-53 | O | 2-OCHF₂ | — |
| VI-54 | O | 3-OCHF₂ | — |
| VI-55 | O | 4-OCHF₂ | — |
| VI-56 | O | 2-OCF₃ | — |
| VI-57 | O | 3-OCF₃ | — |
| VI-58 | O | 4-OCF₃ | — |
| VI-59 | O | 2-OCH₂CH₂OMe | — |
| VI-60 | O | 3-OCH₂CH₂OMe | — |
| VI-61 | O | 4-OCH₂CH₂OMe | — |
| VI-62 | O | 2-OCH₂-(tetrahydrofuran-2-yl) | — |
| VI-63 | O | 3-OCH₂-(tetrahydrofuran-2-yl) | — |
| VI-64 | O | 4-OCH₂-(tetrahydrofuran-2-yl) | — |
| VI-65 | O | 2-OC(=O)Me | — |
| VI-66 | O | 3-OC(=O)Me | — |
| VI-67 | O | 3-OC(=O)Me | — |

TABLE 61-continued

| Compound No. | X¹ | R¹² | R² |
|---|---|---|---|
| VI-68 | O | 2-SMe | — |
| VI-69 | O | 3-SMe | — |
| VI-70 | O | 4-SMe | — |

TABLE 62

| Compound No. | X¹ | R¹² | R² |
|---|---|---|---|
| VI-71 | O | 2-SO₂Me | — |
| VI-72 | O | 3-SO₂Me | — |
| VI-73 | O | 4-SO₂Me | — |
| VI-74 | O | 2-SCF₃ | — |
| VI-75 | O | 3-SCF₃ | — |
| VI-76 | O | 4-SCF₃ | — |
| VI-77 | O | 2-NO₂ | — |
| VI-78 | O | 3-NO₂ | — |
| VI-79 | O | 4-NO₂ | — |
| VI-80 | O | 2-NH₂ | — |
| VI-81 | O | 3-NH₂ | — |
| VI-82 | O | 4-NH₂ | — |
| VI-83 | O | 2-CN | — |
| VI-84 | O | 3-CN | — |
| VI-85 | O | 4-CN | — |
| VI-86 | O | 2-C(=O)Me | — |
| VI-87 | O | 3-C(=O)Me | — |
| VI-88 | O | 4-C(=O)Me | — |
| VI-89 | O | 2-C(=O)OH | — |
| VI-90 | O | 3-C(=O)OH | — |
| VI-91 | O | 4-C(=O)OH | — |
| VI-92 | O | 2-C(=O)OMe | — |
| VI-93 | O | 3-C(=O)OMe | — |
| VI-94 | O | 4-C(=O)OMe | — |
| VI-95 | O | 2-CH₂OMe | — |
| VI-96 | O | 3-CH₂OMe | — |
| VI-97 | O | 4-CH₂OMe | — |
| VI-98 | O | 2,3-F₂ | — |
| VI-99 | O | 2,4-F₂ | — |
| VI-100 | O | 2,5-F₂ | — |
| VI-101 | O | 2,6-F₂ | — |
| VI-102 | O | 3,4-F₂ | — |
| VI-103 | O | 3,5-F₂ | — |
| VI-104 | O | 2,3-Cl₂ | — |
| VI-105 | O | 2,4-Cl₂ | — |
| VI-106 | O | 2,5-Cl₂ | — |
| VI-107 | O | 2,6-Cl₂ | — |
| VI-108 | O | 3,4-Cl₂ | — |
| VI-109 | O | 3,5-Cl₂ | — |

TABLE 63

| Compound No. | X¹ | R¹² | R² |
|---|---|---|---|
| VI-110 | O | 2-F, 3-OMe | — |
| VI-111 | O | 2-Cl, 3-OMe | — |
| VI-112 | O | 2-Me, 3-OMe | — |
| VI-113 | O | 2,3-(OMe)₂ | — |
| VI-114 | O | 3-OMe, 4-F | — |
| VI-115 | O | 3-OMe, 4-Cl | — |
| VI-116 | O | 3-OMe, 4-Me | — |
| VI-117 | O | 3,4-(OMe)₂ | — |
| VI-118 | O | 3-OMe, 5-F | — |
| VI-119 | O | 3-OMe, 5-Cl | — |
| VI-120 | O | 3-OMe, 5-Me | — |
| VI-121 | O | 3,5-(OMe)₂ | — |
| VI-122 | O | 2-F, 4-OMe | — |
| VI-123 | O | 2-Cl, 4-OMe | — |
| VI-124 | O | 2-Me, 4-OMe | — |
| VI-125 | O | 2,4-(OMe)₂ | — |
| VI-126 | O | 3-F, 4-OMe | — |
| VI-127 | O | 3-Cl, 4-OMe | — |
| VI-128 | O | 3-Me, 4-OMe | — |
| VI-129 | O | 2-F, 5-OMe | — |
| VI-130 | O | 2-Cl, 5-OMe | — |
| VI-131 | O | 2-Me, 5-OMe | — |
| VI-132 | O | 2,5-(OMe)₂ | — |

TABLE 63-continued

| Compound No. | X¹ | R¹² | R² |
|---|---|---|---|
| VI-133 | O | 3,4,5-(OMe)$_3$ | — |
| VI-134 | O | 4-OMe | 5-F |
| VI-135 | O | 4-OMe | 6-F |
| VI-136 | O | 4-OMe | 7-F |
| VI-137 | O | 4-OMe | 8-F |
| VI-138 | O | — | 5-Cl |
| VI-139 | O | — | 6-Cl |
| VI-140 | O | — | 7-Cl |
| VI-141 | O | — | 8-Cl |
| VI-142 | O | 4-OMe | 5-Cl |
| VI-143 | O | 4-OMe | 6-Cl |
| VI-144 | O | 4-OMe | 7-Cl |
| VI-145 | O | 4-OMe | 8-Cl |
| VI-146 | S | — | — |
| VI-147 | O | 4-OCH$_2$CN | — |
| VI-148 | O | 3-OCH$_2$—c-Pr | — |

TABLE 64

| Compound No. | X¹ | R¹² | R² |
|---|---|---|---|
| VI-149 | O | 3-OCH$_2$CF$_3$ | — |
| VI-150 | O | 4-OCH$_2$—c-Pr | — |
| VI-151 | O | 4-OCH$_2$CF$_3$ | — |
| VI-152 | O | 4-NMe$_2$ | — |
| VI-153 | O | 3,4-Me$_2$ | — |
| VI-154 | O | 2-F, 4-Me | — |
| VI-155 | O | 3-F, 4-Me | — |
| VI-156 | O | 3-Me, 4-F | — |
| VI-157 | O | 2-Cl, 4-Me | — |
| VI-158 | O | 3-Cl, 4-Me | — |
| VI-159 | O | 3-OEt, 4-OMe | — |
| VI-160 | O | 2,3,4-(OMe)$_3$ | — |
| VI-161 | O | 2,5-F$_2$, 4-OMe | — |
| VI-162 | O | 3,5-F$_2$, 4-OMe | — |
| VI-163 | O | 3,5-Cl$_2$, 4-OMe | — |
| VI-164 | O | 3,4-(CH$_2$CH$_2$CH$_2$)— | — |
| VI-165 | O | 3,4-(CH$_2$CH$_2$CH$_2$CH$_2$)— | — |
| VI-166 | O | 3,4-(CH$_2$OCH$_2$)— | — |
| VI-167 | O | 3,4-(OCH$_2$O)— | 7-F |
| VI-168 | O | 2,3-(OCH$_2$CH$_2$O)— | — |
| VI-169 | O | 3,4-(OCH$_2$CH(Me)O)— | — |
| VI-170 | O | 3,4-(OCH$_2$CH$_2$CH$_2$O)— | — |
| VI-171 | O | — | 5-F |
| VI-172 | O | 3,4,5-(OMe)$_3$ | 5-F |
| VI-173 | O | 3,5-F$_2$, 4-OMe | 5-F |
| VI-174 | O | 3,4-(OCH$_2$CH$_2$O)— | 5-F |
| VI-175 | O | — | 6-F |
| VI-176 | O | 3,4,5-(OMe)$_3$ | 6-F |
| VI-177 | O | 3,4-(OCH$_2$O)— | 6-F |
| VI-178 | O | 3,4-(OCH$_2$CH$_2$O)— | 6-F |
| VI-179 | O | — | 7-F |
| VI-180 | O | 3,4-(OCH$_2$CH$_2$O)— | 7-F |
| VI-181 | O | — | 8-F |
| VI-182 | O | — | 5-Me |
| VI-183 | O | 4-OMe | 5-Me |
| VI-184 | O | 4-OMe | 6-Me |
| VI-185 | O | 4-OMe | 7-Me |
| VI-186 | O | 3,5-F$_2$, 4-OMe | 7-Me |

TABLE 65

| Compound No. | X¹ | R¹² | R² |
|---|---|---|---|
| VI-187 | O | — | 6-CF$_3$ |
| VI-188 | O | — | 6-OMe |
| VI-189 | O | 4-OMe | 6-OMe |
| VI-190 | O | — | 7-OMe |
| VI-191 | O | 4-OMe | 7-OMe |
| VI-192 | O | 2,5-F$_2$, 4-OMe | 7-OMe |
| VI-193 | O | 3,5-F$_2$, 4-OMe | 7-OMe |
| VI-194 | O | — | 8-OMe |
| VI-195 | O | 4-OMe | 8-OMe |

TABLE 65-continued

| Compound No. | X¹ | R¹² | R² |
|---|---|---|---|
| VI-196 | O | 4-OMe | 5,6-F$_2$ |
| VI-197 | O | 4-OMe | 5,7-F$_2$ |
| VI-198 | O | — | 6,7-F$_2$ |
| VI-199 | O | — | 6,8-F$_2$ |
| VI-200 | O | 4-OMe | 5,7-Cl$_2$ |
| VI-201 | O | 4-OMe | 6-F, 7-OMe |
| VI-202 | O | — | 7-c-Pr |
| VI-203 | O | — | 7-OCH$_2$CH=CH$_2$ |
| VI-204 | O | — | 7-OCH$_2$C≡CH |
| VI-205 | O | — | 7-NHMe |
| VI-206 | O | — | 7-C(=O)H |
| VI-207 | O | — | 6-C(=O)Me |
| VI-208 | O | — | 7-C(=O)OH |
| VI-209 | O | — | 7-C(=O)OMe |
| VI-210 | O | — | 7-C(=O)OEt |
| VI-211 | O | — | 7-C(=O)NHNe |
| VI-212 | O | — | 7-C(=O)NMe$_2$ |
| VI-213 | O | — | 6,7-(OCH$_2$CH$_2$O)— |
| VI-214 | O | — | 6,7-(OCH$_2$O)— |
| VI-215 | O | 4-OMe | 6,7-(OCH$_2$CH$_2$O)— |
| VI-216 | O | 4-OMe | 6,7-(OCH$_2$O)— |
| VI-217 | O | 2-CONHMe | — |
| VI-218 | O | 2-CONMe$_2$ | — |
| VI-219 | O | 2-NHCOMe | — |
| VI-220 | O | 4-CH$_2$—c-Pr | — |
| VI-221 | O | 4-CH=CH$_2$ | — |
| VI-222 | O | 4-C≡CMe | — |
| VI-223 | O | 3-CH=CF$_2$ | — |

TABLE 66

| Compound No. | X¹ | R¹² | R² |
|---|---|---|---|
| VI-224 | O | 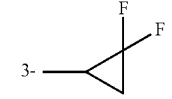 3- | — |
| VI-225 | O |  4-CH$_2$- | — |
| VI-226 | O | 4-CH$_2$OH | — |
| VI-227 | O | 4-CH$_2$SMe | — |
| VI-228 | O | 4-CH$_2$SOMe | — |
| VI-229 | O | 4-CH$_2$SO$_2$Me | — |
| VI-230 | O | 4-CH$_2$SCHF$_2$ | — |
| VI-231 | O | 4-CH$_2$SOCHF$_2$ | — |
| VI-232 | O | 4-CH$_2$SO$_2$CHF$_2$ | — |
| VI-233 | O | 4-CH$_2$CN | — |
| VI-234 | O | 4-NHMe | — |
| VI-235 | O | 4-OCH$_2$OCH$_2$CF$_3$ | — |
| VI-236 | O | 4-C(Me)=NOMe | — |
| VI-237 | O | 2-CONH$_2$ | — |
| VI-238 | O | 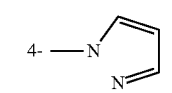 4- | — |
| VI-239 | O | 3-F, 4-OMe | 5-Cl |
| VI-240 | O | 4-OMe | 5,6,8-F$_3$, 7-OMe |
| VI-241 | O | — | 7-CF$_3$ |
| VI-242 | O | 4-F | 7-OMe |
| VI-243 | O | 4-OCHF$_2$ | 7-OMe |
| VI-244 | O | 4-Me | 7-OMe |
| VI-245 | O | 3,4-(OCH$_2$CH$_2$O)— | 6,8-F$_2$ |
| VI-246 | O | 3,4-(OCH$_2$CH$_2$O)— | 8-F |
| VI-247 | O | 4-OMe | 5-Br |
| VI-248 | O | 4-F | 5-F |
| VI-249 | O | 3-F, 4-OEt | — |

TABLE 67

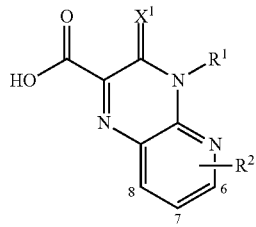

| Compound No. | X$^1$ | R$^1$ | R$^2$ |
|---|---|---|---|
| VII-1 | O | H | — |
| VII-2 | O | Me | — |
| VII-3 | O | Et | — |
| VII-4 | O | n-Pr | — |
| VII-5 | O | i-Pr | — |
| VII-6 | O | c-Pr | — |
| VII-7 | O | n-Bu | — |
| VII-8 | O | s-Bu | — |
| VII-9 | O | i-Bu | — |
| VII-10 | O | t-Bu | — |
| VII-11 | O | c-Bu | — |
| VII-12 | O | n-Pen | — |
| VII-13 | O | c-Pen | — |
| VII-14 | O | n-Hex | — |
| VII-15 | O | c-Hex | — |
| VII-16 | O | n-C$_7$H$_{15}$ | — |
| VII-17 | O | n-C$_8$H$_{17}$ | — |
| VII-18 | O | n-C$_9$H$_{19}$ | — |
| VII-19 | O | n-C$_{10}$H$_{21}$ | — |
| VII-20 | O | n-C$_{11}$H$_{23}$ | — |
| VII-21 | O | n-C$_{12}$H$_{25}$ | — |
| VII-22 | O | CH$_2$CH=CH$_2$ | — |
| VII-23 | O | CH$_2$C≡CH | — |
| VII-24 | O | CH$_2$CF$_3$ | — |
| VII-25 | O | CH$_2$CH$_2$F | — |
| VII-26 | O | CH$_2$CH$_2$Cl | — |
| VII-27 | O | CH$_2$CH$_2$CF$_3$ | — |
| VII-28 | O | CH$_2$CH=CCl$_2$ | — |
| VII-29 | O | CH$_2$OMe | — |
| VII-30 | O | CH$_2$OEt | — |
| VII-31 | O | CH(Me)OMe | — |
| VII-32 | O | CH(Me)OEt | — |
| VII-33 | O | CH$_2$OPh | — |

TABLE 68

| Compound No. | X$^1$ | R$^1$ | R$^2$ |
|---|---|---|---|
| VII-34 | O | CH$_2$OCH$_2$CH$_2$OMe | — |
| VII-35 | O | CH$_2$OCH$_2$CF$_3$ | — |
| VII-36 | O | CH(Me)OCH$_2$CF$_3$ | — |
| VII-37 | O | CH$_2$OCH$_2$-(tetrahydrofuran-2-yl) | — |
| VII-38 | O | CH(Me)OCH$_2$-(tetrahydrofuran-2-yl) | — |
| VII-39 | O | CH$_2$OCH$_2$CH$_2$SO$_2$Me | — |
| VII-40 | O | CH$_2$OCH$_2$CH$_2$CN | — |
| VII-41 | O | CH$_2$OC(=O)t-Bu | — |
| VII-42 | O | CH$_2$SMe | — |
| VII-43 | O | CH$_2$SMe | — |
| VII-44 | O | CH$_2$SEt | — |
| VII-45 | O | CH$_2$S—n-Pr | — |
| VII-46 | O | CH(Me)SMe | — |
| VII-47 | O | CH(Me)SEt | — |
| VII-48 | O | CH(Me)S—n-Pr | — |
| VII-49 | O | CH$_2$SOMe | — |
| VII-50 | O | CH$_2$SOEt | — |

TABLE 68-continued

| Compound No. | X$^1$ | R$^1$ | R$^2$ |
|---|---|---|---|
| VII-51 | O | CH$_2$SO—n-Pr | — |
| VII-52 | O | CH$_2$SO$_2$Me | — |
| VII-53 | O | CH$_2$SO$_2$Et | — |
| VII-54 | O | CH$_2$SO$_2$—n-Pr | — |
| VII-55 | O | CH(Me)SO$_2$Me | — |
| VII-56 | O | CH(Me)SO$_2$Et | — |
| VII-57 | O | CH(Me)SO$_2$—n-Pr | — |
| VII-58 | O | CH$_2$CH$_2$OH | — |
| VII-59 | O | CH$_2$CH$_2$OMe | — |
| VII-60 | O | CH$_2$CH$_2$OEt | — |
| VII-61 | O | CH(Me)CH$_2$OMe | — |
| VII-62 | O | CH$_2$CH$_2$SMe | — |
| VII-63 | O | CH$_2$CH$_2$SO$_2$Me | — |
| VII-64 | O | CH$_2$CH$_2$CH$_2$OMe | — |
| VII-65 | O | CH$_2$C(=O)Me | — |
| VII-66 | O | CH$_2$C(=O)OMe | — |

TABLE 69

| Compound No. | X$^1$ | R$^1$ | R$^2$ |
|---|---|---|---|
| VII-67 | O | CH$_2$C(=O)OEt | — |
| VII-68 | O | CH$_2$C(=O)On-Pr | — |
| VII-69 | O | CH$_2$C(=O)Oi-Pr | — |
| VII-70 | O | CH$_2$C(=O)Ot-Bu | — |
| VII-71 | O | CH$_2$C(=O)NMe$_2$ | — |
| VII-72 | O | CH$_2$C(=O)-morpholino | — |
| VII-73 | O | CH$_2$CN | — |
| VII-74 | O | CH$_2$CH$_2$CN | — |
| VII-75 | O | CH(Me)CH$_2$CN | — |
| VII-76 | O | CH$_2$CH$_2$CH$_2$CN | — |
| VII-77 | O | CH$_2$CH$_2$NO$_2$ | — |
| VII-78 | O | Bn | — |
| VII-79 | O | (2-F)Bn | — |
| VII-80 | O | (3-F)Bn | — |
| VII-81 | O | (4-F)Bn | — |
| VII-82 | O | (2-Cl)Bn | — |
| VII-83 | O | (3-Cl)Bn | — |
| VII-84 | O | (4-Cl)Bn | — |
| VII-85 | O | (2-Me)Bn | — |
| VII-86 | O | (3-Me)Bn | — |
| VII-87 | O | (4-Me)Bn | — |
| VII-88 | O | (2-CF$_3$)Bn | — |
| VII-89 | O | (3-CF$_3$)Bn | — |
| VII-90 | O | (4-CF$_3$)Bn | — |
| VII-91 | O | (2-OMe)Bn | — |
| VII-92 | O | (3-OMe)Bn | — |
| VII-93 | O | (4-OMe)Bn | — |
| VII-94 | O | (2,4-(OMe)$_2$)Bn | — |
| VII-95 | O | (2,6-(OMe)$_2$)Bn | — |
| VII-96 | O | (3,5-(OMe)$_2$)Bn | — |
| VII-97 | O | CH(Me)Ph | — |
| VII-98 | O | 3-methylisoxazol-5-yl | — |
| VII-99 | O | tetrahydrothiophen-3-yl | — |
| VII-100 | O | tetrahydrothiophen-3-yl 1,1-dioxide | — |

TABLE 70
| Compound No. | X¹ | R¹ | R² |
|---|---|---|---|
| VII-101 | O | 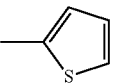 | — |
| VII-102 | O | 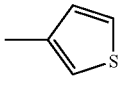 | — |
| VII-103 | O | 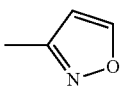 | — |
| VII-104 | O | 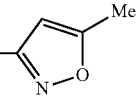 | — |
| VII-105 | O | 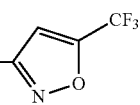 | — |
| VII-106 | O | 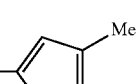 | — |
| VII-107 | O | 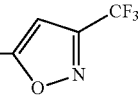 | — |
| VII-108 | O | 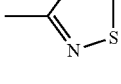 | — |
| VII-109 | O | 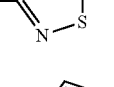 | — |
| VII-110 | O | 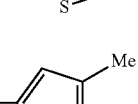 | — |
| VII-111 | O | 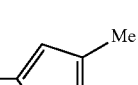 | — |
| VII-112 | O | 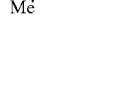 | — |
TABLE 70-continued
| Compound No. | X¹ | R¹ | R² |
|---|---|---|---|
| VII-113 | O | 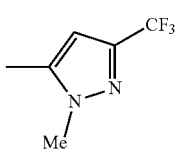 | — |
| VII-114 | O | 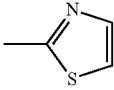 | — |
TABLE 71
| Compound No. | X¹ | R¹ | R² |
|---|---|---|---|
| VII-115 | O | 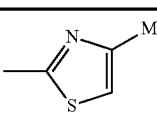 | — |
| VII-116 | O | 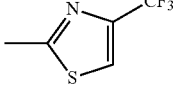 | — |
| VII-117 | O | 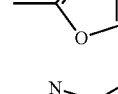 | — |
| VII-118 | O | 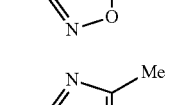 | — |
| VII-119 | O | 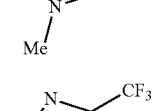 | — |
| VII-120 | O | 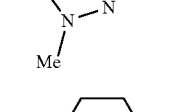 | — |
| VII-121 | O | 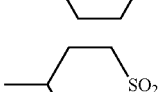 | — |
| VII-122 | O | 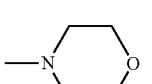 | — |
| VII-123 | O | 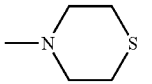 | — |
| VII-124 | O |  | — |

TABLE 71-continued

| Compound No. | X¹ | R¹ | R² |
|---|---|---|---|
| VII-125 | O | —N(CH₂CH₂)₂SO₂ (thiomorpholine-1,1-dioxide) | — |
| VII-126 | O | 2-pyridyl (Me substituent) | — |
| VII-127 | O | 6-chloro-2-methylpyridin-yl | — |
| VII-128 | O | 2,6-dimethylpyridin-yl | — |

TABLE 72

| Compound No. | X¹ | R¹ | R² |
|---|---|---|---|
| VII-129 | O | 6-(CF₃)-2-methylpyridyl | — |
| VII-130 | O | 6-OMe-2-methylpyridyl | — |
| VII-131 | O | 5-F-2-methylpyridyl | — |
| VII-132 | O | 5-Cl-2-methylpyridyl | — |
| VII-133 | O | 5-Me-2-methylpyridyl | — |
| VII-134 | O | 5-CF₃-2-methylpyridyl | — |
| VII-135 | O | 5-OMe-2-methylpyridyl | — |
| VII-136 | O | 4-Cl-2-methylpyridyl | — |

TABLE 72-continued

| Compound No. | X¹ | R¹ | R² |
|---|---|---|---|
| VII-137 | O | 4-Me-2-methylpyridyl | — |
| VII-138 | O | 4-CF₃-2-methylpyridyl | — |
| VII-139 | O | 4-OMe-2-methylpyridyl | — |
| VII-140 | O | 3-pyridyl | — |
| VII-141 | O | 6-Cl-3-methylpyridyl | — |

TABLE 73

| Compound No. | X¹ | R¹ | R² |
|---|---|---|---|
| VII-142 | O | 6-Me-3-methylpyridyl | — |
| VII-143 | O | 6-CF₃-3-methylpyridyl | — |
| VII-144 | O | 6-OMe-3-methylpyridyl | — |
| VII-145 | O | 4-pyridyl | — |
| VII-146 | O | 2-methylpyrimidinyl | — |
| VII-147 | O | 4-CF₃-2-methylpyrimidinyl | — |

TABLE 73-continued

| Compound No. | X¹ | R¹ | R² |
|---|---|---|---|
| VII-148 | O | 2-methyl-4,6-dimethoxypyrimidin-5-yl | — |
| VII-149 | O | 2-methyl-4,6-dimethoxy-1,3,5-triazin-... | — |
| VII-150 | O | methylpyrazinyl | — |
| VII-151 | O | 2-methyl-4,6-diamino-1,3,5-triazinyl | — |
| VII-152 | O | methyl-2,3-dihydrobenzofuranyl | — |
| VII-153 | O | methyl-1,3-benzodioxolyl | — |
| VII-154 | O | methyl-2,2-difluoro-1,3-benzodioxolyl | — |

TABLE 74

| Compound No. | X¹ | R¹ | R² |
|---|---|---|---|
| VII-155 | O | methyl-2,2-dimethyl-1,3-benzodioxolyl | — |
| VII-156 | O | methyl-2,3-dihydro-1,4-benzodioxinyl | — |
| VII-157 | O | methyl-2,2,3,3-tetrafluoro-2,3-dihydro-1,4-benzodioxinyl | — |
| VII-158 | O | CH₂-(tetrahydrofuran-2-yl) | — |
| VII-159 | O | CH₂-(3-methyl-4,5-dihydroisoxazol-5-yl) | — |
| VII-160 | O | CH₂-(3-methylisoxazol-5-yl) | — |
| VII-161 | O | NH₂ | — |
| VII-162 | O | NHMe | — |
| VII-163 | O | NMe₂ | — |
| VII-164 | O | OMe | — |
| VII-165 | O | OEt | — |
| VII-166 | O | Me | 6-F |
| VII-167 | O | Me | 6-Cl |
| VII-168 | O | Me | 6-OMe |
| VII-169 | S | Me | — |
| VII-170 | O | CH₂CH₂CH=CH₂ | — |
| VII-171 | O | CH₂CH₂CH=C(Me)₂ | — |
| VII-172 | O | CH₂CH₂C≡CH | — |
| VII-173 | O | CH₂CH₂C(Me)=CF₂ | — |
| VII-174 | O | CH(Me)C(=O)Ot-Bu | — |
| VII-175 | O | (2-OCHF₂)Bn | — |
| VII-176 | O | CH₂CH₂Ph | — |
| VII-177 | O | CH₂-(thiophen-2-yl) | — |
| VII-178 | O | CH₂-N=CH-CH=C(CF₃) (pyrazole-type) | — |

TABLE 75

| Compound No. | X¹ | R¹ | R² |
|---|---|---|---|
| VII-179 | O | CH₂-(3-trifluoromethyl-1-methyl-1H-pyrazol-4-yl) | — |
| VII-180 | O | CH₂-(5-methylisoxazol-3-yl) | — |
| VII-181 | O | CH₂-(6-chloropyridin-3-yl) | — |

TABLE 75-continued

| Compound No. | X¹ | R¹ | R² |
|---|---|---|---|
| VII-182 | O | CH₂-(2,3-benzodioxine) | — |
| VII-183 | O | CH₂CH₂-(3-Me-isoxazolin-5-yl) | — |
| VII-184 | O | CH₂CH₂-(3-Me-isoxazol-5-yl) | — |
| VII-185 | O | Bn | 8-Me |
| VII-186 | O | Bn | 7-Me |
| VII-187 | O | Bn | 6-Me |
| VII-188 | O | Bn | 6-OMe |

TABLE 76

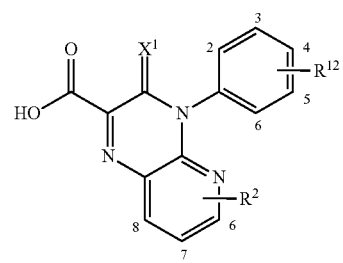

| Compound No. | X¹ | R¹² | R² |
|---|---|---|---|
| VIII-1 | O | — | — |
| VIII-2 | O | 2-F | — |
| VIII-3 | O | 3-F | — |
| VIII-4 | O | 4-F | — |
| VIII-6 | O | 2-Cl | — |
| VIII-6 | O | 3-Cl | — |
| VIII-7 | O | 4-Cl | — |
| VIII-8 | O | 2-Br | — |
| VIII-9 | O | 3-Br | — |
| VIII-10 | O | 4-Br | — |
| VIII-11 | O | 2-Me | — |
| VIII-12 | O | 3-Me | — |
| VIII-13 | O | 4-Me | — |
| VIII-14 | O | 2-Et | — |
| VIII-15 | O | 3-Et | — |
| VIII-16 | O | 4-Et | — |
| VIII-17 | O | 2-n-Pr | — |
| VIII-18 | O | 3-n-Pr | — |
| VIII-19 | O | 4-n-Pr | — |
| VIII-20 | O | 2-i-Pr | — |
| VIII-21 | O | 3-i-Pr | — |
| VIII-22 | O | 4-i-Pr | — |
| VIII-23 | O | 2-c-Pr | — |
| VIII-24 | O | 3-c-Pr | — |
| VIII-25 | O | 4-c-Pr | — |
| VIII-26 | O | 2-CF₃ | — |
| VIII-27 | O | 3-CF₃ | — |
| VIII-28 | O | 4-CF₃ | — |
| VIII-29 | O | 2-OH | — |
| VIII-30 | O | 3-OH | — |
| VIII-31 | O | 4-OH | — |

TABLE 77

| Compound No. | X¹ | R¹² | R² |
|---|---|---|---|
| VIII-32 | O | 2-OMe | — |
| VIII-33 | O | 3-OMe | — |
| VIII-34 | O | 4-OMe | — |
| VIII-35 | O | 2-OEt | — |
| VIII-36 | O | 3-OEt | — |
| VIII-37 | O | 4-OEt | — |
| VIII-38 | O | 2-O-n-Pr | — |
| VIII-39 | O | 3-O-n-Pr | — |
| VIII-40 | O | 4-O-n-Pr | — |
| VIII-41 | O | 2-O-i-Pr | — |
| VIII-42 | O | 3-O-i-Pr | — |
| VIII-43 | O | 4-O-i-Pr | — |
| VIII-44 | O | 2-O-c-Pr | — |
| VIII-45 | O | 3-O-c-Pr | — |
| VIII-46 | O | 4-O-c-Pr | — |
| VIII-47 | O | 2-OCH₂CH=CH₂ | — |
| VIII-48 | O | 3-OCH₂CH=CH₂ | — |
| VIII-49 | O | 4-OCH₂CH=CH₂ | — |
| VIII-50 | O | 2-OCH₂C≡CH | — |
| VIII-51 | O | 3-OCH₂C≡CH | — |
| VIII-52 | O | 4-OCH₂C≡CH | — |
| VIII-53 | O | 2-OCHF₂ | — |
| VIII-54 | O | 3-OCHF₂ | — |
| VIII-55 | O | 4-OCHF₂ | — |
| VIII-56 | O | 2-OCF₃ | — |
| VIII-57 | O | 3-OCF₃ | — |
| VIII-58 | O | 4-OCF₃ | — |
| VIII-59 | O | 2-OCH₂CH₂OMe | — |
| VIII-60 | O | 3-OCH₂CH₂OMe | — |
| VIII-61 | O | 4-OCH₂CH₂OMe | — |
| VIII-62 | O | 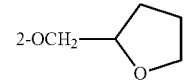 2-OCH₂-(tetrahydrofuran-2-yl) | — |
| VIII-63 | O | 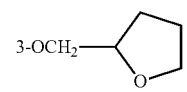 3-OCH₂-(tetrahydrofuran-2-yl) | — |
| VIII-64 | O | 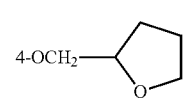 4-OCH₂-(tetrahydrofuran-2-yl) | — |

TABLE 78

| Compound No. | X¹ | R¹² | R² |
|---|---|---|---|
| VIII-65 | O | 2-OC(=O)Me | — |
| VIII-66 | O | 3-OC(=O)Me | — |
| VIII-67 | O | 3-OC(=O)Me | — |
| VIII-68 | O | 2-SMe | — |
| VIII-69 | O | 3-SMe | — |
| VIII-70 | O | 4-SMe | — |
| VIII-71 | O | 2-SO₂Me | — |
| VIII-72 | O | 3-SO₂Me | — |
| VIII-73 | O | 4-SO₂Me | — |
| VIII-74 | O | 2-SCF₃ | — |
| VIII-75 | O | 3-SCF₃ | — |
| VIII-76 | O | 4-SCF₃ | — |
| VIII-77 | O | 2-NO₂ | — |
| VIII-78 | O | 3-NO₂ | — |
| VIII-79 | O | 4-NO₂ | — |
| VIII-80 | O | 2-NH₂ | — |
| VIII-81 | O | 3-NH₂ | — |
| VIII-82 | O | 4-NH₂ | — |
| VIII-83 | O | 2-CN | — |
| VIII-84 | O | 3-CN | — |
| VIII-85 | O | 4-CN | — |
| VIII-86 | O | 2-C(=O)Me | — |
| VIII-87 | O | 3-C(=O)Me | — |
| VIII-88 | O | 4-C(=O)Me | — |
| VIII-89 | O | 2-C(=O)OH | — |

TABLE 78-continued

| Compound No. | $X^1$ | $R^{12}$ | $R^2$ |
|---|---|---|---|
| VIII-90 | O | 3-C(=O)OH | — |
| VIII-91 | O | 4-C(=O)OH | — |
| VIII-92 | O | 2-C(=O)OMe | — |
| VIII-93 | O | 3-C(=O)OMe | — |
| VIII-94 | O | 4-C(=O)OMe | — |
| VIII-95 | O | 2-CH$_2$OMe | — |
| VIII-96 | O | 3-CH$_2$OMe | — |
| VIII-97 | O | 4-CH$_2$OMe | — |
| VIII-98 | O | 2,3-F$_2$ | — |
| VIII-99 | O | 2,4-F$_2$ | — |

TABLE 79

| Compound No. | $X^1$ | $R^{12}$ | $R^2$ |
|---|---|---|---|
| VIII-100 | O | 2,5-F$_2$ | — |
| VIII-101 | O | 2,6-F$_2$ | — |
| VIII-102 | O | 3,4-F$_2$ | — |
| VIII-103 | O | 3,5-F$_2$ | — |
| VIII-104 | O | 2,3-Cl$_2$ | — |
| VIII-105 | O | 2,4-Cl$_2$ | — |
| VIII-106 | O | 2,5-Cl$_2$ | — |
| VIII-107 | O | 2,6-Cl$_2$ | — |
| VIII-108 | O | 3,4-Cl$_2$ | — |
| VIII-109 | O | 3,5-Cl$_2$ | — |
| VIII-110 | O | 2-F, 3-OMe | — |
| VIII-111 | O | 2-Cl, 3-OMe | — |
| VIII-112 | O | 2-Me, 3-OMe | — |
| VIII-113 | O | 2,3-(OMe)$_2$ | — |
| VIII-114 | O | 3-OMe, 4-F | — |
| VIII-115 | O | 3-OMe, 4-Cl | — |
| VIII-116 | O | 3-OMe, 4-Me | — |
| VIII-117 | O | 3,4-(OMe)$_2$ | — |
| VIII-118 | O | 3-OMe, 5-F | — |
| VIII-119 | O | 3-OMe, 5-Cl | — |
| VIII-120 | O | 3-OMe, 5-Me | — |
| VIII-121 | O | 3,5-(OMe)$_2$ | — |
| VIII-122 | O | 2-F, 4-OMe | — |
| VIII-123 | O | 2-Cl, 4-OMe | — |
| VIII-124 | O | 2-Me, 4-OMe | — |
| VIII-125 | O | 2,4-(OMe)$_2$ | — |
| VIII-126 | O | 3-F, 4-OMe | — |
| VIII-127 | O | 3-Cl, 4-OMe | — |
| VIII-128 | O | 3-Me, 4-OMe | — |
| VIII-129 | O | 2-F, 5-OMe | — |
| VIII-130 | O | 2-Cl, 5-OMe | — |
| VIII-131 | O | 2-Me, 5-OMe | — |
| VIII-132 | O | 2,5-(OMe)$_2$ | — |
| VIII-133 | O | 3,4,5-(OMe)$_3$ | — |
| VIII-134 | O | — | 6-F |
| VIII-135 | O | 4-OMe | 6-F |
| VIII-136 | O | — | 6-Cl |

TABLE 80

| Compound No. | $X^1$ | $R^{12}$ | $R^2$ |
|---|---|---|---|
| VIII-137 | O | 4-OMe | 6-Cl |
| VIII-138 | O | — | 6-OMe |
| VIII-139 | O | 4-OMe | 6-OMe |
| VIII-140 | S | — | — |
| VIII-141 | S | 4-OMe | — |
| VIII-142 | O | 2-F, 5-CF$_3$ | — |
| VIII-143 | O | 3-CF$_3$, 4-F | — |
| VIII-144 | O | 2-F, 3-CF$_3$ | — |
| VIII-145 | O | 3-F, 5-CF$_3$ | — |
| VIII-146 | O | 2,3-(Me)$_2$ | — |
| VIII-147 | O | 2,4-(Me)$_2$ | — |
| VIII-148 | O | 2,5-(Me)$_2$ | — |
| VIII-149 | O | 2,6-(Me)$_2$ | — |
| VIII-150 | O | 3,4-(Me)$_2$ | — |
| VIII-151 | O | 3,5-(Me)$_2$ | — |
| VIII-152 | O | 3,5-(CF$_3$)$_2$ | — |
| VIII-153 | O | 2,6-(OMe)$_2$ | — |
| VIII-154 | O | 2-F, 3-Cl | — |
| VIII-155 | O | 2-F, 4-Cl | — |
| VIII-156 | O | 2-F, 5-Cl | — |
| VIII-157 | O | 3-F, 4-Cl | — |
| VIII-158 | O | 4-F, 2-Cl | — |
| VIII-159 | O | 4-F, 3-Cl | — |
| VIII-160 | O | 2-F, 3-Me | — |
| VIII-161 | O | 2-F, 4-Me | — |
| VIII-162 | O | 2-F, 5-Me | — |
| VIII-163 | O | 3-F, 2-Me | — |
| VIII-164 | O | 3-F, 4-Me | — |
| VIII-165 | O | 3-F, 5-Me | — |
| VIII-166 | O | 4-F, 2-Me | — |
| VIII-167 | O | 4-F, 3-Me | — |
| VIII-168 | O | 5-F, 2-Me | — |
| VIII-169 | O | 2-F, 4-CF$_3$ | — |
| VIII-170 | O | 3-F, 4-CF$_3$ | — |
| VIII-171 | O | 4-F, 2-CF$_3$ | — |
| VIII-172 | O | 3-F, 2-OMe | — |
| VIII-173 | O | 4-F, 2-OMe | — |

TABLE 81

| Compound No. | $X^1$ | $R^{12}$ | $R^2$ |
|---|---|---|---|
| VIII-174 | O | 5-F, 2-OMe | — |
| VIII-175 | O | 2-F, 4-OCHF$_2$ | — |
| VIII-176 | O | 3-F, 4-OCHF$_2$ | — |
| VIII-177 | O | 4-F, 2-OCHF$_2$ | — |
| VIII-178 | O | 4-F, 3-CN | — |
| VIII-179 | O | 2-Cl, 4-Me | — |
| VIII-180 | O | 3-Cl, 4-Me | — |
| VIII-181 | O | 3-Cl, 4-OCHF$_2$ | — |
| VIII-182 | O | 4-Me, 3-CF$_3$ | — |
| VIII-183 | O | 4-Me, 2-OMe | — |
| VIII-184 | O | 3-Me, 4-CN | — |
| VIII-185 | O | 4-Me, 3-CN | — |
| VIII-186 | O | 2,3,4-F$_3$ | — |
| VIII-187 | O | 2,3,5-F$_3$ | — |
| VIII-188 | O | 2,4,5-F$_3$ | — |
| VIII-189 | O | 3,4,5-F$_3$ | — |
| VIII-190 | O | 2,3-F$_2$, 4-Me | — |
| VIII-191 | O | 2,6-F$_2$, 4-OMe | — |
| VIII-192 | O | 3,5-F$_2$, 4-OMe | — |
| VIII-193 | O | 4-F, 2-Cl, 5-Me | — |
| VIII-194 | O | — | 7-Cl |
| VIII-195 | O | — | 6-Me |
| VIII-196 | O | — | 7-Me |
| VIII-197 | O | — | 8-Me |
| VIII-198 | O | 3-Me | 8-Me |
| VIII-199 | O | 3-CF$_3$ | 8-Me |
| VIII-200 | O | 4-OMe | 8-Me |
| VIII-201 | O | 3-F, 4-Me | 8-Me |
| VIII-202 | O | 3-F, 4-OMe | 8-Me |
| VIII-203 | O | — | 8-OMe |
| VIII-204 | O | 3-CF$_3$ | 8-OMe |
| VIII-205 | O | 3-F, 4-Me | 8-Cl |
| VIII-206 | O | 3-F, 4-Me | 6-F |
| VIII-207 | O | 3-F, 4-Me | 6-Cl |
| VIII-208 | O | 3-F, 4-Me | 7-Me |
| VIII-209 | O | 3-F, 4-Me | 6-Me |
| VIII-210 | O | — | 8-Cl |
| VIII-211 | O | 3-F, 4-Me | 6-OMe |
| VIII-212 | O | 3-OEt | — |
| VIII-213 | O | 4-OEt | — |
| VIII-214 | O | 4-OMe | 8-Cl |
| VIII-215 | O | — | 6-SMe |
| VIII-216 | O | 3,4-(OCH$_2$CH$_2$O)— | 6-OMe |
| VIII-217 | O | 3-F, 4-OEt | — |
| VIII-218 | O | 3,4-(OCH$_2$O)— | 8-Cl |

Specific preferred examples of the compound represented by formula [J1] and formula [J2] which are production intermediates of the present invention will be shown in the following Table 82 to Table 123. However, the compound is not intended to be limited to these compounds as in the case of the compound of the present invention.

TABLE 82

| Compound No. | $X^1$ | $R^1$ | $R^2$ |
|---|---|---|---|
| IX-1 | O | Me | — |
| IX-2 | O | Et | — |
| IX-3 | O | n-Pr | — |
| IX-4 | O | i-Pr | — |
| IX-5 | O | c-Pr | — |
| IX-6 | O | n-Bu | — |
| IX-7 | O | t-Bu | — |
| IX-8 | O | c-Pen | — |
| IX-9 | O | n-Hex | — |
| IX-10 | O | $CH_2CH=CH_2$ | — |
| IX-11 | O | $CH_2C\equiv CH$ | — |
| IX-12 | O | $CH_2CF_3$ | — |
| IX-13 | O | $CH_2OMe$ | — |
| IX-14 | O | $CH_2OEt$ | — |
| IX-15 | O | $CH_2OPh$ | — |
| IX-16 | O | $CH_2OCH_2CH_2OMe$ | — |
| IX-17 | O | $CH_2OCH_2CF_3$ | — |
| IX-18 | O | $CH_2OCH_2$-(tetrahydrofuran-2-yl) | — |
| IX-19 | O | $CH_2OCH_2CH_2SO_2Me$ | — |
| IX-20 | O | $CH_2OCH_2CH_2CN$ | — |
| IX-21 | O | $CH_2OC(=O)t$-Bu | — |
| IX-22 | O | $CH_2SMe$ | — |
| IX-23 | O | $CH_2SEt$ | — |
| IX-24 | O | $CH_2SO_2Me$ | — |
| IX-25 | O | $CH_2SO_2Et$ | — |
| IX-26 | O | $CH_2CH_2OMe$ | — |
| IX-27 | O | $CH(Me)CH_2OMe$ | — |
| IX-28 | O | $CH_2CH_2SMe$ | — |
| IX-29 | O | $CH_2CH_2SO_2Me$ | — |
| IX-30 | O | $CH_2CH_2CH_2OMe$ | — |

TABLE 83

| Compound No. | $X^1$ | $R^1$ | $R^2$ |
|---|---|---|---|
| IX-31 | O | $CH_2C(=O)Me$ | — |
| IX-32 | O | $CH_2C(=O)O$-t-Bu | — |
| IX-33 | O | $CH_2C(=O)NMe_2$ | — |
| IX-34 | O | 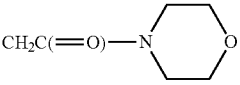 $CH_2C(=O)$-morpholinyl | — |
| IX-35 | O | $CH_2CN$ | — |
| IX-36 | O | $CH_2CH_2CN$ | — |
| IX-37 | O | Bn | — |
| IX-38 | O | (2-Cl)Bn | — |
| IX-39 | O | (3-Cl)Bn | — |
| IX-40 | O | (4-Cl)Bn | — |
| IX-41 | O | (2-OMe)Bn | — |
| IX-42 | O | (3-OMe)Bn | — |
| IX-43 | O | (4-OMe)Bn | — |
| IX-44 | O | $(2,6-(OMe)_2)Bn$ | — |

TABLE 83-continued

| Compound No. | $X^1$ | $R^1$ | $R^2$ |
|---|---|---|---|
| IX-45 | O | 3-methylisoxazol-5-yl-methyl | — |
| IX-46 | O | (tetrahydrothiophen-3-yl)methyl | — |
| IX-47 | O | (1,1-dioxotetrahydrothiophen-3-yl)methyl | — |
| IX-48 | O | (thiophen-3-yl)methyl | — |
| IX-49 | O | isoxazol-3-yl-methyl | — |
| IX-50 | O | (5-methylisoxazol-3-yl)methyl | — |

TABLE 84

| Compound No. | $X^1$ | $R^1$ | $R^2$ |
|---|---|---|---|
| IX-51 | O | (3-methylisothiazol-5-yl)methyl | — |
| IX-52 | O | (3-trifluoromethyl-1-methyl-pyrazol-5-yl)methyl | — |
| IX-53 | O | (thiazol-2-yl)methyl | — |
| IX-54 | O | (4-methylthiazol-2-yl)methyl | — |
| IX-55 | O | (5-methyl-1,3,4-oxadiazol-2-yl)methyl | — |
| IX-56 | O | (3-trifluoromethyl-1-methyl-1,2,4-triazol-5-yl)methyl | — |
| IX-57 | O | (tetrahydrothiopyran-4-yl)methyl | — |

TABLE 84-continued

| Compound No. | X¹ | R¹ | R² |
|---|---|---|---|
| IX-58 | O | 4-(tetrahydro-2H-thiopyran-1,1-dioxide)yl | — |
| IX-59 | O | pyridin-2-yl | — |
| IX-60 | O | 6-methylpyridin-2-yl | — |

TABLE 85

| Compound No. | X¹ | R¹ | R² |
|---|---|---|---|
| IX-61 | O | 5-fluoropyridin-2-yl | — |
| IX-62 | O | 5-chloropyridin-2-yl | — |
| IX-63 | O | 5-methylpyridin-2-yl | — |
| IX-64 | O | 5-trifluoromethylpyridin-2-yl | — |
| IX-65 | O | 5-methoxypyridin-2-yl | — |
| IX-66 | O | 4-methylpyridin-2-yl | — |
| IX-67 | O | pyridin-3-yl | — |
| IX-68 | O | 6-methoxypyridin-3-yl | — |
| IX-69 | O | pyrimidin-2-yl | — |
| IX-70 | O | 4,6-dimethoxypyrimidin-2-yl | — |

TABLE 86

| Compound No. | X¹ | R¹ | R² |
|---|---|---|---|
| IX-71 | O | pyrazin-2-yl | — |
| IX-72 | O | 2,3-dihydrobenzofuran-5-yl | — |
| IX-73 | O | benzo[d][1,3]dioxol-5-yl | — |
| IX-74 | O | 2,2-difluorobenzo[d][1,3]dioxol-5-yl | — |
| IX-75 | O | 2,3-dihydrobenzo[b][1,4]dioxin-6-yl | — |
| IX-76 | O | (tetrahydrofuran-2-yl)methyl | — |
| IX-77 | O | (3-methyl-4,5-dihydroisoxazol-5-yl)methyl | — |
| IX-78 | O | (3-methylisoxazol-5-yl)methyl | — |
| IX-79 | O | NHMe | — |
| IX-80 | O | Me | 6-F |
| IX-81 | O | Me | 7-F |
| IX-82 | O | Me | 5-Cl |
| IX-83 | O | Me | 6-Cl |
| IX-84 | O | Me | 7-Cl |
| IX-85 | O | Me | 8-Cl |

TABLE 87
| Compound No. | X¹ | R¹ | R² |
|---|---|---|---|
| IX-86 | O | CH₂CH₂OMe | 8-Cl |
| IX-87 | O | Me | 7-OMe |
| IX-88 | O | Me | 5-SMe |
| IX-89 | O | Me | 7-SMe |
| IX-90 | O | Me | 5-SO₂Me |
| IX-91 | O | Me | 7-SO₂Me |
| IX-92 | O | Me | 6-NO₂ |
| IX-93 | O | Me | 7-NO₂ |
| IX-94 | S | Me | — |
| IX-95 | O | 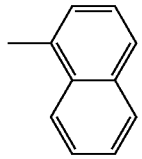 | — |
| IX-96 | O | 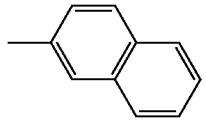 | — |
| IX-97 | O | 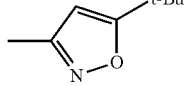 | — |
| IX-98 | O | 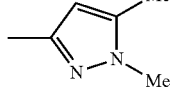 | — |
| IX-99 | O | 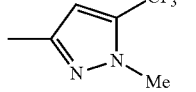 | — |
| IX-100 | O | 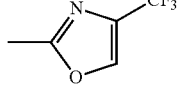 | — |
TABLE 88
| Compound No. | X¹ | R¹ | R² |
|---|---|---|---|
| IX-101 | O | 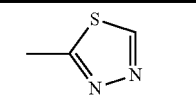 | — |
| IX-102 | O | 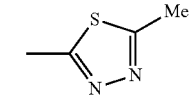 | — |
| IX-103 | O | 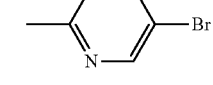 | — |
| IX-104 | O | 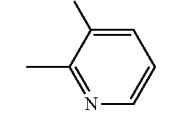 | — |
| IX-105 | O | 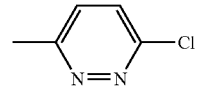 | — |
| IX-106 | O | 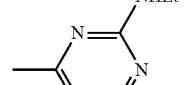 | — |
| IX-107 | O | 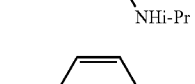 | — |
| IX-108 | O | 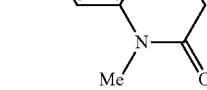 | — |
| IX-109 | O | 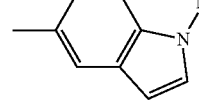 | — |
| IX-110 | O | N(Me)C(=O)Ot-Bu | — |
TABLE 89
| Compound No. | X¹ | R¹ | R² |
|---|---|---|---|
| IX-111 | O | 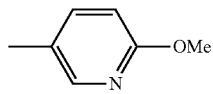 | 5-F |
| IX-112 | O | Bn | 6-F |
| IX-113 | O | 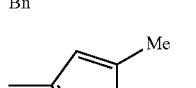 | 7-F |
| IX-114 | O | Me | 5-CH₂OMe |
| IX-115 | O |  | 5,7-F₂ |
| IX-116 | O | 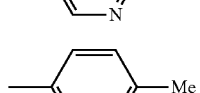 | 7-Cl |
| IX-117 | O | Et | 5-Cl |
| IX-118 | O | n-Bu | 5-Cl |
| IX-119 | O | 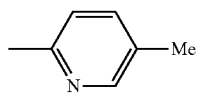 | 7-Me |

TABLE 89-continued

| Compound No. | X¹ | R¹ | R² |
|---|---|---|---|
| IX-120 | O | 2,6-dimethylpyridin-3-yl | 6-CF₃ |
| IX-121 | O | 2,5-dimethylpyrazin-3-yl | — |
| IX-122 | O | 6-methoxy-5-methylpyridin-3-yl | 5-Cl |
| IX-123 | O | 6-methylpyridin-2-yl | 6-F |
| IX-124 | O | 2,5-dimethylthiazol-4-yl | — |
| IX-125 | O | 5-methylpyridin-2-yl | 5-F |
| IX-126 | O | 5-methylpyridin-2-yl | 5-Cl |
| IX-127 | O | 5-methylpyridin-2-yl | 5-Me |
| IX-128 | O | 6-methoxypyridin-3-yl | 5-Me |
| IX-129 | O | 1-methyl-6-(trifluoromethyl)-2-oxo-1,2-dihydropyridin-3-yl | — |

TABLE 90

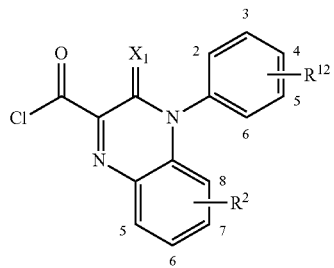

| Compound No. | X¹ | R¹² | R² |
|---|---|---|---|
| X-1 | O | — | — |
| X-2 | O | 2-F | — |
| X-3 | O | 3-F | — |
| X-4 | O | 4-F | — |
| X-5 | O | 2-Cl | — |
| X-6 | O | 3-Cl | — |
| X-7 | O | 4-Cl | — |
| X-8 | O | 3-Me | — |
| X-9 | O | 4-Me | — |
| X-10 | O | 3-Et | — |
| X-11 | O | 4-Et | — |
| X-12 | O | 3-i-Pr | — |
| X-13 | O | 4-c-Pr | — |
| X-14 | O | 3-CF₃ | — |
| X-15 | O | 4-CF₃ | — |
| X-16 | O | 4-OH | — |
| X-17 | O | 2-OMe | — |
| X-18 | O | 3-OMe | — |
| X-19 | O | 4-OMe | — |
| X-20 | O | 3-OEt | — |
| X-21 | O | 4-OEt | — |
| X-22 | O | 3-O-n-Pr | — |
| X-23 | O | 3-O-i-Pr | — |
| X-24 | O | 4-O-i-Pr | — |
| X-25 | O | 4-OCH₂CH=CH₂ | — |
| X-26 | O | 4-OCH₂C≡CH | — |

TABLE 91

| Compound No. | X¹ | R¹² | R² |
|---|---|---|---|
| X-27 | O | 3-OCHF₂ | — |
| X-28 | O | 4-OCHF₂ | — |
| X-29 | O | 3-OCF₃ | — |
| X-30 | O | 4-OCH₂-(tetrahydrofuran-2-yl) | — |
| X-31 | O | 3-SMe | — |
| X-32 | O | 4-SMe | — |
| X-33 | O | 3-SO₂Me | — |
| X-34 | O | 4-SO₂Me | — |
| X-35 | O | 2-NO₂ | — |
| X-36 | O | 3-NO₂ | — |
| X-37 | O | 4-NO₂ | — |
| X-38 | O | 3-CN | — |
| X-39 | O | 4-CN | — |
| X-40 | O | 4-C(=O)Me | — |
| X-41 | O | 4-C(=O)OMe | — |
| X-42 | O | 4-CH₂OMe | — |
| X-43 | O | 3-OMe, 4-Cl | — |
| X-44 | O | 3-OMe, 4-Me | — |
| X-45 | O | 3,4-(OMe)₂ | — |
| X-46 | O | 3,5-(OMe)₂ | — |
| X-47 | O | 2-F, 4-OMe | — |
| X-48 | O | 2-Cl, 4-OMe | — |
| X-49 | O | 2,4-(OMe)₂ | — |
| X-50 | O | 3-F, 4-OMe | — |
| X-51 | O | 3-Cl, 4-OMe | — |

TABLE 91-continued

| Compound No. | $X^1$ | $R^{12}$ | $R^2$ |
|---|---|---|---|
| X-52 | O | 3-Me, 4-OMe | — |
| X-53 | O | 3,4,5-(OMe)$_3$ | — |
| X-54 | O | 4-OMe | 5-F |
| X-55 | O | 4-OMe | 6-F |
| X-56 | O | 4-OMe | 7-F |

TABLE 92

| Compound No. | $X^1$ | $R^{12}$ | $R^2$ |
|---|---|---|---|
| X-57 | O | 4-OMe | 8-F |
| X-58 | O | — | 5-Cl |
| X-59 | O | — | 8-Cl |
| X-60 | O | 4-OMe | 5-Cl |
| X-61 | O | 4-OMe | 6-Cl |
| X-62 | O | 4-OMe | 7-Cl |
| X-63 | O | 4-OMe | 8-Cl |
| X-64 | O | 4-OCH$_2$CN | — |
| X-65 | O | 4-OCH$_2$—c-Pr | — |
| X-66 | O | 4-OCH$_2$CF$_3$ | — |
| X-67 | O | 4-NMe$_2$ | — |
| X-68 | O | 3,4-Me$_2$ | — |
| X-69 | O | 2-F, 4-Me | — |
| X-70 | O | 3-F, 4-Me | — |
| X-71 | O | 3-Me, 4-F | — |
| X-72 | O | 2-Cl, 4-Me | — |
| X-73 | O | 3-Cl, 4-Me | — |
| X-74 | O | 3-OEt, 4-OMe | — |
| X-75 | O | 2,3,4-(OMe)$_3$ | — |
| X-76 | O | 2,5-F$_2$, 4-OMe | — |
| X-77 | O | 3,5-F$_2$, 4-OMe | — |
| X-78 | O | 3,5-Cl$_2$, 4-OMe | — |
| X-79 | O | 3,4-(CH$_2$CH$_2$CH$_2$)— | — |
| X-80 | O | 3,4-(CH$_2$CH$_2$CH$_2$CH$_2$)— | — |
| X-81 | O | 3,4-(CH$_2$OCH$_2$)— | — |
| X-82 | O | 3,4-(OCH$_2$O)— | 7-F |
| X-83 | O | 2,3-(OCH$_2$CH$_2$O)— | — |
| X-84 | O | 3,4-(OCH$_2$CH(Me)O)— | — |
| X-85 | O | 3,4-(OCH$_2$CH$_2$CH$_2$O)— | — |

TABLE 93

| Compound No. | $X^1$ | $R^{12}$ | $R^2$ |
|---|---|---|---|
| X-86 | O | — | 5-F |
| X-87 | O | 3,4,5-(OMe)$_3$ | 5-F |
| X-88 | O | 3,5-F$_2$, 4-OMe | 5-F |
| X-89 | O | 3,4-(OCH$_2$CH$_2$O)— | 5-F |
| X-90 | O | — | 6-F |
| X-91 | O | 3,4,5-(OMe)$_3$ | 6-F |
| X-92 | O | 3,4-(OCH$_2$O)— | 6-F |
| X-93 | O | 3,4-(OCH$_2$CH$_2$O)— | 6-F |
| X-94 | O | — | 7-F |
| X-95 | O | 3,4-(OCH$_2$CH$_2$O)— | 7-F |
| X-96 | O | — | 8-F |
| X-97 | O | — | 5-Me |
| X-98 | O | 4-OMe | 5-Me |
| X-99 | O | 4-OMe | 6-Me |
| X-100 | O | 4-OMe | 7-Me |
| X-101 | O | 3,5-F$_2$, 4-OMe | 7-Me |
| X-102 | O | — | 6-CF$_3$ |
| X-103 | O | — | 6-OMe |
| X-104 | O | 4-OMe | 6-OMe |
| X-105 | O | — | 7-OMe |
| X-106 | O | 4-OMe | 7-OMe |
| X-107 | O | 2,5-F$_2$, 4-OMe | 7-OMe |
| X-108 | O | 3,5-F$_2$, 4-OMe | 7-OMe |
| X-109 | O | — | 8-OMe |
| X-110 | O | 4-OMe | 8-OMe |
| X-111 | O | 4-OMe | 5,6-F$_2$ |
| X-112 | O | 4-OMe | 5,7-F$_2$ |
| X-113 | O | — | 6,7-F$_2$ |

TABLE 94

| Compound No. | $X^1$ | $R^{12}$ | $R^2$ |
|---|---|---|---|
| X-114 | O | — | 6,8-F$_2$ |
| X-115 | O | 4-OMe | 5,7-Cl$_2$ |
| X-116 | O | 4-OMe | 6-F, 7-OMe |
| X-117 | O | 3-F, 4-OMe | 5-Cl |
| X-118 | O | 4-OMe | 5,6,8-F$_3$, 7-OMe |
| X-119 | O | — | 7-CF$_3$ |
| X-120 | O | 4-F | 7-OMe |
| X-121 | O | 4-OCHF$_2$ | 7-OMe |
| X-122 | O | 4-Me | 7-OMe |

TABLE 95

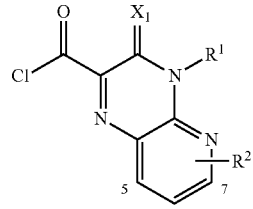

| Compound No. | $X^1$ | $R^1$ | $R^2$ |
|---|---|---|---|
| XI-1 | O | Me | — |
| XI-2 | O | Et | — |
| XI-3 | O | n-Pr | — |
| XI-4 | O | i-Pr | — |
| XI-5 | O | n-Bu | — |
| XI-6 | O | s-Bu | — |
| XI-7 | O | CH$_2$CH═CH$_2$ | — |
| XI-8 | O | CH$_2$C≡CH | — |
| XI-9 | O | CH$_2$CF$_3$ | — |
| XI-10 | O | CH$_2$CH$_2$F | — |
| XI-11 | O | CH$_2$OCH$_2$CF$_3$ | — |
| XI-12 | O | CH$_2$SMe | — |
| XI-13 | O | CH$_2$CH$_2$OMe | — |
| XI-14 | O | CH(Me)CH$_2$OMe | — |
| XI-15 | O | CH$_2$C(═O)OEt | — |
| XI-16 | O | CH$_2$C(═O)Ot-Bu | — |
| XI-17 | O | Bn | — |
| XI-18 | O | (2-F)Bn | — |
| XI-19 | O | (2-Cl)Bn | — |
| XI-20 | O | (2-CF$_3$)Bn | — |
| XI-21 | O | (3-CF$_3$)Bn | — |
| XI-22 | O | (2-OMe)Bn | — |
| XI-23 | O | CH(Me)Ph | — |
| XI-24 | O | 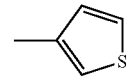 | — |

TABLE 96

| Compound No. | $X^1$ | $R^1$ | $R^2$ |
|---|---|---|---|
| XI-25 | O | 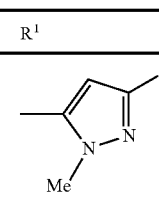 | — |
| XI-26 | O | 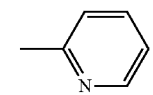 | — |

TABLE 96-continued

| Compound No. | X¹ | R¹ | R² |
|---|---|---|---|
| XI-27 | O | 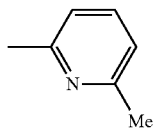 2,6-dimethylpyridyl | — |
| XI-28 | O | 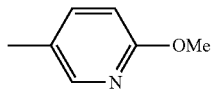 5-methyl-2-methoxypyridyl | — |
| XI-29 | O | 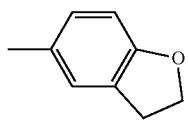 2,3-dihydrobenzofuranyl | — |
| XI-30 | O | 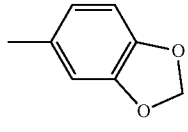 benzodioxolyl | — |
| XI-31 | O | 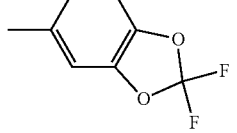 difluorobenzodioxolyl | — |
| XI-32 | O | 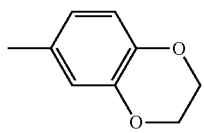 benzodioxinyl | — |
| XI-33 | O | 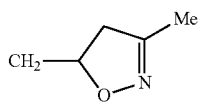 CH₂-(3-Me-isoxazolin-5-yl) | — |
| XI-34 | O | 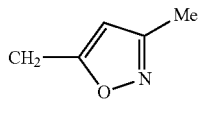 CH₂-(3-Me-isoxazol-5-yl) | — |
| XI-35 | O | Me | 6-Cl |

TABLE 97

| Compound No. | X¹ | R¹ | R² |
|---|---|---|---|
| XI-36 | O | Me | 6-OMe |
| XI-37 | O | CH₂CH₂CH=CH₂ | — |
| XI-38 | O | CH₂CH₂CH=C(Me)₂ | — |
| XI-39 | O | CH₂CH₂C≡CH | — |
| XI-40 | O | CH₂CH₂C(Me)=CF₂ | — |
| XI-41 | O | CH(Me)C(=O)Ot-Bu | — |
| XI-42 | O | (2-OCHF₂)Bn | — |
| XI-43 | O | CH₂CH₂Ph | — |
| XI-44 | O | 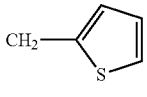 CH₂-thienyl | — |
| XI-45 | O | 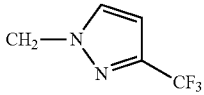 CH₂-(3-CF₃-pyrazolyl) | — |

TABLE 97-continued

| Compound No. | X¹ | R¹ | R² |
|---|---|---|---|
| XI-46 | O | 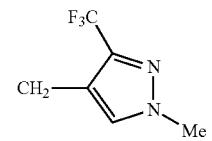 CH₂-(3-CF₃-1-Me-pyrazolyl) | — |
| XI-47 | O | 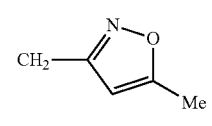 CH₂-(5-Me-isoxazolyl) | — |
| XI-48 | O | 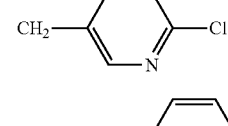 CH₂-(6-Cl-pyridyl) | — |
| XI-49 | O | 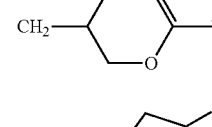 CH₂-benzodioxinyl | — |
| XI-50 | O | 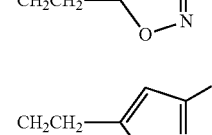 CH₂CH₂-(3-Me-isoxazolin-5-yl) | — |
| XI-51 | O |  CH₂CH₂-(3-Me-isoxazol-5-yl) | — |
| XI-52 | O | Bn | 8-Me |
| XI-53 | O | Bn | 7-Me |
| XI-54 | O | Bn | 6-Me |
| XI-55 | O | Bn | 6-OMe |

TABLE 98

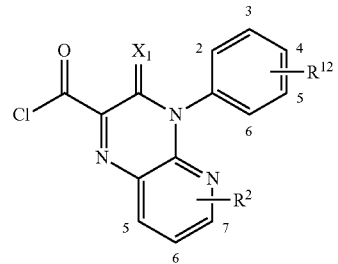

| Compound No. | X¹ | R¹² | R² |
|---|---|---|---|
| XII-1 | O | — | — |
| XII-2 | O | 2-F | — |
| XII-3 | O | 3-F | — |
| XII-4 | O | 4-F | — |
| XII-5 | O | 2-Cl | — |
| XII-6 | O | 3-Cl | — |
| XII-7 | O | 4-Cl | — |
| XII-8 | O | 3-Br | — |
| XII-9 | O | 4-Br | — |
| XII-10 | O | 2-Me | — |
| XII-11 | O | 3-Me | — |
| XII-12 | O | 4-Me | — |
| XII-13 | O | 3-Et | — |
| XII-14 | O | 4-Et | — |
| XII-15 | O | 4-i-Pr | — |

TABLE 98-continued

| Compound No. | X¹ | R¹² | R² |
|---|---|---|---|
| XII-16 | O | 4-c-Pr | — |
| XII-17 | O | 2-CF₃ | — |
| XII-18 | O | 3-CF₃ | — |
| XII-19 | O | 4-CF₃ | — |
| XII-20 | O | 2-OMe | — |
| XII-21 | O | 3-OMe | — |
| XII-22 | O | 4-OMe | — |
| XII-23 | O | 2-OCHF₂ | — |
| XII-24 | O | 3-OCHF₂ | — |
| XII-25 | O | 4-OCHF₂ | — |

TABLE 99

| Compound No. | X¹ | R¹² | R² |
|---|---|---|---|
| XII-26 | O | 2-OCF₃ | — |
| XII-27 | O | 3-OCF₃ | — |
| XII-28 | O | 4-OCF₃ | — |
| XII-29 | O | 4-SCF₃ | — |
| XII-30 | O | 3-CN | — |
| XII-31 | O | 2,3-F₂ | — |
| XII-32 | O | 2,4-F₂ | — |
| XII-33 | O | 2,5-F₂ | — |
| XII-34 | O | 2,6-F₂ | — |
| XII-35 | O | 3,4-F₂ | — |
| XII-36 | O | 3,5-F₂ | — |
| XII-37 | O | 2,3-Cl₂ | — |
| XII-38 | O | 2,4-Cl₂ | — |
| XII-39 | O | 2,5-Cl₂ | — |
| XII-40 | O | 2,6-Cl₂ | — |
| XII-41 | O | 3,4-Cl₂ | — |
| XII-42 | O | 3,5-Cl₂ | — |
| XII-43 | O | 2,3-(OMe)₂ | — |
| XII-44 | O | 3-OMe, 4-F | — |
| XII-45 | O | 3-OMe, 4-Me | — |
| XII-46 | O | 3,4-(OMe)₂ | — |
| XII-47 | O | 3-OMe, 5-F | — |
| XII-48 | O | 3,5-(OMe)₂ | — |
| XII-49 | O | 2-F, 4-OMe | — |
| XII-50 | O | 2,4-(OMe)₂ | — |
| XII-51 | O | 3-F, 4-OMe | — |
| XII-52 | O | 3-Cl, 4-OMe | — |
| XII-53 | O | 3-Me, 4-OMe | — |
| XII-54 | O | 2,5-(OMe)₂ | — |
| XII-55 | O | 3,4,5-(OMe)₃ | — |

TABLE 100

| Compound No. | X¹ | R¹² | R² |
|---|---|---|---|
| XII-56 | O | — | 6-F |
| XII-57 | O | 4-OMe | 6-F |
| XII-58 | O | — | 6-Cl |
| XII-59 | O | 4-OMe | 6-Cl |
| XII-60 | O | 4-OMe | 6-OMe |
| XII-61 | O | 2-F,5-CF₃ | — |
| XII-62 | O | 3-CF₃,4-F | — |
| XII-63 | O | 2-F,3-CF₃ | — |
| XII-64 | O | 3-F,5-CF₃ | — |

TABLE 100-continued

| Compound No. | X¹ | R¹² | R² |
|---|---|---|---|
| XII-65 | O | 2,5-(Me)₂ | — |
| XII-66 | O | 3,4-(Me)₂ | — |
| XII-67 | O | 3,5-(Me)₂ | — |
| XII-68 | O | 3,5-(CF₃)₂ | — |
| XII-69 | O | 2,6-(OMe)₂ | — |
| XII-70 | O | 2-F, 3-Cl | — |
| XII-71 | O | 2-F, 4-Cl | — |
| XII-72 | O | 2-F, 5-Cl | — |
| XII-73 | O | 3-F, 4-Cl | — |
| XII-74 | O | 4-F, 2-Cl | — |
| XII-75 | O | 4-F, 3-Cl | — |
| XII-76 | O | 2-F, 3-Me | — |
| XII-77 | O | 2-F, 4-Me | — |
| XII-78 | O | 2-F, 5-Me | — |
| XII-79 | O | 3-F, 2-Me | — |
| XII-80 | O | 3-F, 4-Me | — |

TABLE 101

| Compound No. | X¹ | R¹² | R² |
|---|---|---|---|
| XII-81 | O | 3-F, 5-Me | — |
| XII-82 | O | 4-F, 2-Me | — |
| XII-83 | O | 4-F, 3-Me | — |
| XII-84 | O | 5-F, 2-Me | — |
| XII-85 | O | 2-F, 4-CF₃ | — |
| XII-86 | O | 3-F, 4-CF₃ | — |
| XII-87 | O | 4-F, 2-CF₃ | — |
| XII-88 | O | 3-F, 2-OMe | — |
| XII-89 | O | 4-F, 2-OMe | — |
| XII-90 | O | 5-F, 2-OMe | — |
| XII-91 | O | 2-F, 4-OCHF₂ | — |
| XII-92 | O | 3-F, 4-OCHF₂ | — |
| XII-93 | O | 4-F, 2-OCHF₂ | — |
| XII-94 | O | 4-F, 3-CN | — |
| XII-95 | O | 2-Cl, 4-Me | — |
| XII-96 | O | 3-Cl, 4-Me | — |
| XII-97 | O | 3-Cl, 4-OCHF₂ | — |
| XII-98 | O | 4-Me, 3-CF₃ | — |
| XII-99 | O | 4-Me, 2-OMe | — |
| XII-100 | O | 3-Me, 4-CN | — |
| XII-101 | O | 4-Me, 3-CN | — |
| XII-102 | O | 2,3,4-F₃ | — |
| XII-103 | O | 2,3,5-F₃ | — |
| XII-104 | O | 2,4,5-F₃ | — |
| XII-105 | O | 3,4,5-F₃ | — |
| XII-106 | O | 2,3-F₂, 4-Me | — |
| XII-107 | O | 2,6-F₂, 4-OMe | — |

TABLE 102

| Compound No. | X¹ | R¹² | R² |
|---|---|---|---|
| XII-108 | O | 3,5-F₂, 4-OMe | — |
| XII-109 | O | 4-F, 2-Cl, 5-Me | — |
| XII-110 | O | — | 7-Cl |
| XII-111 | O | — | 6-Me |
| XII-112 | O | — | 7-Me |
| XII-113 | O | — | 8-Me |
| XII-114 | O | 3-Me | 8-Me |
| XII-115 | O | 3-CF₃ | 8-Me |
| XII-116 | O | 4-OMe | 8-Me |
| XII-117 | O | 3-F, 4-Me | 8-Me |
| XII-118 | O | 3-F, 4-OMe | 8-Me |
| XII-119 | O | — | 8-OMe |
| XII-120 | O | 3-CF₃ | 8-OMe |
| XII-121 | O | 3-F, 4-Me | 8-Cl |
| XII-122 | O | 3-F, 4-Me | 6-F |
| XII-123 | O | 3-F, 4-Me | 6-Cl |
| XII-124 | O | 3-F, 4-Me | 7-Me |
| XII-125 | O | 3-F, 4-Me | 6-Me |
| XII-126 | O | — | 8-Cl |
| XII-127 | O | 3-F, 4-Me | 6-OMe |

TABLE 102-continued

| Compound No. | $X^1$ | $R^{12}$ | $R^2$ |
|---|---|---|---|
| XII-128 | O | 3-OEt | — |
| XII-129 | O | 4-OEt | — |
| XII-130 | O | 4-OMe | 8-Cl |
| XII-131 | O | — | 6-SMe |
| XII-132 | O | 3,4-(OCH$_2$CH$_2$O)— | 6-OMe |
| XII-133 | O | 3-F, 4-OEt | — |
| XII-134 | O | 3,4-(OCH$_2$O)— | 8-Cl |

TABLE 103

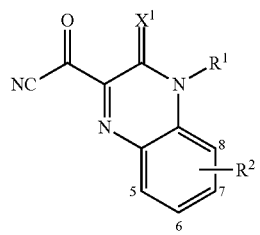

| Compound No. | $X^1$ | $R^1$ | $R^2$ |
|---|---|---|---|
| XIII-1 | O | Me | — |
| XIII-2 | O | Et | — |
| XIII-3 | O | n-Pr | — |
| XIII-4 | O | i-Pr | — |
| XIII-5 | O | c-Pr | — |
| XIII-6 | O | n-Bu | — |
| XIII-7 | O | t-Bu | — |
| XIII-8 | O | c-Pen | — |
| XIII-9 | O | n-Hex | — |
| XIII-10 | O | CH$_2$CH=CH$_2$ | — |
| XIII-11 | O | CH$_2$C≡CH | — |
| XIII-12 | O | CH$_2$CF$_3$ | — |
| XIII-13 | O | CH$_2$OMe | — |
| XIII-14 | O | CH$_2$OEt | — |
| XIII-15 | O | CH$_2$OPh | — |
| XIII-16 | O | CH$_2$OCH$_2$CH$_2$OMe | — |
| XIII-17 | O | CH$_2$OCH$_2$CF$_3$ | — |
| XIII-18 | O | CH$_2$OCH$_2$-(tetrahydrofuran-2-yl) | — |
| XIII-19 | O | CH$_2$OCH$_2$CH$_2$SO$_2$Me | — |
| XIII-20 | O | CH$_2$OCH$_2$CH$_2$CN | — |
| XIII-21 | O | CH$_2$OC(=O)t-Bu | — |
| XIII-22 | O | CH$_2$SMe | — |
| XIII-23 | O | CH$_2$SEt | — |
| XIII-24 | O | CH$_2$SO$_2$Me | — |
| XIII-25 | O | CH$_2$SO$_2$Et | — |
| XIII-26 | O | CH$_2$CH$_2$OMe | — |
| XIII-27 | O | CH(Me)CH$_2$OMe | — |
| XIII-28 | O | CH$_2$CH$_2$SMe | — |
| XIII-29 | O | CH$_2$CH$_2$SO$_2$Me | — |
| XIII-30 | O | CH$_2$CH$_2$CH$_2$OMe | — |

TABLE 104

| Compound No. | $X^1$ | $R^1$ | $R^2$ |
|---|---|---|---|
| XIII-31 | O | CH$_2$C(=O)Me | — |
| XIII-32 | O | CH$_2$C(=O)O-t-Bu | — |
| XIII-33 | O | CH$_2$C(=O)NMe$_2$ | — |
| XIII-34 | O | CH$_2$C(=O)-morpholino | — |
| XIII-35 | O | CH$_2$CN | — |

TABLE 104-continued

| Compound No. | $X^1$ | $R^1$ | $R^2$ |
|---|---|---|---|
| XIII-36 | O | CH$_2$CH$_2$CN | — |
| XIII-37 | O | Bn | — |
| XIII-38 | O | (2-Cl)Bn | — |
| XIII-39 | O | (3-Cl)Bn | — |
| XIII-40 | O | (4-Cl)Bn | — |
| XIII-41 | O | (2-OMe)Bn | — |
| XIII-42 | O | (3-OMe)Bn | — |
| XIII-43 | O | (4-OMe)Bn | — |
| XIII-44 | O | (2,6-(OMe)$_2$)Bn | — |
| XIII-45 | O | 3-methylisoxazol-5-yl | — |
| XIII-46 | O | 3-methyltetrahydrothiophen-3-yl | — |
| XIII-47 | O | 3-methyltetrahydrothiophene-1,1-dioxide-3-yl | — |
| XIII-48 | O | 3-methylthiophen-3-yl | — |
| XIII-49 | O | 3-methylisoxazol-3-yl | — |
| XIII-50 | O | 3,5-dimethylisoxazol-3-yl | — |

TABLE 105

| Compound No. | $X^1$ | $R^1$ | $R^2$ |
|---|---|---|---|
| XIII-51 | O | 3,5-dimethylisothiazol-5-yl | — |
| XIII-52 | O | 1,5-dimethyl-3-(trifluoromethyl)pyrazol-5-yl | — |
| XIII-53 | O | thiazol-2-yl | — |
| XIII-54 | O | 4-methylthiazol-2-yl | — |
| XIII-55 | O | 5-methyl-1,3,4-oxadiazol-2-yl | — |

TABLE 105-continued
| Compound No. | X¹ | R¹ | R² |
|---|---|---|---|
| XIII-56 | O | 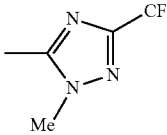 | — |
| XIII-57 | O | 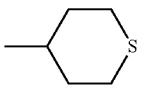 | — |
| XIII-58 | O | 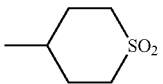 | — |
| XIII-59 | O | 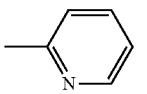 | — |
| XIII-60 | O | 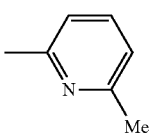 | — |
TABLE 106
| Compound No. | X¹ | R¹ | R² |
|---|---|---|---|
| XIII-61 | O | 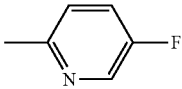 | — |
| XIII-62 | O | 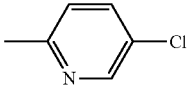 | — |
| XIII-63 | O | 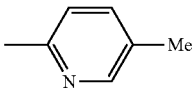 | — |
| XIII-64 | O | 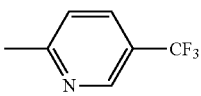 | — |
| XIII-65 | O | 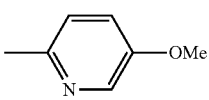 | — |
| XIII-66 | O | 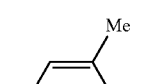 | — |
| XIII-67 | O | 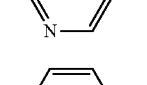 | — |
| XIII-68 | O | 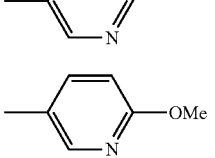 | — |
TABLE 106-continued
| Compound No. | X¹ | R¹ | R² |
|---|---|---|---|
| XIII-69 | O | 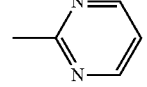 | — |
| XIII-70 | O | 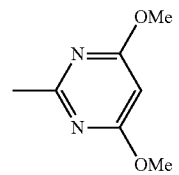 | — |
TABLE 107
| Compound No. | X¹ | R¹ | R² |
|---|---|---|---|
| XIII-71 | O | 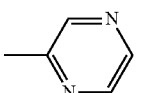 | — |
| XIII-72 | O | 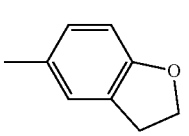 | — |
| XIII-73 | O | 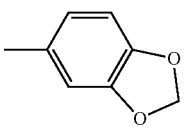 | — |
| XIII-74 | O | 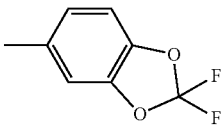 | — |
| XIII-75 | O | 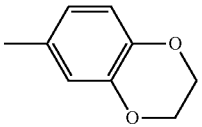 | — |
| XIII-76 | O | 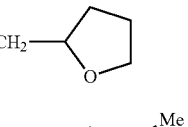 | — |
| XIII-77 | O | 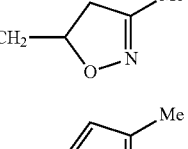 | — |
| XIII-78 | O | 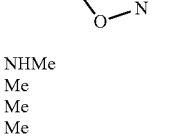 | — |
| XIII-79 | O | NHMe | — |
| XIII-80 | O | Me | 6-F |
| XIII-81 | O | Me | 7-F |
| XIII-82 | O | Me | 5-Cl |
| XIII-83 | O | Me | 6-Cl |
| XIII-84 | O | Me | 7-Cl |
| XIII-85 | O | Me | 8-Cl |

TABLE 108

| Compound No. | X¹ | R¹ | R² |
|---|---|---|---|
| XIII-86 | O | CH$_2$CH$_2$OMe | 8-Cl |
| XIII-87 | O | Me | 7-OMe |
| XIII-88 | O | Me | 5-SMe |
| XIII-89 | O | Me | 7-SMe |
| XIII-90 | O | Me | 5-SO$_2$Me |
| XIII-91 | O | Me | 7-SO$_2$Me |
| XIII-92 | O | Me | 6-NO$_2$ |
| XIII-93 | O | Me | 7-NO$_2$ |
| XIII-94 | S | Me | — |
| XIII-95 | O | 1-methylnaphthalen-yl | — |
| XIII-96 | O | 2-methylnaphthalen-yl | — |
| XIII-97 | O | 3-methyl-5-t-Bu-isoxazolyl | — |
| XIII-98 | O | 1,3,5-trimethylpyrazol-yl (3-Me, 5-Me, N-Me) | — |
| XIII-99 | O | 3-methyl-5-CF$_3$-1-methylpyrazolyl | — |
| XIII-100 | O | 2-methyl-4-CF$_3$-oxazolyl | — |

TABLE 109

| Compound No. | X¹ | R¹ | R² |
|---|---|---|---|
| XIII-101 | O | 2-methyl-1,3,4-thiadiazolyl | — |
| XIII-102 | O | 2-methyl-5-Me-1,3,4-thiadiazolyl | — |
| XIII-103 | O | 2-methyl-5-Br-pyridinyl | — |
| XIII-104 | O | 2-methyl-3-Me-pyridinyl | — |
| XIII-105 | O | 3-methyl-6-Cl-pyridazinyl | — |
| XIII-106 | O | 6-methyl-2-NHEt-4-NHi-Pr-1,3,5-triazinyl | — |
| XIII-107 | O | 6-methyl-4-Me-3-oxo-benzoxazin-yl | — |
| XIII-108 | O | 5-methyl-1-Me-indolyl | — |
| XIII-109 | O | 5-methyl-benzofuranyl | — |
| XIII-110 | O | N(Me)C(=O)Ot-Bu | — |

TABLE 110

| Compound No. | X¹ | R¹ | R² |
|---|---|---|---|
| XIII-111 | O | 5-methyl-2-OMe-pyridinyl | 5-F |
| XIII-112 | O | Bn | 6-F |
| XIII-113 | O | 3-methyl-5-Me-isoxazolyl | 6-F |
| XIII-114 | O | Me | 5-CH$_2$OMe |
| XIII-115 | O | 5-methyl-2-OMe-pyridinyl | 5,7-F$_2$ |
| XIII-116 | O | 2-methyl-5-Me-pyridinyl | 7-Cl |
| XIII-117 | O | Et | 5-Cl |
| XIII-118 | O | n-Bu | 5-Cl |
| XIII-119 | O | 2-methyl-5-Me-pyridinyl | 7-Me |

TABLE 110-continued

| Compound No. | X¹ | R¹ | R² |
|---|---|---|---|
| XIII-120 | O | 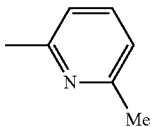 2,6-dimethylpyridin-3-yl | 6-CF₃ |
| XIII-121 | O | 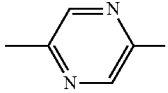 2,5-dimethylpyrazin-3-yl | — |
| XIII-122 | O | 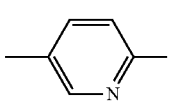 6-methoxy-5-methylpyridin-3-yl | 5-Cl |
| XIII-123 | O | 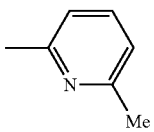 2,6-dimethylpyridin-3-yl | 6-F |
| XIII 124 | O | 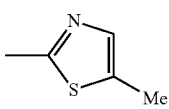 2-methyl-5-methylthiazole | — |
| XIII-125 | O | 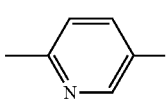 2,5-dimethylpyridin-3-yl | 5-F |
| XIII-126 | O | 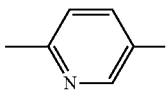 2,5-dimethylpyridin-3-yl | 5-Cl |
| XIII-127 | O | 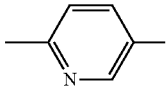 2,5-dimethylpyridin-3-yl | 5-Me |
| XIII-128 | O | 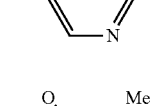 6-methoxy-5-methylpyridin-3-yl | 6-Me |
| XIII-129 | O | 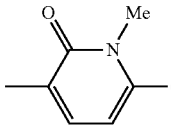 N-methyl-6-trifluoromethylpyridinone | — |

TABLE 111

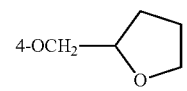

| Compound No. | X¹ | R¹² | R² |
|---|---|---|---|
| XIV-1 | O | — | — |
| XIV-2 | O | 2-F | — |
| XIV-3 | O | 3-F | — |
| XIV-4 | O | 4-F | — |
| XIV-5 | O | 2-Cl | — |
| XIV-6 | O | 3-Cl | — |
| XIV-7 | O | 4-Cl | — |
| XIV-8 | O | 3-Me | — |
| XIV-9 | O | 4-Me | — |
| XIV-10 | O | 3-Et | — |
| XIV-11 | O | 4-Et | — |
| XIV-12 | O | 3-i-Pr | — |
| XIV-13 | O | 4-c-Pr | — |
| XIV-14 | O | 3-CF₃ | — |
| XIV-15 | O | 4-CF₃ | — |
| XIV-16 | O | 4-OH | — |
| XIV-17 | O | 2-OMe | — |
| XIV-18 | O | 3-OMe | — |
| XIV-19 | O | 4-OMe | — |
| XIV-20 | O | 3-OEt | — |
| XIV-21 | O | 4-OEt | — |
| XIV-22 | O | 3-O—n-Pr | — |
| XIV-23 | O | 3-O—i-Pr | — |
| XIV-24 | O | 4-O—i-Pr | — |
| XIV-25 | O | 4-OCH₂CH=CH₂ | — |
| XIV-26 | O | 4-OCH₂C≡CH | — |

TABLE 112

| Compound No. | X¹ | R¹² | R² |
|---|---|---|---|
| XIV-27 | O | 3-OCHF₂ | — |
| XIV-28 | O | 4-OCHF₂ | — |
| XIV-29 | O | 3-OCF₃ | — |
| XIV-30 | O | 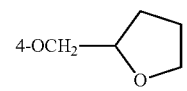 4-OCH₂-(tetrahydrofuran-2-yl) | — |
| XIV-31 | O | 3-SMe | — |
| XIV-32 | O | 4-SMe | — |
| XIV-33 | O | 3-SO₂Me | — |
| XIV-34 | O | 4-SO₂Me | — |
| XIV-35 | O | 2-NO₂ | — |
| XIV-36 | O | 3-NO₂ | — |
| XIV-37 | O | 4-NO₂ | — |
| XIV-38 | O | 3-CN | — |
| XIV-39 | O | 4-CN | — |
| XIV-40 | O | 4-C(=O)Me | — |
| XIV-41 | O | 4-C(=O)OMe | — |
| XIV-42 | O | 4-CH₂OMe | — |
| XIV-43 | O | 3-OMe, 4-Cl | — |
| XIV-44 | O | 3-OMe, 4-Me | — |
| XIV-45 | O | 3,4-(OMe)₂ | — |
| XIV-46 | O | 3,5-(OMe)₂ | — |
| XIV-47 | O | 2-F, 4-OMe | — |
| XIV-48 | O | 2-Cl, 4-OMe | — |
| XIV-49 | O | 2,4-(OMe)₂ | — |
| XIV-50 | O | 3-F, 4-OMe | — |
| XIV-51 | O | 3-Cl, 4-OMe | — |

TABLE 112-continued

| Compound No. | $X^1$ | $R^{12}$ | $R^2$ |
|---|---|---|---|
| XIV-52 | O | 3-Me, 4-OMe | — |
| XIV-53 | O | 3,4,5-(OMe)$_3$ | — |
| XIV-54 | O | 4-OMe | 5-F |
| XIV-55 | O | 4-OMe | 6-F |
| XIV-56 | O | 4-OMe | 7-F |

TABLE 113

| Compound No. | $X^1$ | $R^{12}$ | $R^2$ |
|---|---|---|---|
| XIV-57 | O | 4-OMe | 8-F |
| XIV-58 | O | — | 5-Cl |
| XIV-59 | O | — | 8-Cl |
| XIV-60 | O | 4-OMe | 5-Cl |
| XIV-61 | O | 4-OMe | 6-Cl |
| XIV-62 | O | 4-OMe | 7-Cl |
| XIV-63 | O | 4-OMe | 8-Cl |
| XIV-64 | O | 4-OCH$_2$CN | — |
| XIV-65 | O | 4-OCH$_2$—c-Pr | — |
| XIV-66 | O | 4-OCH$_2$CF$_3$ | — |
| XIV-67 | O | 4-NMe$_2$ | — |
| XIV-68 | O | 3,4-Me$_2$ | — |
| XIV-69 | O | 2-F, 4-Me | — |
| XIV-70 | O | 3-F, 4-Me | — |
| XIV-71 | O | 3-Me, 4-F | — |
| XIV-72 | O | 2-Cl, 4-Me | — |
| XIV-73 | O | 3-Cl, 4-Me | — |
| XIV-74 | O | 3-OEt, 4-OMe | — |
| XIV-75 | O | 2,3,4-(OMe)$_3$ | — |
| XIV-76 | O | 2,5-F$_2$, 4-OMe | — |
| XIV-77 | O | 3,5-F$_2$, 4-OMe | — |
| XIV-78 | O | 3,5-Cl$_2$, 4-OMe | — |
| XIV-79 | O | 3,4-(CH$_2$CH$_2$CH$_2$)— | — |
| XIV-80 | O | 3,4-(CH$_2$CH$_2$CH$_2$CH$_2$)— | — |
| XIV-81 | O | 3,4-(CH$_2$OCH$_2$)— | — |
| XIV-82 | O | 3,4-(OCH$_2$O)— | 7-F |
| XIV-83 | O | 2,3-(OCH$_2$CH$_2$O)— | — |
| XIV-84 | O | 3,4-(OCH$_2$CH(Me)O)— | — |
| XIV-85 | O | 3,4-(OCH$_2$CH$_2$CH$_2$O)— | — |

TABLE 114

| Compound No. | $X^1$ | $R^{12}$ | $R^2$ |
|---|---|---|---|
| XIV-86 | O | — | 5-F |
| XIV-87 | O | 3,4,5-(OMe)$_3$ | 5-F |
| XIV-88 | O | 3,5-F$_2$, 4-OMe | 5-F |
| XIV-89 | O | 3,4-(OCH$_2$CH$_2$O)— | 5-F |
| XIV-90 | O | — | 6-F |
| XIV-91 | O | 3,4,5-(OMe)$_3$ | 6-F |
| XIV-92 | O | 3,4-(OCH$_2$O)— | 6-F |
| XIV-93 | O | 3,4-(OCH$_2$CH$_2$O)— | 6-F |
| XIV-94 | O | — | 7-F |
| XIV-95 | O | 3,4-(OCH$_2$CH$_2$O)— | 7-F |
| XIV-96 | O | — | 8-F |
| XIV-97 | O | — | 5-Me |
| XIV-98 | O | 4-OMe | 5-Me |
| XIV-99 | O | 4-OMe | 6-Me |
| XIV-100 | O | 4-OMe | 7-Me |
| XIV-101 | O | 3,5-F$_2$, 4-OMe | 7-Me |
| XIV-102 | O | — | 6-CF$_3$ |
| XIV-103 | O | — | 6-OMe |
| XIV-104 | O | 4-OMe | 6-OMe |
| XIV-105 | O | — | 7-OMe |
| XIV-106 | O | 4-OMe | 7-OMe |
| XIV-107 | O | 2,5-F$_2$, 4-OMe | 7-OMe |
| XIV-108 | O | 3,5-F$_2$, 4-OMe | 7-OMe |
| XIV-109 | O | — | 8-OMe |
| XIV-110 | O | 4-OMe | 8-OMe |
| XIV-111 | O | 4-OMe | 5,6-F$_2$ |
| XIV-112 | O | 4-OMe | 5,7-F$_2$ |
| XIV-113 | O | — | 6,7-F$_2$ |

TABLE 115

| Compound No. | $X^1$ | $R^{12}$ | $R^2$ |
|---|---|---|---|
| XIV-114 | O | — | 6,8-F$_2$ |
| XIV-115 | O | 4-OMe | 5,7-Cl$_2$ |
| XIV-116 | O | 4-OMe | 6-F, 7-OMe |
| XIV-117 | O | 3-F, 4-OMe | 5-Cl |
| XIV-118 | O | 4-OMe | 5,6,8-F$_3$, 7-OMe |
| XIV-119 | O | — | 7-CF$_3$ |
| XIV-120 | O | 4-F | 7-OMe |
| XIV-121 | O | 4-OCHF$_2$ | 7-OMe |
| XIV-122 | O | 4-Me | 7-OMe |
| XIV-123 | O | 4-OMe | 5-Br |
| XIV-124 | O | 4-F | 5-F |
| XIV-125 | O | 3-F, 4-OEt | — |

TABLE 116

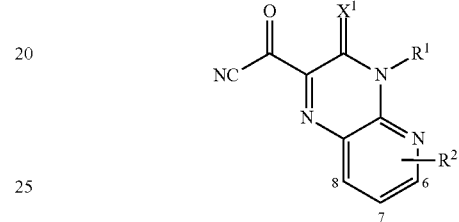

| Compound No. | $X^1$ | $R^1$ | $R^2$ |
|---|---|---|---|
| XV-1 | O | Me | — |
| XV-2 | O | Et | — |
| XV-3 | O | n-Pr | — |
| XV-4 | O | i-Pr | — |
| XV-5 | O | n-Bu | — |
| XV-6 | O | s-Bu | — |
| XV-7 | O | CH$_2$CH=CH$_2$ | — |
| XV-8 | O | CH$_2$C≡CH | — |
| XV-9 | O | CH$_2$CF$_3$ | — |
| XV-10 | O | CH$_2$CH$_2$F | — |
| XV-11 | O | CH$_2$OCH$_2$CF$_3$ | — |
| XV-12 | O | CH$_2$SMe | — |
| XV-13 | O | CH$_2$CH$_2$OMe | — |
| XV-14 | O | CH(Me)CH$_2$OMe | — |
| XV-15 | O | CH$_2$C(=O)OEt | — |
| XV-16 | O | CH$_2$C(=O)Ot-Bu | — |
| XV-17 | O | Bn | — |
| XV-18 | O | (2-F)Bn | — |
| XV-19 | O | (2-Cl)Bn | — |
| XV-20 | O | (2-CF$_3$)Bn | — |
| XV-21 | O | (3-CF$_3$)Bn | — |
| XV-22 | O | (2-OMe)Bn | — |
| XV-23 | O | CH(Me)Ph | — |
| XV-24 | O | 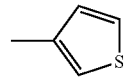 | — |

TABLE 117

| Compound No. | $X^1$ | $R^1$ | $R^2$ |
|---|---|---|---|
| XV-25 | O | | — |
| XV-26 | O | | — |

TABLE 117-continued

| Compound No. | X¹ | R¹ | R² |
|---|---|---|---|
| XV-27 | O | 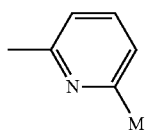 | — |
| XV-28 | O | 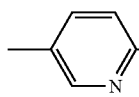 | — |
| XV-29 | O | 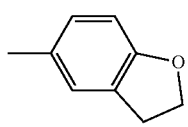 | — |
| XV-30 | O | 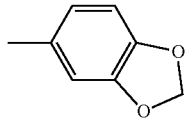 | — |
| XV-31 | O | 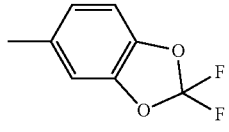 | — |
| XV-32 | O | 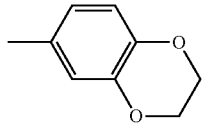 | — |
| XV-33 | O | 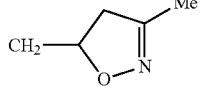 | — |
| XV-34 | O | 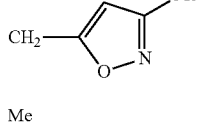 | — |
| XV-35 | O | Me | 6-Cl |

TABLE 118

| Compound No. | X¹ | R¹ | R² |
|---|---|---|---|
| XV-36 | O | Me | 6-OMe |
| XV-37 | O | CH₂CH₂CH=CH₂ | — |
| XV-38 | O | CH₂CH₂CH=C(Me)₂ | — |
| XV-39 | O | CH₂CH₂C≡CH | — |
| XV-40 | O | CH₂CH₂C(Me)=CF₂ | — |
| XV-41 | O | CH(Me)C(=O)Ot-Bu | — |
| XV-42 | O | (2-OCHF₂)Bn | — |
| XV-43 | O | CH₂CH₂Ph | — |
| XV-44 | O | 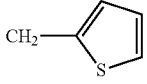 | — |
| XV-45 | O | 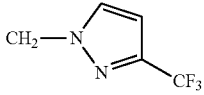 | — |

TABLE 118-continued

| Compound No. | X¹ | R¹ | R² |
|---|---|---|---|
| XV-46 | O | 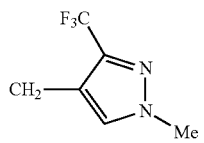 | — |
| XV-47 | O | 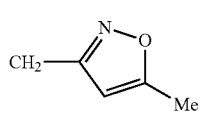 | — |
| XV-48 | O | 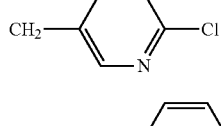 | — |
| XV-49 | O | 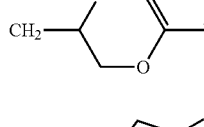 | — |
| XV-50 | O | 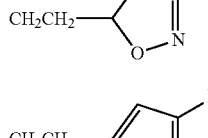 | — |
| XV-51 | O |  | — |
| XV-52 | O | Bn | 8-Me |
| XV-53 | O | Bn | 7-Me |
| XV-54 | O | Bn | 6-Me |
| XV-55 | O | Bn | 6-OMe |

TABLE 119

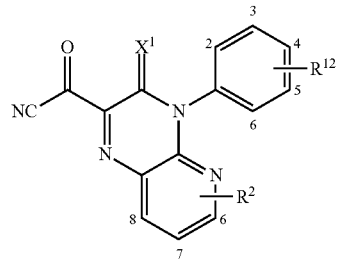

| Compound No. | X¹ | R¹² | R² |
|---|---|---|---|
| XVI-1 | O | — | — |
| XVI-2 | O | 2-F | — |
| XVI-3 | O | 3-F | — |
| XVI-4 | O | 4-F | — |
| XVI-5 | O | 2-Cl | — |
| XVI-6 | O | 3-Cl | — |
| XVI-7 | O | 4-Cl | — |
| XVI-8 | O | 3-Br | — |
| XVI-9 | O | 4-Br | — |
| XVI-10 | O | 2-Me | — |
| XVI-11 | O | 3-Me | — |
| XVI-12 | O | 4-Me | — |
| XVI-13 | O | 3-Et | — |
| XVI-14 | O | 4-Et | — |
| XVI-15 | O | 4-i-Pr | — |

TABLE 119-continued

| Compound No. | X¹ | R¹² | R² |
|---|---|---|---|
| XVI-16 | O | 4-c-Pr | — |
| XVI-17 | O | 2-CF₃ | — |
| XVI-18 | O | 3-CF₃ | — |
| XVI-19 | O | 4-CF₃ | — |
| XVI-20 | O | 2-OMe | — |
| XVI-21 | O | 3-OMe | — |
| XVI-22 | O | 4-OMe | — |
| XVI-23 | O | 2-OCHF₂ | — |
| XVI-24 | O | 3-OCHF₂ | — |
| XVI-25 | O | 4-OCHF₂ | — |

TABLE 120

| Compound No. | X¹ | R¹² | R² |
|---|---|---|---|
| XVI-26 | O | 2-OCF₃ | — |
| XVI-27 | O | 3-OCF₃ | — |
| XVI-28 | O | 4-OCF₃ | — |
| XVI-29 | O | 4-SCF₃ | — |
| XVI-30 | O | 3-CN | — |
| XVI-31 | O | 2,3-F₂ | — |
| XVI-32 | O | 2,4-F₂ | — |
| XVI-33 | O | 2,5-F₂ | — |
| XVI-34 | O | 2,6-F₂ | — |
| XVI-35 | O | 3,4-F₂ | — |
| XVI-36 | O | 3,5-F₂ | — |
| XVI-37 | O | 2,3-Cl₂ | — |
| XVI-38 | O | 2,4-Cl₂ | — |
| XVI-39 | O | 2,5-Cl₂ | — |
| XVI-40 | O | 2,6-Cl₂ | — |
| XVI-41 | O | 3,4-Cl₂ | — |
| XVI-42 | O | 3,5-Cl₂ | — |
| XVI-43 | O | 2,3-(OMe)₂ | — |
| XVI-44 | O | 3-OMe, 4-F | — |
| XVI-45 | O | 3-OMe, 4-Me | — |
| XVI-46 | O | 3,4-(OMe)₂ | — |
| XVI-47 | O | 3-OMe, 5-F | — |
| XVI-48 | O | 3,5-(OMe)₂ | — |
| XVI-49 | O | 2-F, 4-OMe | — |
| XVI-50 | O | 2,4-(OMe)₂ | — |
| XVI-51 | O | 3-F, 4-OMe | — |
| XVI-52 | O | 3-Cl, 4-OMe | — |
| XVI-53 | O | 3-Me, 4-OMe | — |
| XVI-54 | O | 2,5-(OMe)₂ | — |
| XVI-55 | O | 3,4,5-(OMe)₃ | — |

TABLE 121

| Compound No. | X¹ | R¹² | R² |
|---|---|---|---|
| XVI-56 | O | — | 6-F |
| XVI-57 | O | 4-OMe | 6-F |
| XVI-58 | O | — | 6-Cl |
| XVI-59 | O | 4-OMe | 6-Cl |
| XVI-60 | O | 4-OMe | 6-OMe |
| XVI-61 | O | 2-F,5-CF₃ | — |
| XVI-62 | O | 3-CF₃,4-F | — |
| XVI-63 | O | 2-F,3-CF₃ | — |
| XVI-64 | O | 3-F,5-CF₃ | — |

TABLE 121-continued

| Compound No. | X¹ | R¹² | R² |
|---|---|---|---|
| XVI-65 | O | 2,5-(Me)₂ | — |
| XVI-66 | O | 3,4-(Me)₂ | — |
| XVI-67 | O | 3,5-(Me)₂ | — |
| XVI-68 | O | 3,5-(CF₃)₂ | — |
| XVI-69 | O | 2,6-(OMe)₂ | — |
| XVI-70 | O | 2-F, 3-Cl | — |
| XVI-71 | O | 2-F, 4-Cl | — |
| XVI-72 | O | 2-F, 5-Cl | — |
| XVI-73 | O | 3-F, 4-Cl | — |
| XVI-74 | O | 4-F, 2-Cl | — |
| XVI-75 | O | 4-F, 3-Cl | — |
| XVI-76 | O | 2-F, 3-Me | — |
| XVI-77 | O | 2-F, 4-Me | — |
| XVI-78 | O | 2-F, 5-Me | — |
| XVI-79 | O | 3-F, 2-Me | — |
| XVI-80 | O | 3-F, 4-Me | — |

TABLE 122

| Compound No. | X¹ | R¹² | R² |
|---|---|---|---|
| XVI-81 | O | 3-F, 5-Me | — |
| XVI-82 | O | 4-F, 2-Me | — |
| XVI-83 | O | 4-F, 3-Me | — |
| XVI-84 | O | 5-F, 2-Me | — |
| XVI-85 | O | 2-F, 4-CF₃ | — |
| XVI-86 | O | 3-F, 4-CF₃ | — |
| XVI-87 | O | 4-F, 2-CF₃ | — |
| XVI-88 | O | 3-F, 2-OMe | — |
| XVI-89 | O | 4-F, 2-OMe | — |
| XVI-90 | O | 5-F, 2-OMe | — |
| XVI-91 | O | 2-F, 4-OCHF₂ | — |
| XVI-92 | O | 3-F, 4-OCHF₂ | — |
| XVI-93 | O | 4-F, 2-OCHF₂ | — |
| XVI-94 | O | 4-F, 3-CN | — |
| XVI-95 | O | 2-Cl, 4-Me | — |
| XVI-96 | O | 3-Cl, 4-Me | — |
| XVI-97 | O | 3-Cl, 4-OCHF₂ | — |
| XVI-98 | O | 4-Me, 3-CF₃ | — |
| XVI-99 | O | 4-Me, 2-OMe | — |
| XVI-100 | O | 3-Me, 4-CN | — |
| XVI-101 | O | 4-Me, 3-CN | — |
| XVI-102 | O | 2,3,4-F₃ | — |
| XVI-103 | O | 2,3,5-F₃ | — |
| XVI-104 | O | 2,4,5-F₃ | — |
| XVI-105 | O | 3,4,5-F₃ | — |
| XVI-106 | O | 2,3-F₂, 4-Me | — |
| XVI-107 | O | 2,6-F₂, 4-OMe | — |

TABLE 123

| Compound No. | X¹ | R¹² | R² |
|---|---|---|---|
| XVI-108 | O | 3,5-F₂, 4-OMe | — |
| XVI-109 | O | 4-F, 2-Cl, 5-Me | — |
| XVI-110 | O | — | 7-Cl |
| XVI-111 | O | — | 6-Me |
| XVI-112 | O | — | 7-Me |
| XVI-113 | O | — | 8-Me |
| XVI-114 | O | 3-Me | 8-Me |
| XVI-115 | O | 3-CF₃ | 8-Me |
| XVI-116 | O | 4-OMe | 8-Me |
| XVI-117 | O | 3-F, 4-Me | 8-Me |
| XVI-118 | O | 3-F, 4-OMe | 8-Me |
| XVI-119 | O | — | 8-OMe |
| XVI-120 | O | 3-CF₃ | 8-OMe |
| XVI-121 | O | 3-F, 4-Me | 8-Cl |
| XVI-122 | O | 3-F, 4-Me | 6-F |
| XVI-123 | O | 3-F, 4-Me | 6-Cl |
| XVI-124 | O | 3-F, 4-Me | 7-Me |
| XVI-125 | O | 3-F, 4-Me | 6-Me |
| XVI-126 | O | — | 8-Cl |
| XVI-127 | O | 3-F, 4-Me | 6-OMe |

TABLE 123-continued

| Compound No. | $X^1$ | $R^{12}$ | $R^2$ |
|---|---|---|---|
| XVI-128 | O | 3-OEt | — |
| XVI-129 | O | 4-OEt | — |
| XVI-130 | O | 4-OMe | 8-Cl |
| XVI-131 | O | — | 6-SMe |
| XVI-132 | O | 3,4-(OCH$_2$CH$_2$O)— | 6-OMe |
| XVI-133 | O | 3-F, 4-OEt | — |
| XVI-134 | O | 3,4-(OCH$_2$O)— | 8-Cl |

Representative methods for producing the compound of the present invention represented by formula [I] will be-illustrated below, but the method is not to be limited to these methods.

<Production Method 1>

The compound of the present invention represented by the following formula [1a] can be produced by the methods based on the reaction scheme as-illustrated in the following.

(Process 1)

Enol ester compounds represented by formulas [4a] and [4b] can be produced by allowing a compound represented by formula [2] to react with a compound represented by formula [3a] in a solvent in the presence of a base.

(Hereinafter, for example, the "compound represented by formula [2]" may also be simply described as "formula [2].")

The amount of use of the formula [3a] as used herein may be appropriately selected in the range of 0.5 to 10 moles, and preferably 1.0 to 1.2 moles, based on 1 mole of the formula [2].

As the base that can be used in the present process, for example, organic amines such as triethylamine, pyridine, 4-dimethylaminopyridine, N,N-dimethylaniline and 1,8-di-azabicyclo[5.4.0]-7-undecene; carboxylic acid metal salts represented by metal carbonates such as sodium carbonate, potassium carbonate, magnesium carbonate and calcium car-

[Chemical Formula 12]

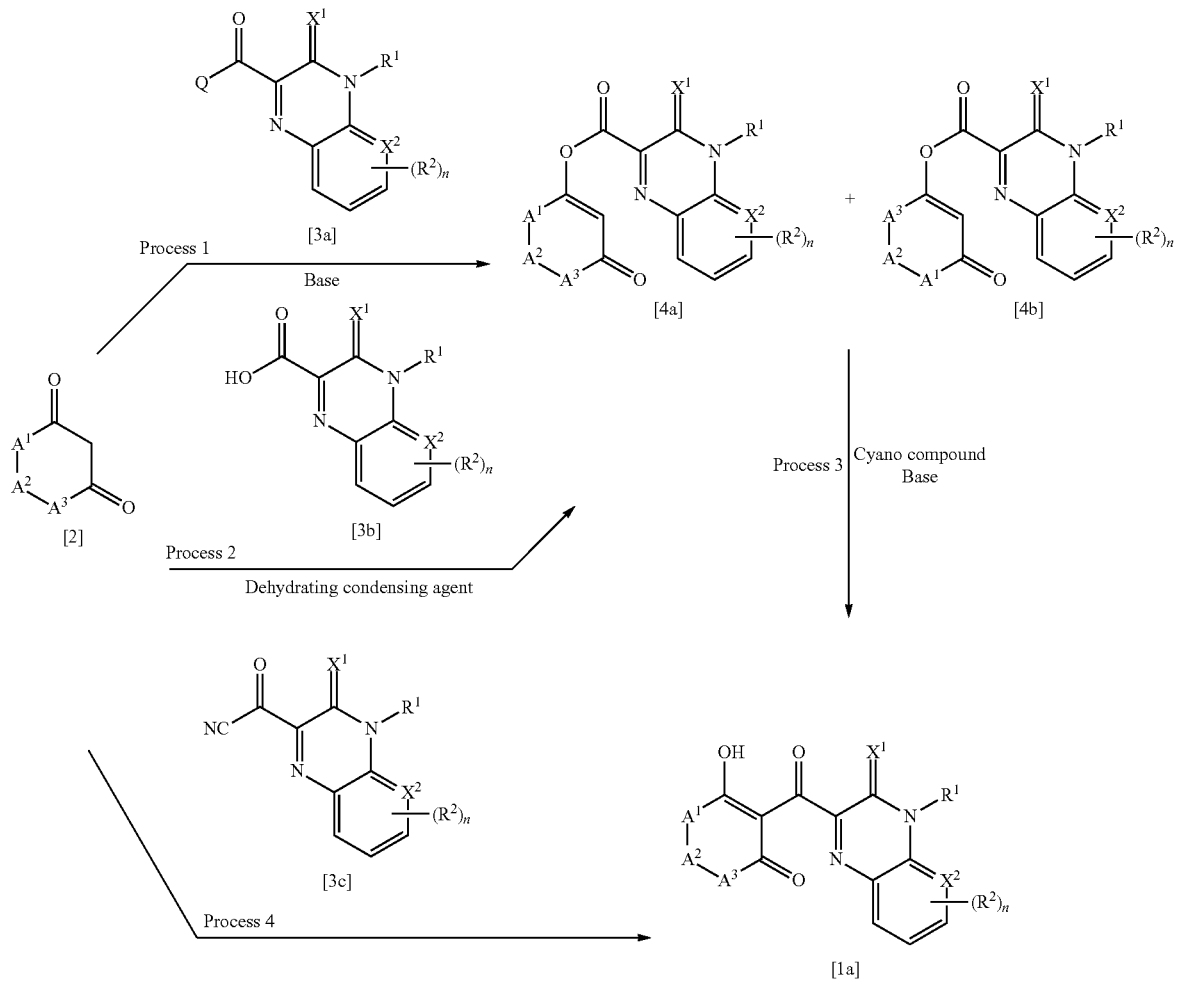

wherein $R^1$, $R^2$, $A^1$, $A^2$, $A^3$, n, $X^1$ and $X^2$ respectively have the same meanings as defined above; and Q represents a leaving group such as halogen, an alkylcarbonyloxy group, an alkoxycarbonyloxy group, a haloalkylcarbonyloxy group, a haloalkoxycarbonyloxy group, a benzoyloxy group, a pyridyl group or an imidazolyl group.

bonate; metal hydrogen carbonates such as sodium hydrogen carbonate and potassium hydrogen carbonate; and metal acetates such as sodium acetate, potassium acetate, calcium acetate and magnesium acetate; metal alkoxides such as sodium methoxide, sodium ethoxide, sodium tertiary butox-ide, potassium methoxide and potassium tertiary butoxide;

metal hydroxides such as sodium hydroxide, potassium hydroxide, calcium hydroxide and magnesium hydroxide; metal hydrides such as lithium hydride, sodium hydride, potassium hydride and calcium hydride; and the like may be included.

The amount of use of the base may be appropriately selected in the range of 0.5 to 10 moles, and preferably 1.0 to 1.2 moles, based on one mole of the formula [2].

The solvent that can be used in the present process may be any solvent as long as it does not inhibit the progress of the present reaction, and for example, nitriles such as acetonitrile; ethers such as diethyl ether, diisopropyl ether, tetrahydrofuran, dioxane, monoglyme and diglyme; halogenated hydrocarbons such as dichloroethane, chloroform, tetrachlorocarbon and tetrachloroethane; aromatic hydrocarbons such as benzene, chlorobenzene, nitrobenzene and toluene; amides such as N,N-dimethylformamide and N,N-dimethylacetamide; imidazolinones such as 1,3-dimethyl-2-imidazolinone; sulfur compounds such as dimethylsulfoxide; and the like can be used. Further, solvent mixtures of these can also be used.

The amount of use of the solvent is 0.01 to 100 L, and preferably 0.1 to 10 L, based on the formula [2].

The reaction temperature may be selected in the range of −20° C. to the boiling point region of the inert solvent used, and is preferably selected in the range of 0° C. to 100° C.

Furthermore, the reaction can be performed using a phase transfer catalyst such as a quaternary ammonium salt. In the case of using a phase transfer catalyst, the amount of use thereof is 0.0001 to 1.0 mole, and preferably 0.001 to 0.1 moles, based on one mole of the formula [2].

The reaction time may vary depending on the reaction temperature, reaction substrate, the extent of reaction and the like, but is usually from 10 minutes to 48 hours.

The compounds of formula [4a] and formula [4b], which are the target products of the reaction, can be collected from the reaction system by a conventional method after completion of the reaction, and then can be purified by operations such as column chromatography and recrystallization, as necessary.

(Process 2)

The formulas [4a] and [4b] can also be produced by allowing the formula [2] and the formula [3b] to react in a solvent in the presence of a dehydrating condensing agent in the presence or absence of a base.

The amount of use of the formula [3b] as used in the present process may be appropriately selected in the range of 0.5 to 10 moles, and preferably 1.0 to 1.2 moles, based on one mole of the formula [2].

As the dehydrating condensing agent, dicyclohexylcarbodiimide (DCC), N-(3-dimethylaminopropyl)-N'-ethylcarbodiimide (EDC or WSC), N,N-carbonyldiimidazole, 2-chloro-1,3-dimethylimidazolium chloride, 2-chloro-1-pyridinium iodide and the like can be used.

The base and the solvent that can be used in the present process may be exemplified by those described in the Process 1.

The amount of the base used in the reaction of the present process is 0 to 100 moles, and preferably 0 to 10 moles, based on one mole of the formula [2].

The amount of use of the solvent is 0.01 to 100 L, and preferably 0.1 to 10 L, based on one mole of the formula [2].

The reaction temperature may be appropriately selected in the range of −20° C. to the boiling point region of the inert solvent used, and is preferably selected in the range of 0° C. to 100° C.

The reaction time may vary depending on the reaction temperature, reaction substrate, the extent of reaction and the like, but is usually from 10 minutes to 48 hours.

(Process 3)

The formula [1a] can be produced by reacting the formula [4a] and the formula [4b] produced in the process 2 or 3, with a cyano compound in the presence of a base.

The base that can be used in the present process may be exemplified by the same bases as those described with regard to the process 1.

The amount of use of the base may be appropriately selected in the range of 0.5 to 10 moles, and preferably 1.0 to 1.2 moles, based on one mole of the formula [4a] and formula [4b].

The cyano compound that can be used in the present process may be exemplified by potassium cyanide, sodium cyanide, acetone cyanohydrin, hydrogen cyanide, a polymer carrying hydrogen cyanide, and the like.

The amount of use of the cyano compound may be appropriately selected in the range of 0.01 to 1.0 moles, and preferably 0.05 to 0.2 moles, based on one mole of the formulas [4a] and [4b].

Furthermore, in the present process, a phase transfer catalyst such as crown ether may also be used.

The amount of use of the phase transfer catalyst is 0.001 to 10 moles, and preferably 0.01 to 1.0 mole, based on one mole of the formulas [4a] and [4b].

The solvent that can be used in the present reaction may be exemplified by the same solvents as those described with regard to the process 1, and the amount of use thereof is 0.01 to 100 L, and preferably 0.1 to 10 L, based on one mole of the formulas [4a] and [4b].

The reaction temperature may be selected in the range of −20° C. to the boiling point region of the inert solvent used, and is preferably selected in the range of 0° C. to 100° C.

The reaction time may vary depending on the reaction temperature, reaction substrate, the extent of reaction and the like, but is usually from 10 minutes to 48 hours.

Additionally, in the present process, the formula [1a] can still be produced, even if the formulas [4a] and [4b] produced in the process 1 or process 2 are used without being isolated.

(Process 4)

The compound of the formula [1a] can also be produced by reacting the formula [2] with the formula [3c] in the presence of a base or a Lewis acid. In addition, the production intermediate of the formula [3c] can be produced by reacting a compound represented by formula [3a-1] with a cyanogenating agent. The amount of use of the formula [3c] used in the present process may be appropriately selected in the range of 0.5 to 10 moles, and preferably 1.0 to 1.2 moles, based on one mole of the formula [2].

The Lewis acid that can be used includes zinc chloride, aluminum chloride and the like.

In the case of using a Lewis acid, the amount of use of the Lewis acid may be appropriately selected in the range of 0.01 to 100 moles, and preferably 0.1 to 10 moles, based on one mole of the formula [2].

The base that can be used in the present process may be exemplified by the same bases as those described with regard to the process 1.

In the case of using a base, the amount of use of the base may be appropriately selected in the range of 0.5 to 10 moles, and preferably 1.0 to 1.2 moles, based on one mole of the formula [2].

The solvent that can be used in the present process may be exemplified by the same solvents as those described with regard to the process 1, and the amount of use thereof is 0.01 to 100 L, and preferably 0.1 to 10 L, based on one mole of the formula [2].

The reaction temperature may be selected in the range of −20° C. to the boiling point region of the inert solvent used, and is preferably selected in the range of 0° C. to 100° C.

The reaction time may vary depending on the reaction temperature, reaction substrate, the extent of reaction and the like, but is usually from 10 minutes to 48 hours.

<Production Method 2>

Furthermore, compounds represented by formula [1b] and [1c] of the present invention can be produced from the compound represented by the formula [1a] of the present invention, according to the following production method.

[Chemical Formula 13]

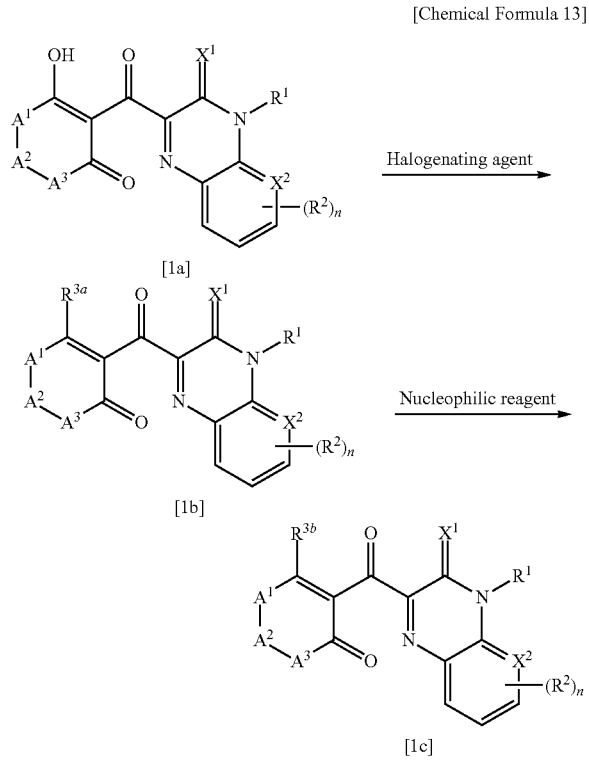

wherein $X^1, X^2, R^1, R^2, A^1, A^2, A^3$ and n respectively have the same meanings as defined above; $R^{3a}$ represents a halogen atom such as chlorine or bromine; and $R^{3b}$ represents an amino group, a $C_1$-$C_6$ alkylthio group, a $C_1$-$C_6$ alkyl-$C_1$-$C_6$ haloalkylthio group, a $C_2$-$C_6$ alkenylthio group, a $C_2$-$C_6$ alkynylthio group, a $C_1$-$C_6$ alkylcarbonyloxy group, a $C_2$-$C_6$ alkenylcarbonyloxy group, a $C_2$-$C_6$ alkynylcarbonyloxy group, a phenoxy group (the group may be substituted with one or two or more identical or different $R^{14}$s), a phenylthio group (the group may be substituted with one or two or more identical or different $R^{14}$s), a phenylcarbonyloxy group (the group may be substituted with one or two or more identical or different $R^{14}$s), a 1,2,4-triazol-1-yl group, a 1,2,3-triazol-1-yl group, a 1,2,3-triazol-2-yl group, an imidazol-1-yl group, a pyrazol-1-yl group, a tetrazol-1-yl group, or a tetrazol-2-yl group.

In other words, the compound of formula [1b] can be produced by reacting the compound of formula [1a] with a halogenating agent, and the compound of formula [1c] can be produced by reacting the compound of formula [1b] with a nucleophilic reagent in the presence of a base.

The halogenating agent that can be used in the process of converting from the formula [1a] to the formula [1b], includes thionyl chloride, thionyl bromide, phosphorus oxychloride, phosphorus oxybromide, phenyltrimethylammonium tribromide, a bromide of Meldrums acid, and the like. The amount of use of the halogenating agent may be appropriately selected in the range of 0.5 to 10 moles, and preferably 1.0 to 1.2 moles, based on one mole of the compound of formula [1a].

The solvent that can be used may be exemplified by the same solvents as those described with regard to the process 1 of the production method 1.

The reaction temperature may be selected in the range of −20° C. to the boiling point region of the inert solvent used, and is preferably selected in the range of 0° C. to 100° C. The reaction time may vary depending on the reaction temperature, reaction substrate, the extent of reaction, and the like, but is usually from 10 minutes to 48 hours.

As the nucleophilic reagent that can be used in the process of converting from the formula [1b] to the formula [1c], alcohols such as methanol, ethanol and benzyl alcohol; mercaptans such as methyl mercaptan and ethyl mercaptan; amines such as ammonia, methylamine and ethylamine; and the like may be included. The amount of use of the nucleophilic reagent may be appropriately selected in the range of 0.5 to 10 moles, and preferably 1.0 to 1.2 moles, based on one mole of the compound of formula [1a].

The base that can be used may be exemplified by the same bases as those described with regard to the process 1 of the production method 1, and the solvent that can be used may be exemplified by the same solvents as those described with regard to the process 1 of the production method 1.

The reaction temperature may be selected in the range of −20° C. to the boiling point region of the inert solvent used, and is preferably selected in the range of 0° C. to 100° C. The reaction time may vary depending on the reaction temperature, reaction substrate, the extent of reaction, and the like, but is usually from 10 minutes to 48 hours.

<Production Method 3>

The compound of the present invention represented by the following formula [1d] can be produced by a method as shown in the reaction scheme-illustrated below.

[Chemical Formula 14]

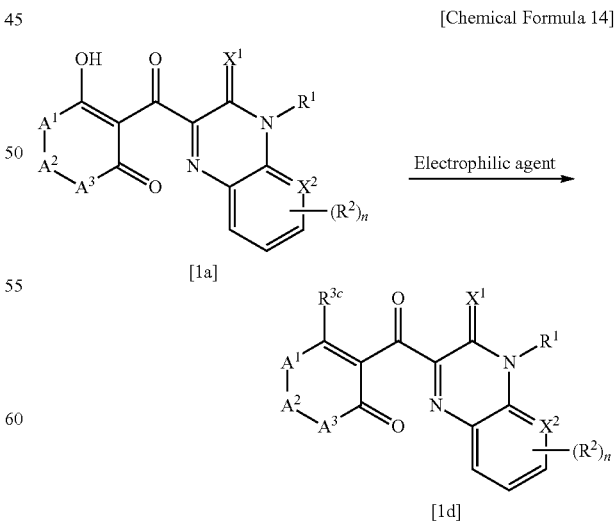

wherein $X^1, X^2, R^1, R^2, A^1, A^2, A^3$ and n respectively have the same meanings as defined above; and $R^{3c}$ represents a $C_1$-$C_6$ alkoxy group, a $C_1$-$C_6$ alkylsulfonyloxy group, a $C_1$-$C_6$ alkylcarbonyloxy group, a $C_2$-$C_6$ alkenylcarbonyloxy group, a $C_2$-$C_6$ alkynylcarbonyloxy group, a phenylsulfonyloxy group (the group may be substituted with one or two or more identical or different $R^{14}$s) or a phenylcarbonyloxy group (the group may be substituted with one or two or more identical or different $R^{14}$s).

In other words, the compound of formula [1d] can be produced by reacting the compound of formula [1a] with an electrophilic reagent in a solvent in the presence/absence of a base.

As the electrophilic reagent that can be used, halides such as iodomethane and benzyl bromide; acid chlorides such as acetyl chloride and benzoyl chloride; sulfonic acid chlorides such as methanesulfonyl chloride and p-toluenesulfonyl chloride; sulfuric acid esters such as dimethyl sulfuric acid and diethyl sulfuric acid; and the like may be included, for example. The amount of use of the electrophilic reagent may be appropriately selected in the range of 0.1 to 10 moles, and preferably 1.0 to 1.2 moles, based on one mole of the compound of formula [1a].

The base that can be used may be exemplified by the same bases as those described with regard to the process 1 of the production method 1, and the amount of use of the base may be appropriately selected in the range of 0 to 10 moles, and preferably 1.0 to 1.2 moles, based on one mole of the compound of formula [1a].

The solvent that can be used may be exemplified by the same solvents as those described with regard to the process 1 of the production method 1.

The reaction temperature may be selected in the range of –20° C. to the boiling point region of the inert solvent used, and is preferably selected in the range of 0° C. to 100° C. The reaction time may vary depending on the reaction temperature, reaction substrate, the extent of reaction, and the like, but is usually from 10 minutes to 48 hours.

The method for producing a production intermediate for the compound of the present invention will be described.

<Intermediate Production Method 1>

[Chemical Formula 15]

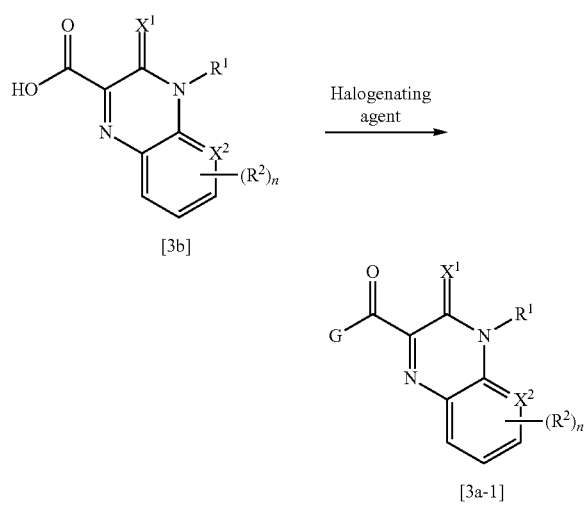

wherein $R^1$, $R^2$, n, $X^1$ and $X^2$ respectively have the same meanings as defined above; and G represents a halogen atom such as chlorine or bromine.

The formula [3a-1] which is a production intermediate for the compound of the present invention, can be produced by reacting the formula [3b] with an appropriate halogenating agent in a solvent or without solvent.

As the halogenating agent that can be used in the present process, oxalyl chloride, thionyl chloride and the like may be included, for example.

The amount of use of the halogenating agent may be appropriately selected in the range of 0.01 to 100 moles, and preferably 0.1 to 10 moles, based on one mole of the formula [3b].

Examples of the solvent include halogenated hydrocarbons such as dichloromethane and chloroform; ethers such as diethyl ether and tetrahydrofuran; and aromatic hydrocarbons such as benzene and toluene.

The amount of use of the solvent is 0 to 100 L, and preferably 0.01 to 10 L, based on one mole of the formula [3b].

The reaction temperature may be selected in the range of –100° C. to 200° C., and is preferably selected to be from 0° C. to 100° C.

The reaction time may vary with the reaction temperature, reaction substrate, the extent of reaction and the like, but is usually from 10 minutes to 24 hours.

<Intermediate Production Method 2>

[Chemical Formula 16]

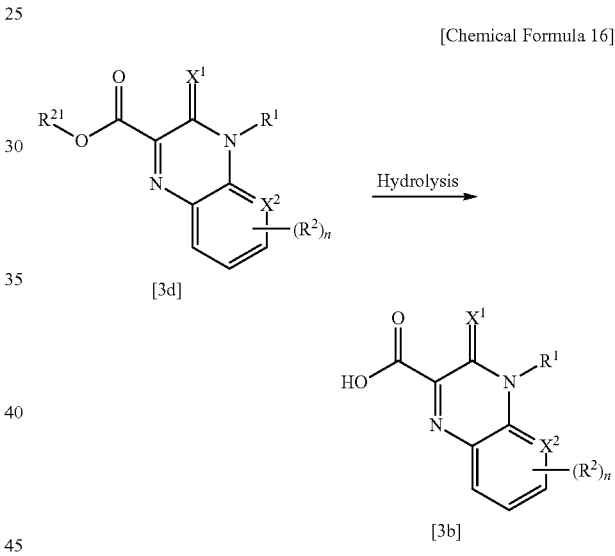

wherein $R^1$, $R^2$, n, $X^1$ and $X^2$ respectively have the same meanings as defined above; and $R^{21}$ represents a lower alkyl group, a benzyl group which may be substituted, or a phenyl group which may be substituted.

The production intermediate of formula [3b] can be produced by hydrolyzing the formula [3d] in water or a solvent mixture, in the presence of an acid or in the presence of a base.

As the base that can be used in the present process, inorganic bases such as potassium carbonate, sodium hydride and sodium hydroxide; and organic bases such as 1,8-diazabicyclo[5,4,0]-7-undecene may be included, for example.

The amount of use of the base may be appropriately selected in the range of 0.01 to 100 moles, and preferably 0.1 to 10 moles, based on one mole of the compound [3d].

As the acid that can be used in the present process, inorganic acids such as hydrochloric acid, hydrobromic acid and sulfuric acid; and organic acids such as acetic acid and trifluoroacetic acid may be included, for example.

The amount of use of the acid can be from 1 mole to a large excess, and preferably 1 to 100 moles, based on one mole of the compound of formula [3d].

The solvent mixture that can be used in the present process is a solvent mixture of water and an organic solvent, and examples of the organic solvent include alcohols such as methanol and ethanol; ethers such as tetrahydrofuran; ketones such as acetone and methyl isobutyl ketone; amides such as N,N-dimethylformamide and N,N-dimethylacetamide; sulfur compounds such as dimethylsulfoxide and sulfolane; acetonitrile; and mixtures thereof.

The amount of use of the solvent is 0.01 to 100 L, and preferably 0.1 to 10 L, based on one mole of the formula [3d].

The reaction temperature may be selected in the range of −100 to 200° C., and is preferably selected in the range of 0° C. to 100° C.

The reaction time may vary depending on the reaction temperature, reaction substrate, the extent of reaction and the like, but is usually from 10 minutes to 24 hours.

<Intermediate Production Method 3>

[Chemical Formula 17]

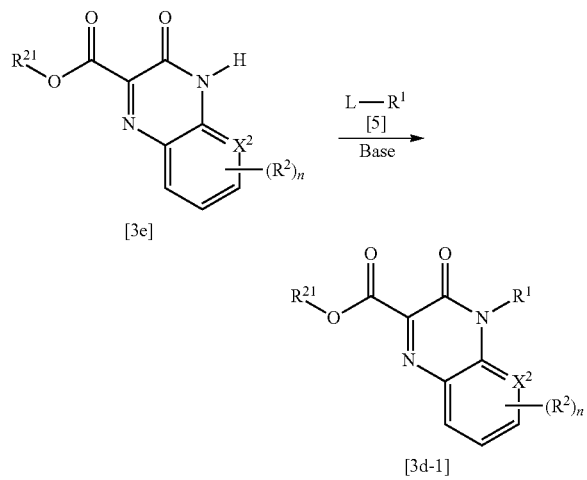

wherein L represents a leaving group such as a halogen atom, a $C_1$-$C_4$ alkylsulfonyloxy group, a $C_1$-$C_4$ alkylsulfonyl group, a benzylsulfonyl group which may be substituted, a phenylsulfonyl group which may be substituted, a phenylsulfonyloxy group which may be substituted, or a benzylsulfonyloxy group which may be substituted; and $R^1$, $R^2$, $R^{21}$, n and $X^2$ respectively have the same meanings as defined above; provided that when $R^1$ is a haloalkyl group, L represents a leaving group having higher reactivity than the halogen atom remaining behind after haloalkylation. For example, when $R^1$ is a $CHF_2$ group, L represents a chlorine atom or a bromine atom, and when $R^1$ is a $CH_2CF_3$ group, L represents a leaving group such as a chlorine atom, a bromine atom, a p-toluenesulfonyloxy group, a methylsulfonyloxy group, or a trifluoromethanesulfonyloxy group.

The production intermediate for the formula [3d-1] can be produced by reacting the formula [3e] with the formula [5] in the presence or absence of a base, in a solvent or without solvent.

The amount of use of the formula [5] used in the present process may be appropriately selected in the range of 0.01 to 100 moles, and preferably 0.1 to 10 moles, based on one mole of the formula [3e].

As the base that can be used in the present process, alkali metal carbonates such as sodium carbonate and potassium carbonate; alkali metal hydroxides such as sodium hydroxide and potassium hydroxide; alkali metal hydrides such as potassium hydride and sodium hydride; alkali metal alcoholates such as sodium ethoxide and sodium methoxide; and organic bases such as 1,8-diazabicyclo[5,4,0]-7-undecene may be included, for example.

The amount of use of the base that can be used in the present process may be appropriately selected in the range of 0 to 100 moles, and preferably 0.1 to 10 moles, based on one mole of the formula [3e].

As the solvent that can be used in the present process, halogenated hydrocarbons such as dichloromethane and chloroform; ethers such as diethyl ether and tetrahydrofuran; aromatic hydrocarbons such as benzene and toluene; aliphatic hydrocarbons such as hexane and heptane; ketones such as acetone and methyl isobutyl ketone; ester such as ethyl acetate and methyl acetate; amides such as N-methylpyrrolidone and N,N-dimethylformamide; sulfur compounds such as dimethylsulfoxide and sulfolane; nitriles such as acetonitrile; and mixtures thereof.

The amount of use of the solvent that can be used in the present process may be appropriately selected in the range of 0 to 100 L, and preferably 0 to 10 L, based on one mole of the formula [3e].

The reaction temperature of the present process may be selected in the range of −100° C. to the boiling point region of the inert solvent used, and is preferably selected in the range of −20° C. to 100° C.

The reaction time of the present process may vary depending on the reaction temperature, reaction substrate, the extent of reaction and the like, but is usually from 1 hour to 168 hours.

<Intermediate Production Method 4>

[Chemical Formula 18]

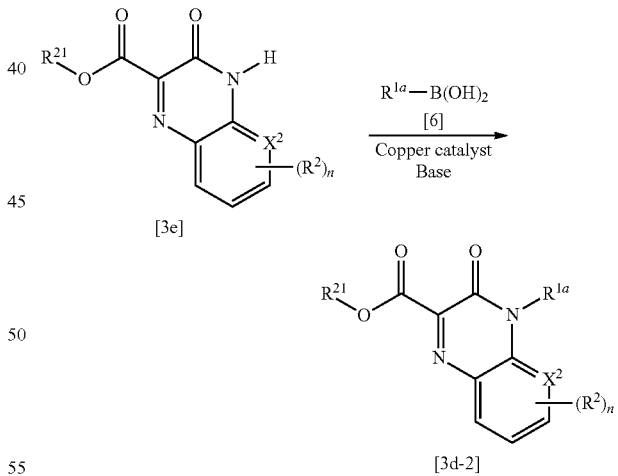

wherein $R^{1a}$ represents a $C_6$-$C_{10}$ aryl group or a heterocyclic group having 2 to 10 carbon atoms and 1 to 5 heteroatoms selected from an oxygen atom, a sulfur atom and a nitrogen atom; and $R^2$, $R^{21}$, n and $X^2$ respectively have the same meanings as defined above.

The production intermediate of formula [3d-2] can be produced by reacting the formula [3e] with the formula [6] in the presence of a copper catalyst and a base, according to the method described in Tetrahedron, Vol. 55, pp. 12757-12770 (1999).

<Intermediate Production Method 5>

[Chemical Formula 19]

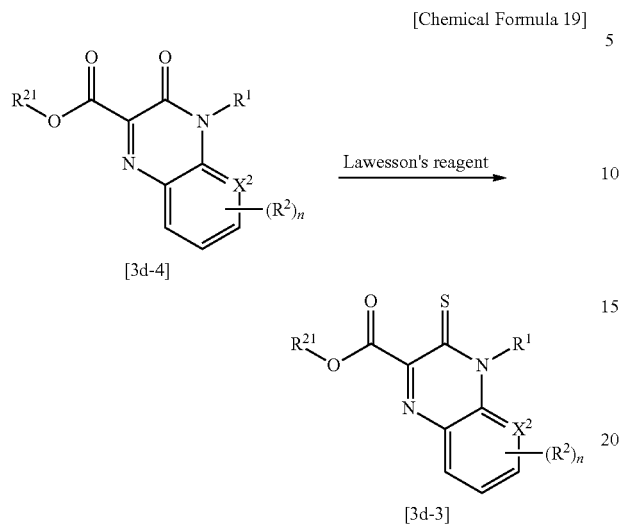

wherein $R^1$, $R^2$, $R^{21}$, n and $X^2$ respectively have the same meanings as defined above.

The production intermediate of formula [3d-3] can be produced by reacting a compound represented by formula [3d-4] with Lawesson's reagent, according to the method described in US2005/256000.

<Intermediate Production Method 6>

[Chemical Formula 20]

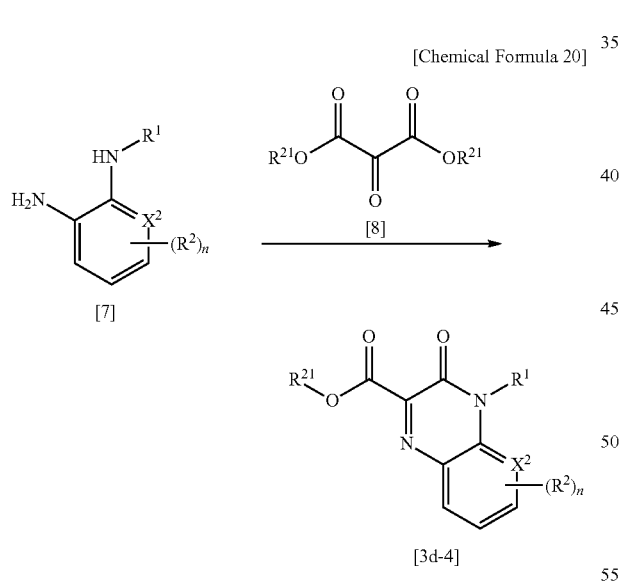

wherein $R^1$, $R^2$, $R^{21}$, n and $X^2$ respectively have the same meanings as defined above.

The production intermediate of formula [3d-4] can be produced by reacting the formula [7] with a ketomalonic acid diester represented by formula [8], according to the methods described in U.S. Pat. No. 6,329,389, U.S. Pat. No. 6,348,461; Journal of the Chemical Society, pp. 430-439 (1957); WO 2005/21547, U.S. Pat. No. 4,296,114; Journal of the Chemical Society, Perkin Transactions 1, pp. 75-84 (1987), and the like.

<Intermediate Production Method 7>

[Chemical Formula 21]

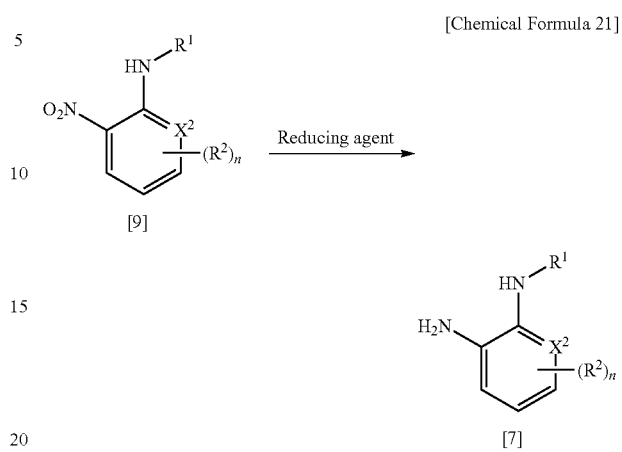

wherein $R^1$, $R^2$, n and $X^2$ respectively have the same meanings as defined above.

The formula [7] can be produced by reducing a nitro compound represented by formula [9] according to the descriptions in the Lectures on Experimental Chemistry, 4$^{th}$ Edition, Vol. 26, "Reduction in General", published by Maruzen Co., Ltd.

<Intermediate Production Method 8>

[Chemical Formula 22]

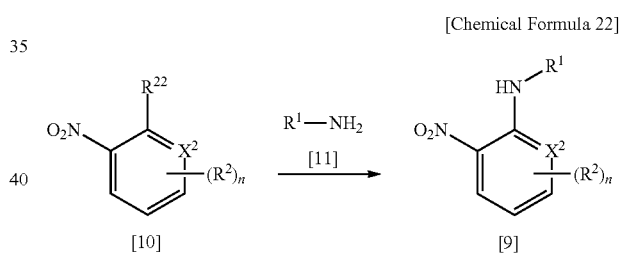

wherein $R^1$, $R^2$, n and $X^2$ respectively have the same meanings as defined above; and $R^{22}$ represents a halogen atom such as a fluorine atom, a chlorine atom or a bromine atom.

The production intermediate of formula [9] can be produced by reacting the formula [10] with the formula [11] according to the methods described in WO 2004/817, U.S. Pat. No. 6,348,461; Journal of Medicinal Chemistry, Vol. 41, pp. 5457-5465 (1998); Journal of the Chemical Society, Perkin Transactions 1, pp. 2387-2391 (1980), and the like.

<Intermediate Production Method 9>

[Chemical Formula 23]

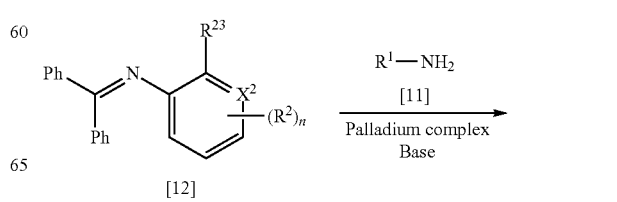

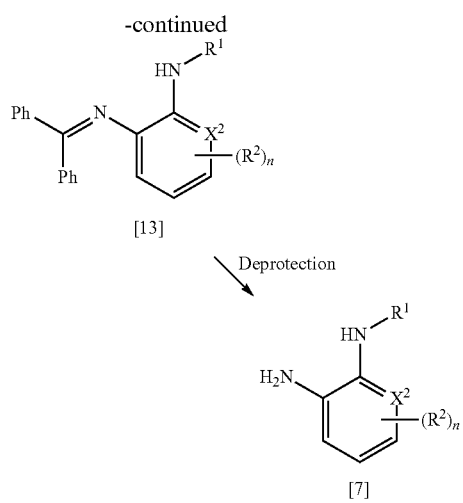

[13]

↓ Deprotection

[7]

wherein $R^1$, $R^2$, n and $X^2$ respectively have the same meanings as defined above; and $R^{23}$ represents a chlorine atom, a bromine atom or an iodine atom.

The production intermediate of formula [7] can be produced by the process shown above.

The production intermediate of formula [13] can be produced by reacting a compound represented by formula [12] with a compound represented by formula [11] in the presence of a palladium complex and a base, according to the methods described in Journal of Organic Chemistry, Vol. 65, pp. 1144-1157 (2000); Journal of Organic Chemistry, Vol. 65, pp. 1158-1174 (2000); and the like.

The production intermediate of formula [7] can also be produced by deprotecting the amino group of the compound represented by formula [13], according to the methods described in Tetrahedron Letters, pp. 2641-2644 (1978); Synthesis, pp. 359-363; Journal of the Chemical Society, Perkin Transactions 1, pp. 3081-3084 (1988); and the like.

<Intermediate Production Method 10>

[Chemical Formula 24]

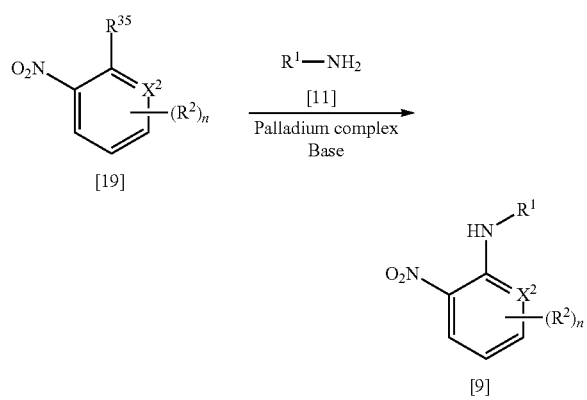

wherein $R^1$, $R^2$, n and $X^2$ respectively have the same meanings as defined above; and $R^{35}$ represents a chlorine atom, a bromine atom, an iodine atom or a trifluoromethanesulfonyloxy group.

The production intermediate of formula [9] can be produced by reacting the compound of formula [19] with the compound of formula [11] in the presence of a palladium complex and a base, according to the method for producing production intermediate of formula [13] in <intermediate production method 9>.

<Intermediate Production Method 11>

[Chemical Formula 25]

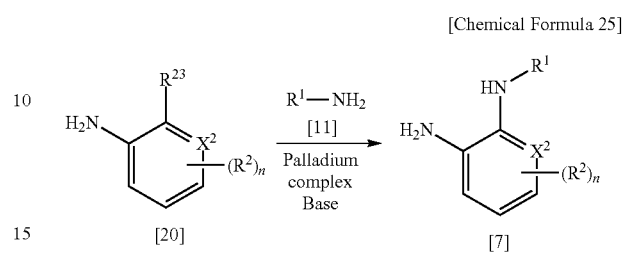

wherein $R^1$, $R^2$, $R^{23}$, n and $X^2$ respectively have the same meanings as defined above.

The production intermediate of formula [7] can be produced by reacting the compound of formula [20] with the compound of formula [11] in the presence of a palladium complex and a base, according to the method for producing production intermediate of formula [13] in <intermediate production method 9>.

<Intermediate Production Method 12>

[Chemical Formula 26]

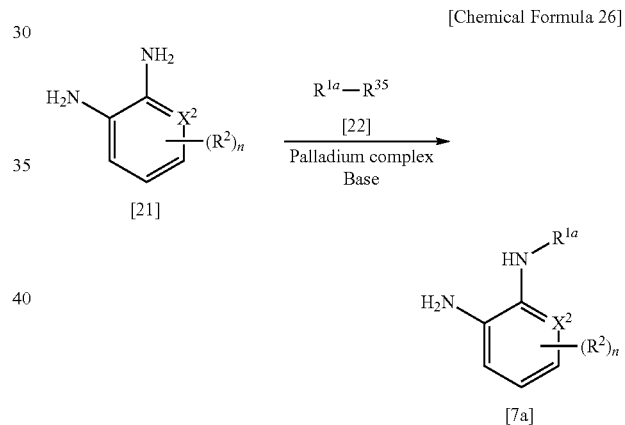

wherein $R^{1a}$, $R^2$, $R^{35}$, n and $X^2$ respectively have the same meanings as defined above.

The production intermediate of formula [7a] can be produced by reacting the compound of formula [21] with the compound of formula [22] in the presence of a palladium complex and a base, according to the method for producing production intermediate of formula [13] in <intermediate production method 9>.

<Intermediate Production Method 13>

[Chemical Formula 27]

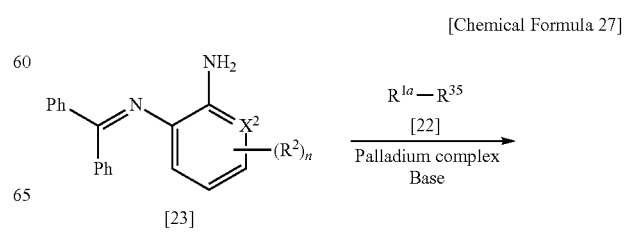

-continued

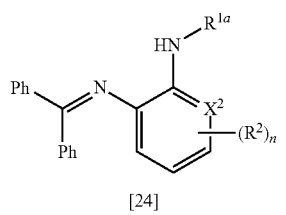

[24]

↓ Deprotection

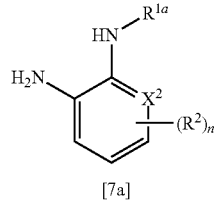

[7a]

wherein $R^{1a}$, $R^2$, $R^{35}$, n and $X^2$ respectively have the same meanings as defined above.

The production intermediate of formula [7a] can also be produced by deprotecting the amino group of the compound represented by formula [24] which is produced by reacting the compound of formula [23] with the compound of formula [22] in the presence of a palladium complex and a base, according to the production method of <intermediate production method 9>.

<Intermediate Production Method 14>

[Chemical Formula 28]

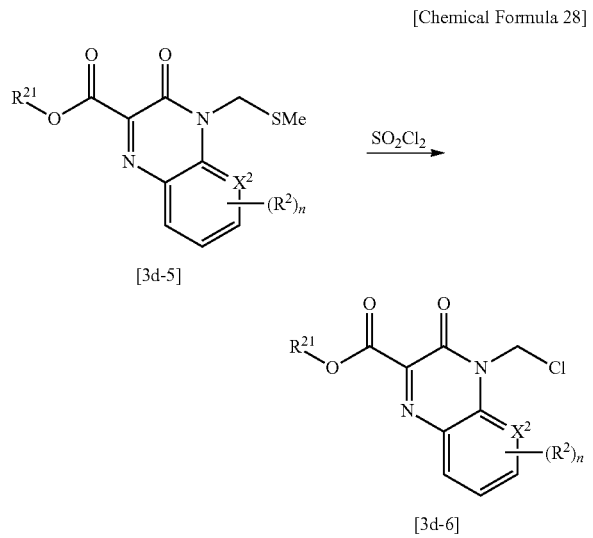

-continued

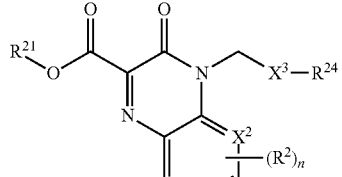

[3d-7]

wherein $R^2$, $R^{21}$, n and $X^2$ respectively have the same meanings as defined above; $R^{24}$ represents a $C_1$-$C_6$ alkoxy group, a $C_3$-$C_8$ cycloalkyloxy group, a $C_1$-$C_6$ haloalkoxy group, a phenoxy group, a $C_1$-$C_6$ alkylcarbonyloxy group, a $C_1$-$C_6$ alkoxy-$C_1$-$C_6$ alkoxy group, a $C_1$-$C_6$ alkylsulfonyl-$C_1$-$C_6$ alkoxy group, a cyano-$C_1$-$C_6$ alkoxy group, a heterocyclic-$C_1$-$C_6$ alkoxy group having 2 to 10 carbon atoms and 1 to 5 heteroatoms, which may be identical or different, selected from an oxygen atom, a sulfur atom and a nitrogen atom, or a $C_1$-$C_6$ alkylthio group; $M^{l+}$ represents an alkali metal cation; and $X^3$ represents an oxygen atom or a sulfur atom.

The production intermediate of formula [3d-7] can be produced by the process shown above.

Specifically, the formula [3d-6] can be produced by reacting the formula [3d-5] with sulfuryl chloride according to the methods described in US2003/195169; Tetrahedron Letters, Vol. 37, No. 6, pp. 759-762 (1996); and the like.

The formula [3d-7] can be produced by reacting the formula [3d-6] with a compound represented by formula [14] or formula [15], according to the methods described in U.S. Pat. No. 5,155,272, EP-1228067, U.S. Pat. No. 4,058,392; Journal of the Chemical Society, Perkin Transactions 1, pp. 781-790 (1987); and the like.

<Intermediate Production Method 15>

[Chemical Formula 29]

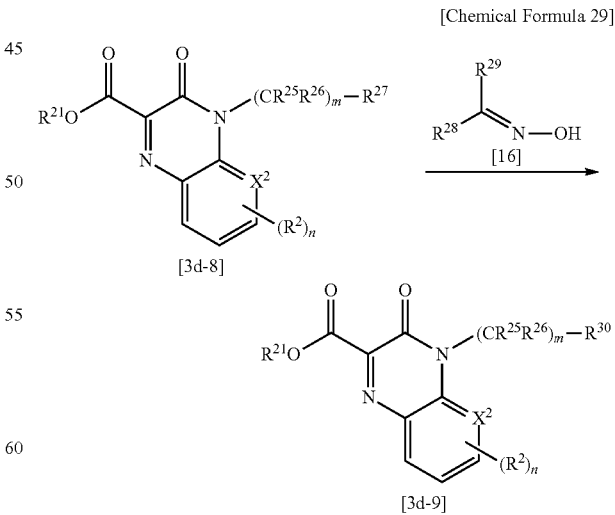

wherein $R^2$, $R^{21}$, $X^2$ and n respectively have the same meanings as defined above; $R^{27}$ represents a group represented by the following formula [17a] or formula [17b]:

[Chemical Formula 30]

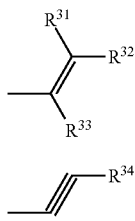

[17a]

[17b]

$R^{30}$ represents a group represented by the following formula [18a] or [18b]:

[Chemical Formula 31]

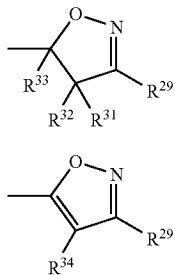

[18a]

[18b]

$R^{25}$, $R^{26}$, $R^{31}$, $R^{32}$, $R^{33}$ and $R^{34}$ each independently represent a hydrogen atom, an alkyl group, an alkenyl group, an alkynyl group, a cycloalkyl group or a haloalkyl group; $R^{29}$ represents an alkyl group, an alkenyl group, an alkynyl group, an alkoxy group, a cycloalkyl group, a haloalkyl group or a haloalkenyl group; $R^{28}$ represents a halogen atom; and t represents an integer from 0 to 6; provided that when $R^{27}$ is the formula [17a], $R^{30}$ is the formula [18a], and when $R^{27}$ is the formula [17b], $R^{30}$ is the formula [18b].

The production intermediate of formula [3d-9] can be produced by reacting the formula [3d-8] with the formula [16] according to the methods described in WO 2005/26123; Tetrahedron, Vol. 40, p. 2985 (1984); Synthetic Communications, Vol. 18, p. 1171 (1988); and the like.

<Intermediate Production Method 16>

[Chemical Formula 32]

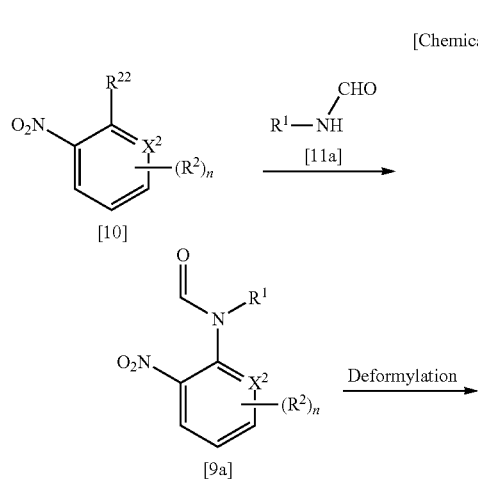

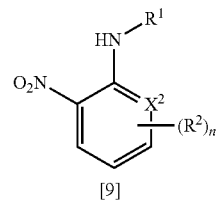

wherein $R^1$, $R^2$, $R^{22}$, n and $X^2$ respectively have the same meanings as defined above.

The production intermediate of formula [9] can also be produced by the process mentioned above.

The production intermediate of formula [9a] can be produced by reacting the formula [10] with the formula [11a] in the presence of a base, in a solvent or without solvent.

The amount of use of the formula [11a] as used in the present process may be appropriately selected in the range of 0.1 to 10 moles, and preferably 1.0 to 1.1 moles, based on one mole of the formula [10].

As the base that can be used in the present process, for example, alkali metal carbonates such as sodium carbonate or potassium carbonate; alkali metal hydroxides such as sodium hydroxide or potassium hydroxide; alkali metal hydrides such as potassium hydride or sodium hydride; alkali metal alcoholates such as sodium ethoxide or sodium methoxide; or organic bases such as 1,8-diazabicyclo[5,4,0]-7-undecene and the like may be included.

The amount of use of the base as used in the present process may be appropriately selected in the range of 0.1 to 10 moles, and preferably 1.0 to 1.1 moles, based on one mole of the formula [10].

As the solvent that can be used in the present process, halogenated hydrocarbons such as dichloromethane and chloroform; ethers such as diethyl ether and tetrahydrofuran; aromatic hydrocarbons such as benzene and toluene; aliphatic hydrocarbons such as hexane and heptane; ketones such as acetone and methyl isobutyl ketone; esters such as ethyl acetate and methyl acetate; amides such as N-methylpyrrolidone and N,N-dimethylformamide; sulfur compounds such as dimethylsulfoxide and sulfolane; nitriles such as acetonitrile; and mixtures thereof.

The amount of use of the solvent that can be used in the present process may be appropriately selected in the range of 0 to 100 L, and preferably 1 to 2 L, based on one mole of the formula [10].

The reaction temperature of the present process may be selected in the range of −100° C. to the boiling point region of the inert solvent used, and is preferably selected in the range of 15° C. to 140° C.

The reaction time of the present process may vary depending on the reaction temperature, reaction substrate, the extent of reaction and the like, but is usually from 1 hour to 168 hours.

Additionally, the production intermediate of formula [9] can be produced by deformylating the formula [9a] in water or a solvent mixture, in the presence of an acid or in the presence of a base.

As the base that can be used in the present process, inorganic bases such as potassium carbonate, sodium hydride and sodium hydroxide; and organic bases such as 1,8-diazabicyclo[5,4,0]-7-undecene may be included, for example.

The amount of use of the base may be appropriately selected in the range of 0.1 to 10 moles, and preferably 1.0 to 1.2 moles, based on one mole of the compound [9a].

As the acid that can be used in the present process, inorganic acids such as hydrochloric acid, hydrobromic acid and sulfuric acid; and organic acids such as acetic acid and trifluoroacetic acid may be included, for example.

The amount of use of the acid can be from 1 mole to a large excess, and preferably 1 to 100 moles, based on one mole of the compound of formula [9a].

The solvent mixture that can be used in the present process is a solvent mixture of water and an organic solvent, and examples of the organic solvent include alcohols such as methanol and ethanol; ethers such as tetrahydrofuran; ketones such as acetone and methyl isobutyl ketone; amides such as N,N-dimethylformamide and N,N-dimethylacetamide; sulfur compounds such as dimethylsulfoxide and sulfolane; acetonitrile; and mixtures thereof.

The amount of use of the solvent is 0.1 to 100 L, and preferably 1.0 to 10 L, based on one mole of the formula [9a].

The reaction temperature may be selected in the range of −100 to 200° C., and is preferably selected in the range of 0° C. to 100° C.

The reaction time may vary depending on the reaction temperature, reaction substrate, the extent of reaction and the like, but is usually from 10 minutes to 24 hours.

<Intermediate Production Method 17>

[Chemical Formula 33]

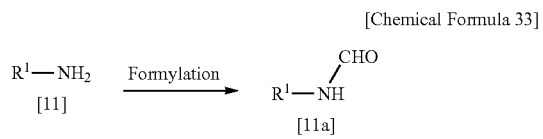

wherein $R^1$ has the same meaning as defined above.

The production intermediate of formula [11a] can be produced by formylating the formula [11], according to the method described in Journal of the American Chemical Society, Vol. 80, pp. 1154 and US2004/198981.

The herbicide and agrochemical composition of the present invention are characterized by containing the oxopyrazine derivative represented by formula [I] of the present invention or an agrochemically acceptable salt thereof, as an active ingredient. The present invention also relates to an agrochemical composition, more particularly a herbicidal composition, containing the oxopyrazine derivative represented by formula [I] of the present invention, or one or two or more of agrochemically acceptable salts thereof, and a carrier allowed to be used in agrochemical preparations.

The herbicide of the present invention can contain additive components (carrier) that are conventionally used in agrochemical preparations, as necessary.

Examples of these additive components include carriers such as solid carriers or liquid carriers, surfactants, binders or adhesiveness imparting agents, thickeners, colorants, extending agents, spreading agents, antifreezing agents, anticaking agents, disintegrants, stabilizers, and the like. In addition to these, antiseptics, plant pieces and the like may also be used as additive components, according to necessity.

These additive components may be used individually, or may also be used in combination of two or more species.

The above-mentioned additive components will be discussed.

Examples of the solid carrier include naturally occurring minerals such as quartz, clay, kaolinite, pyrophillite, seriate, talc, bentonite, acid clay, attapulgite, zeolite and diatomaceous earth; inorganic salts such as calcium carbonate, ammonium sulfate, sodium sulfate and potassium chloride; organic solid carriers such as synthetic silicic acid, synthetic silicates, starch, celluloses and plant powders; plastic carriers such as polyethylene, polypropylene and polyvinylidene chloride; and the like. These may be used individually, or may be used in combination of two or more species.

Examples of the liquid carrier include alcohols which are largely classified into monohydric alcohols such as methanol, ethanol, propanol, isopropanol and butanol; and polyhydric alcohols such as ethylene glycol, diethylene glycol, propylene glycol, hexylene glycol, polyethylene glycol, polypropylene glycol and glycerin; polyhydric alcohol derivatives such as propylene-based glycol ethers; ketones such as acetone, methyl ethyl ketone, methyl isobutyl ketone, diisobutyl ketone, cyclohexanone and isophorone; ethers such as ethyl ether, dioxane, cellosolve, dipropyl ether and tetrahydrofuran; aliphatic hydrocarbons such as normal paraffin, naphthene, isoparaffin, kerosene and mineral oil; aromatic hydrocarbons such as benzene, toluene, xylene, solvent naphtha and alkylnaphthalene; halogenated hydrocarbons such as dichloroethane, chloroform and tetrachlorocarbon; esters such as ethyl acetate, diisopropyl phthalate, dibutyl phthalate, dioctyl phthalate and dimethyl adipate; lactones such as γ-butylolactone; amides such as dimethylformamide, diethylformamide, dimethylacetamide and N-alkylpyrrolidinone; nitriles such as acetonitrile; sulfur compounds such as dimethylsulfoxide; plant oils such as soybean oil, rapeseed oil, cotton seed oil and castor oil; water; and the like. These may be used individually, or may be used in combination of two or more species.

The surfactant is not particularly limited, but is preferably a surfactant which gelates or shows swellability in water. Examples thereof include nonionic surfactants such as sorbitan fatty acid esters, polyoxyethylene sorbitan fatty acid esters, sucrose fatty acid esters, polyoxyethylene fatty acid esters, polyoxyethylene resin acid esters, polyoxyethylene fatty acid diesters, polyoxyethylene alkyl ethers, polyoxyethylene alkyl phenyl ethers, polyoxyethylene dialkylphenyl ethers, polyoxyethylene alkyl phenyl ether-formalin condensates, polyoxyethylene-polyoxypropylene block polymers, alkyl polyoxyethylene-polypropylene block polymer ethers, polyoxyethylene alkylamines, polyoxyethylene fatty acid amides, polyoxyethylene fatty acid bisphenyl ethers, polyalkylene benzyl phenyl ethers, polyoxyalkylene styryl phenyl ethers, acetylenediol, polyoxyalkylene addition acetylenediol, polyoxyethylene ether type silicones, ester type silicones, fluorine-based surfactants, polyoxyethylene castor oil and polyoxyethylene hydrogenated castor oil; anionic surfactants such as alkyl sulfates, polyoxyethylene alkyl ether sulfates, polyoxyethylene alkyl phenyl ether sulfates, polyoxyethylene styryl phenyl ether sulfates, alkyl benzenesulfonates, lignin sulfonates, alkyl sulfosuccinates, naphthalenesulfonates, alkyl naphthalenesulfonates, salts of naphthalenesulfonic acid-formalin condensate, salts of alkyl naphthalenesulfonic acid-formalin condensate, fatty acid salts, polycarboxylic acid salts, N-methyl-fatty acid sarcosinate, resin acid salts, polyoxyethylene alkyl ether phosphates and polyoxyethylene alkyl phenyl ether phosphates; cationic surfactants such as alkylamine salts such as laurylamine hydrochlorides, stearylamine hydrochlorides, oleylamine hydrochlorides, stearylamine acetates, stearylaminopropylamine acetates, alkyltrimethylammonium chlorides and alkyldimethylbenzalkonium chlorides; amphoteric surfactants such as amino acid type or betaine type surfactants; and the like.

These surfactants may be used individually, or may be used in combination of two or more species.

Examples of the binder or adhesiveness imparting agent include carboxymethylcellulose or salts thereof, dextrin, water-soluble starch, xanthan gum, guar gum, sucrose, polyvinylpyrrolidone, gum arabic, polyvinyl alcohol, polyvinyl acetate, sodium polyacrylate, polyethylene glycol having an average molecular weight of 6000 to 20000, polyethylene oxide having an average molecular weight of 100000 to 5000000, naturally occurring phospholipids (for example, cephalic acid, lecithin, etc.), and the like.

Examples of the thickener include water-soluble polymers such as xanthan gum, guar gum, carboxymethylcellulose, polyvinylpyrrolidone, carboxyvinyl polymers, acrylic polymers, starch derivatives and polysaccharides; inorganic fine powders such as high purity bentonite and white carbon; and the like.

Examples of the colorant include inorganic pigments such as iron oxide, titanium oxide and Prussian Blue; organic pigments such as alizarin dyes, azo dyes and metal phthalocyanine dyes; and the like.

Examples of the extending agent include silicone-based surfactants, powdered celluloses, dextrin, processed starch, polyaminocarboxylic acid chelate compounds, crosslinked polyvinylpyrrolidone, maleic acid and styrenes, methacrylic acid copolymers, half esters of a polyhydric alcohol polymer and a dicarboxylic acid anhydride, water-soluble salts of polystyrenesulfonic acid, and the like.

Examples of the spreading agent include various surfactants such as sodium dialkylsulfosuccinate, polyoxyethylene alkyl ethers, polyoxyethylene alkyl phenyl ethers and polyoxyethylene fatty acid esters; paraffins, terpenes, polyamide resins, polyacrylates, polyoxyethylene, waxes, polyvinyl alkyl ethers, alkylphenol-formalin condensates, synthetic resin emulsions, and the like.

Examples of the antifreezing agent include polyhydric alcohols such as ethylene glycol, diethylene glycol, propylene glycol and glycerin; and the like.

Examples of the anticaking agent include polysaccharides such as starch, alginic acid, mannose and galactose; polyvinylpyrrolidone, white carbon, ester gums, petroleum resins, and the like.

Examples of the disintegrants include sodium tripolyphosphate, sodium hexametaphosphate, stearic acid metal salts, powdered cellulose, dextrin, copolymers of methacrylic acid esters, polyvinylpyrrolidone, polyaminocarboxylic acid chelate compounds, sulfonated styrene-isobutylene-maleic anhydride copolymers, starch-polyacrylonitrile graft copolymers, and the like.

Examples of the stabilizer include drying agents such as zeolites, quicklime and magnesium oxide; antioxidants of phenol type, amine type, sulfur type, phosphoric acid type and the like; ultraviolet absorbents of salicylic acid type, benzophenone type and the like; and the like.

Examples of the antiseptic include potassium sorbate, 1,2-benzothiazolin-3-one and the like.

Examples of the plant pieces include sawdust, coconut shell, corncob, tobacco stalk, and the like.

In the case of incorporating the additive components into the herbicide of the present invention, the content proportion is selected in the range of usually 5 to 95%, and preferably 20 to 90%, for the carrier; usually 0.1% to 30%, and preferably 0.5 to 10%, for the surfactant; and usually 0.1 to 30%, and preferably 0.5 to 10%, for the other additives, all based on the mass of the herbicide.

The herbicide of the present invention is used after being formulated into any formulation such as a liquid formulation, an emulsifiable concentrate, a wettable powder formulation, a dust formulation, an oil formulation, a water dispersible granule formulation, a flowable formulation, an emulsified suspension, a granule formulation, a jumbo formulation, a suspoemulsion or a Mametsubu (registered trademark) formulation.

During this formulation, the herbicide can be prepared into a mixed composition with at least one of agrochemicals such as other herbicides, insecticides, bactericides and plant growth regulators, a safeners, a fertilizer and the like, or the herbicide can be used in combination with these components.

At the time of use, the herbicide of the present invention may be diluted to an appropriate concentration and sprayed, or may be directly applied.

The oxopyrazine derivative represented by formula [I] of the present invention or an agrochemically acceptable salt thereof can be used alone as an active ingredient, but can also be used as a mixture or in combination with other active ingredients.

Examples of known herbicidal compounds and plant growth regulators which may be mixed or used in combination, will be listed in the following.

2,3,6-TBA, 2,4-D, 2,4-DB, DNOC, EPTC, ethoxyfenethyl, MCPA, MCPA-thioethyl, MCPS, S-metolachlor, TCA, ioxynil, aclonifen, azafenidin, acifluorfen, azimsulfuron, asulam, acetochlor, atrazine, anilofos, amicarbazone, amidosulfuron, amitrole, aminopyralid, amiprophos-methyl, ametryn, alachlor, alloxydim, ancymidol, iodosulfulon-methyl-sodium, isouron, isoxachlortole, isoxaflutole, isoxaben, isoproturon, imazaquin, imazapyr, imazamethabenz-methyl, imazapic, imazamox, imazethapyr, imazosulfuron, indanofan, esprocarb, ethametsulfuron-methyl, ethalfluralin, ethidimuron, ethoxysulfuron, ethofumesate, etobenzanid, oxadiazon, oxadiargyl, oxaziclomefone, oxasulfuron, oxyfluorfen, oryzalin, orbencarb, cafenstrole, carfentrazone-ethyl, karbutilate, carbetamide, quizalofop, quizalofop-P-ethyl, quizalofop-P-tefuryl, quizalofop-ethyl, quinclorac, quinmerac, cumyluron, glyphosate, glyphosate-trimesium, glufosinate-ammonium, glufosinate-sodium, clethodim, clodinafop-propargyl, clopyralid, clomazone, chlomethoxyfen, clomeprop, cloransulam-methyl, chloramben, chloridazon, chlorimuron-ethyl, chlorsulfuron, chlorthal-dimethyl, chlorthiamid, chlorpropham, chlormequatchloride, chloroxuron, chlorotoluron, chlorobromuron, cyanazine, diuron, dicamba, cycloate, cycloxydim, diclosulam, cyclosulfamuron, dichlobenil, diclofop-methyl, dichlorprop, dichlorprop-P, diquatdibromide, dithiopyr, siduron, dinitramine, cinidon-ethyl, cinosulfuron, dinoseb, dinoterb, cyhalofop-butyl, diphenamid, difenzoquat, diflufenican, diflufenzopyr, diflumetorim, simazine, dimethachlor, dimethametryn, dimethenamid, simetryn, dimepiperate, dimefuron, cinmethylin, sulcotrione, sulfentrazone, sulfosulfuron, sulfometuron-methyl, sethoxydim, terbacil, daimuron, dalapon, thiazopyr, tiocarbazil, thiobencarb, thidiazimin, thidiazuron, thifensulfuron-methyl, desmedipham, desmetryne, thenylchlor, tebutam, tebuthiuron, tepraloxydim, tefuryltrion, terbuthylazine, terbutryn, terbumeton, tembotrione, topramezone, tralkoxydim, triaziflam, triasulfuron, triallate, trietazine, triclopyr, triflusulfuron-methyl, tritosulfuron, trifluralin, trifloxysulfuron-sodium, tribenuron-methyl, naptalam, naproanilide, napropamide, nicosulfuron, neburon, norflurazon, vernolate, paraquat dichloride, haloxyfop, haloxyfop-P-methyl, halosulfuron-methyl, pinoxaden, picloram, picolinafen, bispyribac-sodium, bifenox, piperophos, pyraclonil, pyrasulfotole, pyrazoxyfen, pyrazosulfuron-ethyl, pyrazolynate, bilanafos, pyraflufen-ethyl, pyridafol, pyrithiobac-sodium, pyridate, pyriftalid, pyributicarb, pyribenzoxim, pyrimisulfan, primisulfuron-methyl, pyriminobac-methyl, pyroxysulam, fenuron, fenoxaprop-P-ethyl, fenoxaprop-ethyl, fenclorim, fentrazamide, phenmedipham, foramsulfuron, butachlor, butafenacil, butamifos, butylate, butralin, butroxydim, flazasulfuron, flamprop-M, fluazifop-butyl, fluazifop-P-butyl, fluazolate, fluometuron, fluoroglycofen-ethyl, flucarbazone-sodium, flucetosulfuron, fluthiacet-methyl, flupyrsulfuron-methyl-sodium, flufenacet, flufenpyr-ethyl, flupropanate, flupoxame, flumioxazin, flumiclorac-pentyl, flumetsulam, fluridone, flurtamone, flurprimidol, fluoroxypyr, fluorochloridone, pretilachlor, prodiamine, prosulfuron, prosulfocarb, propaquizafop, propachlor, propazine, propanil, propyzamide, propisochlor, propham, profluazol, propoxycarbazone, propoxycarbazone-sodium, profoxydim, bromacil, prometryn, prometon, bromoxynil, bromofenoxim, bromobutide, florasulam, hexazinone, pethoxamid, benazolin, penoxsulam, beflubutamid, pebulate, bencarbazone, pendimethalin, benzfendizone, bensulide, bensulfuron-methyl, benzobicyclon, benzofenap, bentazone, pentanochlor, pentoxazone, benfluralin, benfuresate, fosamine, fomesafen, forchlorfenuron, maleic hydrazide, mecoprop, mecoprop-P, mesosulfuron-methyl, mesotrione, metazachlor, methabenzthiazuron, metamitron, metamifop, methyl-dimuron, metoxuron, metosulam, metsulfuron-methyl, metobromuron, metobenzuron, metolachlor, metribuzin, mepiquat chloride, mefenacet, monolinuron, molinate, lactofen, linuron, rimsulfuron, lenacil, prohexadione-calcium, trinexapac-ethyl, pyroxasulfone, an isoxazoline derivative represented by the following formula [C]:

[Chemical Formula 34]

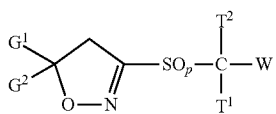

wherein p represents an integer from 0 to 2; $T^1$ and $T^2$ each independently represent a hydrogen atom, a halogen atom, a cyano group, a lower alkoxycarbonyl group or a $C_1$-$C_6$ alkyl group; $G^1$ and $G^2$ each independently represent a hydrogen atom, a $C_1$-$C_6$ alkyl group or a $C_1$-$C_6$ haloalkyl group; W represents a phenyl group (substituted with 1 to 5 identical or different Vs); and V represents a hydrogen atom, a $C_1$-$C_6$ alkyl group {which may be substituted with 1 to 3 identical or different halogen atoms, a $C_1$-$C_6$ alkoxy group, a hydroxyl group, a $C_1$-$C_6$ alkylthio group, a $C_1$-$C_6$ alkylsulfinyl group, a $C_1$-$C_6$ alkylsulfonyl group, a $C_1$-$C_6$ alkylamino group, a $C_1$-$C_6$ dialkylamino group, a cyano group or a phenoxy group (which may be substituted)}, a $C_1$-$C_6$ alkoxy group (which may be substituted with 1 to 3 identical or different halogen atoms, a $C_1$-$C_6$ alkoxy group, a $C_2$-$C_6$ alkenyl group, a $C_2$-$C_6$ alkynyl group, a $C_1$-$C_6$ alkoxycarbonyl group, a $C_1$-$C_6$ alkylcarbonyl group or a $C_3$-$C_8$ cycloalkyl group), a $C_3$-$C_8$ cycloalkyloxy group or a halogen atom, and the like may be included.

Furthermore, examples of known bactericidal compounds which may be mixed or used in combination, will be listed in the following.

Benomyl, carbendazim, fuberidazole, thiabendazole, thiophanate, thiophanate-methyl, chlozolinate, iprodione, procymidone, vinclozolin, azaconazole, bitertanol, bromuconazole, cyproconazole, difenoconazole, diniconazole, epoxiconazole, fenarimol, fenbuconazole, fluquinconazole, flusilazole, flutriafol, hexaconazole, imazalil, imibenconazole, ipconazole, metconazole, myclobutanil, nuarimol, oxpoconazole fumarate, paclobutrazol, pefurazoate, penconazole, prochloraz, propiconazole, prothioconazole, pyrifenox, simeconazole, tebuconazole, tetraconazole, triadimefon, triadimenol, triflumizole, triforine, triticonazole, benalaxyl, furalaxyl, mefenoxam, metalaxyl, metalaxyl-M, ofurace, oxadixyl, aldimorph, dodemorph, fenpropidin, fenpropimorph, piperalin, spiroxamine, tridemorph, edifenphos, iprobenfos, isoprothiolane, pyrazophos, benodanil, boscalid, carboxin, fenfuram, flutolanil, furametpyr, mepronil, oxycarboxin, penthiopyrad, thifluzamide, bupirimate, dimethirimol, ethirimol, cyprodinil, mepanipyrim, pyrimethanil, diethofencarb, azoxystrobin, dimoxystrobin, enestrobin, famoxadone, fenamidone, fluoxastrobin, kresoxim-methyl, metominostrobin, orysastrobin, picoxystrobin, pyraclostrobin, trifloxystrobin, fenpiclonil, fludioxonil, quinoxyfen, biphenyl, chloroneb, dicloran, etridiazole, quintozene, tecnazene, tolclofos-methyl, fthalide, pyroquilon, tricyclazole, carpropamid, diclocymet, fenoxanil, fenhexamid, pyributicarb, polyoxin, pencycuron, cyazofamid, zoxamide, blasticidin-S, kasugamycin, streptomycin, validamycin, cymoxanil, iodocarb, propamocarb, prothiocarb, binapacryl, dinocap, ferimzone, fluazinam, TPTA (fentin acetate), TPTC (fentin chloride), TPTH (fentin hydroxide), oxolinic acid, hymexazol, octhilinone, fosetyl, phosphoric acid and salts thereof, tecloftalam, triazoxide, flusulfamide, diclomezine, silthiofam, diflumetorim, benthiavalicarb-isopropyl, dimethomorph, flumorph, iprovalicarb, mandipropamid, oxytetracycline, methasulfocarb, chinomethionate, fluoroimide, milneb, copperhydroxide, copper octanoate, copper oxychloride, copper sulfate, cuprous oxide, mancopper, oxine-copper, sulfur, ferbam, mancozeb, maneb, metiram, propineb, thiram, zineb, ziram, captafol, captan, folpet, chlorothalonil, dichlofluanid, tolylfluanid, anilazine, dodine, guazatine, iminoctadine, dithianon, acibenzolar-S-methyl, probenazole, tiadinil, ethaboxam, cyflufenamid, proquinazid, metrafenone, fluopicolide, dazomet, difenzoquat, amisubrom, Bordeaux mixture, F-991, nabam, phenazine oxide, polycarbamate, pyribencarb, and the like may be included.

Examples of known insecticidal and nematocidal compounds which may be mixed or used in combination, will be listed in the following.

Acetamiprid, clothianidin, dinotefuran, imidacloprid, nitenpyram, thiacloprid, thiamethoxam, ethiprole, fipronil, acetoprol, chromafenozide, halofenozide, methoxyfenozide, tebufenozide, acrinathrin, allethrin, alpha-cypermethrin, beta-cyfluthrin, beta-cypermethrin, bifenthrin, bioallethrin, bioresmethrin, cycloprothrin, cyfluthrin, cyhalothrin, cypermethrin, cyphenothrin, deltamethrin, empenthrin, esfenvalerate, fenpropathrin, fenvalerate, flucythrinate, flumethrin, gamma-cyhalothrin, imiprothrin, lambda-cyhalothrin, methothrin, permethrin, phenothrin, prallethrin, resmethrin, kadethrin, tau-fluvalinate, tefluthrin, tetramethrin, zeta-cypermethrin, tralomethrin, transfluthrin, etofenprox, halfenprox, silafluofen, bensultap, cartap, thiocyclam, thiosultap-sodium, acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos, dicrotophos, dimethoate, dimethylvinphos, disulfoton, EPN, ethion, ethoprophos, famphur, fenamiphos, fenitrothion, fenthion, fosthiazate, heptenophos, isocarbophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion, imicyafos, flupyrazofos, aldicarb, bendiocarb, benfuracarb, carbaryl, carbofuran, carbosulfan, ethiofencarb, fenobucarb, formetanate, furathiocarb, isoprocarb, methiocarb, methomyl, metolcarb, oxamyl, pirimicarb, propoxur, trimethacarb, XMC, xylylcarb, alanycarb, butocarboxim, butoxycarboxim, thiodicarb, thiofanox, bistrifluoron, chlorfluazuron, diflubenzuron, flucycloxuron, flufenoxuron, hexaflumuron, lufenuron, novaluron, noviflumuron, teflubenzuron, triflumuron, abamectin, emamectin, chlorfenapyr, fenoxycarb, hydroprene, kinoprene, methoprene, pyriproxyfen, dienochlor, cyenopyrafen, cyflumetofen, spiromesifen, spirodiclofen, spirotetramat, flubendiamide, flurimfen (flufenerim), flonicamid, metaflumizon, rynaxypyr, lepmectin, pyridalyl, fluacrypyrim, indoxacarb, bromopropylate, triazamate, fenazaquin, fenpyroximate, pyridaben, tebufenpyrad, clofentezine, etoxazole, hexythiazox, pymetrozine, buprofezin, 1,3-dichloropropene (1,3-D), isocarbophos, ammonium N-methyldithiocarbamate (NCS), azocyclotin, endosulfan, chlordane, chloropicrin, cyhexatin, spinosad, sodium dimethyldithiocarbamate, fenbutatin oxide, flusulfamide, methyl isothiocyanate (MITC), rotenone, CL900167, sodium aluminium fluoride, pyrifluquinazon, RU-15525, XDE-175, ZXI-8901 and the like may be included.

Examples of known safeners which may be mixed or used in combination, will be listed in the following.

Benoxacor, furilazole, dichlormid, dicyclonone, DKA-24 (N1,N2-diallyl-N2-dichloroacetylglycinamide), AD-67 (4-dichloroacetyl-1-oxa-4-azaspiro[4.5]decane), PPG-1292 (2,2-dichloro-N-(1,3-dioxan-2-ylmethyl)-N-(2-propenyl)acetamide), R-29148 (3-dichloroacetyl-2,2,5-trimethyl-1,3-oxazolidine), cloquintcet-mexyl, 1,8-naphthalicanhydride, mefenpyr-diethyl, mefenpyr, fenchlorazole-ethyl, fenclorim, MG-191 (2-dichloromethyl-2-methyl-1,3-dioxane), cyometrinil, flurazole, fluxofenim, isoxadifen-ethyl, mecoprop, MCPA, daimuron, 2,4-D, isoxadifen, MON4660, oxabetrinil, cyprosulfamide, and the like may be included.

The proportion of incorporation of the active ingredient in the herbicide of the present invention is appropriately selected according to necessity, and may be appropriately selected in the range of 0.01 to 10% by weight, and preferably 0.05 to 5% by weight, in the case of a dust formulation or a granule formulation. The proportion of incorporation may be appropriately selected in the range of 1 to 50% by weight, and preferably 5 to 30% by weight, in the case of an emulsion or a wettable powder formulation. The proportion of incorporation may be appropriately selected in the range of 1 to 40% by weight, and preferably 5 to 30% by weight, in the case of a flowable formulation and the like.

The amount of application of the herbicide of the present invention may vary depending on the type of the compound used, weed to be treated, tendency of occurrence, environmental conditions, formulation used, and the like, but in the case of using the herbicide directly such as in the form of a dust formulation or a granule formulation as it is, the amount of application may be appropriately selected in the range of 1 g to 50 kg, and preferably 10 g to 10 kg, per one hectare in terms of the active ingredient. In the case of using the herbicide in the liquid state such as in the form of an emulsifiable concentrate, a wettable powder formulation or a flowable formulation, the amount of application may be appropriately selected in the range of 0.1 to 50000 ppm, and preferably 10 to 10000 ppm.

The herbicide of the present invention can be used through foliar application, soil application or submerged application, to upland fields, paddy fields, orchards and the like. The herbicide of the present invention can also be used for the purpose of controlling general weeds in fallow fields, ridges between rice fields, farm roads, drainage ditches, reclaimed pastures, burial grounds, parklands, streets, playgrounds, vacant lots around buildings, reclaimed lands, track ends, forests, and the like.

The herbicide of the present invention exhibits excellent herbicidal effects over a wide range from pre-emergence to the growing period of weeds including, for example, *Persicaria* spp. such as *Polygonum lapathifolium* L., *Polygonum longisetum* De Bruyn and *Rumex japonicus* Houtt.; *Amaranthus* spp. such as *Amaranthus viridis* L., *Amaranthus palmeri* S. Wats. and *Amaranthus retroflexus* L.; broad leaf weeds such as *Solanum carolinense* L., *Solanum nigrum* L., *Chenopodium album* L., *Abutilon theophrasti medicus*, *Sida spinosa* L., *Sesbania exaltata* Cory, *Ambrosia elatior* L., *Papaver rhoeas* L., *Ipomoea* spp., *Xanthium strumarium* L., *Stellaria media* Villars, *Matricaria chamomilla* L., *Galium spurium* L. var. *echinospermon* Hayek, *Viola mandshurica*, *Veronica persica* Poiret, *Veronica hederifolia* L., *Lamium amplexicaule* L., *Viola angustifolia* L., *Senecio vulgaris* L., and *Capsella Bursa-pastoris* (L.) medik; perennial or annual cyperaceous weeds such as *Cyperus rotundus* L., *Cyperus esculentus* L., *Cyperus brevifolius* Hassk. var. *leiolepis* T. Koyama, *Cyperus microiria* Steud., and *Cyperus iria*; and graminaceous weeds such as *Echinochloa esculenta* (A. Braun) H. Scholz, *Digitaria ciliaris* (Retz.) Koel., *Setaria viridis* (L.) P. Beauv., *Poa annua* L., *Alopecurus aequalis* Sobol. var. *amurensis* Ohwi, *Sorghum halepense* Pers., *Alopecurus myosuroides* Huds., *Lolium multiflorum* Lamarck., and *Avena sativa* L. The herbicide of the present invention can also control annual weeds growing in paddy fields, such as *Echinochloa oryzicola* Vasing, *Echinochloa crus-galli* (L.) P. Beauv. var. *crus-galli*, *Cyperus difformis* L., *Leptochloa chinensis* (L.) Nees, *Monochoria vaginalis* (Burm. f.) Presl var. *plantaginea* (Roxb.) Solms-Laub., *Lindernia dubia* (L.) Pennell, *Lindernia procumbens* (Krock.) Philcox., *Rotala indica* (Willd.) Koehne var. *uliginosa* (Miq.) Koehne, *Vandellia angustifolia* Benth., *Limnophila sessiliflora*, *Ammannia multiflora* Roxb., *Elatine triandra* Schk. var. *pedicellata* Krylov., *Monochoria korsakowii* Regel et Maack, *Ludwigia prostrata* Roxb., *Eclipta prostrata* L., *Bidens frondosa* L., *Aeschynomene indica* L., and *Murdannia keisak* Hand-Mazz.; and perennial weeds such as *Sagittaria pygmaea* Miq., *Sagittaria triflolia* L., *Cyperus serotinus* Rottb., *Eleocharis kuroguwai* Ohwi, *Scirpus juncoides* Roxb., *Alisma canaliculatum* A. Br. et Bouche, *Potamogeton distinctus* A. Bennett, *Leersia japonica* Makino, *Paspalum distichum* L., *Leersia oryzoides* (L.) Swartz, and *Eleocharis acicularis* Roem. et Schult. var. *longiseta* Svenson.

Furthermore, the herbicide of the present invention is highly safe for useful plants and useful crops, and exhibits high safety for, for example, crops such as rice, wheat, barley, common oat, rye, foxtail millet, common millet, corn and grain sorghum; soybean, cotton, sugarbeet, sugarcane, onion, sunflower, oilseed rape, peanut, flax, tobacco, coffee, sweet potato, potato, tomato and other vegetables, or turf and the like.

The useful crops and useful plants as used herein include so-called genetically modified crops and breedings which have been transformed by genetic engineering technologies to exhibit resistance to herbicides, pests, diseases and the like, such as corn, soybean, cotton, oilseed rape and sugarcane; and plants exhibiting resistance to herbicides, pests, diseases and the like through screening.

Hereinafter, the method for producing the compound of formula [I] according to the present invention, preparation examples and uses will be-illustrated in detail by the following Examples, but should not be construed to be limited thereto.

In addition, in the following description, "%" represents percentage by weight, and "parts" represents parts by weight.

Example 1

Production of 3-(2-hydroxy-6-oxo-1-cyclohexen-ecarbonyl)-1-methylquinoxalin-2(1H)-one (Compound No. I-2 of the invention (see Table 1))

(1) Production of 3-oxo-1-cyclohexenyl 1-methyl-2-oxo-1,2-dihydroquinoxaline-3-carboxylate 4.6 g (22.5 mmol) of 1-methyl-2-oxo-1,2-dihydroquinoxaline-3-carboxylic acid was dissolved in dichloromethane (200 mL), and N,N-dimethylformamide (0.5 mL) and 4.3 g (33.9 mmol) of oxalyl chloride were added thereto. The mixture was stirred for 1 hour at room temperature. The reaction mixture was concentrated under reduced pressure, and the obtained residue was dissolved in dichloromethane (100 mL). This solution was added dropwise at room temperature to a solution prepared by dissolving 2.8 g (25.0 mmol) of 1,3-cyclohexanedione and 2.7 g (26.7 mmol) of triethylamine in dichloromethane (100 mL). The mixture was stirred for 1 hour at room temperature, and then, the reaction mixture was washed with water, and dried over anhydrous sodium sulfate. The inorganic matter was separated by filtration, and then the solvent was distilled off under reduced pressure, to obtain 6.3 g (yield 94%) of 3-oxo-1-cyclohexenyl 1-methyl-2-oxo-1,2-dihydroquinoxaline-3-carboxylate as a yellow solid.

$^1$H-NMR (CDCl$_3$/TMS δ (ppm)): 2.11-2.18 (2H, m), 2.96-2.49 (2H, m), 2.76-2.78 (2H, m), 3.77 (3H, s), 6.13 (1H, s), 7.39-7.97 (2H, m), 7.73 (1H, t), 8.00 (1H, d)

(2) Production of 3-(2-hydroxy-6-oxo-1-cyclohexen-ecarbonyl)-1-methylquinoxalin-2(1H)-one 6.3 g (21.1 mmol) of 3-oxo-1-cyclohexenyl 1-methyl-2-oxo-1,2-dihydroquinoxaline-3-carboxylate was dissolved in dichloromethane (100 mL), and to this solution, 2.4 g (23.7 mmol) of triethylamine and acetone cyanohydrin (1 mL) were added. The mixture was stirred for a day at room temperature. The reaction mixture was washed with 10% hydrochloric acid and dried over anhydrous sodium sulfate, and the solvent was distilled off under reduced pressure. The residue was recrystallized from methanol, to obtain 4.3 g (yield: 68%) of 3-(2-hydroxy-6-oxo-1-cyclohexenecarbonyl)-1-methylquinoxalin-2(1H)-one as a white powder (melting point 191 to 192° C.).

$^1$H-NMR (CDCl$_3$/TMS δ (ppm)): 2.05-2.12 (2H, m), 2.45-2.47 (2H, m), 2.76-2.80 (2H, m), 3.71 (3H, s), 7.33-7.38 (2H, m), 7.60 (1H, t), 7.85 (1H, d), 16.3 (1H, s)

Example 2

Production of 2-(2-hydroxy-6-oxo-1-cyclohexen-ecarbonyl)-4-phenyl-pyrido[2,3-b]pyrazin-3(4H)-one (Compound No. IV-1 of the invention (see Table 38))

6.50 g (24 mmol) of 3-oxo-4-phenyl-3,4-dihydropyrido[2,3-b]pyrazine-2-carboxylic acid was dissolved in dichloromethane (100 mL), and to this solution, N,N-dimethylformamide (0.5 mL) and 3.8 g (30 mmol) of oxalyl chloride were added sequentially. The mixture was stirred for one hour at room temperature. After confirming the completion of the reaction, the solvent was distilled off under reduced pressure. The obtained residue was dissolved in dichloromethane (30 mL), and this solution was added dropwise at 0° C. over 5 minutes to a solution prepared by dissolving 2.7 g (24 mmol) of 1,3-cyclohexanedione and 2.5 g (24 mmol) of triethylamine in dichloromethane (30 mL). The reaction solution was returned to room temperature and stirred for 3 hours, and then acetone cyanohydrin (1 mL) and 2.5 g (24 mmol) of triethylamine were added thereto. The mixture was stirred for 12 hours at room temperature. After confirming the completion of the reaction, water (50 mL) was added to the reaction solution, the reaction solution was adjusted to pH 12 using a 10% aqueous solution of sodium hydroxide, and the reaction solution was separated. The aqueous layer was adjusted to pH 1 by adding 6 N hydrochloric acid, and then the aqueous layer was extracted with dichloromethane. The obtained organic layer was dried over anhydrous magnesium sulfate, and then the solvent was distilled off under reduced pressure. The residue thus obtained was washed with methanol, to obtain 6.5 g (yield: 73%) of 2-(2-hydroxy-6-oxo-1-cyclohexenecarbonyl)-4-phenyl-pyrido[2,3-b]pyrazin-3(4H)-one.

$^1$H-NMR (CDCl$_3$/TMS δ (ppm)): 2.06 (2H, t), 2.44 (2H, s), 2.77 (2H, t), 7.30 (3H, d), 7.53 (3H, m), 8.18 (1H, m), 8.47 (1H, d), 16.10 (1H, s)

Example 3

Production of 2-(2-hydroxy-6-oxo-1-cyclohexen-ecarbonyl)-4-(4-methoxyphenyl)-pyrido[2,3-b]pyrazin-3(4H)-one (Compound No. IV-62 of the invention (see Table 39))

4.4 g (15 mmol) of 4-(4-methoxyphenyl)-3-oxo-3,4-dihydropyrido[2,3-b]pyrazine-2-carboxylic acid was dissolved in dichloromethane (100 mL), and to this solution, N,N-dimethylformamide (0.5 mL) and 3.8 g (30 mmol) of oxalyl chloride were added sequentially. The mixture was heated to reflux for one hour while stirring. After confirming the completion of the reaction, the reaction solution was cooled to room temperature, and the solvent was distilled off under reduced pressure. The residue thus obtained was dissolved in dichloromethane (30 mL), and this solution was added dropwise at 0° C. over 5 minutes to a solution prepared by dissolving 1.8 g (16 mmol) of 1,3-cyclohexanedione and 1.8 g (18 mmol) of triethylamine in dichloromethane (30 mL). The reaction solution was returned to room temperature and stirred for 3 hours, and then acetone cyanohydrin (1 mL) and 1.8 g (18 mmol) of triethylamine were further added thereto. The mixture was stirred for 12 hours at room temperature. After confirming the completion of the reaction, water (20 mL) was added to the reaction solution, the reaction solution was adjusted to pH 12 using a 10% aqueous solution of sodium hydroxide, and the reaction solution was separated. The aqueous layer was adjusted to pH 1 by adding 6 N hydrochloric acid, and then the aqueous layer was extracted with dichloromethane. The obtained organic layer was dried over anhydrous magnesium sulfate, and then the solvent was distilled off under reduced pressure. The residue thus obtained was washed with methanol, to obtain 4.5 g (yield: 78%) of 2-(2-hydroxy-6-oxo-1-cyclohexenecarbonyl)-4-(4-methoxyphenyl)-pyrido[2,3-b]pyrazin-3(4H)-one.

$^1$H-NMR (CDCl$_3$/TMS δ (ppm)): 2.06 (2H, s), 2.44 (2H, s), 2.77 (2H, t), 3.86 (3H, s), 7.07 (2H, d), 7.28 (2H, d), 8.17 (1H, d), 8.49 (1H, d)

Example 4

Production of 3-hydroxy-2-(1-methyl-2-thioxo-1,2-dihydroquinoxalin-3-yl-carbonyl)-2-cyclohexen-1-one (Compound No. I-256 of the invention (see Table 11))

2.4 g (10.3 mmol) of ethyl 1-methyl-2-oxo-1,2-dihydroquinoxaline-3-carboxylate and 4.2 g (10.4 mmol) of Lawesson's reagent were added to toluene (50 mL), and the mixture was stirred for a day while maintaining the liquid temperature at 100° C. The reaction mixture was cooled to room temperature, and then the solvent was distilled off under reduced pressure. Chloroform was added to the residue, the insoluble was separated by filtration, and the filtrate was concentrated under reduced pressure. The residue thus obtained was dissolved in ethanol (300 mL), 4.9 g of a 25% aqueous solution of sodium hydroxide was added at room temperature, and the mixture was stirred for a day at room temperature. The reaction mixture was concentrated under reduced pressure, water was added thereto, and the mixture was adjusted to pH 1 using 10% hydrochloric acid. A solid precipitated therefrom was collected by filtration, and was washed with water. The solid thus obtained was dried, and this solid was dissolved in chloroform (50 mL). 1.7 g (13.4 mmol) of oxalyl chloride and one droplet of N,N-dimethylformamide were added to the solution, and the reaction solution was stirred for 2 hours at room temperature, and concentrated under reduced pressure. The residue thus obtained was dissolved in chloroform (20 mL), 0.84 g (7.49 mmol) of 1,3-cyclohexanedione and 0.83 g (8.20 mmol) of triethylamine were added thereto, and the mixture was stirred for one hour at room temperature. 0.83 g (8.20 mmol) of triethylamine and 0.64 g (7.52 mmol) of acetone cyanohydrin were further added at room temperature, and the mixture was stirred for two days at room temperature. The reaction mixture was washed with 10% hydrochloric acid, and dried over anhydrous magnesium sulfate, and the solvent was distilled off under reduced pressure. The residue thus obtained was purified by silica gel chromatography (developing solvent: ethyl acetate/chloroform=1/1). The resulting solid was washed with ethyl acetate, to obtain 0.40 g of 3-hydroxy-2-(1-methyl-2-thioxo-1,2-dihydroquinoxaline-3-car bonyl)-2-cyclohexen-1-one as a yellow powder (melting point 300° C. or above).

$^1$H-NMR (CDCl$_3$/TMS δ (ppm)): 2.01-2.11 (2H, m), 2.38-2.44 (2H, m), 2.75-2.81 (2H, m), 4.19 (3H, s), 7.44 (1H, t), 7.55 (1H, d), 7.68 (1H, t), 7.88 (1H, d), 16.3 (1H, s)

Example 5

Production of 5-fluoro-3-(2-hydroxy-6-oxo-1-cyclohexenecarbonyl)-1-(4-methoxyphenyl)-quinoxalin-2(1H)-one (Compound No. 11-186 of the invention (see Table 24))

11.1 g (35 mmol) of 5-fluoro-1-(4-methoxyphenyl)-2-oxo-1,2-dihydroquinoxaline-3-carboxylic acid was dissolved in chloroform (300 mL), and to this solution, N,N-dimethylformamide (0.5 mL) and 6.7 g (53 mmol) of oxalyl chloride were added sequentially. The mixture was stirred for one hour at room temperature. After confirming the completion of the reaction, the solvent was distilled off under reduced pressure. The residue thus obtained was dissolved in chloroform (100 mL), and this solution was added dropwise at 0° C. over 5 minutes to a solution prepared by dissolving 4.4 g (39 mmol) of 1,3-cyclohexanedione and 4.3 g (43 mmol) of triethylamine in chloroform (200 mL). The reaction solution was returned to room temperature and stirred for 3 hours, and then 1.5 g (18 mmol) of acetone cyanohydrin and 4.3 g (43 mmol) of triethylamine were added thereto. The mixture was stirred for 12 hours at room temperature. The reaction solution was washed with 10% hydrochloric acid and dried over anhydrous sodium sulfate, and then the solvent was distilled off under reduced pressure. The residue thus obtained was washed with methanol, to obtain 13.6 g (yield: 94%) of 5-fluoro-3-(2-hydroxy-6-oxo-1-cyclohexenecarbonyl)-1-(4-methoxyphenyl)-quinoxalin-2(1H)-one as a pale orange-colored powder.

$^1$H-NMR (CDCl$_3$/TMS δ (ppm)): 2.06 (2H, m), 2.43 (2H, br), 2.75 (2H, t), 3.88 (3H, s), 6.57 (1H, d), 7.01-7.10 (3H, m), 7.26-7.35 (3H, m), 16.19 (1H, s)

Example 6

Production of 5-chloro-3-(2-hydroxy-6-oxo-1-cyclohexenecarbonyl)-1-(4-methoxyphenyl)-quinoxalin-2(1H)-one (Compound No. 11-194 of the invention (see Table 24))

6.7 g (20 mmol) of 5-chloro-1-(4-methoxyphenyl)-2-oxo-1,2-dihydroquinoxaline-3-carboxylic acid was dissolved in chloroform (300 mL), and to this solution, N,N-dimethylformamide (0.5 mL) and 5.2 g (41 mmol) of oxalyl chloride were added sequentially. The mixture was stirred for one hour at room temperature. After confirming the completion of the reaction, the solvent was distilled off under reduced pressure. The residue thus obtained was dissolved in chloroform (70 mL), and this solution was added dropwise at 0° C. over 5 minutes to a solution prepared by dissolving 2.5 g (22 mmol) of 1,3-cyclohexanedione and 2.5 g (25 mmol) of triethylamine in chloroform (70 mL). The reaction solution was returned to room temperature and stirred for 3 hours, and then 0.86 g (10 mmol) of acetone cyanohydrin and 2.5 g (25 mmol) of triethylamine were added thereto. The mixture was stirred for 12 hours at room temperature. The reaction solution was washed with 10% hydrochloric acid and dried over anhydrous sodium sulfate, and then the solvent was distilled off under reduced pressure. The residue thus obtained was washed with ethyl acetate, to obtain 6.0 g (yield: 70%) of 5-chloro-3-(2-hydroxy-6-oxo-1-cyclohexenecarbonyl)-1-(4-methoxyphenyl)quinoxalin-2(1H)-one as a pale orange-colored powder.

$^1$H-NMR (CDCl$_3$/TMS δ (ppm)): 2.06 (2H, m), 2.44 (2H, br), 2.75 (2H, t), 3.88 (3H, s), 6.71 (1H, d), 7.09 (2H, d), 7.25-7.30 (3H, m), 7.39 (1H, d), 16.23 (1H, s)

Example 7

Production of 1-(benzo[d][1,3]dioxol-5-yl)-3-(2-hydroxy-6-oxo-1-cyclohexenecarbonyl)-quinoxalin-2(1H)-one (Compound No. I-202 of the invention (see Table 9))

5.7 g (19 mmol) of 1-(benzo[d][1,3]dioxol-5-yl)-2-oxo-1,2-dihydroquinoxaline-3-carboxylic acid and 3.1 g (24 mmol) of oxalyl chloride were dissolved in dichloromethane (10 mL), and 0.026 g (0.35 mmol) of dimethylformamide was added thereto. The mixture was heated to reflux for 2 hours while stirring. After confirming the completion of the reaction, the solvent was distilled off under reduced pressure to obtain 1-(benzo[d][1,3]dioxol-5-yl)-2-oxo-1,2-dihydroquinoxaline-3-carbonyl chloride as yellow crystals (Compound No. of Production Intermediate: IX-73).

$^1$H-NMR (CDCl$_3$/TMS δ (ppm)): 6.12 (2H, d), 6.74-6.76 (2H, m), 6.88 (1H, d), 7.01 (1H, d), 7.43 (1H, t), 7.57 (1H, t), 8.04 (1H, d)

The 1-(benzo[d][1,3]dioxol-5-yl)-2-oxo-1,2-dihydroquinoxaline-3-carbonyl chloride thus obtained was dissolved in dichloromethane (30 mL), and the solution was added dropwise to a liquid mixture containing 2.7 g (24 mmol) of 1,3-cyclohexanedione, 3.7 g (36 mmol) of triethylamine and dichloromethane (20 mL), under ice-cooling. After stirring the reaction solution for 3 hours at room temperature, 0.04 g (0.53 mmol) of acetone cyanohydrin and 3.7 g (36 mmol) of triethylamine were added to the liquid mixture, and the mixture was stirred for 12 hours at room temperature. The reaction solution was poured into water, and the aqueous layer was acidified with 10% hydrochloric acid, and extracted with dichloromethane. The obtained organic layer was dried over anhydrous magnesium sulfate, and the inorganic matter was separated by filtration. The solvent was distilled off under reduced pressure, and to the residue thus obtained, a mixed solution of methanol and water was added to obtain a solid. The solid was collected by filtration and dried, to obtain 5.5 g (yield: 75%) of 1-(benzo[d][1,3]dioxol-5-yl)-3-(2-hydroxy-6-oxo-1-cyclohexenecarbonyl)-quinoxalin-2(1H)-one as a yellow amorphous matter.

$^1$H-NMR (CDCl$_3$/TMS δ (ppm)): 2.03-2.05 (2H, m), 2.43 (2H, brs), 2.73 (2H, t), 6.08 (2H, d), 6.38-6.87 (3H, m), 6.99 (1H, d), 7.29-7.43 (2H, m), 7.88 (1H, d), 16.27 (1H, s)

Example 8

Production of 1-(2,3-dihydrobenzo[b]1,4-dioxin-6-yl)-3-(2-hydroxy-6-oxo-1-cyclohexenecarbonyl)-quinoxalin-2(1H)-one (Compound No. 1-209 of the invention (see Table 10))

9.9 g (31 mmol) of 1-(2,3-dihydrobenzo[b] 1,4-dioxin-6-yl)-2-oxo-1,2-dihydroquinoxaline-3-carboxylic acid was dissolved in dichloromethane (100 mL), and to this solution, N,N-dimethylformamide (0.5 mL) and 4.7 g (37 mmol) of oxalyl chloride were added sequentially. The mixture was stirred for one hour at room temperature. After confirming the completion of the reaction, the solvent was distilled off under reduced pressure to obtain 1-(2,3-dihydrobenzo[b]1,4-dioxin-6-yl)-2-oxo-1,2-dihydroquinoxaline-3-carbonyl chloride as yellow crystals (Compound No. of Production Intermediate: IX-75).

$^1$H-NMR (CDCl$_3$/TMS δ (ppm)): 4.33 (4H, s), 6.74-6.89 (3H, m), 7.08 (1H, d), 7.44 (1H, t), 7.55 (1H, t), 8.02 (1H, d)

The 1-(2,3-dihydrobenzo[b]1,4-dioxin-6-yl)-2-oxo-1,2-dihydroquinoxaline-3-carbonyl chloride thus obtained was dissolved in dichloromethane (30 mL), and this solution was added dropwise at 0° C. over 5 minutes to a solution prepared by dissolving 4.2 g (37 mmol) of 1,3-cyclohexanedione and 6.2 g (61 mmol) of triethylamine in dichloromethane (30 mL). The reaction solution was returned to room temperature and stirred for 3 hours, and then acetone cyanohydrin (1 mL) and 6.2 g (61 mmol) of triethylamine were added thereto. The mixture was stirred for 12 hours at room temperature. After confirming the completion of the reaction, water (50 mL) was added to the reaction solution, the reaction solution was adjusted to pH 12 using a 10% aqueous solution of sodium hydroxide, and the reaction solution was separated. The aqueous layer was adjusted to pH 1 by adding 6 N hydrochloric acid, and then the aqueous layer was extracted with dichloromethane. The obtained organic layer was dried over anhydrous magnesium sulfate, and then the solvent was distilled off under reduced pressure. The residue thus obtained was washed with methanol, to obtain 5.2 g (yield: 40%) of 1-(2,3-dihydrobenzo[b]1,4-dioxin-6-yl)-3-(2-hydroxy-6-oxo-1-cyclohexenecarbonyl)-quinoxalin-2(1H)-one as milky white crystals.

$^1$H-NMR (CDCl$_3$/TMS δ (ppm)): 2.02-2.09 (2H, m), 2.44 (2H, br), 2.73-2.77 (2H, m), 4.32 (4H, s), 6.84-6.87 (3H, m), 7.04 (1H, d), 7.28-7.42 (2H, m), 7.87 (1H, d), 16.3 (1H, s)

Example 9

Production of 4-(3-fluoro-4-methylphenyl)-2-(2-hydroxy-6-oxo-1-cyclohexenecarbonyl)-pyrido[2,3-b]pyrazin-3(4H)-one (Compound No. IV-222 of the invention (see Table 43))

24 g (80 mmol) of 4-(3-fluoro-4-methylphenyl)-3-oxo-3,4-dihydropyrido[2,3-b]pyrazine-2-carboxylic acid was dissolved in chloroform (180 ml), and N,N-dimethylformamide (1 mL) and 20 g (160 mmol) of oxalyl chloride were added thereto. The mixture was stirred for one hour at 40° C. After confirming the completion of the reaction, the solvent was distilled off under reduced pressure. The residue thus obtained was dissolved in chloroform (180 mL), and this solution was added dropwise at 0° C. over 5 minutes to a solution prepared by dissolving 10 g (90 mmol) of 1,3-cyclohexanedione and 9.0 g (90 mmol) of triethylamine in chloroform (180 mL). The reaction solution was returned to room temperature, and stirred for 3 hours, and then 0.8 g (10 mmol) of acetone cyanohydrin and 9.0 g (90 mmol) of triethylamine were added thereto. The mixture was stirred for 12 hours at room temperature.

After confirming the completion of the reaction, the solvent was distilled off under reduced pressure, and the residue was extracted with ethyl acetate. A 10% aqueous solution of sodium hydroxide was added, and the mixture was adjusted to pH 12. Subsequently, the obtained aqueous layer was adjusted to pH 1 by adding 6 N hydrochloric acid, and the aqueous layer was extracted again with chloroform. Anhydrous magnesium sulfate and florisil were added to the organic layer to dry the layer, and the solvent was distilled off under reduced pressure. The residue thus obtained was washed with methanol, to obtain 15 g (yield: 48%) of 4-(3-fluoro-4-methylphenyl)-2-(2-hydroxy-6-oxo-1-cyclohexenecarbonyl)-pyrido[2,3-b]pyrazin-3(4H)-one.

$^1$H-NMR (CDCl$_3$/TMS δ (ppm)): 2.07 (2H, t), 2.35 (3H, d), 2.44 (2H, brs), 2.78 (2H, t), 7.06 (2H, d), 7.29-7.41 (2H, m), 8.18 (1H, dd), 8.48 (1H, dd), 16.06 (1H, brs)

Example 10

Production of 3-(2-hydroxy-6-oxo-1-cyclohexenecarbonyl)-1-(6-methyl-2-pyridyl)-quinoxalin-2(1H)-one (Compound No. I-173 of the invention (see Table 7))

(1) Production of 3-oxo-1-cyclohexenyl 1-(6-methyl-2-pyridyl)-2-oxo-1,2-dihydroquinoxaline-3-carboxylate 23.3 g of 1-(6-methyl-2-pyridyl)-2-oxo-1,2-dihydroquinoxaline-3-carboxylic acid was dissolved in chloroform (100 mL), and 21.0 g of oxalyl chloride was added thereto. The mixture was stirred for one hour at room temperature. The solvent was distilled off under reduced pressure, and the residue was dissolved in 100 mL of chloroform. 10.2 g of 1,3-cyclohexadione and 10.1 g of triethylamine were added, and the mixture was stirred for 2 hours at room temperature. The reaction mixture was poured into water, and extracted with chloroform. The organic layer was washed with saturated brine, and dried over anhydrous magnesium sulfate, and then the solvent was distilled off under reduced pressure, to obtain 28.8 g of 3-oxo-1-cyclohexenyl 1-(6-methyl-2-pyridyl)-2-oxo-1,2-dihydroquinoxaline-3-carboxylate.

$^1$H-NMR (CDCl$_3$/TMS δ (ppm)): 2.12 (2H, m), 2.46 (2H, t), 2.65 (3H, s), 2.74 (2H, t), 6.11 (1H, s), 6.68 (1H, d), 7.28 (1H, d), 7.51 (3H, m), 7.93 (1H, d), 8.03 (1H, d)

(2) Production of 3-(2-hydroxy-6-oxo-1-cyclohexenecarbonyl)-1-(6-methyl-2-pyridyl)-quinoxalin-2(1H)-one 28.8 g of 3-oxo-1-cyclohexenyl 1-(6-methyl-2-pyridyl)-2-oxo-1,2-dihydroquinoxaline-3-carboxylate was dissolved in 100 mL of acetonitrile, and 9.3 g of triethylamine and 7.2 g of acetone cyanohydrin were added thereto. The mixture was stirred for one hour at 80° C. The solvent was distilled off under reduced pressure, the residue was dissolved in chloroform, and the solution was adjusted to below pH 4. The organic layer was washed with saturated brine, and dried over anhydrous magnesium sulfate, and then the solvent was distilled off under reduced pressure, to obtain 24.2 g of 3-(2-hydroxy-6-oxo-1-cyclohexenecarbonyl)-1-(6-methyl-2-pyridyl)-quinoxalin-2(1H)-one.

$^1$H-NMR (CDCl$_3$/TMS δ (ppm)): 2.06 (m, 2H), 2.45 (t, 2H), 2.64 (s, 3H), 2.76 (t, 2H), 6.68 (s, 1H), 7.39 (m, 9H), 7.89 (m, 2H), 16.32 (s, 1H)

The property values of the compounds obtained in the above Examples 1 to 10, and the compounds of the present invention produced in the same manner as in these Examples are presented in Table 124 to Table 134.

TABLE 124

| Compound No. | Melting Point (° C.) or Refractive Rate ($n_D^{20}$) | |
|---|---|---|
| I-1 | Melting Point | 84-86 |
| I-2 | Melting Point | 191-192 |
| I-5 | Melting Point | 193-195 |
| I-7 | Melting Point | 155-157 |
| I-12 | Melting Point | 164-165 |
| I-13 | Melting Point | 151-152 |
| I-14 | Melting Point | 172-174 |
| I-15 | Refractive Rate | 1.6148 |
| I-18 | Melting Point | 157-159 |
| I-21 | Melting Point | 144-147 |
| I-22 | Melting Point | 125-128 |
| I-30 | Melting Point | 171-172 |
| I-35 | Melting Point | 205-206 |
| I-40 | Melting Point | 190-192 |
| I-49 | Melting Point | 140-141 |
| I-50 | Melting Point | 144-145 |
| I-57 | Melting Point | 201-203 |
| I-58 | | Incapable measurement |
| I-59 | Melting Point | 1.5663 |
| I-62 | Melting Point | 164-166 |
| I-65 | Refractive Rate | 1.6070 |
| I-67 | Melting Point | 184-185 |
| I-68 | Melting Point | 151-152 |
| I-69 | Melting Point | 216-218 |
| I-70 | Melting Point | 179-181 |
| I-71 | Melting Point | 203-205 |
| I-72 | Melting Point | 179-181 |
| I-80 | Melting Point | 249-251 |
| I-81 | Melting Point | 272-274 |
| I-82 | Melting Point | 226-228 |
| I-88 | Melting Point | 142-144 |
| I-90 | Melting Point | 153-155 |
| I-91 | Melting Point | 148-149 |
| I-92 | Melting Point | 218-222 |
| I-93 | | Oily |
| I-94 | Melting Point | 186-187 |

TABLE 124-continued

| Compound No. | Melting Point (° C.) or Refractive Rate ($n_D^{20}$) | |
|---|---|---|
| I-99 | Melting Point | 187-189 |
| I-100 | Melting Point | 217-219 |
| I-101 | Melting Point | 239-241 |
| I-102 | Melting Point | 181-183 |
| I-103 | Melting Point | 184-186 |
| I-107 | Melting Point | 181-183 |
| I-111 | Melting Point | 214-216 |
| I-112 | Melting Point | 192-194 |
| I-113 | Melting Point | 195-196 |
| I-120 | Melting Point | 215-218 |
| I-125 | Melting Point | 203-204 |
| I-126 | Melting Point | 207-210 |
| I-128 | Melting Point | 233-235 |

TABLE 125

| Compound No. | Melting Point (° C.) or Refractive Rate ($n_D^{20}$) | |
|---|---|---|
| I-131 | Melting Point | 207-208 |
| I-136 | Melting Point | 178-181 |
| I-137 | Melting Point | 126-127 |
| I-139 | Melting Point | 189-192 |
| I-144 | Melting Point | 171-174 |
| I-145 | Melting Point | 87-88 |
| I-148 | Melting Point | 207-208 |
| I-149 | Melting Point | 73-75 |
| I-156 | Melting Point | 105-107 |
| I-158 | Melting Point | 133-135 |
| I-159 | | Oily |
| I-160 | Melting Point | 168-169 |
| I-163 | Melting Point | 182-183 |
| I-165 | Melting Point | 185-187 |
| I-166 | Melting Point | 99-101 |
| I-167 | Melting Point | 150-153 |
| I-171 | Melting Point | 177-179 |
| I-173 | Melting Point | 177-179 |
| I-176 | Melting Point | 170-171 |
| I-177 | Melting Point | 125-128 |
| I-178 | Melting Point | 115-117 |
| I-179 | Melting Point | 116-118 |
| I-180 | Melting Point | 129-130 |
| I-182 | Melting Point | 208-210 |
| I-185 | Melting Point | 168-170 |
| I-189 | Melting Point | 141-144 |
| I-195 | Melting Point | 237-239 |
| I-197 | Melting Point | 217-219 |
| I-199 | Melting Point | 187-189 |
| I-201 | Melting Point | 156-157 |
| I-202 | Melting Point | 150-151 |
| I-207 | Melting Point | 146-147 |
| I-209 | Melting Point | 246-248 |
| I-211 | Melting Point | 151-153 |
| I-212 | Melting Point | 199-200 |
| I-213 | Melting Point | 172-175 |
| I-220 | Melting Point | 235-237 |
| I-221 | Melting Point | 187-189 |
| I-223 | Melting Point | 213-216 |
| I-225 | Melting Point | 225-228 |
| I-227 | Melting Point | 205-207 |
| I-229 | Melting Point | 162-163 |
| I-230 | Melting Point | 161-164 |
| I-238 | Melting Point | 179-181 |
| I-241 | Melting Point | 161-164 |
| I-243 | Melting Point | 170-171 |
| I-245 | Melting Point | 229-231 |
| I-247 | Melting Point | 233-235 |
| I-249 | Melting Point | 225-226 |
| I-250 | Melting Point | 195-197 |
| I-256 | Melting Point | 300 or more |
| I-263 | Melting Point | 148-150 |

TABLE 126

| Compound No. | Melting Point (° C.) or Refractive Rate ($n_D^{20}$) | |
|---|---|---|
| I-264 | Melting Point | 170-173 |
| I-265 | Melting Point | 193-195 |
| I-266 | Melting Point | 199-200 |
| I-267 | Melting Point | 163-166 |
| I-268 | Melting Point | 127-129 |
| I-269 | Melting Point | 211-213 |
| I-270 | Melting Point | 167-169 |
| I-271 | Melting Point | 138-140 |
| I-272 | Melting Point | 173-174 |
| I-273 | Melting Point | 141-143 |
| I-274 | Melting Point | 148-150 |
| I-275 | Melting Point | 204-205 |
| I-276 | | Incapable measurement |
| I-277 | Melting Point | 135-137 |
| I-278 | Melting Point | 144-145 |
| I-279 | Melting Point | 166-168 |
| I-280 | Melting Point | 186-188 |
| I-281 | Melting Point | 139-141 |
| I-282 | Melting Point | 164-165 |
| I-283 | Melting Point | 190-192 |
| I-284 | Melting Point | 160-162 |
| I-363 | Melting Point | 250-252 |
| I-364 | Melting Point | 168-170 |
| I-365 | Melting Point | 182-183 |
| I-366 | Melting Point | 212-214 |
| I-367 | Melting Point | 208-210 |
| I-368 | Melting Point | 152-154 |
| I-371 | Melting Point | 189-190 |
| I-372 | Melting Point | 205-207 |
| I-373 | Melting Point | 124-126 |
| I-379 | Melting Point | 208-209 |
| I-380 | Melting Point | 146-147 |
| I-385 | Melting Point | 194-196 |
| I-388 | Melting Point | 172-175 |
| I-395 | Melting Point | 140-142 |

TABLE 127

| Compound No. | Melting Point (° C.) or Refractive Rate ($n_D^{20}$) | |
|---|---|---|
| II-1 | Melting Point | 68-71 |
| II-4 | Melting Point | 203-204 |
| II-5 | Melting Point | 180-182 |
| II-6 | Melting Point | 172-174 |
| II-7 | Melting Point | 177-178 |
| II-8 | Melting Point | 70-72 |
| II-9 | Melting Point | 100-101 |
| II-11 | Melting Point | 202-204 |
| II-13 | Melting Point | 201-202 |
| II-14 | Melting Point | 105-107 |
| II-15 | Melting Point | 176-179 |
| II-20 | Melting Point | 93-94 |
| II-21 | Melting Point | 123-126 |
| II-23 | Melting Point | 136-138 |
| II-24 | Melting Point | 101-104 |
| II-29 | Melting Point | 169-171 |
| II-33 | Melting Point | 147-149 |
| II-39 | Melting Point | 125-127 |
| II-44 | Melting Point | 112-114 |
| II-51 | Melting Point | 264-266 |
| II-52 | Melting Point | 201-202 |
| II-57 | Melting Point | 124-125 |
| II-62 | Melting Point | 112-114 |
| II-63 | Melting Point | 175-177 |
| II-64 | Melting Point | 174-176 |
| II-68 | Melting Point | 164-167 |
| II-69 | Melting Point | 88-90 |
| II-71 | Melting Point | 78-80 |
| II-74 | Melting Point | 106-108 |
| II-75 | Melting Point | 173-175 |
| II-81 | Melting Point | 135-136 |
| II-84 | Melting Point | 149-150 |
| II-90 | Melting Point | 103-105 |

TABLE 127-continued

| Compound No. | Melting Point (° C.) or Refractive Rate ($n_D^{20}$) | |
|---|---|---|
| II-95 | Melting Point | 111-113 |
| II-101 | Melting Point | 61-64 |
| II-116 | Melting Point | 93-96 |
| II-121 | Melting Point | 125-128 |
| II-122 | Melting Point | 172-174 |
| II-124 | Melting Point | 91-94 |
| II-125 | Melting Point | 274-277 |
| II-129 | Melting Point | 230-232 |
| II-130 | Melting Point | 96-99 |
| II-131 | Melting Point | 136-137 |
| II-136 | Melting Point | 143-146 |
| II-137 | Melting Point | 107-110 |

TABLE 128

| Compound No. | Melting Point (° C.) or Refractive Rate ($n_D^{20}$) | |
|---|---|---|
| II-140 | Melting Point | 128-130 |
| II-146 | Melting Point | 111-113 |
| II-149 | Melting Point | 101-103 |
| II-167 | Melting Point | 108-110 |
| II-168 | Melting Point | 122-123 |
| II-169 | Melting Point | 215-216 |
| II-173 | Melting Point | 185-188 |
| II-174 | Melting Point | 98-101 |
| II-175 | Melting Point | 110-112 |
| II-177 | Melting Point | 136-138 |
| II-178 | Melting Point | 113-115 |
| II-179 | Melting Point | 190-193 |
| II-180 | Melting Point | 106-109 |
| II-185 | Melting Point | 124-126 |
| II-186 | Melting Point | 242-245 |
| II-187 | Melting Point | 114-116 |
| II-188 | Melting Point | 136-138 |
| II-189 | Melting Point | 187-189 |
| II-190 | Melting Point | 217-219 |
| II-193 | Melting Point | 173-175 |
| II-194 | Melting Point | 105-107 |
| II-195 | Melting Point | 191-193 |
| II-196 | Melting Point | 120-122 |
| II-197 | Melting Point | 205-207 |
| II-205 | Melting Point | 139-142 |
| II-208 | Melting Point | 102-104 |
| II-209 | Melting Point | 109-111 |
| II-210 | Melting Point | 98-100 |
| II-211 | Melting Point | 113-115 |
| II-212 | Melting Point | 126-129 |
| II-213 | Melting Point | 171-172 |
| II-214 | Melting Point | 97-99 |
| II-215 | Melting Point | 116-117 |
| II-216 | Melting Point | 181-183 |
| II-217 | Melting Point | 197-199 |
| II-218 | Melting Point | 138-140 |
| II-219 | Melting Point | 183-185 |
| II-220 | Melting Point | 128-130 |
| II-221 | Melting Point | 106-109 |
| II-222 | Melting Point | 91-92 |
| II-223 | Melting Point | 110-111 |
| II-224 | Melting Point | 143-145 |
| II-225 | Melting Point | 135-138 |
| II-226 | Melting Point | 141-143 |
| II-227 | Melting Point | 201-203 |
| II-228 | Melting Point | 182-185 |
| II-229 | Melting Point | 145-148 |

TABLE 129

| Compound No. | Melting Point (° C.) or Refractive Rate ($n_D^{20}$) | |
|---|---|---|
| II-230 | Melting Point | 161-163 |
| II-231 | Melting Point | 154-157 |
| II-232 | Melting Point | 205-208 |

TABLE 129-continued

| Compound No. | Melting Point (° C.) or Refractive Rate ($n_D^{20}$) | |
|---|---|---|
| II-233 | Melting Point | 212-214 |
| II-234 | Melting Point | 118-121 |
| II-235 | Melting Point | 97-98 |
| II-236 | Melting Point | 232-234 |
| II-237 | Melting Point | 182-183 |
| II-238 | Melting Point | 213-216 |
| II-239 | Melting Point | 153-155 |
| II-240 | Melting Point | 135-137 |
| II-241 | Melting Point | 121-123 |
| II-242 | Melting Point | 145-146 |
| II-243 | Melting Point | 176-179 |
| II-244 | Melting Point | 257-260 |
| II-245 | Melting Point | 165-166 |
| II-246 | Melting Point | 155-158 |
| II-247 | Melting Point | 201-204 |
| II-248 | Melting Point | 113-116 |
| II-249 | Melting Point | 165-167 |
| II-250 | Melting Point | 197-198 |
| II-251 | Melting Point | 129-131 |
| II-252 | Melting Point | 162-164 |
| II-253 | Melting Point | 202-204 |
| II-254 | Melting Point | 104-106 |
| II-255 | Melting Point | 118-120 |
| II-256 | Melting Point | 189-190 |
| II-257 | Melting Point | 91-92 |
| II-258 | Melting Point | 195-197 |
| II-259 | Melting Point | 214-216 |
| II-260 | Melting Point | 224-226 |
| II-261 | Melting Point | 181-183 |
| II-262 | Melting Point | 264-267 |
| II-263 | Melting Point | 194-196 |
| II-301 | Melting Point | 222-223 |
| II-302 | Melting Point | 190-192 |
| II-303 | Melting Point | 102-103 |
| II-304 | Melting Point | 183-185 |
| II-305 | Melting Point | 93-95 |
| II-306 | Melting Point | 156-157 |
| II-307 | Melting Point | 227-229 |
| II-317 | Melting Point | 107-109 |
| II-323 | Melting Point | 106-108 |

TABLE 130

| Compound No. | Melting Point (° C.) or Refractive Rate ($n_D^{20}$) | |
|---|---|---|
| III-2 | Melting Point | 177-180 |
| III-5 | Melting Point | 101-103 |
| III-7 | Melting Point | 105-106 |
| III-12 | Refractive Rate | 1.5852 |
| III-13 | Melting Point | 124-126 |
| III-15 | Refractive Rate | 1.5521 |
| III-30 | Melting Point | 128-130 |
| III-35 | Melting Point | 198-200 |
| III-40 | Melting Point | 163-165 |
| III-45 | Melting Point | 141-142 |
| III-59 | Melting Point | 87-88 |
| III-70 | Melting Point | 158-159 |
| III-88 | Melting Point | 119-121 |
| III-90 | Melting Point | 126-128 |
| III-96 | Melting Point | 132-134 |
| III-99 | Melting Point | 142-144 |
| III-107 | Melting Point | 178-180 |
| III-108 | Melting Point | 155-157 |
| III-111 | Melting Point | 170-172 |
| III-117 | Melting Point | 185-188 |
| III-118 | Melting Point | 149-151 |
| III-120 | Melting Point | 167-168 |
| III-130 | Melting Point | 184-185 |
| III-139 | Melting Point | 226-229 |
| III-158 | Melting Point | 185-187 |
| III-173 | Melting Point | 202-204 |
| III-189 | Melting Point | 196-198 |
| III-201 | Melting Point | 135-138 |

TABLE 130-continued

| Compound No. | Melting Point (° C.) or Refractive Rate ($n_D^{20}$) | |
|---|---|---|
| III-202 | Melting Point | 197-199 |
| III-207 | Melting Point | 201-203 |
| III-209 | Melting Point | 231-233 |
| III-212 | Melting Point | 93-96 |
| III-213 | Melting Point | 139-141 |
| III-220 | Melting Point | 148-151 |
| III-221 | Melting Point | 182-185 |
| III-229 | Melting Point | 87-88 |
| III-230 | Melting Point | 113-115 |
| III-231 | Melting Point | 143-144 |
| III-232 | Melting Point | 108-110 |
| III-233 | Melting Point | 83-85 |
| III-234 | Melting Point | 168-170 |
| III-235 | Melting Point | 136-138 |
| III-236 | Melting Point | 168-171 |
| III-237 | Melting Point | 128-130 |
| III-238 | Melting Point | 136-137 |
| III-239 | Melting Point | 122-124 |
| III-240 | Melting Point | 222-224 |

TABLE 131

| Compound No. | Melting Point (°C.) or Refractive Rate ($n_D^{20}$) | |
|---|---|---|
| III-241 | Melting Point | 159-160 |
| III-242 | Melting Point | 71-73 |
| III-243 | Melting Point | 88-89 |
| III-244 | Melting Point | 178-180 |
| III-245 | Melting Point | 161-162 |
| III-246 | Melting Point | 129-131 |
| III-247 | Melting Point | 133-134 |

TABLE 132

| Compound No. | Melting Point (°C.) or Refractive Rate ($n_D^{20}$) | |
|---|---|---|
| IV-1 | Melting Point | 253-255 |
| IV-2 | Melting Point | 158-159 |
| IV-3 | Melting Point | 216-218 |
| IV-4 | Melting Point | 224-226 |
| IV-6 | Melting Point | 216-217 |
| IV-7 | Melting Point | 231-232 |
| IV-8 | Melting Point | 231-232 |
| IV-9 | Melting Point | 181-183 |
| IV-11 | Melting Point | 224-227 |
| IV-13 | Melting Point | 203-206 |
| IV-17 | Melting Point | 264-266 |
| IV-18 | Melting Point | 237-239 |
| IV-19 | Melting Point | 251-253 |
| IV-20 | Melting Point | 163-165 |
| IV-21 | Melting Point | 203-205 |
| IV-23 | Melting Point | 110-112 |
| IV-24 | Melting Point | 117-119 |
| IV-30 | Melting Point | 123-125 |
| IV-33 | Melting Point | 198-199 |
| IV-34 | Melting Point | 183-185 |
| IV-39 | Melting Point | 168-171 |
| IV-40 | Melting Point | 176-178 |
| IV-41 | Melting Point | 203-205 |
| IV-44 | Melting Point | 94-96 |
| IV-52 | Melting Point | 171-172 |
| IV-57 | Melting Point | 177-180 |
| IV-62 | Melting Point | 133-135 |
| IV-68 | | Incapable measurement |
| IV-69 | Melting Point | 102-104 |
| IV-85 | Melting Point | 185-186 |
| IV-90 | Melting Point | 172-174 |
| IV-95 | Melting Point | 133-136 |
| IV-100 | Melting Point | 100-102 |
| IV-101 | Melting Point | 155-156 |

TABLE 132-continued

| Compound No. | Melting Point (° C.) or Refractive Rate ($n_D^{20}$) | |
|---|---|---|
| IV-106 | Melting Point | 166-169 |
| IV-128 | Melting Point | 176-178 |
| IV-136 | Melting Point | 196-197 |
| IV-150 | Melting Point | 201-202 |
| IV-151 | Melting Point | 177-178 |
| IV-152 | Melting Point | 230-232 |
| IV-153 | Melting Point | 242-245 |
| IV-154 | Melting Point | 226-228 |
| IV-155 | Melting Point | 260-261 |
| IV-156 | Melting Point | 215-217 |
| IV-157 | Melting Point | 121-124 |

TABLE 133

| Compound No. | Melting Point (° C.) or Refractive Rate ($n_D^{20}$) | |
|---|---|---|
| IV-158 | Melting Point | 251-253 |
| IV-159 | Melting Point | 183-185 |
| IV-160 | Melting Point | 208-211 |
| IV-161 | Melting Point | 237-240 |
| IV-165 | Melting Point | 228-231 |
| IV-166 | Melting Point | 196-199 |
| IV-168 | Melting Point | 199-201 |
| IV-169 | Melting Point | 171-173 |
| IV-170 | Melting Point | 216-217 |
| IV-173 | Melting Point | 208-210 |
| IV-174 | Melting Point | 196-197 |
| IV-177 | Melting Point | 204-207 |
| IV-178 | Melting Point | 167-169 |
| IV-179 | Melting Point | 153-155 |
| IV-180 | Melting Point | 177-179 |
| IV-184 | Melting Point | 181-182 |
| IV-185 | Melting Point | 104-106 |
| IV-186 | Melting Point | 221-223 |
| IV-187 | Melting Point | 214-216 |
| IV-188 | Melting Point | 217-219 |
| IV-189 | Melting Point | 194-196 |
| IV-191 | Melting Point | 118-120 |
| IV-200 | Melting Point | 237-239 |
| IV-201 | Melting Point | 167-168 |
| IV-202 | Melting Point | 155-157 |
| IV-203 | Melting Point | 189-191 |
| IV-206 | Melting Point | 122-125 |
| IV-208 | Melting Point | 171-172 |
| IV-209 | Melting Point | 242-245 |
| IV-210 | Melting Point | 222-224 |
| IV-211 | | Incapable measurement |
| IV-212 | Melting Point | 208-210 |
| IV-213 | Melting Point | 177-179 |
| IV-214 | Melting Point | 219-222 |
| IV-215 | Melting Point | 176-178 |
| IV-216 | Melting Point | 118-122 |
| IV-217 | Melting Point | 231-232 |
| IV-218 | Melting Point | 180-182 |
| IV-219 | Melting Point | 200-202 |
| IV-220 | Melting Point | 225-228 |
| IV-221 | Melting Point | 185-187 |
| IV-222 | Melting Point | 185-186 |
| IV-223 | Melting Point | 210-212 |
| IV-224 | Melting Point | 254-257 |
| IV-225 | Melting Point | 167-169 |
| IV-226 | Melting Point | 186-189 |
| IV-227 | Melting Point | 200-202 |
| IV-228 | Melting Point | 182-184 |
| IV-229 | Melting Point | 177-178 |
| IV-230 | Melting Point | 142-144 |

TABLE 134

| Compound No. | Melting Point (° C.) or Refractive Rate ($n_D^{20}$) | |
|---|---|---|
| IV-231 | Melting Point | 262-265 |
| IV-232 | Melting Point | 181-183 |
| IV-233 | Melting Point | 200-203 |
| IV-234 | Melting Point | 125-127 |
| IV-235 | Melting Point | 88-89 |
| IV-236 | Melting Point | 170-172 |
| IV-237 | Melting Point | 179-182 |
| IV-238 | Melting Point | 146-149 |
| IV-239 | Melting Point | 207-209 |
| IV-240 | Melting Point | 135-137 |
| IV-241 | Melting Point | 208-211 |
| IV-242 | Melting Point | 137-139 |
| IV-243 | Melting Point | 128-130 |
| IV-244 | Melting Point | 181-182 |
| IV-245 | Melting Point | 92-94 |
| IV-246 | Melting Point | 198-201 |
| IV-247 | Melting Point | 98-100 |
| IV-248 | Melting Point | 122-124 |
| IV-249 | Melting Point | 104-107 |
| IV-250 | Melting Point | 119-122 |
| IV-251 | Melting Point | 184-187 |
| IV-252 | Melting Point | 119-121 |
| IV-253 | Melting Point | 204-205 |
| IV-254 | Melting Point | 233-235 |
| IV-255 | Melting Point | 247-249 |
| IV-256 | Melting Point | 230-232 |
| IV-257 | Melting Point | 234-236 |
| IV-258 | Melting Point | 191-192 |
| IV-259 | Melting Point | 228-229 |
| IV-260 | Melting Point | 202-204 |
| IV-261 | Melting Point | 126-128 |
| IV-262 | Melting Point | 235-237 |
| IV-263 | Melting Point | 216-218 |
| IV-264 | Melting Point | 197-199 |
| IV-265 | Melting Point | 266-268 |
| IV-266 | Melting Point | 210-211 |
| IV-267 | Melting Point | 208-210 |
| IV-268 | Melting Point | 217-219 |
| IV-269 | Melting Point | 207-210 |
| IV-270 | Melting Point | 217-220 |
| IV-271 | Melting Point | 74-76 |
| IV-273 | Melting Point | 268-271 |
| IV-274 | Melting Point | 196-199 |
| IV-284 | Melting Point | 181-183 |
| IV-285 | Melting Point | 100-103 |
| IV-286 | Melting Point | 103-105 |
| IV-287 | Melting Point | 217-219 |

[NMR Data]

For Compound Nos. I-15, I-58, I-65, I-93, I-159, I-276, III-12, III-15 and IV-211, the $^1$H-NMR data (CDCl$_3$/TMS δ (ppm) value) are presented in the following.

Compound No. I-15:

1.02 (3H, t), 1.55 (2H, m), 1.81 (2H, m), 2.07 (2H, t), 2.44 (2H, s), 2.77 (2H, t), 9.27 (2H, t), 7.36 (2H, m), 7.58 (1H, t), 7.86 (1H, d), 16.32 (1H, s)

Compound No. I-58:

2.07 (2H, s), 2.92 (2H, s), 2.77 (2H, t), 3.34 (3H, s), 3.51 (2H, s), 3.78 (2H, s), 5.79 (2H, s), 7.35 (1H, t), 7.69 (2H, m), 7.83 (1H, d), 16.27 (1H, s)

Compound No. I-65:

1.42-2.09 (9H, m), 2.07 (2H, s), 2.43 (2H, s), 3.01 (2H, s), 3.59-9.05 (5H, m), 5.75 (1H, d), 5.85 (1H, d), 7.36 (1H, t), 7.54-7.65 (2H, m), 7.82 (1H, d), 16.3 (1H, br)

Compound No. I-68:

1.41 (3H, t), 2.07 (2H, s), 2.49 (2H, s), 2.77 (2H, t), 9.09 (2H, q), 6.87 (1H, m), 7.02 (1H, d), 7.31 (1H, m), 7.96 (1H, t), 8.18 (1H, d), 8.99 (1H, d), 1.98 (3H, t), 9.13 (2H, q), 7.15 (2H, d), 7.23 (2H, d), 7.56 (1H, m), 8.63 (1H, d), 8.72 (1H, d)

Compound No. I-93:
2.00-2.08 (4H, m), 2.43 (2H, br), 2.77 (2H, t), 3.36 (3H, s), 3.47 (2H, t), 4.36 (2H, t), 7.34 (1H, t), 7.50 (1H, d), 7.57 (1H, t), 7.86 (1H, d), 16.33 (1H, br).

Compound No. I-159:
2.07 (2H, t), 2.46 (2H, br), 2.78 (2H, t), 7.25 (1H, s), 7.36 (1H, t), 7.46 (1H, t), 7.61 (1H, d), 7.87 (1H, d), 7.89 (1H, d), 16.23 (1H, br).

Compound No. I-276:
2.04 (2H, m), 2.42 (2H, m), 2.53 (2H, m), 3.84 (3H, s), 6.52-6.60 (2H, m), 7.06-7.59 (6H, m), 7.86 (1H, d), 18.1 (1H, s)

Compound No. III-12:
1.06 (3H, s), 1.83 (2H, m), 2.08 (2H, t), 2.44 (2H, s), 2.65 (2H, s), 4.41 (2H, t), 7.27 (1H, d), 8.13 (1H, d), 8.61 (1H, d), 16.13 (1H, s)

Compound No. III-15:
1.01 (3H, s), 1.52 (2H, m), 1.79 (2H, m), 2.05 (2H, t), 2.45 (2H, s), 2.76 (2H, t), 4.47 (2H, t), 7.28 (1H, d), 8.13 (1H, d), 8.61 (1H, d), 16.16 (1H, s)

Compound No. IV-211:
2.06 (2H, t), 2.95 (2H, brs), 2.78 (2H, brs), 3.73 (6H, s), 6.72 (2H, d), 7.25 (1H, d), 7.92 (1H, t), 8.16 (1H, dd), 8.46 (1H, dd), 16.11 (1H, brs)

Reference Example 1

(Production Intermediate) Production of 1-methyl-2-oxo-1,2-dihydroquinoxaline-3-carboxylic acid (Compound No. of Production Intermediate: V-2)

(1) Production of ethyl 1-methyl-2-oxo-1,2-dihydroquinoxaline-3-carboxylate 4.0 g (18.3 mmol) of ethyl 2-oxo-1,2-dihydroquinoxaline-3-carboxylate was dissolved in N,N-dimethylformamide (100 mL), and under a nitrogen stream, 0.81 g (20.3 mmol) of 60% sodium hydride (oily) was added thereto, while maintaining the liquid temperature in the range of 5° C. to 10° C. After stirring the mixture for one hour at room temperature, 3.9 g (27.5 mmol) of iodomethane was added dropwise to the reaction solution. The mixture was stirred for a day at room temperature, and then the reaction mixture was poured into water, and extracted with ethyl acetate. The organic layer was washed with water and a saturated aqueous solution of sodium chloride, and dried over anhydrous sodium sulfate. The inorganic matter was separated by filtration, and then the solvent was distilled off under reduced pressure. The residue thus obtained was purified by silica gel chromatography (developing solvent: ethyl acetate:hexane=3:2), to obtain 3.0 g (yield: 71%) of ethyl 1-methyl-2-oxo-1,2-dihydroquinoxaline-3-carboxylate as a white powder.
$^1$H-NMR (CDCl$_3$/TMS δ (ppm)): 1.45 (3H, t), 3.74 (3H, s), 4.51 (2H, q), 7.35-7.43 (2H, m), 7.67 (1H, t), 7.96 (1H, d)

(2) Production of 1-methyl-2-oxo-1,2-dihydroquinoxaline-3-carboxylic acid 3.0 g (12.9 mmol) of ethyl 1-methyl-2-oxo-1,2-dihydroquinoxaline-3-carboxylate was dissolved in ethanol (100 mL), and 4.1 g (25.6 mmol) of a 25% aqueous solution of sodium hydroxide was added dropwise thereto at room temperature. The mixture was stirred for a day at room temperature, and then the reaction mixture was concentrated under reduced pressure. Water was added to the reaction mixture, and the solution was acidified using 10% hydrochloric acid, and extracted with chloroform. The organic layer was dried over anhydrous sodium sulfate, and then the inorganic matter was separated by filtration. Then, the solvent was distilled off under reduced pressure, to obtain 2.6 g (yield: 99%) of 1-methyl-2-oxo-1,2-dihydroquinoxaline-3-carboxylic acid as a milky yellow powder.
$^1$H-NMR (CDCl$_3$/TMS δ (ppm)): 3.89 (3H, s), 7.52 (1H, d), 7.58 (1H, t), 7.86 (1H, t), 8.28 (1H, d), 14.23 (1H, br)

Reference Example 2

(Production Intermediate) Production of 3-oxo-4-phenyl-3,4-dihydropyrido[2,3-b]pyrazine-2-carboxylic acid (Compound No. of Production Intermediate: VIII-1)

(1) Production of ethyl 3-oxo-4-phenyl-3,4-dihydropyrido[2,3-b]pyrazine-2-carboxylate 11.68 g (63 mmol) of 3-amino-2-anilinopyridine was dissolved in ethanol (150 mL), and 12.07 g (69 mmol) of diethyl ketomalonate was added thereto. The mixture was heated to reflux for 4 hours while stirring. After confirming the completion of the reaction, the reaction solution was cooled to room temperature, and the solvent was distilled off under reduced pressure. The residue thus obtained was washed using diisopropyl ether, to obtain 10.74 g (yield: 58%) of ethyl 3-oxo-4-phenyl-3,4-dihydropyrido[2,3-b]pyrazine-2-carboxylate as pale yellow crystals.
$^1$H-NMR (CDCl$_3$/TMS δ (ppm)): 1.44 (3H, t), 9.51 (2H, q), 7.30 (2H, d), 7.35 (1H, q), 7.56 (3H, m), 8.30 (1H, q), 8.52 (1H, q)

(2) Production of 3-oxo-4-phenyl-3,4-dihydropyrido[2,3-b]pyrazine-2-carboxylic acid 10.74 g (36 mmol) of ethyl 3-oxo-4-phenyl-3,4-dihydropyrido[2,3-b]pyrazine-2-carboxylate was dissolved in acetic acid (270 mL), and 6N hydrochloric acid (80 mL) was added thereto at room temperature. Then, the mixture was stirred overnight at room temperature. After confirming the completion of the reaction, the solvent was distilled off under reduced pressure, and water (100 mL) was added. The solid thus obtained was separated by filtration and dried, to obtain 6.50 g (yield: 67%) of 3-oxo-4-phenyl-3,4-dihydropyrido[2,3-b]pyrazine-2-carboxylic acid as pale brown crystals.
$^1$H-NMR (CDCl$_3$/TMS δ (ppm)): 7.33 (2H, d), 7.57 (1H, m), 7.65 (3H, m), 8.64 (1H, q), 8.70 (1H, q)

Reference Example 3

(Production Intermediate) Production of 4-(4-methoxyphenyl)-3-oxo-3,4-dihydropyrido[2,3-b]pyrazine-2-carboxylic acid (Compound No. of Production Intermediate: VIII-34)

(1) Production of N-(4-methoxyphenyl)-3-nitropyridin-2-amine 5.0 g (32 mmol) of 2-chloro-3-nitropyridine was dissolved in 2-ethoxyethanol (150 mL), and water (150 mL) was added thereto. To the mixed solution, 3.9 g (32 mmol) of 4-methoxyaniline and 6 N hydrochloric acid (1 mL) were added, and the mixture was heated to reflux for 12 hours while stirring. After confirming the completion of the reaction, the reaction solution was cooled to room temperature, and the solvent was distilled off under reduced pressure. The residue was extracted with ethyl acetate, and washed with saturated brine, and then the obtained organic layer was dried over anhydrous magnesium sulfate. The inorganic matter was separated by filtration, and then the solvent was distilled off under reduced pressure, to obtain 6.6 g (yield: 85%) of N-(4-methoxyphenyl)-3-nitropyridin-2-amine as orange-colored crystals.

$^1$H-NMR (CDCl$_3$/TMS δ (ppm)): 3.83 (3H, s), 6.78 (1H, q), 6.94 (2H, d), 7.99 (2H, d), 8.44 (1H, q), 8.51 (1H, q), 9.96 (1H, brs)

(2) Production of 3-amino-2-(4-methoxyphenyl)aminopyridine 6.6 g (27 mmol) of 2-(4-methoxyphenyl)amino-3-nitropyridine was dissolved in methanol (150 mL). A solution in which tin (II) chloride dihydrate was dissolved in 12 N hydrochloric acid (40 mL) was prepared, and this solution was added dropwise to the reaction solution at 0° C. over 5 minutes. The reaction solution was returned to room temperature, and then stirred for 3 hours. After confirming the completion of the reaction, the solvent was distilled off under reduced pressure, and water (100 mL) was added. The reaction solution was adjusted to pH 12 using a 10% aqueous solution of sodium hydroxide, subsequently filtered, and extracted with dichloromethane. The obtained organic layer was dried over anhydrous magnesium sulfate, and then the inorganic matter was separated by filtration. The solvent was distilled off under reduced pressure, to obtain 5.2 g (yield: 90%) of 3-amino-2-(4-methoxyphenyl)aminopyridine as orange-colored crystals.

$^1$H-NMR (CDCl$_3$/TMS δ (ppm)): 3.39 (2H, s), 3.79 (3H, s), 6.06 (1H, brs), 6.69 (1H, q), 6.87 (2H, d), 6.97 (1H, q), 7.22 (2H, d), 7.80 (1H, q)

(3) Production of ethyl 4-(4-methoxyphenyl)-3-oxo-3,4-dihydropyrido[2,3-b]pyrazine-2-carboxylate 5.2 g (24 mmol) of 3-amino-2-(4-methoxyphenyl)aminopyridine was dissolved in ethanol (150 mL), and 4.6 g (27 mmol) of diethyl ketomalonate was added thereto. The mixture was heated to reflux for 9 hours while stirring. After confirming the completion of the reaction, the reaction solution was cooled to room temperature, and the solvent was distilled off under reduced pressure. The residue thus obtained was purified by column chromatography (developing solvent: ethyl acetate:hexane=1:2), to obtain 2.9 g (yield: 37%) of ethyl 4-(4-methoxyphenyl)-3-oxo-3,4-dihydropyrido[2,3-b]pyrazine-2-carboxylate as yellow crystals $^1$H-NMR (CDCl$_3$/TMS δ (ppm)): 1.44 (3H, t), 3.88 (2H, s), 4.51 (2H, q), 7.09 (2H, d), 7.22 (2H, d), 7.35 (1H, q), 8.29 (1H, q), 8.54 (1H, q)

(4) Production of 4-(4-methoxyphenyl)-3-oxo-3,4-dihydropyrido[2,3-b]pyrazine-2-carboxylic acid 2.9 g (9 mmol) of ethyl 4-(4-methoxyphenyl)-3-oxo-3,4-dihydropyrido[2,3-b]pyrazine-2-carboxylate was dissolved in 1,4-dioxane (30 mL). A solution in which 1.8 g (13 mmol) of potassium carbonate was dissolved in water (60 mL) was prepared, and was added to the reaction solution at room temperature, and then the mixture was stirred for one hour at 50° C. After confirming the completion of the reaction, the reaction solution was cooled to room temperature, and the solvent was distilled off under reduced pressure. Water (50 mL) was added, and then the reaction solution was cooled to 0° C., and adjusted to pH 1 using 6 N hydrochloric acid. Subsequently, a solid was separated by filtration and dried, to obtain 2.6 g (yield: 98%) of 4-(4-methoxyphenyl)-3-oxo-3,4-dihydropyrido[2,3-b]pyrazine-2-carboxylic acid as yellow crystals.

$^1$H-NMR (CDCl$_3$/TMS δ (ppm)): 3.91 (3H, s), 7.15 (2H, d), 7.23 (2H, d), 7.56 (1H, q), 8.63 (1H, q), 8.72 (1H, q)

Reference Example 4

(Production Intermediate) Production of ethyl 1-(3-methoxyphenyl)-2-oxo-1,2-dihydroquinoxaline-3-carboxylate 2.0 g (9.2 mmol) of ethyl 2-oxo-1,2-dihydroquinoxaline-3-carboxylate was dissolved in dichloromethane (100 mL), and 2.8 g (1.8 mmol) of 3-methoxyphenylboric acid, 3.3 g (1.8 mmol) of anhydrous copper (II) acetate and 1.4 g (1.8 mmol) of pyridine were added thereto. The mixture was stirred for 72 hours at room temperature. After completion of the reaction, the inorganic matter was separated by filtration, and then the solvent was distilled off under reduced pressure. The residue thus obtained was purified by column chromatography (developing solvent: ethyl acetate:hexane=1:1), to obtain 1.2 g (yield: 42%) of ethyl 1-(3-methoxyphenyl)-2-oxo-1,2-dihydroquinoxaline-3-carboxylate as a white powder.

$^1$H-NMR (CDCl$_3$/TMS δ (ppm)): 1.43 (3H, t), 3.83 (3H, s), 4.51 (2H, q), 6.77-6.88 (2H, m), 7.08 (2H, d), 7.35 (1H, t), 7.39-7.53 (2H, m), 7.98 (1H, d)

Reference Example 5

(Production Intermediate) Production of 1-[(3-methylisoxazol-5-yl)methyl]-2-oxo-1,2-dihydroquinoxaline-3-carboxylic acid (Compound No. of Production Intermediate: V-103)

(1) Production of ethyl 2-oxo-1-(2-propynyl)-1,2-dihydroquinoxaline-3-carboxylate 9.2 g (62.9 mmol) of N-(2-propynyl) 1,2-phenylenediamine and 12.1 g (69.2 mmol) of diethyl ketomalonate were dissolved in toluene (100 mL), and the solution was refluxed for 3 hours. After confirming the completion of the reaction, the reaction solution was concentrated under reduced pressure, and the solid matter thus obtained was washed with diisopropyl ether, to obtain 15.0 g (yield: 93%) of ethyl 2-oxo-1-(2-propynyl)-1,2-dihydroquinoxaline-3-carboxylate as a white powder.

$^1$H-NMR (CDCl$_3$/TMS δ (ppm)): 1.45 (3H, t), 2.32 (1H, t), 4.51 (2H, q), 5.08 (2H, d), 7.43 (1H, t), 7.52 (1H, d), 7.70 (1H, t), 7.97 (1H, d)

(2) Production of Chloroacetaldoxime 10.4 g (77.9 mmol) of N-chlorosuccinimide was dissolved in N,N-dimethylformamide (65 mL), and 3.6 g (60.9 mmol) of acetaldoxime was added dropwise at a temperature in the range of 0° C. to 5° C. The mixture was stirred for 3 hours at 10° C. Water was added to the reaction solution, and the mixture was extracted with diethyl ether. The organic layer was washed with a saturated aqueous solution of sodium chloride, dried and concentrated, to obtain chloroacetaldoxime as a yellow liquid. The obtained chloroacetaldoxime was used in the subsequent reaction without purification.

(3) Production of ethyl 1-[(3-methylisoxazol-5-yl) methyl]-2-oxo-1,2-dihydroquinoxaline-3-carboxylate 3.0 g (11.7 mmol) of ethyl 2-oxo-1-(2-propynyl)-1,2-dihydroquinoxaline-3-carboxylate and 3.28 g (35.1 mmol) of chloroacetaldoxime were dissolved in tetrahydrofuran (30 mL), and 3.55 g (35.1 mmol) of triethylamine was added dropwise at a temperature in the range of 0° C. to 5° C. The mixture was stirred for 3 days at room temperature. After confirming the completion of the reaction, the solvent was distilled off under reduced pressure, and the residue was extracted with ethyl acetate. The organic layer was washed with an aqueous solution of citric acid, dried over anhydrous sodium sulfate, and concentrated. The solid matter thus obtained was washed with diisopropyl ether, to obtain 3.4 g (yield: 93%) of ethyl 1-[(3-methylisoxazol-5-yl)methyl]-2-oxo-1,2-dihydroquinoxaline-3-carboxylate as a white powder.

$^1$H-NMR (CDCl$_3$/TMS δ (ppm)): 1.45 (3H, t), 2.25 (3H, s), 9.52 (2H, q), 5.52 (2H, s), 6.19 (1H, s), 7.42 (1H, t), 7.52 (1H, d), 7.68 (1H, t), 7.98 (1H, d)

(4) Production of 1-[(3-methylisoxazol-5-yl)methyl]-2-oxo-1,2-dihydroquinoxaline-3-carboxylic acid 3.0 g (9.58 mmol) of ethyl 1-[(3-methylisoxazol-5-yl)methyl]-2-oxo-1,2-dihydroquinoxaline-3-carboxylate and 0.46 g (11.5 mmol) of lithium hydroxide monohydrate were dissolved in a solvent mixture of ethanol (30 mL) and water (30 mL), and the solution was stirred for 2 hours at room temperature. The reaction solution was concentrated to a half the original volume, and water was added to the residue. The mixture was acidified using 10% hydrochloric acid, and then extracted with ethyl acetate. The organic layer was washed with water, dried over anhydrous sodium sulfate, and concentrated, to obtain 2.3 g (yield: 84%) of 1-[(3-methylisoxazol-5-yl)methyl]-2-oxo-1,2-dihydroquinoxaline-3-carboxylic acid as a white powder.

$^1$H-NMR (CDCl$_3$/TMS δ (ppm)): 2.28 (3H, s), 5.66 (2H, s), 7.62 (1H, t), 7.71 (1H, d), 7.87 (1H, t), 8.28 (1H, d)

Reference Example 6

Production of 2-oxo-1-[(2,2,2-trifluoroethoxy)methyl]-1,2-dihydroquinoxaline-3-carboxylic acid (Compound No. of Production Intermediate: V-35)

(1) Production of ethyl 1-(methylthiomethyl)-2-oxo-1,2-dihydroquinoxaline-3-carboxy late 5.0 g (22.9 mmol) of ethyl 2-oxo-1,2-dihydroquinoxaline-3-carboxylate, 3.8 g (27.5 mmol) of potassium carbonate, 4.56 g (27.5 mmol) of potassium iodide and 2.43 g (25.2 mmol) of chloromethyl methyl sulfide were dissolved in acetone (100 mL), and the solution was refluxed for 5 hours. After completion of the reaction, the solvent was distilled off under reduced pressure, and to the residue thus obtained, a mixture of water and ethyl acetate was added. The resulting mixture was separated. The organic layer was dried over anhydrous magnesium sulfate, and the inorganic matter was separated by filtration. The solvent was distilled off under reduced pressure, and the residue thus obtained was solidified using diethyl ether, to obtain 3.5 g (yield: 55%) of ethyl 1-(methylthiomethyl)-2-oxo-1,2-dihydroquinoxaline-3-carboxy late as a white powder.

$^1$H-NMR (CDCl$_3$/TMS δ (ppm)): 1.44 (3H, t), 2.32 (3H, s), 4.51 (2H, q), 5.39 (2H, s), 7.40 (2H, m), 7.67 (1H, t), 7.98 (1H, d)

(2) Production of ethyl 1-(chloromethyl)-2-oxo-1,2-dihydroquinoxaline-3-carboxylate 2.1 g (7.5 mmol) of ethyl 1-(methylthiomethyl)-2-oxo-1,2-dihydroquinoxaline-3-carboxy late was dissolved in dichloromethane (10 mL), and 1.3 g (9.8 mmol) of sulfuryl chloride was added dropwise at or below 10° C. The mixture was stirred for 2 hours at room temperature. After completion of the reaction, the solvent was distilled off under reduced pressure, to obtain ethyl 1-(chloromethyl)-2-oxo-1,2-dihydroquinoxaline-3-carboxylate. The chloromethylation product thus obtained was used in the subsequent reaction without purification.

(3) Production of ethyl 2-oxo-1-[(2,2,2-trifluoroethoxy)methyl]-1,2-dihydroquinoxaline-3-carboxylate 1.2 g (9.0 mmol) of 2,2,2,-trifluoroethanol was dissolved in N,N-dimethylformamide (20 mL), and 0.36 g (9.0 mmol) of 60% sodium hydride (oily) was added in small portions. The mixture was stirred for one hour at room temperature. To this reaction solution, the ethyl 1-(chloromethyl)-2-oxo-1,2-dihydroquinoxaline-3-carboxylate obtained previously was added at or below 10° C. The mixture was stirred for 3 hours at room temperature, and then poured into ice water, and a solid matter precipitated therefrom was collected by filtration. The solid matter thus obtained was washed with water, and then dried under reduced pressure, to obtain 2.0 g (yield: 81%) of ethyl 2-oxo-1-[(2,2,2-trifluoroethoxy)methyl]-1,2-dihydroquinoxaline-3-carboxylate as a yellow powder.

$^1$H-NMR (CDCl$_3$/TMS δ (ppm)): 1.45 (3H, t), 9.10 (2H, q), 9.52 (2H, q), 5.85 (2H, s), 7.95 (1H, t), 7.54 (1H, d), 7.68 (1H, t), 7.97 (1H, d)

(4) Production of 2-oxo-1-[(2,2,2-trifluoroethoxy)methyl]-1,2-dihydroquinoxaline-3-carboxylic acid 1.5 g (4.54 mmol) of ethyl 2-oxo-1-[(2,2,2-trifluoroethoxy)methyl]-1,2-dihydroquinoxaline-3-carboxylate and 0.28 g (6.81 mmol) of lithium hydroxide monohydrate were dissolved in a solvent mixture of ethanol (30 mL) and water (30 mL), and the solution was stirred for 2 hours at room temperature. The reaction solution was concentrated to a half the original volume, and then water was added to the residue. The mixture was acidified using 10% hydrochloric acid, and then extracted with ethyl acetate. The organic layer was washed with water, dried over anhydrous sodium sulfate, and concentrated, to obtain 2.4 g (yield: 53%) of 2-oxo-1-[(2,2,2-trifluoroethoxy)methyl]-1,2-dihydroquinoxaline-3-carboxylic acid as a white powder.

$^1$H-NMR (CDCl$_3$/TMS δ (ppm)): 9.14 (2H, q), 5.98 (2H, s), 7.69 (2H, m), 7.86 (1H, t), 8.26 (1H, d)

Reference Example 7

Production of 5-fluoro-1-(4-methoxyphenyl)-2-oxo-1,2-dihydroquinoxaline-3-carboxylic acid (Compound No. of Production Intermediate: VI-134)

(1) Production of 3-fluoro-N-(4-methoxyphenyl)-2-nitroaniline 20.0 g (126 mmol) of 2,6-difluoronitrobenzene and 17.0 g (138 mmol) of p-anisidine were dissolved in N,N-dimethylformamide (60 ml), and 20.8 g (150 mmol) of potassium carbonate was added thereto. The mixture was heated with stirring for 12 hours at 75° C. The reaction mixture was poured into water, and extracted with ethyl acetate. The extracted organic layer was washed with water, 10% hydrochloric acid, water, and a saturated aqueous solution of sodium chloride in this order, dried over anhydrous magnesium sulfate, and concentrated under reduced pressure. The residue thus obtained was purified by silica gel chromatography (developing solvent: ethyl acetate:hexane=1:9), to obtain 21.2 g (yield: 64%) of 3-fluoro-N-(4-methoxyphenyl)-2-nitroaniline as a brown liquid.

$^1$H-NMR (CDCl$_3$/TMS δ (ppm)): 3.84 (s, 3H), 6.50 (t, 1H), 6.73 (d, 1H), 6.94 (d, 2H), 7.15-7.21 (m, 3H), 8.51 (br, 1H)

(2) Production of 3-fluoro-N$^1$-(4-methoxyphenyl)-1,2-phenylenediamine 21.2 g (80.8 mmol) of 3-fluoro-N-(4-methoxyphenyl)-2-nitroaniline was dissolved in ethanol (600 ml), and 2.1 g of 5% palladium-activated carbon was added thereto. The mixture was stirred for 12 hours in a hydrogen atmosphere. The reaction mixture was filtered, and the filtrate was concentrated under reduced pressure. The residue thus obtained was purified by silica gel chromatography (developing solvent: ethyl acetate:hexane=1:4), to obtain 15.4 g (yield 82%) of 3-fluoro-N$^1$-(4-methoxyphenyl)-1,2-phenylenediamine as a pale yellow liquid.

$^1$H-NMR (CDCl$_3$/TMS δ (ppm)): 3.63 (br, 2H), 3.78 (s, 3H), 5.12 (br, 1H), 6.61-6.83 (m, 7H)

(3) Production of ethyl 5-fluoro-1-(4-methoxyphenyl)-2-oxo-1,2-dihydroquinoxaline-3-carboxylate 15.4 g (66.3 mmol) of 3-fluoro-N$^1$-(4-methoxyphenyl)-1,2-phenylenediamine and 11.6 g (66.6 mmol) of diethyl ketomalonate were dissolved in benzene (400 ml), and the solution was heated to reflux for 2 hours while removing water using a Dean-Stark apparatus. The reaction mixture was concentrated under reduced pressure, and then the residue thus obtained was dissolved in ethyl acetate, and washed with water, 10% hydrochloric acid and a saturated aqueous solution of sodium chloride. The organic layer was dried over anhydrous magnesium sulfate, and concentrated under reduced pressure. The residue thus obtained was recrystallized from ethanol, to obtain 14.5 g (yield: 64%) of ethyl 5-fluoro-1-(4-methoxyphenyl)-2-oxo-1,2-dihydroquinoxaline-3-carboxylate as pale magenta-colored acicular crystals.

$^1$H-NMR (CDCl$_3$/TMS δ (ppm)): 1.43 (t, 3H), 3.89 (s, 3H), 4.50 (q, 2H), 6.56 (d, 1H), 7.05-7.22 (m, 5H), 7.39 (m, 1H)

(4) Production of 5-fluoro-1-(4-methoxyphenyl)-2-oxo-1,2-dihydroquinoxaline-3-carboxylic acid 14.3 g (41.8 mmol) of ethyl 5-fluoro-1-(4-methoxyphenyl)-2-oxo-1,2-dihydroquinoxaline-3-carboxylate was dissolved in ethanol (100 ml), and 10.0 g (62.5 mmol) of a 25% aqueous solution of sodium hydroxide was added thereto. The mixture was stirred for 2 hours at room temperature. The reaction mixture was concentrated under reduced pressure, and water was added to the residue thus obtained. The mixture was acidified using 10% hydrochloric acid. A solid precipitated therefrom was separated by filtration, washed with water, and then dried, to obtain 11.1 g (yield: 84%) of 5-fluoro-1-(4-methoxyphenyl)-2-oxo-1,2-dihydroquinoxaline-3-carboxylic acid as a pale yellow powder.

$^1$H-NMR (CDCl$_3$/TMS δ (ppm)): 3.93 (s, 3H), 6.71 (d, 1H), 7.15-7.29 (m, 5H), 7.60 (m, 1H)

Reference Example 8

Production of 5-chloro-1-(4-methoxyphenyl)-2-oxo-1,2-dihydroquinoxaline-3-carboxylic acid (Compound No. of Production Intermediate: VI-142)

(1) Production of 3-chloro-1,2-phenylenediamine 12.5 g (72.4 mmol) of 3-chloro-2-nitroaniline was dissolved in methanol (250 ml), and a solution prepared by dissolving 57.2 g (253 mmol) of tin (II) chloride dihydrate in concentrated hydrochloric acid (75 mL) was added dropwise. The reaction mixture was heated with stirring for 3 hours, and concentrated under reduced pressure. Water was added to the residue thus obtained, and the solution was alkalinized with a 25% aqueous solution of sodium hydroxide, and extracted with methylene chloride. The extracted organic layer was dried over anhydrous magnesium sulfate, and then concentrated under reduced pressure, to obtain 10.5 g (yield: >99%) of 3-chloro-1,2-phenylenediamine as a pale magenta-colored liquid.

$^1$H-NMR (CDCl$_3$/TMS δ (ppm)): 3.58 (br, 4H), 6.60-6.65 (m, 2H), 6.82 (m, 1H)

(2) Production of ethyl 5-chloro-2-oxo-1,2-dihydroquinoxaline-3-carboxylate 10.5 g (73.6 mmol) of 3-chloro-1,2-phenylenediamine and 12.8 g (73.5 mmol) of diethyl ketomalonate were dissolved in ethanol, and the solution was heated to reflux for 3 hours. While heating to reflux, ethanol was added thereto until precipitated crystals dissolved. The reaction mixture was cooled to room temperature, and then precipitated crystals were separated by filtration. The filter cake was washed with cold ethanol, and then dried, to obtain 10.5 g (yield: 51%) of ethyl 5-chloro-2-oxo-1,2-dihydroquinoxaline-3-carboxylate as pale yellow acicular crystals.

$^1$H-NMR (CDCl$_3$/TMS δ (ppm)): 1.44 (t, 3H), 4.51 (q, 2H), 7.26-7.46 (m, 3H), 12.79 (br, 1H)

(3) Production of ethyl 5-chloro-1-(4-methoxyphenyl)-2-oxo-1,2-dihydroquinoxaline-3-carboxylate To a slurry containing 5.7 g (22.6 mmol) of ethyl 5-chloro-2-oxo-1,2-dihydroquinoxaline-3-carboxylate, 6.9 g (45.4 mmol) of 4-methoxyphenylboric acid, 8.2 g (45.1 mmol) of anhydrous copper (II) acetate and chloroform (200 ml), 3.6 g (45.5 mmol) of pyridine and 4.6 g (45.5 mmol) of triethylamine were added dropwise, and the mixture was stirred for 72 hours at room temperature. The reaction mixture was washed with 10% hydrochloric acid, dried over anhydrous magnesium sulfate, and concentrated under reduced pressure. The residue thus obtained was isolated by silica gel chromatography (developing solvent: ethyl acetate:hexane=2:3), and the isolated solid was washed with diisopropyl ether, to obtain 6.3 g (yield: 78%) of ethyl 5-chloro-1-(4-methoxyphenyl)-2-oxo-1,2-dihydroquinoxaline-3-carboxylate as a pale yellow powder.

$^1$H-NMR (CDCl$_3$/TMS δ (ppm)): 1.43 (t, 3H), 3.89 (s, 3H), 9.51 (q, 2H), 6.69 (d, 1H), 7.11 (d, 2H), 7.18 (d, 2H), 7.33 (t, 1H), 7.49 (d, 1H)

(4) Production of 5-chloro-1-(4-methoxyphenyl)-2-oxo-1,2-dihydroquinoxaline-3-carboxylic acid 7.7 g (21.5 mmol) of ethyl 5-chloro-1-(4-methoxyphenyl)-2-oxo-1,2-dihydroquinoxaline-3-carboxylate was dissolved in ethanol (100 ml), and 6.9 g (43.1 mmol) of a 25% aqueous solution of sodium hydroxide was added thereto. The mixture was stirred for 12 hours at room temperature. The reaction mixture was concentrated under reduced pressure, water was added to the residue thus obtained, and the mixture was acidified using 10% hydrochloric acid. A solid precipitated therefrom was separated by filtration, washed with water, and then dried, to obtain 6.7 g (yield: 94%) of 5-chloro-1-(4-methoxyphenyl)-2-oxo-1,2-dihydroquinoxaline-3-carboxylic acid as a pale yellow powder.

$^1$H-NMR (CDCl$_3$/TMS δ (ppm)): 3.93 (s, 3H), 6.82 (d, 1H), 7.17 (d, 2H), 7.22 (d, 2H), 7.55 (t, 1H), 7.62 (d, 1H)

Reference Example 9

Production of 1-(benzo[d][1,3]dioxol-5-yl)-2-oxo-1,2-dihydroquinoxaline-3-carboxylic acid (production intermediate of Compound No. V-155)

(1) Production of N-(2-nitrophenyl)benzo[d][1,3]dioxol-5-ylamine 9.3 g (66 mmol) of 2-fluoro-nitrobenzene and 10 g (73 mmol) of benzo[d][1,3]dioxol-5-ylamine were dissolved in N,N-dimethylformamide (60 mL) and 10.9 g (79 mmol) of potassium carbonate was added thereto. Mixed solution was heated to reflux for 10 hours while stirring. The reaction mixture was poured into water, and extracted with ethyl acetate. The extracted organic layer was washed with saturated aqueous solution of sodium chloride, dried over anhydrous magnesium sulfate, and concentrated under reduced pressure. The residue thus obtained was purified by silica gel chromatography (developing solvent: ethyl acetate:hexane=1:3), to obtain 11 g (yield: 65%) of N-(2-nitrophenyl)benzo[d][1,3]dioxol-5-ylamine as red-purple crystals.

$^1$H-NMR (CDCl$_3$/TMS δ (ppm)): 6.02 (1H, s), 6.76-6.87 (3H, m), 7.23 (1H, d), 7.46 (1H, d), 7.62 (1H, d), 7.99 (1H, d), 8.47 (1H, s)

(2) Production of N-(benzo[d][1,3]dioxol-5-yl)benzene-1,2-diamine 13.6 g (244 mmol) of iron powder and 10.5 g (40 mmol) of N-(2-nitrophenyl)benzo[d][1,3]dioxol-5-ylamine were added to a solvent mixture of ethyl acetate (130 ml), water (65 mL) and acetic acid (15 mL), and the mixture was stirred for 1 hour at 70° C. The reaction solution was cooled to room temperature, and the waste was separated by filtration using a filter aid. The organic layer of the filtrate was batched off, washed with water, dried over anhydrous magnesium sulfate, and concentrated under reduced pressure to obtain 9.2 g (yield: 99%) of N-(benzo[d][1,3]dioxol-5-yl)benzene-1,2-diamine as white crystals.

$^1$H-NMR (CDCl$_3$/TMS δ (ppm)): 3.72 (2H, brs), 5.02 (1H, brs), 5.89 (2H, s), 6.20-6.24 (1H, m), 6.38-6.39 (1H, m), 6.67 (1H, d), 6.71-6.80 (2H, m), 6.94-7.05 (2H, m)

(3) Production of ethyl 1-(benzo[d][1,3] dioxol-5-yl)-2-oxo-1,2-dihydroquinoxaline-3-carboxylate 9.2 g (40 mmol) of N-(benzo[d][1,3]dioxol-5-yl)benzene-1,2-diamine was dissolved in toluene (200 mL), and 8.4 g (48 mmol) of diethyl ketomalonate was added thereto. The mixture was heated to reflux for 2 hours while removing water using a Dean-Stark apparatus. The reaction solution was cooled to room temperature, and the solvent was distilled off under reduced pressure. The residue thus obtained was solidified using ethanol to obtain 13.6 g (yield: 49%) of ethyl 1-(benzo)[d][1,3]dioxol-5-yl)-2-oxo-1,2-dihydroquinoxaline-3-carboxylate as a yellow crystal.

$^1$H-NMR (CDCl$_3$/TMS δ (ppm)): 1.44 (3H, t), 4.50 (2H, q), 6.09 (2H, d), 6.74-6.77 (2H, m), 6.83 (1H, d), 7.01 (1H, d), 7.36 (1H, t), 7.47 (1H, t), 7.97 (1H, d)

(4) Production of 1-(benzo[d][1,3]dioxol-5-yl)-2-oxo-1,2-dihydroquinoxaline-2-carboxylic acid 6.7 g (18 mmol) of ethyl 1-(benzo[d][1,3]dioxol-5-yl)-2-oxo-1,2-dihydroquinoxaline-3-carboxylate and 0.9 g (21 mmol) of lithium hydroxide monohydrate were dissolved in a solvent mixture of ethanol (60 mL) and water (60 mL), and the solution was stirred for 2 hours at room temperature. The reaction mixture was concentrated under reduced pressure and water was added to the residue thus obtained. The mixture was acidified using 10% hydrochloric acid. A solid precipitated therefrom was separated by filtration, washed with water, and then dried to obtain 5.0 g (yield: 93%) of 1-(benzo[d][1,3]dioxol-5-yl)-2-oxo-1,2-dihydroquinoxaline-2-carboxylic acid as yellow crystals.

$^1$H-NMR (CDCl$_3$/TMS δ (ppm)): 6.15 (2H, s), 6.73 (1H, d), 6.88 (1H, d), 7.05 (1H, s), 7.13 (1H, d), 7.90 (1H, t), 7.52 (1H, t), 7.89 (1H, d)

Reference Example 10

Production of 1-(2,3-dihydrobenzo[b][1.4]dioxin-6-yl)-2-oxo-1,2-dihydroquinoxaline-3-carboxylic acid (production intermediate of Compound No. V-158)

(1) Production of N-(2-nitrophenyl)-2,3-dihydrobenzo[b][1,4]dioxin-6-amine 5.9 g (39 mmol) of 2,3-dihydrobenzo[b]1,4-dioxin-6-amine and 5.0 g (35 mmol) of 2-fluoronitrobenzene were dissolved in N-methylpyrrolidone (70 mL) and 20.8 g (150 mmol) of potassium carbonate was added thereto. The solvent was heated with stirring for 10 hours at 120° C. The reaction mixture was poured into water, and extracted with ethyl acetate. The extracted organic layer was washed with water, 10% hydrochloric acid, water, and a saturated aqueous solution of sodium chloride in this order, dried over anhydrous magnesium sulfate, and concentrated under reduced pressure. The residue thus obtained was purified by silica gel chromatography (developing solvent: ethyl acetate:hexane=1:4), to obtain 6.4 g (yield: 66%) of N-(2-nitrophenyl)-2,3-dihydrobenzo[b][1,4]dioxin-6-amine as a red liquid.

$^1$H-NMR (CDCl$_3$/TMS δ (ppm)): 4.29 (4H, s), 6.70-6.76 (2H, m), 6.81 (1H, d), 6.90 (1H, d), 7.09 (1H, d), 7.33 (1H, t), 8.18 (1H, d), 9.36 (1H, s)

(2) Production of N-(2,3-dihydrobenzo[b][1,4]dioxin-6-yl)benzene-1,2-diamine

A mixture of 6.3 g (23 mmol) of N-(2-nitrophenyl)-2,3-dihydrobenzo[b][1,4]dioxin-6-amine, 9.0 g (161 mmol) of iron powder, acetic acid (1 ml), water (35 ml) and toluene (70 ml) were heated to reflux for 8 hours. The reaction mixture was filtered aid to separate the waste. The organic layer of the filtrate was batched off, washed with water, dried over anhydrous magnesium sulfate, and concentrated under reduced pressure to obtain 5.1 g (yield: 91%) of N-(2,3-dihydrobenzo[b][1,4]dioxin-6-yl)benzene-1,2-diamine) as a brown liquid.

¹H-NMR (CDCl₃/TMS δ (ppm)): 3.71 (2H, br), 4.18-4.25 (4H, m), 4.97 (1H, br), 6.29-6.32 (2H, m), 6.70-6.79 (3H, m), 6.95 (1H, t), 7.06 (1H, d)

(3) Production of ethyl 1-(2,3-dihydrobenzo[b][1,4]dioxin-6-yl)-2-oxo-1,2-dihydroquinoxaline-3-carboxylate 5.0 g (21 mmol) of N-(2,3-dihydrobenzo[b][1,4]dioxin-6-yl)benzene-1,2-diamine and 3.9 g (22 mmol) of diethyl ketomalonate were dissolved in toluene (60 ml), and the solution was heated to reflux for 12 hours while removing water using a Dean-Stark apparatus. The reaction solution was washed with water, dried over anhydrous magnesium sulfate, and concentrated under reduced pressure. The residue thus obtained was purified by silica gel chromatography (developing solvent: ethyl acetate:hexane=2:3) to obtain 4.6 g (yield: 63%) of ethyl 1-(2,3-dihydrobenzo[b][1,4]dioxin-6-yl)-2-oxo-1,2-dihydroquinoxaline-3-carboxylate as a milky yellow powder.
¹H-NMR (CDCl₃/TMS δ (ppm)): 1.43 (3H, t), 4.30-4.36 (4H, m), 4.50 (2H, q), 6.74-6.85 (3H, m), 7.06 (1H, d), 7.32-7.49 (2H, m), 7.97 (1H, d)

(4) Production of 1-(2,3-dihydrobenzo[b][1,4]dioxin-6-yl)-2-oxo-1,2-dihydroquinoxaline-3-carboxylic acid 4.5 g (13 mmol) of ethyl 1-(2,3-dihydrobenzo[b][1,4]dioxin-6-yl)-2-oxo-1,2-dihydroquinoxaline-3-carboxylate was dissolved in ethanol (100 ml), and 4.1 g (26 mmol) of a 25% aqueous solution of sodium hydroxide was added thereto. The solution was stirred for 2 hours at room temperature. The reaction mixture was concentrated under reduced pressure and water was added to the residue thus obtained. The mixture was acidified using 10% hydrochloric acid. A solid precipitated therefrom was separated by filtration, washed with water, and then dried to obtain 3.9 g (yield: 94%) of 1-(2,3-dihydrobenzo[b][1,4]dioxin-6-yl)-2-oxo-1,2-dihydroquinoxaline-3-carboxylic acid as a pale yellow powder.
¹H-NMR (CDCl₃/TMS δ (ppm)): 4.35-4.39 (4H, m), 6.77 (1H, d), 6.85 (1H, s), 6.99 (1H, d), 7.14 (1H, d), 7.53-7.67 (2H, m), 8.28 (1H, d)

Reference Example 11

Production of 4-(3-fluoro-4-methylphenyl)-3-oxo-3,4-dihydropyrido[2,3-b]pyrazine-2-carboxylic acid (Compound No. of Production Intermediate: VIII-164)

(1) Production of N-(3-fluoro-4-methylphenyl)-3-nitro-2-pyridylamine 45 g (0.28 mmol) of 2-chloro-3-nitropyridine was dissolved in 2-ethoxyethanol (300 ml), and 36 g (0.28 mmol) of 3-fluoro-4-methylaniline, 12N-hydrochloric acid and water (300 ml) were added thereto. Mixed solution was heated to reflux for 24 hours while stirring. The reaction solution was cooled to room temperature, and the solvent was distilled off under reduced pressure. The solution was extracted with ethyl acetate, and washed with saturated brine, and then the obtained organic layer was dried over anhydrous magnesium sulfate. The mixture was concentrated under reduced pressure, and the residue thus obtained was washed with diisopropyl ether to obtain 57 g (yield: 82%) of N-(3-fluoro-4-methylphenyl)-3-nitro-2-pyridylamine.

¹H-NMR (CDCl₃/TMS δ (ppm)): 2.27 (3H, d), 6.85 (1H, q), 7.16 (2H, d), 7.60 (1H, d), 8.50 (1H, m), 8.54 (1H, d), 10.10 (1H, brs)

(2) Production of N²-(3-fluoro-4-methylphenyl)-2,3-pyridinediamine 57 g (0.23 mol) of N-(3-fluoro-4-methylphenyl)-3-nitro-2-pyridylamine was dissolved in ethyl acetate (250 ml), and water (125 ml) and acetic acid (80 ml) were added thereto, and the solution was heated to 50° C. 77 g (1.40 mol) of iron powder was added to the reaction solution so that the temperature thereof would not exceed 60° C., and then stirred for 1 hour at 60° C. The reaction solution was cooled to room temperature, and the inorganic matter was separated by filtration. The solution was extracted with ethyl acetate, and washed with saturated brine, and then the obtained organic layer was dried over anhydrous magnesium sulfate. The solvent was distilled off under reduced pressure, and the residue thus obtained was washed with hexane to obtain 45 g (yield: 90%) of N²-(3-fluoro-4-methylphenyl)-2,3-pyridinediamine.
¹H-NMR (CDCl₃/TMS δ (ppm)): 2.20 (3H, d), 3.27 (2H, s), 6.26 (1H, brs), 6.74-6.86 (2H, m), 6.98-7.14 (3H, m), 7.83 (1H, dd)

(3) Production of ethyl 4-(3-fluoro-4-methylphenyl)-3-oxo-3,4-dihydropyrido[2,3-b]pyrazine-2-carboxylate 46 g (0.21 mol) of N²-(3-fluoro-4-methylphenyl)-2,3-pyridinediamine was dissolved in toluene (400 ml), and 40 g (0.23 mol) of diethyl ketomalonate and 92 g of 4 A molecular sieve were added thereto. The solution was heated to reflux for 12 hours while removing water using a Dean-Stark apparatus. The reaction solution was cooled to room temperature, inorganic material was filtered off and the solvent was distilled off under reduced pressure. The residue thus obtained was washed with diisopropyl ether to obtain 50 g (yield: 73%) of 4-(3-fluoro-4-methylphenyl)-3-oxo-3,4-dihydropyrido[2,3-b]pyrazine-2-carboxylate.
¹H-NMR (CDCl₃/TMS δ (ppm)): 1.44 (3H, t), 2.37 (3H, d), 4.52 (2H, q), 7.01 (2H, d), 7.35-7.42 (2H, m), 8.30 (1H, dd), 8.54 (1H, d)

(4) Production of 4-(3-fluoro-4-methylphenyl)-3-oxo-3,4-dihydropyrido[2,3-b]pyrazine-2-carboxylic acid 45 g (0.14 mol) of ethyl 4-(3-fluoro-4-methylphenyl)-3-oxo-3,4-dihydropyrido[2,3-b]pyrazine-2-carboxylate was dissolved in 1,4-dioxan (300 ml), and a solution of 39 g (0.28 mol) of potassium carbonate and water (300 ml) was added thereto. The solution was stirred for 1 hour at 60° C. The reaction solution was cooled to room temperature, and the solvent was distilled off under reduced pressure. Water was added to the residue thus obtained and was washed with chloroform. Then, the aqueous layer was adjusted to pH 1 by adding 6 N hydrochloric acid, and the aqueous layer was extracted again with chloroform. Anhydrous magnesium sulfate was added to the organic layer to dry the layer, and the solvent was distilled off under reduced pressure to obtain 32 g (yield: 76%) of 4-(3-fluoro-4-methylphenyl)-3-oxo-3,4-dihydropyrido[2,3-b]pyrazine-2-carboxylic acid.
¹H-NMR (CDCl₃/TMS δ (ppm)): 2.41 (3H, d), 7.04 (2H, d), 7.48 (1H, t), 7.55-7.60 (1H, m), 8.63 (1H, dd), 8.70-8.72 (1H, m)

Reference Example 12

Production of 1-(6-methylpyridine-2-yl)-2-oxo-1,2-dihydroquinoxaline-3-carboxylic acid (production intermediate of Compound No. V-127)

(1) Production of $N^1$-(diphenylmethylene)-$N^2$-(6-methylpyridine-2-yl)benzene-1,2-diamine 37.8 g (0.11 mol) of 2-bromo-N-(diphenylmethylene) aniline was dissolved in toluene (100 ml), and 14.6 g (0.13 mol) of 2-amino-6-picoline, 5.2 g (5.5 mmol) of tris(dibenzylideneacetone)dipalladium(0), 11.2 g (17.6 mmol) of 2,2'-bis(diphenylphosphino)-1,1'-binaphthyl, and 15.2 g (0.15 mol) of sodium-t-butoxide were added thereto. The mixture was stirred for 2 hours at 100° C. The reaction mixture was poured into water, and extracted with ethyl acetate. The organic layer was washed with saturated brine and dried over anhydrous magnesium sulfate. The solvent was distilled off under reduced pressure, and the residue was washed with methanol to obtain 42.1 g (yield:>99%) of $N^1$-(diphenylmethylene)-$N^2$-(6-methylpyridine-2-yl)benzene-1,2-diamine.

$^1$H-NMR (CDCl$_3$/TMS δ (ppm)): 2.44 (3H, s), 6.32 (1H, d), 6.64 (3H, m), 6.95 (2H, m), 7.14 (2H, d), 7.25-7.51 (7H, m), 7.75 (2H, d), 7.96 (1H, m)

(2) Production of N-(6-methylpyridine-2-yl)benzene-1,2-diamine 42.1 g (0.11 mol) of $N^1$-(diphenylmethylene)-$N^2$-(6-methylpyridine-2-yl)benzene-1,2-diamine was dissolved in tetrahydrofuran (100 ml), and 10% hydrochloric acid (45 ml) was added thereto, and was stirred for 2 hours at room temperature. The solvent was distilled off under reduced pressure, and water was added to the residue thus obtained and washed with ethyl acetate. Then, the aqueous layer was adjusted to pH>11, and the aqueous layer was extracted with methylene chloride. The organic layer was washed with saturated brine, and dried over anhydrous magnesium sulfate, and then the solvent was distilled off under reduced pressure to obtain 19.8 g (yield: 83%) of N-(6-methylpyridine-2-yl)benzene-1,2-diamine.

$^1$H-NMR (CDCl$_3$/TMS δ (ppm)): 2.43 (3H, s), 3.86 (2H, s), 5.99 (1H, s), 6.21 (1H, d), 6.57 (1H, d), 6.80 (2H, m), 7.05 (1H, t), 7.16 (1H, d), 7.33 (1H, t)

(3) Production of ethyl 1-(6-methylpyridine-2-yl)-2-oxo-1,2-dihydroquinoxaline-3-carboxylate 19.8 g (0.1 mol) of N-(6-methylpyridine-2-yl)benzene-1,2-diamine was dissolved in toluene (100 ml), and 19.0 g (0.11 mol) of diethyl ketomalonate and 57.1 g of 4 A molecular sieve were added thereto. The solution was heated to reflux for 3 hours while removing water using a Dean-Stark apparatus. Reaction mixture was filtered, and the filtrate was concentrated under reduced pressure to obtain 27.2 g (yield: 89%) of ethyl 1-(6-methylpyridine-2-yl)-2-oxo-1,2-dihydroquinoxaline-3-carboxylate.

$^1$H-NMR (CDCl$_3$/TMS δ (ppm)): 1.42 (3H, t), 2.64 (3H, s), 4.51 (2H, q), 6.65 (1H, d), 7.24 (1H, d), 7.43 (3H, m), 7.90 (1H, t), 8.00 (1H, d)

(4) Production of 1-(6-methylpyridine-2-yl)-2-oxo-1,2-dihydroquinoxaline-3-carboxylic acid 27.2 g (88 mmol) of ethyl 1-(6-methylpyridine-2-yl)-2-oxo-1,2-dihydroquinoxaline-3-carboxylate was dissolved in 1,4-dioxane (50 ml) and water (50 ml), and 18.3 g (0.13 mol) of potassium carbonate was added thereto, and the solution was stirred for 1 hour at 60° C. The solvent was distilled off under reduced pressure and the aqueous layer was adjusted to pH<4. The precipitated crystals were filtered to obtain 23.3 g (yield: 94%) of 1-(6-methylpyridine-2-yl)-2-oxo-1,2-dihydroquinoxaline-3-carboxylic acid.

$^1$H-NMR (CDCl$_3$/TMS δ (ppm)): 2.55 (3H, s), 6.57 (1H, d), 7.47 (4H, m), 7.94 (1H, d), 8.07 (1H, t)

The property values of the production intermediates obtained in the above Reference Examples 1 to 12, and the production intermediates produced in the same manner as in these Reference Examples are presented in Table 135 to Table 137.

TABLE 135

| Compound No. | Melting Point (° C.) or Refractive Rate ($n_D^{20}$) | |
|---|---|---|
| V-2 | Melting Point | 175-176 |
| V-3 | Melting Point | 173-175 |
| V-4 | Melting Point | 165-167 |
| V-5 | Melting Point | 189-190 |
| V-6 | Melting Point | 204-207 |
| V-10 | Melting Point | 253-256 |
| V-37 | Melting Point | 125-127 |
| V-42 | Melting Point | 177-179 |
| V-52 | Melting Point | 179-181 |
| V-97 | Melting Point | 171-173 |
| V-102 | Melting Point | 165-167 |
| V-103 | Melting Point | 152-154 |
| V-120 | Melting Point | 191-193 |
| V-121 | Melting Point | 291-293 |
| V-125 | Malting Point | 176-178 |
| V-127 | Melting Point | 185-186 |
| V-130 | Melting Point | 164-166 |
| V-131 | Melting Point | 159-161 |
| V-132 | Melting Point | 156-159 |
| V-133 | Melting Point | 167-169 |
| V-134 | Melting Point | 185-188 |
| V-136 | Melting Point | 173-176 |
| V-139 | Melting Point | 161-163 |
| V-155 | Melting Point | 183-185 |
| V-158 | Melting Point | 197-198 |
| V-164 | Melting Point | 158-160 |
| V-169 | Melting Point | 190-192 |
| V-170 | Melting Point | 175-177 |
| V-172 | Melting Point | 185-186 |
| V-174 | Melting Point | 190-192 |
| V-176 | Melting Point | 204-205 |
| V-178 | Melting Point | 164-166 |
| V-189 | Melting Point | 207-208 |
| V-191 | Melting Point | 209-210 |
| V-193 | Melting Point | 207-209 |
| V-195 | Melting Point | 214-216 |
| V-198 | Melting Point | 181-183 |

TABLE 136

| Compound No. | Melting Point (° C.) or Refractive Rate ($n_D^{20}$) | |
|---|---|---|
| V-207 | Melting Point | 145-147 |
| V-212 | Melting Point | 187-189 |
| V-213 | Melting Point | 170-172 |
| V-214 | Melting Point | 172-173 |
| V-217 | Melting Point | 210-212 |
| V-221 | Melting Point | 187-188 |
| V-222 | Melting Point | 173-175 |
| V-223 | Melting Point | 167-169 |
| V-224 | Melting Point | 197-199 |
| V-225 | Melting Point | 179-180 |
| V-305 | Melting Point | 170-173 |
| V-306 | Melting Point | 138-140 |
| V-307 | Melting Point | 181-183 |

TABLE 136-continued

| Compound No. | Melting Point (° C.) or Refractive Rate ($n_D^{20}$) | |
|---|---|---|
| V-308 | Melting Point | 202-204 |
| V-311 | Melting Point | 187-188 |
| V-313 | Melting Point | 163-165 |
| V-314 | Melting Point | 140-143 |
| V-315 | Melting Point | 167-169 |
| V-316 | Melting Point | 197-199 |
| V-317 | Melting Point | 180-182 |
| V-318 | Melting Point | 201-203 |
| VI-34 | Melting Point | 173-175 |
| VI-54 | Melting Point | 162-163 |
| VI-77 | Melting Point | 183-185 |
| VI-122 | Melting Point | 176-178 |
| VI-135 | Melting Point | 195-197 |
| VI-136 | Melting Point | 191-192 |
| VI-137 | Melting Point | 165-166 |
| VI-138 | Melting Point | 182-184 |
| VI-141 | Melting Point | 159-161 |
| VI-142 | Melting Point | 198-200 |
| VI-154 | Melting Point | 163-165 |
| VI-156 | Melting Point | 179-180 |
| VI-161 | Melting Point | 182-183 |
| VI-163 | Melting Point | 196-198 |
| VI-167 | Melting Point | 154-156 |
| VI-170 | Melting Point | 185-187 |
| VI-171 | Melting Point | 208-209 |
| VI-174 | Melting Point | 220-222 |
| VI-175 | Melting Point | 156-159 |
| VI-177 | Melting Point | 200-201 |
| VI-179 | Melting Point | 175-176 |
| VI-180 | Melting Point | 199-200 |
| VI-181 | Melting Point | 174-176 |
| VI-182 | Melting Point | 186-189 |
| VI-184 | Melting Point | 182-184 |

TABLE 137

| Compound No. | Melting Point (° C.) or Refractive Rate ($n_D^{20}$) | |
|---|---|---|
| VI-187 | Melting Point | 192-193 |
| VI-188 | Melting Roint | 186-187 |
| VI-190 | Melting Point | 193-194 |
| VI-191 | Melting Point | >300 |
| VI-192 | Melting Point | 99-101 |
| VI-193 | Melting Point | 177-180 |
| VI-194 | Melting Point | 177-178 |
| VI-196 | Melting Point | 166-168 |
| VI-197 | Melting Point | 184-186 |
| VI-199 | Melting Point | 164-165 |
| VI-200 | Melting Point | 200-201 |
| VI-201 | Melting Point | 192-195 |
| VI-239 | Melting Point | 195-196 |
| VI-240 | Melting Point | 155-157 |
| VI-241 | Melting Point | 141-143 |
| VI-244 | Melting Point | 215-217 |
| VI-245 | Melting Point | 183-184 |
| VI-246 | Melting Point | 197-198 |
| VI-247 | Melting Point | 198-200 |
| VII-3 | Melting Point | 143-144 |
| VII-4 | Melting Point | 144-147 |
| VII-5 | Melting Point | 157-158 |
| VII-7 | Melting Point | 119-120 |
| VII-8 | Melting Point | 140-141 |
| VII-61 | Melting Point | 127-129 |
| VII-78 | Melting Point | 131-132 |
| VII-79 | Melting Point | 159-160 |
| VII-82 | Melting Point | 162-165 |
| VII-88 | Melting Point | 182-184 |
| VII-89 | Melting Point | 176-178 |
| VII-126 | Melting Point | 232-235 |
| VII-128 | Melting Point | 161-163 |
| VIII-175 | Melting Point | 160-162 |
| VIII-1 | Melting Point | 178-179 |
| VIII-7 | Melting Point | 159-161 |

TABLE 137-continued

| Compound No. | Melting Point (° C.) or Refractive Rate ($n_D^{20}$) | |
|---|---|---|
| VIII-13 | Melting Point | 182-183 |
| VIII-27 | Melting Point | 104-107 |
| VIII-125 | Melting Point | 123-126 |

[NMR Data]

For Compound Nos. V-7, V-14, V-29, V-35, V-40, V-51, V-58, V-60, V-61, V-62, V-64, V-71, V-72, V-73, V-101, V-113, V-117, V-119, V-152, V-154, V-156, V-158, V-160, V-162, V-179, V-186, V-197, V-205, V-211, V-216, V-217, V-218, V-226, V-310, V-319, VI-1, VI-6, VI-7, VI-13, VI-21, VI-27, VI-31, VI-33, VI-36, VI-37, VI-49, VI-54, VI-55, VI-57, VI-88, VI-94, VI-115, VI-116, VI-117, VI-121, VI-122, VI-123, VI-125, VI-133, VI-134, VI-144, VI-150, VI-152, VI-153, VI-156, VI-157, VI-159, VI-160, VI-161, VI-162, VI-165, VI-170, VI-173, VI-185, VI-189, VI-195, VI-198, VI-242, VI-243, VI-248, VII-59, VII-67, VII-91, VII-97, VII-102, VII-153, VII-154, VII-156, VII-171, VII-173, VII-176, VII-177, VII-178, VII-180, VII-181, VII-185, VII-186, VII-187, VII-188, VIII-2, VIII-3, VIII-4, VIII-5, VIII-6, VIII-11, VIII-12, VIII-15, VIII-16, VIII-22, VIII-28, VIII-53, VIII-54, VIII-55, VIII-56, VIII-57, VIII-58, VIII-76, VIII-84, VIII-98, VIII-99, VIII-100, VIII-101, VIII-102, VIII-103, VIII-104, VIII-106, VIII-107, VIII-108, VIII-109, VIII-113, VIII-114, VIII-116, VIII-117, VIII-118, VIII-121, VIII-126, VIII-127, VIII-128, VIII-132, VIII-133, VIII-134, VIII-135, VIII-136, VIII-137, VIII-139, VIII-142, VIII-143, VIII-144, VIII-145, VIII-150, VIII-152, VIII-153, VIII-154, VIII-155, VIII-156, VIII-157, VIII-158, VIII-159, VIII-160, VIII-161, VIII-162, VIII-163, VIII-164, VIII-165, VIII-166, VIII-167, VIII-168, VIII-169, VIII-170, VIII-171, VIII-172, VIII-173, VIII-174, VIII-175, VIII-176, VIII-177, VIII-178, VIII-179, VIII-180, VIII-181, VIII-182, VIII-183, VIII-184, VIII-185, VIII-187, VIII-190, VIII-192, VIII-193, VIII-194, VIII-195, VIII-196, VIII-197, VIII-198, VIII-199, VIII-200, VIII-201, VIII-202, VIII-203, VIII-204, VIII-208, VIII-209, VIII-210, VIII-211, VIII-212, VIII-213, VIII-214, VIII-215, VIII-216 and VIII-218, the $^1$H-NMR data (CDCl$_3$/TMS δ (ppm) value) are presented in the following.

Compound No. V-7:
 1.09 (3H, t), 1.93-1.56 (2H, m), 1.78-1.86 (2H, m), 4.91 (2H, t), 7.51 (1H, d), 7.58 (1H, dd), 7.89 (1H, m), 8.28 (1H, dd), 14.33 (1H, brs)

Compound No. V-14:
 0.92 (3H, t), 1.35-1.38 (4H, m), 1.49 (2H, m), 1.83 (2H, m), 9.39 (2H, t), 7.51 (1H, d), 7.58 (1H, m), 7.84 (1H, m), 8.28 (1H, d), 19.33 (1H, brs)

Compound No. V-29:
 3.49 (3H, s), 5.86 (2H, s), 7.59 (1H, t), 7.70 (1H, d), 7.83 (1H, t), 8.25 (1H, dd)

Compound No. V-35:
 4.19 (2H, q), 5.98 (2H, s), 7.60-7.68 (2H, m), 7.86 (1H, t), 8.26 (1H, d)

Compound No. V-40:
 2.65 (2H, t), 3.93 (2H, t), 5.95 (2H, s), 7.62 (1H, t), 7.71 (1H, d), 7.86 (1H, t), 8.26 (1H, dd), 13.66 (1H, bs)

Compound No. V-51:
 3.18 (3H, s), 5.86 (2H, s), 7.50 (1H, m), 7.72-7.80 (2H, m), 7.91 (1H, d)

Compound No. V-58:
 3.33 (3H, s), 3.89 (2H, t), 9.62 (2H, t), 7.59 (1H, t), 7.71 (1H, d), 7.82 (1H, t), 8.25 (1H, dd), 19.20 (1H, bs)

Compound No. V-60:
1.68 (3H, d), 3.31 (3H, s), 3.79-3.84 (1H, m), 4.21-4.28 (1H, m), 4.87-5.28 (1H, m), 7.55 (1H, t), 7.72 (1H, d), 7.79 (1H, t), 8.26 (1H, dd), 14.28 (1H, bs)

Compound No. V-61:
2.28 (3H, s), 2.92 (2H, m), 4.63 (2H, m), 7.51-7.62 (2H, m), 7.86 (1H, m), 8.28 (1H, dd)

Compound No. V-62:
3.11 (3H, s), 3.54 (2H, t), 4.89 (2H, t), 7.61-7.69 (2H, m), 7.91 (1H, dd), 8.30 (1H, d)

Compound No. V-64:
2.44 (3H, s), 5.26 (2H, t), 7.15 (1H, d), 7.58 (1H, t), 7.78 (1H, t), 8.27 (1H, dd), 13.70 (1H, bs)

Compound No. V-71:
3.66-3.78 (6H, m), 3.84-3.87 (3H, m), 7.31 (1H, d), 7.53 (1H, t), 7.77 (1H, t), 8.15 (1H, dd)

Compound No. V-72:
5.38 (2H, t), 7.50-7.57 (2H, m), 7.80 (1H, t), 8.04 (1H, dd)

Compound No. V-73:
2.99 (2H, t), 4.55 (2H, t), 7.46 (1H, t), 7.43 (1H, t), 7.82 (1H, d), 7.89 (1H, d), 13.98 (1H, bs)

Compound No. V-101:
7.04 (1H, d), 7.11 (1H, d), 7.52-7.54 (2H, m), 7.57-7.71 (2H, m), 8.29 (1H, d)

Compound No. V-113:
7.08 (1H, d), 7.61 (1H, t), 7.71 (1H, t), 7.77 (1H, d), 8.04 (1H, d), 8.30 (1H, d)

Compound No. V-117:
2.84 (3H, s), 6.98 (1H, d), 7.62 (1H, t), 7.74 (1H, t), 8.30 (1H, d)

Compound No. V-119:
3.91 (3H, s), 6.90 (1H, d), 7.67 (1H, t), 7.79 (1H, t), 8.31 (1H, d)

Compound No. V-152:
6.74 (1H, d), 7.64 (2H, m), 8.33 (1H, d), 8.85 (2H, s), 8.93 (1H, s), 13.32 (1H, bs)

Compound No. V-154:
3.33-3.38 (2H, m), 4.79 (2H, t), 2.37-2.44 (1H, m), 2.90-2.92 (2H, m), 6.98 (1H, d), 7.03 (2H, s), 7.12 (1H, s), 7.55 (1H, t), 7.65 (1H, t), 8.29 (1H, d)

Compound No. V-156:
6.89 (1H, d), 7.09 (2H, m), 7.37 (1H, d), 7.59 (1H, t), 7.68 (1H, t), 8.32 (1H, d)

Compound No. V-158:
4.35-4.39 (4H, m), 6.78 (1H, dd), 6.85 (1H, d), 6.99 (1H, dd), 7.14 (1H, d), 7.55 (1H, m), 7.66 (1H, d), 8.29 (1H, dd), 13.97 (1H, brs)

Compound No. V-160:
1.78-1.82 (1H, m), 1.96-2.03 (2H, m), 1.29-2.22 (1H, m), 3.76 (1H, q), 3.90 (1H, q), 4.37-4.48 (2H, m), 4.59 (1H, dd), 4.56 (1H, t), 7.72 (1H, d), 7.81 (1H, t), 8.24 (1H, d), 14.05 (1H, bs)

Compound No. V-162:
2.28 (3H, s), 5.66 (2H, s), 7.62 (1H, t), 7.71 (1H, d), 7.87 (1H, t), 8.28 (1H, d)

Compound No. V-179:
3.34 (3H, s), 3.81 (2H, t), 5.20 (2H, t), 7.49 (1H, t), 7.84 (1H, dd), 8.20 (1H, t), 13.96 (1H, bs)

Compound No. V-186:
3.67 (3H, s), 3.96 (3H, s), 7.05-7.11 (2H, m), 7.82 (1H, d), 13.88 (1H, br)

Compound No. V-197:
3.82 (3H, m), 7.58 (1H, d), 8.53 (1H, d), 8.88 (1H, s)

Compound No. V-205:
6.68 (1H, d), 7.20 (1H, d), 7.48-7.64 (5H, m), 7.74 (1H, d), 8.06 (1H, d), 8.17 (1H, d), 8.37 (1H, d)

Compound No. V-211:
6.98 (1H, s), 7.51 (1H, t), 7.64 (1H, t), 7.95 (1H, s), 9.32 (1H, s)

Compound No. V-216:
1.20-1.31 (9H, m), 3.44 (1H, m), 3.55 (1H, m), 4.12 (1H, m), 5.31 (2H, br), 7.13 (1H, br), 7.56 (1H, br), 7.71 (1H, br), 8.25 (1H, br)

Compound No. V-217:
3.36 (3H, s), 4.77 (2H, s), 6.95 (3H, m), 7.27 (1H, d), 7.58 (1H, t), 7.67 (1H, t), 8.31 (1H, d)

Compound No. V-218:
3.70 (3H, s), 3.91 (3H, s), 6.61 (1H, d), 6.92 (1H, d), 7.08 (1H, d), 7.25 (2H, s), 7.51-7.61 (4H, m), 8.30 (1H, d)

Compound No. V-226:
2.55 (3H, s), 6.77 (1H, d), 7.37 (1H, d), 7.50 (1H, d), 7.93 (1H, d), 8.22 (1H, d), 8.65 (1H, s)

Compound No. V-310:
4.06 (3H, s), 6.84 (1H, d), 7.05 (1H, d), 7.52-7.66 (m, 3H), 8.15 (1H, s)

Compound No. V-319:
3.75 (3H, s), 6.97 (2H, t), 7.58 (1H, t), 7.66-7.72 (2H, m), 8.30 (1H, d)

Compound No. VI-1:
6.87 (1H, d), 7.34 (2H, d), 7.54-7.74 (5H, m), 8.31 (1H, d)

Compound No. VI-6:
6.87 (1H, d), 7.27 (1H, m), 7.38 (1H, s), 7.56-7.70 (4H, m), 8.31 (1H, d), 13.33 (1H, brs)

Compound No. VI-7:
6.88 (1H, dd), 7.30-7.33 (2H, m), 7.57 (1H, m), 7.58-7.70 (3H, m), 8.30 (1H, dd), 13.71 (1H, brs)

Compound No. VI-13:
2.52 (3H, s), 6.92 (1H, dd), 7.21-7.24 (2H, m), 7.47-7.67 (4H, m), 8.29 (1H, dd), 13.91 (1H, brs)

Compound No. VI-21:
1.32 (6H, d), 3.05 (1H, m), 6.87 (1H, dd), 7.13-7.18 (2H, m), 7.52-7.66 (4H, m), 8.31 (1H, dd), 13.99 (1H, brs)

Compound No. VI-27:
6.81 (1H, d), 7.58-7.62 (2H, m), 7.66-7.71 (2H, m), 7.88 (1H, dd), 7.95 (1H, d), 8.32 (1H, d), 13.58 (1H, brs)

Compound No. VI-31:
6.89 (1H, d), 7.05-7.13 (4H, m), 7.47 (1H, t), 7.58 (1H, t), 8.09 (1H, d)

Compound No. VI-33:
3.88 (3H, s), 6.85 (1H, dd), 6.89-6.94 (2H, m), 7.19 (1H, dd), 7.54-7.68 (3H, m), 8.31 (1H, dd), 13.76 (1H, brs)

Compound No. VI-36:
1.45 (3H, t), 4.09 (2H, m), 6.83-6.94 (3H, m), 7.17 (1H, dd), 7.53-7.67 (3H, m), 8.30 (1H, dd)

Compound No. VI-37:
1.50 (3H, t), 4.15 (2H, q), 6.94 (1H, d), 7.19-7.28 (4H, m), 7.53-7.66 (2H, m), 8.30 (1H, dd), 13.98 (1H, brs)

Compound No. VI-49:
4.65 (2H, d), 5.37 (1H, d), 5.48 (1H, d), 6.06-6.15 (1H, m), 6.93 (1H, d), 7.17-7.26 (4H, m), 7.56 (1H, t), 7.64 (1H, t), 8.30 (1H, d).

Compound No. VI-54:
6.62 (1H, t), 6.86 (1H, m), 7.15 (1H, m), 7.21 (1H, d), 7.44 (1H, d), 7.67 (3H, m), 8.32 (1H, d)

Compound No. VI-55:
6.82 (1H, t), 6.84 (1H, d), 7.30-7.44 (4H, m), 7.59 (1H, t), 7.61 (1H, t), 8.17 (1H, d)

Compound No. VI-57:
6.85 (1H, dd), 7.32 (1H, d), 7.53-7.62 (2H, m), 7.68 (1H, m), 7.77 (1H, dd), 8.33 (1H, dd)

Compound No. VI-88:
2.73 (3H, s), 6.83 (1H, d), 7.48 (1H, d), 7.59 (1H, t), 7.64 (1H, t), 8.27-8.39 (3H, m)

Compound No. VI-94:
4.01 (3H, s), 6.81 (1H, d), 7.93-7.65 (4H, m), 8.31-8.43 (3H, m)

Compound No. VI-115:
3.94 (3H, s), 6.87-6.93 (3H, m), 7.58 (1H, dd), 7.65-7.70 (2H, m), 8.31 (1H, m)

Compound No. VI-116:
2.35 (3H, s), 3.85 (3H, s), 6.72 (1H, d), 6.82 (1H, dd), 6.95 (1H, dd), 7.42 (1H, d), 7.56 (1H, m), 7.65 (1H, m), 8.30 (1H, dd)

Compound No. VI-117:
3.90 (3H, s), 4.00 (3H, s), 6.79 (1H, d), 6.89-6.97 (2H, m), 7.13 (1H, d), 7.57 (1H, m), 7.66 (1H, m), 8.30 (1H, d), 13.76 (1H, brs)

Compound No. VI-121:
3.84 (6H, s), 6.43-6.45 (2H, m), 6.70 (1H, dd), 6.98 (1H, d), 7.56 (1H, m), 7.66 (1H, m), 8.30 (1H, m)

Compound No. VI-122:
3.90 (3H, s), 6.92-6.99 (2H, m), 7.08 (1H, d), 7.25 (1H, d), 7.57 (1H, t), 7.68 (1H, t), 8.30 (1H, d)

Compound No. VI-123:
3.93 (3H, s), 6.81 (1H, d), 7.08 (1H, d), 7.23-7.30 (2H, m), 7.57 (1H, t), 7.66 (1H, t), 8.32 (1H, d)

Compound No. VI-125:
3.74 (1H, s), 3.92 (1H, s), 6.72 (2H, m), 6.91 (1H, d), 7.16 (1H, m), 7.53 (1H, t), 7.63 (1H, t), 8.29 (1H, d)

Compound No. VI-133:
3.88 (6H, s), 3.97 (3H, s), 6.54 (2H, s), 6.97 (1H, d), 7.58 (1H, m), 7.69 (1H, m), 8.30 (1H, d), 13.60 (1H, brs)

Compound No. VI-134:
3.93 (s, 3H), 6.71 (d, 1H), 7.16-7.29 (m, 5H), 7.58 (m, 1H)

Compound No. VI-144:
3.94 (3H, s), 6.89 (1H, s), 7.18-7.24 (4H, m), 7.52 (1H, d), 8.22 (1H, d)

Compound No. VI-150:
0.39-0.43 (2H, m), 0.69-0.74 (2H, m), 1.31-1.37 (1H, m), 3.91 (2H, d), 6.93 (1H, d), 7.16-7.24 (2H, m), 7.57 (1H, t), 7.65 (1H, t), 8.29 (1H, d)

Compound No. VI-152:
3.08 (6H, s), 6.88 (2H, d), 6.90 (1H, d), 7.13 (2H, d), 7.53 (1H, t), 7.61 (1H, t), 8.28 (1H, d)

Compound No. VI-153:
2.38 (3H, s), 2.41 (3H, s), 6.91 (1H, d), 7.01-7.08 (2H, m), 7.44 (1H, d), 7.55 (1H, t), 7.61 (1H, t), 8.29 (1H, d)

Compound No. VI-156:
2.40 (3H, d), 6.88 (1H, d), 7.15 (2H, m), 7.33 (1H, t), 7.57 (1H, t), 7.66 (1H, m), 8.30 (1H, d)

Compound No. VI-157:
2.51 (3H, s), 6.78 (1H, d), 7.25 (1H, d), 7.39 (1H, d), 7.55-7.68 (3H, m), 8.32 (1H, d)

Compound No. VI-159:
1.49 (3H, t), 3.99 (3H, s), 4.12 (2H, m), 6.77 (1H, d), 6.88 (1H, m), 6.95 (1H, d), 7.11 (1H, d), 7.56 (1H, t), 7.65 (1H, t), 8.30 (1H, d)

Compound No. VI-160:
3.81 (3H, s), 3.97 (6H, d), 6.88-6.96 (3H, m), 7.57 (1H, t), 7.65 (1H, t), 8.29 (1H, d)

Compound No. VI-161:
4.01 (3H, s), 6.95 (1H, d), 7.05 (1H, m), 7.12 (1H, m), 7.58 (1H, t), 7.70 (1H, m), 8.32 (1H, m)

Compound No. VI-162:
4.16 (3H, s), 6.97 (3H, m), 7.60 (1H, t), 7.70 (1H, t), 8.31 (1H, d)

Compound No. VI-165:
1.68-1.81 (4H, m), 2.10-2.16 (1H, m), 2.37-2.44 (1H, m), 2.90-2.92 (2H, m), 6.99-7.02 (2H, m), 7.37 (2H, t), 7.56-7.68 (2H, m), 8.31 (1H, d)

Compound No. VI-170:
2.30 (2H, m), 4.30 (2H, m), 4.43 (2H, m), 6.86 (1H, m), 6.93 (2H, m), 7.22 (2H, d), 7.55 (1H, t), 7.65 (1H, t), 8.29 (1H, d)

Compound No. VI-173:
4.16 (3H, s), 6.70 (1H, d), 6.95 (2H, m), 7.25 (1H, t), 7.65 (1H, m))

Compound No. VI-185:
2.43 (3H, s), 3.94 (3H, s), 6.67 (1H, s), 7.22 (4H, m), 7.35 (1H, s), 8.16 (1H, s), 13.99 (1H, s)

Compound No. VI-189:
3.91 (3H, s), 3.92 (3H, s), 6.86 (1H, d), 7.20 (5H, m), 7.71 (1H, s)

Compound No. VI-195:
3.45 (3H, s), 3.90 (3H, s), 7.05 (2H, d), 7.19 (3H, d), 7.48 (1H, t), 7.92 (1H, d)

Compound No. VI-198:
6.67 (1H, dd), 7.32 (2H, d), 7.68-7.76 (3H, m), 8.12 (1H, dd)

Compound No. VI-242:
3.80 (3H, s), 6.17 (1H, d), 7.13 (1H, m), 7.35 (4H, m), 8.20 (1H, d)

Compound No. VI-243:
3.81 (3H, s), 6.18 (1H, d), 6.66 (1H, t), 7.14 (1H, m), 7.35 (2H, d), 7.44 (2H, d), 8.22 (1H, d)

Compound No. VI-248:
6.64 (1H, d), 7.28-7.43 (5H, m), 7.62 (1H, m)

Compound No. VII-59:
3.56 (3H, s), 3.86 (2H, t), 4.91 (2H, t), 7.55-7.59 (1H, m), 8.58 (1H, dd), 8.84 (1H, dd), 14.01 (1H, bs)

Compound No. VII-67:
1.32 (3H, t), 2.28 (2H, q), 5.38 (2H, s), 7.56-7.61 (1H, m), 8.60 (1H, d), 8.79 (1H, d)

Compound No. VII-91:
3.86 (3H, s), 5.87 (2H, s), 6.78 (2H, q), 6.92 (1H, d), 7.29 (1H, s), 7.55 (1H, q), 8.60 (1H, d), 8.80 (1H, d)

Compound No. VII-97:
2.08 (3H, d), 7.32 (9H, m), 7.99 (2H, m), 7.57 (1H, m), 8.57 (1H, m), 8.82 (1H, d)

Compound No. VII-102:
7.12 (1H, d), 7.43-7.47 (1H, m), 7.55-7.58 (2H, m), 8.31 (H, d), 8.56 (1H, d)

Compound No. VII-153:
6.13 (1H, s), 6.77 (2H, m), 7.09 (1H, m), 7.57 (1H, m), 8.62 (1H, m), 8.73 (1H, d)

Compound No. VII-154:
7.05 (2H, m), 7.32 (1H, d), 7.60 (1H, q), 8.68 (2H, m)

Compound No. VII-156:
4.35 (9H, m), 6.77 (1H, q), 6.85 (1H, d), 7.11 (1H, d), 7.56 (1H, q), 8.62 (1H, q), 8.79 (1H, q)

Compound No. VII-171:
1.57 (3H, s), 1.67 (3H, s), 2.51 (2H, q), 9.63 (2H, t), 5.22 (1H, t), 7.59-7.58 (1H, m), 8.56 (1H, d), 8.85 (1H, d), 14.12 (1H, bs)

Compound No. VII-173:
1.79 (3H, t), 2.52 (2H, t), 4.75 (2H, t), 7.56-7.67 (1H, m), 8.58 (1H, d), 8.89 (1H, d), 14.00 (1H, bs)

Compound No. VII-176:
3.10 (2H, t), 9.86 (2H, t), 7.29-7.31 (5H, m), 7.56 (1H, q), 8.57 (1H, d), 8.89 (1H, d)

Compound No. VII-177:
5.99 (2H, s), 6.95 (1H, q), 7.25 (1H, q), 7.36 (1H, d), 7.60 (1H, q), 8.57 (1H, dd), 8.93 (1H, dd)

Compound No. VII-178:
6.59 (1H, d), 6.98 (2H, s), 7.69 (1H, q), 8.05 (1H, d), 8.58 (1H, dd), 8.92 (1H, dd)

Compound No. VII-180:
2.37 (3H, s), 5.75 (2H, s), 6.07 (1H, s), 7.47 (1H, q), 8.34 (1H, dd), 8.71 (1H, dd)
Compound No. VII-181:
5.81 (2H, s), 7.30 (1H, d), 7.62 (1H, q), 7.95 (1H, dd), 8.59 (1H, dd), 8.72 (1H, d), 8.89 (1H, dd)
Compound No. VII-185:
2.86 (3H, s), 5.82 (2H, s), 7.28-7.33 (3H, m), 7.39 (1H, d), 7.59 (2H, t), 8.69 (1H, d)
Compound No. VII-186:
2.59 (3H, s), 5.82 (2H, s), 7.28-7.33 (3H, m), 7.55 (2H, t), 8.39 (1H, d), 8.72 (1H, d)
Compound No. VII-187:
2.81 (3H, s), 5.83 (2H, s), 7.29-7.36 (3H, m), 7.91 (1H, d), 7.58 (2H, t), 8.92 (1H, d)
Compound No. VII-188:
4.19 (3H, s), 5.76 (2H, s), 6.96 (1H, d), 7.32-7.37 (3H, m), 7.49 (2H, dd), 8.36 (1H, d)
Compound No. VIII-2:
7.36-7.46 (3H, m), 7.56-7.67 (2H, m), 8.63-8.70 (2H, m), 13.36 (1H, br)
Compound No. VIII-3:
7.08-7.15 (2H, m), 7.31-7.38 (1H, m), 7.57-7.68 (2H, m), 8.63-8.71 (2H, m), 13.32 (1H, br)
Compound No. VIII-4:
7.27-7.38 (4H, m), 7.58 (1H, dd), 8.63-8.71 (2H, m), 13.57 (1H, br)
Compound No. VIII-5:
7.36-7.40 (1H, m), 7.55-7.72 (4H, m), 8.64-8.69 (2H, m), 13.08 (1H, br)
Compound No. VIII-6:
7.22-7.26 (1H, m), 7.36 (1H, s), 7.57-7.61 (3H, m), 8.64 (1H, dd), 8.70 (1H, dd), 13.29 (1H, br)
Compound No. VIII-11:
2.07 (3H, s), 7.18 (1H, d), 7.44-7.59 (4H, m), 8.62 (1H, d), 8.70-8.72 (1H, m), 13.40 (1H, br)
Compound No. VIII-12:
2.48 (3H, s), 7.10-7.13 (2H, m), 7.44 (1H, d), 7.53-7.58 (2H, m), 8.64 (1H, dd), 8.71 (1H, dd), 13.71 (1H, br)
Compound No. VIII-15:
1.31 (3H, t), 2.79 (2H, q), 7.13 (2H, m), 7.46 (1H, d), 7.55 (2H, m), 8.63 (1H, m), 8.71 (1H, m)
Compound No. VIII-16:
1.39 (3H, t), 2.80 (2H, q), 7.24 (2H, d), 7.48 (2H, d), 7.55 (1H, q), 8.63 (1H, m), 8.72 (1H, m)
Compound No. VIII-22:
1.35 (6H, d), 3.06 (1H, m), 7.25 (2H, m), 7.54 (3H, m), 8.63 (1H, m), 8.71 (1H, m)
Compound No. VIII-28:
7.49 (2H, d), 7.60 (1H, q), 7.93 (2H, d), 8.63-8.69 (2H, m), 13.25 (1H, br)
Compound No. VIII-53:
6.40 (1H, t), 7.55 (5H, m), 8.66 (2H, m)
Compound No. VIII-54:
6.60 (1H, t), 7.13 (1H, s), 7.20 (1H, d), 7.39 (1H, d), 7.58 (1H, q), 7.67 (1H, t), 8.69 (2H, m)
Compound No. VIII-55:
6.65 (1H, t), 7.36 (4H, m), 7.58 (1H, m), 8.67 (2H, m)
Compound No. VIII-56:
7.43 (1H, d), 7.53-7.64 (3H, m), 7.68 (1H, d), 8.63-8.68 (2H, m)
Compound No. VIII-57:
7.24-7.32 (2H, m), 7.49 (2H, d), 7.59 (1H, q), 7.70 (1H, t), 8.63-8.70 (2H, m), 13.12 (1H, br)
Compound No. VIII-58:
7.37-7.41 (2H, m), 7.49 (2H, d), 7.58-7.61 (1H, m), 8.64-8.70 (2H, m), 13.48 (1H, br)
Compound No. VIII-76:
7.40 (2H, d), 7.59 (1H, q), 7.93 (2H, d), 8.65 (2H, m)
Compound No. VIII-84:
7.61 (2H, q), 7.67 (1H, s), 7.79 (1H, t), 7.91 (1H, d), 8.66 (2H, q)
Compound No. VIII-98:
7.15-7.18 (1H, m), 7.37-7.41 (1H, m), 7.43-7.50 (1H, m), 7.59-7.62 (1H, m), 8.64-8.70 (2H, m), 13.20 (1H, br)
Compound No. VIII-99:
7.13-7.18 (1H, m), 7.36-7.41 (1H, m), 7.58-7.61 (1H, m), 8.59-8.70 (2H, m), 13.27 (1H, br)
Compound No. VIII-100:
7.13-7.18 (1H, m), 7.30-7.39 (2H, m), 7.59-7.62 (1H, m), 8.63-8.70 (2H, m), 10.81 (1H, br)
Compound No. VIII-101:
7.18-7.27 (2H, m), 7.57-7.63 (2H, m), 8.63-8.70 (1H, m), 12.55 (1H, br)
Compound No. VIII-102:
7.10-7.15 (1H, m), 7.20-7.27 (1H, m), 7.41-7.50 (1H, m), 7.58-7.62 (1H, m), 8.63-8.71 (2H, m), 12.80 (1H, br)
Compound No. VIII-103:
6.91-6.95 (2H, m), 7.06-7.13 (1H, m), 7.58-7.62 (1H, m), 8.63-8.71 (2H, m), 13.20 (1H, br)
Compound No. VIII-104:
7.32 (1H, dd), 7.43-7.49 (2H, m), 7.69 (1H, dd), 8.53 (1H, dd)
Compound No. VIII-106:
7.42-7.52 (3H, m), 7.59 (1H, d), 8.39 (1H, dd), 8.54 (1H, dd)
Compound No. VIII-107:
7.52-7.62 (4H, m), 8.65-8.68 (2H, m)
Compound No. VIII-108:
7.20 (1H, dd), 7.47 (1H, d), 7.60 (1H, q), 7.73 (1H, d), 8.64 (1H, dd), 8.70 (1H, dd)
Compound No. VIII-109:
7.28 (1H, s), 7.40 (1H, s), 7.46 (1H, q), 7.54 (1H, t), 8.38 (1H, dd), 8.60 (1H, dd)
Compound No. VIII-113:
3.69 (3H, s), 3.95 (3H, s), 6.84 (1H, dd), 7.15 (1H, dd), 7.25 (1H, t), 7.44 (1H, q), 8.39 (1H, dd), 8.56 (1H, dd)
Compound No. VIII-114:
3.91 (1H, s), 6.84-6.92 (2H, m), 7.34 (1H, dd), 7.58 (1H, dd), 8.64 (1H, dd), 8.72 (1H, dd), 13.55 (1H, br)
Compound No. VIII-116:
2.29 (3H, s), 3.81 (3H, s), 6.78 (1H, s), 6.80 (1H, dd), 7.33 (1H, d), 7.44 (1H, q), 8.37 (1H, dd), 8.58 (1H, dd)
Compound No. VIII-117:
3.88 (3H, s), 3.97 (3H, s), 6.80 (1H, d), 6.89 (1H, dd), 7.09 (1H, d), 7.51 (1H, q), 8.53 (1H, dd), 8.68 (1H, dd)
Compound No. VIII-118:
3.86 (3H, s), 6.64-6.68 (2H, m), 6.87 (1H, dt), 7.59 (1H, q), 8.64 (1H, dd), 8.72 (1H, dd)
Compound No. VIII-121:
3.82 (6H, s), 6.44 (1H, d), 6.65 (1H, d), 7.50 (1H, q), 8.51 (1H, dd), 8.67 (1H, dd)
Compound No. VIII-126:
7.09 (2H, m), 7.21 (1H, t), 7.58 (1H, q), 8.63 (1H, m), 8.72 (1H, m)
Compound No. VIII-127:
4.01 (3H, s), 7.21 (2H, m), 7.38 (1H, d), 7.58 (1H, q), 8.62 (1H, m), 8.71 (1H, m)
Compound No. VIII-128:
2.30 (3H, s), 3.93 (3H, s), 7.04-7.15 (3H, m), 7.56 (1H, q), 8.63 (1H, dd), 8.74 (1H, dd)
Compound No. VIII-132:
3.70 (3H, s), 3.82 (3H, s), 6.83 (1H, s), 7.11 (2H, s), 7.54 (1H, q), 8.62 (1H, d), 8.70 (1H, dd)

Compound No. VIII-133:
3.87 (6H, s), 3.97 (3H, s), 6.51 (2H, s), 7.56 (1H, q), 8.63 (1H, m), 8.76 (1H, m)
Compound No. VIII-134:
7.16 (1H, dd), 7.30 (2H, m), 7.61-7.69 (3H, m), 8.71 (1H, q)
Compound No. VIII-135:
3.91 (3H, s), 7.12-7.24 (5H, m), 8.70 (1H, q)
Compound No. VIII-136:
7.29-7.32 (2H, m), 7.53 (1H, d), 7.59-7.69 (3H, m), 8.54 (1H, d)
Compound No. VIII-137:
3.92 (3H, s), 7.13 (2H, d), 7.21 (2H, d), 7.52 (1H, d), 8.53 (1H, d)
Compound No. VIII-139:
3.73 (3H, s), 3.91 (3H, s), 6.93 (1H, d), 7.10 (2H, d), 7.23 (2H, d), 8.39 (1H, d)
Compound No. VIII-142:
7.52 (1H, t), 7.61 (1H, m), 7.70 (1H, d), 7.91 (1H, m), 8.67 (2H, m)
Compound No. VIII-143:
7.56 (4H, m), 8.67 (2H, m)
Compound No. VIII-144:
7.59 (3H, m), 7.90 (1H, t), 8.67 (2H, m)
Compound No. VIII-145:
7.31 (1H, d), 7.44 (1H, s), 7.61 (2H, m), 8.65 (2H, m)
Compound No. VIII-150:
2.37 (3H, s), 2.39 (3H, s), 7.07 (2H, m), 7.42 (1H, d), 7.55 (1H, q), 8.63 (1H, m), 8.72 (1H, m)
Compound No. VIII-152:
7.62 (1H, q), 7.85 (2H, s), 8.12 (1H, s), 8.65-8.68 (2H, m)
Compound No. VIII-153:
3.73 (6H, s), 6.80 (2H, d), 7.97-7.53 (2H, m), 8.59 (1H, dd), 8.69 (1H, dd)
Compound No. VIII-154:
7.29-7.45 (2H, m), 7.54-7.69 (2H, m), 8.60-8.68 (2H, m)
Compound No. VIII-155:
7.30 (1H, t), 7.92 (2H, d), 7.59 (1H, q), 8.64 (1H, d), 8.68 (1H, d)
Compound No. VIII-156:
7.30-7.46 (2H, m), 7.56-7.66 (2H, m), 8.64 (1H, dd), 8.69 (1H, d)
Compound No. VIII-157:
7.11 (1H, d), 7.19 (1H, dd), 7.60 (1H, q), 7.69 (1H, t), 8.65 (1H, d), 8.69 (1H, d)
Compound No. VIII-158:
7.28-7.37 (1H, m), 7.38-7.45 (2H, m), 7.59 (1H, m), 8.62-8.68 (2H, m)
Compound No. VIII-159:
7.22-7.26 (1H, m), 7.40-7.95 (2H, m), 7.59 (1H, dd), 8.62-8.71 (1H, m)
Compound No. VIII-160:
2.41 (3H, d), 7.18 (1H, t), 7.32 (1H, t), 7.47 (1H, t), 7.58 (1H, q), 8.69 (1H, dd), 8.70 (1H, dd)
Compound No. VIII-161:
2.51 (3H, s), 7.18-7.29 (3H, m), 7.55-7.60 (1H, m), 8.63 (1H, d), 8.71 (1H, d), 13.35 (1H, br)
Compound No. VIII-162:
2.45 (3H, s), 7.16 (1H, dd), 7.27 (1H, t), 7.38-7.43 (1H, m), 7.58 (1H, q), 8.64 (1H, dd), 8.71 (1H, dd)
Compound No. VIII-163:
1.94 (3H, d), 7.01 (1H, d), 7.31 (1H, d), 7.43 (1H, q), 7.59 (1H, q), 8.67 (1H, dd), 8.70 (1H, dd)
Compound No. VIII-164:
2.41 (3H, d), 7.02 (2H, d), 7.48 (1H, d), 7.57 (1H, q), 8.63 (1H, m), 8.70 (1H, m)
Compound No. VIII-165:
2.48 (3H, s), 6.88 (1H, d), 6.94 (1H, s), 7.15 (1H, d), 7.58 (1H, q), 8.64 (1H, dd), 8.72 (1H, dd)
Compound No. VIII-166:
7.12-7.18 (3H, m), 7.59 (1H, q), 8.64-8.72 (2H, m), 11.85 (1H, br)
Compound No. VIII-167:
7.11-7.19 (2H, m), 7.26-7.31 (1H, m), 7.58 (1H, dd), 8.64 (1H, dd), 8.72 (1H, dd), 13.22 (1H, br)
Compound No. VIII-168:
1.99 (3H, s), 6.95 (1H, dd), 7.22-7.28 (1H, m), 7.46 (1H, q), 7.59 (1H, q), 8.66 (1H, dd), 8.71 (1H, dd)
Compound No. VIII-169:
7.59-7.72 (4H, m), 8.62-8.68 (2H, m), 9.57 (1H, br)
Compound No. VIII-170:
7.26-7.30 (2H, d), 7.62 (1H, dd), 7.91 (1H, t), 8.64-8.70 (2H, m), 12.16 (1H, br)
Compound No. VIII-171:
7.37-7.41 (1H, m), 7.52-7.60 (2H, m), 7.65-7.69 (1H, m), 8.62-8.65 (2H, m), 13.20 (1H, br)
Compound No. VIII-172:
3.87 (3H, d), 7.05 (1H, d), 7.22-7.28 (1H, m), 7.35-7.40 (1H, m), 7.57 (1H, q), 8.64 (1H, dd), 8.69 (1H, dd)
Compound No. VIII-173:
3.75 (1H, s), 6.88-6.95 (2H, m), 7.21-7.27 (1H, m), 7.56 (1H, dd), 8.63 (1H, dd), 8.69 (1H, dd), 13.67 (1H, br)
Compound No. VIII-174:
3.73 (3H, s), 7.05 (1H, dd), 7.12 (1H, dd), 7.28-7.34 (1H, m), 7.56 (1H, q), 8.62 (1H, dd), 8.68 (1H, dd)
Compound No. VIII-175:
6.65 (1H, t), 7.20 (2H, m), 7.39 (1H, t), 7.59 (1H, q), 8.68 (2H, m)
Compound No. VIII-176:
6.69 (1H, t), 7.14 (1H, m), 7.22 (1H, m), 7.52 (1H, t), 7.59 (1H, q), 8.63 (1H, m), 8.69 (1H, m)
Compound No. VIII-177:
6.42 (1H, t), 7.18-7.25 (2H, m), 7.37-7.42 (1H, m), 7.59 (1H, m), 8.62-8.68 (2H, m), 12.34 (1H, br)
Compound No. VIII-178:
7.51 (1H, t), 7.60-7.67 (3H, m), 8.65 (2H, d)
Compound No. VIII-179:
2.49 (3H, s), 7.23 (1H, d), 7.36 (1H, m), 7.52 (1H, s), 7.57 (1H, q), 8.66 (2H, m)
Compound No. VIII-180:
2.51 (3H, s), 7.14 (1H, d), 7.34 (1H, s), 7.56 (2H, m), 8.63 (1H, d), 8.70 (1H, m)
Compound No. VIII-181:
6.67 (1H, t), 7.25 (2H, m), 7.50 (2H, m), 7.59 (1H, q), 8.68 (2H, m)
Compound No. VIII-182:
2.64 (3H, s), 7.42 (1H, d), 7.60 (3H, t), 865 (1H, d), 8.70 (1H, t)
Compound No. VIII-183:
2.49 (3H, s), 3.73 (3H, s), 6.98 (1H, s), 7.02 (1H, d), 7.13 (1H, d), 7.53 (1H, q), 8.62 (1H, dd), 8.70 (1H, dd)
Compound No. VIII-184:
2.68 (3H, s), 7.29 (1H, dd), 7.33 (1H, s), 7.60 (1H, q), 7.89 (1H, d), 8.65 (1H, dd), 8.68 (1H, dd)
Compound No. VIII-185:
2.70 (3H, s), 7.47 (1H, dd), 7.58-7.63 (3H, m), 8.65 (1H, dd), 8.68 (1H, dd)
Compound No. VIII-187:
6.96 (6H, m), 7.24 (1H, m), 7.62 (1H, q), 8.66 (2H, m)
Compound No. VIII-190:
2.45 (3H, s), 7.04 (1H, t), 7.22 (1H, t), 7.59 (1H, q), 8.63 (1H, m), 8.69 (1H, m)

Compound No. VIII-192:
4.14 (3H, s), 6.93 (2H, m), 7.59 (1H, q), 8.63 (1H, m), 8.70 (1H, m)

Compound No. VIII-193:
2.36 (3H, s), 7.20 (1H, d), 7.36 (1H, d), 7.59 (1H, q), 8.63 (1H, m), 8.69 (1H, m)

Compound No. VIII-194:
7.30 (2H, dd), 7.60-7.71 (3H, m), 8.61 (2H, q)

Compound No. VIII-195:
2.56 (3H, s), 7.30 (2H, d), 7.40 (1H, d), 7.58-7.66 (3H, m), 8.47 (1H, d)

Compound No. VIII-196:
2.53 (3H, s), 7.31 (2H, m), 7.65 (3H, m), 8.90 (1H, s), 8.52 (1H, s)

Compound No. VIII-197:
2.92 (3H, s), 7.30 (2H, d), 7.38 (1H, d), 7.59-7.68 (3H, m), 8.51 (1H, d)

Compound No. VIII-198:
2.48 (3H, s), 2.92 (3H, s), 7.10 (2H, d), 7.40 (2H, q), 7.54 (1H, t), 8.53 (1H, d)

Compound No. VIII-199:
2.91 (3H, s), 7.40 (1H, d), 7.52 (1H, d), 7.60 (1H, s), 7.79 (1H, t), 7.87 (1H, d), 8.49 (1H, d)

Compound No. VIII-200:
2.91 (3H, s), 3.90 (3H, s), 7.19 (2H, d), 7.22 (2H, d), 7.37 (1H, d), 8.59 (1H, d)

Compound No. VIII-201:
2.40 (3H, d), 2.91 (3H, s), 7.00 (2H, d), 7.39 (1H, d), 7.46 (1H, d), 8.52 (1H, d)

Compound No. VIII-202:
2.91 (3H, s), 3.99 (3H, s), 7.09-7.09 (2H, m), 7.17 (1H, t), 7.39 (1H, d), 8.53 (1H, d)

Compound No. VIII-203:
4.17 (3H, s), 6.95 (1H, d), 7.28-7.32 (2H, m), 7.58-7.69 (3H, m), 8.51 (1H, d)

Compound No. VIII-204:
4.18 (3H, s), 6.97 (1H, d), 7.52 (1H, d), 7.60 (1H, s), 7.81 (1H, t), 7.87 (1H, d), 8.48 (1H, d)

Compound No. VIII-208:
2.41 (3H, d), 2.53 (3H, s), 7.02 (2H, d), 7.47 (1H, t), 8.40 (1H, q), 8.53 1H, d)

Compound No. VIII-209:
2.42 (3H, d), 2.59 (3H, s), 7.00 (2H, d), 7.43 (2H, q), 8.46 (1H, d)

Compound No. VIII-210:
7.30 (2H, d), 7.61-7.70 (4H, m), 8.53 (1H, d)

Compound No. VIII-211:
2.41 (3H, s), 3.74 (3H, s), 6.94 (1H, d), 7.02 (2H, m), 7.43 (1H, t), 8.40 (1H, d)

Compound No. VIII-212:
1.49 (3H, t), 9.08 (2H, q), 6.82 (1H, s), 6.87 (1H, d), 7.13 (1H, d), 7.53-7.58 (2H, m), 8.63 (1H, d), 8.72 (1H, d)

Compound No. VIII-213:
1.48 (3H, t), 9.13 (2H, q), 7.15 (2H, d), 7.23 (2H, d), 7.56 (1H, m), 8.63 (1H, d), 8.72 (1H, d)

Compound No. VIII-214:
3.91 (3H, s), 7.12 (2H, d), 7.21 (2H, d), 7.59 (1H, d), 8.55 (1H, d)

Compound No. VIII-215:
2.15 (3H, s), 7.31-7.36 (3H, m), 7.59-7.66 (3H, m), 8.27 (1H, d)

Compound No. VIII-216:
3.77 (3H, s), 9.35 s), 6.77 (1H, dd), 6.85 (1H, d), 6.93 (1H, d), 7.05 (1H, d), 8.39 (1H, d)

Compound No. VIII-218:
6.13 (2H, s), 6.72-6.77 (2H, m), 7.03 (1H, d), 7.61 (1H, d), 8.57 (1H, d)

For production intermediates obtained in Example 7 and Example 8 as well as a intermediate produced in the same manner, the $^1$H-NMR data (CDCl$_3$/TMS δ (ppm) value) are presented in the following.

Compound No. X-1:
6.77 (1H, d), 7.29-7.67 (7H, m), 8.06 (d, 1H)

Compound No. X-6:
6.78 (1H, d), 7.21-7.62 (6H, m), 8.06 (1H, d)

Compound No. X-7:
6.77 (1H, d), 7.26 (2H, d), 7.45 (1H, t), 7.55-7.63 (3H, m), 8.09 (1H, d)

Compound No. X-9:
2.48 (1H, s), 6.80 (1H, d), 7.17 (2H, d), 7.39-7.45 (3H, m), 7.54 (1H, t), 8.04 (1H, d)

Compound No. X-12:
1.29 (d, 6H), 3.00 (1H, m), 6.77 (1H, d), 7.09-7.14 (2H, m), 7.40-7.46 (2H, m), 7.52-7.57 (2H, m), 8.05 (1H, d)

Compound No. X-14:
6.71 (1H, d), 7.45-7.62 (4H, m), 7.78-7.89 (2H, m), 8.09 (1H, d)

Compound No. X-17:
3.74 (3H, s), 6.74 (1H, d), 7.14-7.24 (3H, m), 7.41 (1H, t), 7.51-7.58 (2H, m), 8.05 (1H, d)

Compound No. X-18:
3.84 (3H, s), 6.80-6.89 (3H, m), 7.12 (1H, d), 7.43 (1H, t), 7.49-7.61 (2H, m), 8.05 (1H, d)

Compound No. X-20:
1.43 (3H, t), 4.06 (2H, m), 6.79 (3H, m), 7.11 (1H, d), 7.40-7.58 (3H, m), 8.04 (1H, d)

Compound No. X-21:
1.48 (3H, t), 4.12 (2H, q), 6.83 (1H, d), 7.10 (2H, d), 7.19 (2H, d), 7.44 (1H, t), 7.54 (1H, t), 8.04 (1H, d)

Compound No. X-29:
6.75 (1H, d), 7.22-7.29 (2H, m), 7.56-7.72 (4H, m), 8.08 (1H, d)

Compound No. X-43:
3.91 (3H, s), 6.80-6.88 (3H, m), 7.46 (1H, t), 7.55-7.64 (2H, m), 8.07 (1H, d)

Compound No. X-44:
2.31 (3H, s), 3.82 (3H, s), 6.70 (3H, s), 6.76-6.85 (2H, m), 7.35-7.57 (3H, m), 8.04 (1H, d)

Compound No. X-45:
3.87 (3H, s), 3.98 (3H, s), 6.76 (1H, d), 6.85 (1H, dd), 7.07 (1H, d), 7.43 (1H, t), 7.56 (1H, t), 8.05 (1H, d)

Compound No. X-46:
3.82 (6H, s), 6.42 (2H, s), 6.64 (1H, s), 6.87 (1H, d), 7.43 (1H, t), 7.57 (1H, t), 8.04 (1H, d)

Compound No. X-53:
3.85 (6H, s), 3.94 (3H, s), 6.50 (2H, s), 6.86 (1H, d), 7.45 (1H, t), 7.59 (1H, t), 8.05 (1H, d)

Compound No. IX-6:
1.01 (3H, t), 1.47 (2H, m), 1.78 (2H, m), 4.32 (2H, m), 7.39-7.53 (2H, m), 7.76 (1H, t), 8.03 (1H, d)

Compound No. IX-9:
0.90 (3H, t), 1.30-1.51 (6H, m), 1.78 (2H, m), 4.29 (2H, t), 7.40-7.47 (2H, m), 7.75 (1H, t), 8.09 (1H, d)

Compound No. IX-28:
2.28 (3H, s), 2.85 (2H, t), 4.51 (2H, t), 7.41-7.70 (2H, m), 7.79 (1H, t), 8.12 (1H, d)

Compound No. IX-29:
3.09 (3H, t), 3.49 (2H, t), 4.77 (2H, t), 7.50-7.58 (2H, m), 7.89 (1H, t), 8.08 (1H, d)

Compound No. IX-73:
6.12 (2H, d), 6.79-6.76 (2H, m), 6.88 (1H, d), 7.01 (1H, d), 7.43 (1H, t), 7.57 (1H, t), 8.09 (1H, d)

Compound No. IX-75:
4.33 (4H, s), 6.74-6.89 (3H, m), 7.08 (1H, d), 7.94 (1H, t), 7.55 (1H, t), 8.02 (1H, d)

Hereinafter, preparation methods will be described in detail with reference to representative Preparation Examples. The type of the compounds and additives, and the incorporation ratios can be altered in a wide range, without being limited to those given below. In the following description, the "part" means parts by weight.

Preparation Example 1

Wettable Powder Formulation

| | |
|---|---|
| Compound of Compound No. I-12 | 10 parts |
| Polyoxyethylene octyl phenyl ether | 0.5 parts |
| Sodium salt of β-naphthalenesulfonic acid-formalin condensate | 0.5 parts |
| Diatomaceous earth | 20 parts |
| Clay | 69 parts |

The above-mentioned components were uniformly mixed and pulverized to obtain a wettable powder formulation. Furthermore, wettable powder formulations could be obtained in the same manner, using the respective compounds described in Table 1 to Table 45 instead of the compound of Compound No. I-12.

Preparation Example 2

Flowable Formulation

| | |
|---|---|
| Compound of Compound No. I-13 | 20 parts |
| Water | 69 parts |
| Polyoxyethylene styrenated phenyl ether sulfate | 4 parts |
| Ethylene glycol | 7 parts |

To the above-mentioned components, silicone AF-118N (manufactured by Asahi Kasei Corp.) was added in an amount of 200 ppm based on the total amount, and the mixture was mixed for 30 minutes in a high speed stirrer, and pulverized in a wet type pulverizer, to obtain a flowable formulation. Furthermore, flowable formulations can be obtained in the same manner, using the respective compounds described in Table 1 to Table 45 instead of the compound of Compound No. I-13.

Preparation Example 3

Emulsifiable Concentrate

| | |
|---|---|
| Compound of Compound No. I-59 | 30 parts |
| Mixture of equal amounts of xylene and isophoron | 60 parts |
| Polyoxyethylene sorbitan alkylate | 4 parts |
| Polyoxyethylene polyalkylaryl ether | 4 parts |
| Alkylaryl sulfonate | 2 parts |

The above-mentioned components were dissolved uniformly to obtain an emulsifiable concentrate. Furthermore, emulsions can be obtained in the same manner, using the respective compounds described in Table 1 to Table 45 instead of the compound of Compound No. 1-59.

Preparation Example 4

Granule Formulation

| | |
|---|---|
| Compound of Compound No. I-58 | 10 parts |
| Mixture of talc and bentonite (1:3) | 80 parts |
| White carbon | 5 parts |
| Polyoxyethylene sorbitan alkylate | 2 parts |
| Polyoxyethylene polyalkylaryl ether | 2 parts |
| Alkylaryl sulfonate | 1 part |

The above-mentioned components were uniformly mixed and pulverized. To this mixture, water was added in an amount equivalent to 10 parts, and the resulting mixture was kneaded. The kneaded mixture was extruded through an orifice having a diameter of 0.7 mm using an extrusion type granulator, dried, and then cut to a length of 0.5 to 1 mm, to obtain a granular formulation. Furthermore, granule formulations can be obtained in the same manner, using the respective compounds described in Table 1 to Table 45 instead of the compound of Compound No. I-58.

The compounds described in Tables 1 to 45 can be formulated into various formulations in the same manner according to the methods described in Preparation Examples 1 to 4.

Hereinafter, the herbicidal activity of the compound of the present invention will be described with reference to Test Examples.

Test Example 1

Test for Herbicidal Effects in Paddy Field Soil Treatment

A 100-cm$^2$ plastic pot was filled with paddy field soil. After puddling and leveling, seeds of *Echinochloa oryzicola* Vasing, *Monochoria vaginalis* (*Burm. f.*) Presl var. *plantaginea* (Roxb.) Solms-Laub., and *Scirpus juncoides* Roxb. var. *ohwianus*. *T. Koyama* were sowed, and the soil was waterlogged to a water depth of 3 cm. On the next day, a wettable powder formulation prepared according to Preparation Example 1 was diluted with water, and was added dropwise on the water surface. The amount of application was an amount equivalent to 1000 g of the active ingredient per hectare. Thereafter, the plants were grown in a greenhouse, and on the 21$^{st}$ day after the treatment, the herbicidal effects were investigated according to the criteria described in Table 138.

TABLE 138

| Index No. | Herbicidal effects (of the degree of suppressing the growth) and phytotoxicity |
|---|---|
| 5 | 90% or more suppressing herbicidal effects, phytotoxicity |
| 4 | 70% or more and less than 90% of herbicidal effects, phytotoxicity |
| 3 | 50% or more and less than 70% of herbicidal effects, phytotoxicity |
| 2 | 30% or more and less than 50% of herbicidal effects, phytotoxicity |
| 1 | 10% or more and less than 30% of herbicidal effects, phytotoxicity |
| 0 | 0% or more and less than 10% of herbicidal effects, phytotoxicity |

The results are presented in the following Table 139 to Table 146.

TABLE 139

| Compound No. | Echinochloa oryzicola Vasing | Monochoria vaginalis (Burm. f.) Presl var. plantaginea (Roxb.) Solms-Laub. | Scirpus juncoides Roxb. var. ohwianus. T. Koyama |
|---|---|---|---|
| I-2 | 4 | 5 | 5 |
| I-7 | 5 | 5 | 5 |
| I-12 | 5 | 5 | 5 |
| I-13 | 5 | 5 | 5 |
| I-14 | 4 | 5 | 5 |
| I-15 | 5 | 5 | 5 |
| I-22 | 5 | 5 | 5 |
| I-30 | 5 | 5 | 5 |
| I-35 | 5 | 5 | 5 |
| I-40 | 5 | 5 | 5 |
| I-49 | 5 | 5 | 5 |
| I-50 | 5 | 5 | 5 |
| I-57 | 4 | 5 | 5 |
| I-58 | 5 | 5 | 5 |
| I-59 | 5 | 5 | 5 |
| I-62 | 5 | 5 | 5 |
| I-65 | 4 | 5 | 5 |
| I-67 | 4 | 5 | 5 |
| I-68 | 4 | 5 | 5 |
| I-70 | 5 | 5 | 5 |
| I-72 | 5 | 5 | 5 |
| I-82 | 5 | 5 | 5 |
| I-88 | 5 | 5 | 5 |
| I-90 | 5 | 5 | 5 |
| I-91 | 5 | 5 | 5 |
| I-92 | 4 | 5 | 5 |
| I-93 | 5 | 5 | 5 |
| I-94 | 5 | 5 | 5 |
| I-99 | 5 | 5 | 5 |
| I-102 | 5 | 4 | 5 |
| I-103 | 5 | 5 | 5 |
| I-107 | 4 | 5 | 5 |
| I-111 | 5 | 5 | 5 |
| I-112 | 5 | 5 | 5 |
| I-113 | 5 | 5 | 5 |
| I-120 | 4 | 5 | 5 |
| I-125 | 4 | 5 | 5 |
| I-126 | 4 | 5 | 5 |
| I-131 | 5 | 5 | 5 |
| I-137 | 5 | 5 | 5 |
| I-139 | 5 | 5 | 5 |
| I-144 | 5 | 5 | 5 |
| I-145 | 5 | 5 | 5 |
| I-148 | 5 | 5 | 5 |
| I-149 | 5 | 5 | 4 |
| I-156 | 5 | 5 | 5 |
| I-158 | 5 | 5 | 5 |
| I-159 | 5 | 5 | 5 |
| I-160 | 5 | 5 | 5 |
| I-163 | 4 | 5 | 5 |

TABLE 140

| Compound No. | Echinochloa oryzicola Vasing | Monochoria vaginalis (Burm. f.) Presl var. plantaginea (Roxb.) Solms-Laub. | Scirpus juncoides Roxb. var. ohwianus. T. Koyama |
|---|---|---|---|
| I-165 | 5 | 5 | 5 |
| I-166 | 4 | 5 | 5 |
| I-171 | 5 | 5 | 5 |
| I-173 | 5 | 5 | 5 |
| I-176 | 5 | 5 | 5 |
| I-177 | 5 | 5 | 5 |
| I-178 | 4 | 5 | 5 |
| I-179 | 5 | 5 | 5 |
| I-180 | 4 | 5 | 5 |
| I-182 | 5 | 5 | 5 |
| I-185 | 5 | 5 | 5 |
| I-189 | 5 | 5 | 5 |
| I-197 | 5 | 5 | 5 |
| I-199 | 5 | 5 | 5 |

TABLE 140-continued

| Compound No. | Echinochloa oryzicola Vasing | Monochoria vaginalis (Burm. f.) Presl var. plantaginea (Roxb.) Solms-Laub. | Scirpus juncoides Roxb. var. ohwianus. T. Koyama |
|---|---|---|---|
| I-201 | 5 | 5 | 5 |
| I-202 | 5 | 5 | 5 |
| I-207 | 4 | 5 | 5 |
| I-209 | 4 | 5 | 5 |
| I-211 | 4 | 5 | 5 |
| I-212 | 5 | 5 | 5 |
| I-213 | 4 | 5 | 5 |
| I-220 | 5 | 5 | 5 |
| I-221 | 5 | 5 | 5 |
| I-223 | 4 | 5 | 5 |
| I-225 | 5 | 5 | 4 |
| I-227 | 5 | 5 | 5 |
| I-229 | 4 | 5 | 5 |
| I-230 | 5 | 5 | 5 |
| I-238 | 5 | 4 | 5 |
| I-263 | 5 | 5 | 5 |
| I-264 | 4 | 5 | 5 |
| I-265 | 4 | 5 | 5 |
| I-266 | 5 | 5 | 5 |
| I-267 | 5 | 5 | 5 |
| I-268 | 5 | 5 | 5 |
| I-269 | 5 | 5 | 5 |
| I-270 | 5 | 5 | 5 |
| I-271 | 5 | 5 | 5 |
| I-272 | 5 | 5 | 5 |
| I-273 | 5 | 5 | 5 |
| I-274 | 5 | 5 | 4 |
| I-275 | 4 | 5 | 5 |
| I-276 | 5 | 5 | 5 |
| I-277 | 5 | 5 | 5 |
| I-278 | 4 | 5 | 5 |
| I-279 | 4 | 5 | 5 |
| I-280 | 5 | 5 | 5 |
| I-281 | 5 | 5 | 5 |
| I-283 | 4 | 5 | 5 |
| I-363 | 5 | 5 | 5 |
| I-364 | 4 | 5 | 5 |
| I-368 | 4 | 5 | 5 |
| I-371 | 5 | 5 | 5 |
| I-372 | 5 | 5 | 5 |
| I-373 | 5 | 5 | 5 |
| I-379 | 5 | 5 | 5 |
| I-380 | 4 | 5 | 5 |

TABLE 141

| Compound No. | Echinochloa oryzicola Vasing | Monochoria vaginalis (Burm. f.) Presl var. plantaginea (Roxb.) Solms-Laub. | Scirpus juncoides Roxb. var. ohwianus. T. Koyama |
|---|---|---|---|
| II-1 | 5 | 5 | 5 |
| II-4 | 5 | 5 | 5 |
| II-5 | 5 | 5 | 5 |
| II-6 | 5 | 5 | 5 |
| II-7 | 5 | 5 | 5 |
| II-8 | 5 | 5 | 5 |
| II-9 | 5 | 5 | 5 |
| II-11 | 5 | 5 | 5 |
| II-13 | 5 | 5 | 5 |
| II-14 | 5 | 5 | 5 |
| II-15 | 5 | 5 | 5 |
| II-20 | 5 | 5 | 5 |
| II-21 | 5 | 5 | 5 |
| II-23 | 5 | 5 | 5 |
| II-24 | 5 | 5 | 5 |
| II-29 | 5 | 5 | 5 |
| II-33 | 5 | 5 | 5 |
| II-39 | 5 | 5 | 5 |
| II-44 | 5 | 5 | 5 |
| II-51 | 5 | 5 | 5 |
| II-52 | 5 | 5 | 5 |

TABLE 141-continued

| Compound No. | Echinochloa oryzicola Vasing | Monochoria vaginalis (Burm. f.) Presl var. plantaginea (Roxb.) Solms-Laub. | Scirpus juncoides Roxb. var. ohwianus. T. Koyama |
| --- | --- | --- | --- |
| II-57 | 5 | 5 | 5 |
| II-62 | 5 | 5 | 5 |
| II-63 | 5 | 5 | 5 |
| II-64 | 5 | 5 | 4 |
| II-68 | 5 | 5 | 5 |
| II-69 | 5 | 5 | 5 |
| II-71 | 4 | 5 | 5 |
| II-74 | 5 | 5 | 5 |
| II-75 | 5 | 5 | 5 |
| II-81 | 5 | 5 | 5 |
| II-84 | 5 | 5 | 5 |
| II-90 | 5 | 5 | 5 |
| II-95 | 5 | 5 | 5 |
| II-101 | 5 | 5 | 5 |
| II-116 | 5 | 5 | 5 |
| II-121 | 4 | 5 | 5 |
| II-122 | 5 | 5 | 5 |
| II-124 | 4 | 5 | 5 |
| II-125 | 5 | 5 | 5 |
| II-129 | 5 | 5 | 5 |
| II-130 | 5 | 5 | 5 |
| II-131 | 5 | 5 | 5 |
| II-136 | 5 | 5 | 5 |
| II-137 | 5 | 5 | 5 |
| II-140 | 5 | 5 | 4 |
| II-149 | 5 | 5 | 5 |
| II-167 | 5 | 5 | 5 |
| II-168 | 5 | 5 | 5 |
| II-169 | 5 | 5 | 5 |

TABLE 142

| Compound No. | Echinochloa oryzicola Vasing | Monochoria vaginalis (Burm. f.) Presl var. plantaginea (Roxb.) Solms-Laub. | Scirpus juncoides Roxb. var. ohwianus. T. Koyama |
| --- | --- | --- | --- |
| II-173 | 5 | 5 | 5 |
| II-174 | 5 | 5 | 5 |
| II-175 | 4 | 5 | 5 |
| II-177 | 4 | 5 | 5 |
| II-178 | 4 | 5 | 5 |
| II-179 | 4 | 5 | 5 |
| II-180 | 5 | 5 | 5 |
| II-185 | 4 | 5 | 5 |
| II-186 | 4 | 5 | 5 |
| II-187 | 5 | 5 | 5 |
| II-188 | 5 | 5 | 5 |
| II-189 | 5 | 5 | 5 |
| II-190 | 5 | 5 | 5 |
| II-193 | 5 | 5 | 5 |
| II-194 | 4 | 5 | 5 |
| II-195 | 5 | 5 | 5 |
| II-196 | 4 | 5 | 5 |
| II-197 | 5 | 5 | 5 |
| II-208 | 5 | 5 | 5 |
| II-209 | 5 | 5 | 5 |
| II-210 | 5 | 5 | 5 |
| II-211 | 5 | 5 | 5 |
| II-212 | 5 | 5 | 5 |
| II-213 | 5 | 5 | 5 |
| II-214 | 5 | 5 | 5 |
| II-215 | 5 | 5 | 5 |
| II-216 | 5 | 5 | 5 |
| II-217 | 4 | 5 | 5 |
| II-218 | 4 | 5 | 5 |
| II-219 | 5 | 5 | 5 |
| II-220 | 5 | 5 | 5 |
| II-221 | 4 | 5 | 5 |
| II-222 | 5 | 5 | 5 |
| II-223 | 5 | 5 | 5 |
| II-224 | 4 | 5 | 5 |

TABLE 142-continued

| Compound No. | Echinochloa oryzicola Vasing | Monochoria vaginalis (Burm. f.) Presl var. plantaginea (Roxb.) Solms-Laub. | Scirpus juncoides Roxb. var. ohwianus. T. Koyama |
| --- | --- | --- | --- |
| II-225 | 5 | 5 | 5 |
| II-226 | 5 | 5 | 5 |
| II-227 | 5 | 5 | 5 |
| II-228 | 5 | 5 | 5 |
| II-229 | 5 | 5 | 5 |
| II-230 | 4 | 5 | 5 |
| II-231 | 5 | 5 | 5 |
| II-232 | 4 | 5 | 5 |
| II-233 | 5 | 5 | 5 |
| II-235 | 4 | 5 | 5 |
| II-236 | 4 | 5 | 5 |
| II-237 | 5 | 5 | 5 |
| II-238 | 5 | 5 | 5 |
| II-239 | 5 | 5 | 5 |

TABLE 143

| Compound No. | Echinochloa oryzicola Vasing | Monochoria vaginalis (Burm. f.) Presl var. plantaginea (Roxb.) Solms-Laub. | Scirpus juncoides Roxb. var. ohwianus. T. Koyama |
| --- | --- | --- | --- |
| II-240 | 4 | 5 | 5 |
| II-241 | 5 | 5 | 5 |
| II-242 | 5 | 5 | 5 |
| II-243 | 5 | 5 | 5 |
| II-244 | 5 | 5 | 5 |
| II-245 | 5 | 5 | 5 |
| II-246 | 4 | 5 | 5 |
| II-247 | 4 | 5 | 5 |
| II-248 | 5 | 5 | 5 |
| II-249 | 5 | 5 | 5 |
| II-252 | 5 | 5 | 5 |
| II-253 | 5 | 5 | 5 |
| II-254 | 5 | 5 | 5 |
| II-255 | 5 | 5 | 5 |
| II-256 | 5 | 5 | 5 |
| II-257 | 5 | 5 | 5 |
| II-258 | 4 | 5 | 5 |
| II-259 | 4 | 5 | 5 |
| II-260 | 5 | 5 | 5 |
| II-261 | 5 | 5 | 5 |
| II-263 | 5 | 5 | 5 |
| II-301 | 5 | 5 | 5 |
| II-303 | 5 | 5 | 5 |
| II-304 | 5 | 5 | 5 |
| II-305 | 5 | 5 | 5 |
| II-306 | 5 | 5 | 5 |
| III-2 | 5 | 5 | 5 |
| III-5 | 5 | 5 | 5 |
| III-7 | 5 | 5 | 5 |
| III-12 | 5 | 5 | 5 |
| III-13 | 5 | 5 | 5 |
| III-15 | 5 | 5 | 5 |
| III-30 | 4 | 5 | 5 |
| III-35 | 4 | 5 | 5 |
| III-40 | 5 | 5 | 5 |
| III-45 | 4 | 5 | 5 |
| III-59 | 5 | 5 | 5 |
| III-70 | 4 | 5 | 5 |
| III-88 | 5 | 5 | 4 |
| III-90 | 5 | 5 | 5 |
| III-96 | 5 | 5 | 5 |
| III-99 | 5 | 5 | 5 |
| III-107 | 5 | 5 | 5 |
| III-108 | 5 | 5 | 5 |
| III-111 | 5 | 5 | 5 |
| III-117 | 5 | 5 | 5 |
| III-118 | 5 | 5 | 5 |
| III-120 | 5 | 5 | 5 |
| III-130 | 5 | 5 | 5 |
| III-139 | 5 | 5 | 5 |

TABLE 143-continued

| Compound No. | Echinochloa oryzicola Vasing | Monochoria vaginalis (Burm. f.) Presl var. plantaginea (Roxb.) Solms-Laub. | Scirpus juncoides Roxb. var. ohwianus. T. Koyama |
|---|---|---|---|
| III-158 | 5 | 5 | 5 |
| III-173 | 5 | 5 | 5 |
| III-189 | 5 | 5 | 5 |
| III-201 | 5 | 5 | 5 |

TABLE 144

| Compound No. | Echinochloa oryzicola Vasing | Monochoria vaginalis (Burm. f.) Presl var. plantaginea (Roxb.) Solms-Laub. | Scirpus juncoides Roxb. var. ohwianus. T. Koyama |
|---|---|---|---|
| III-202 | 5 | 5 | 5 |
| III-207 | 5 | 5 | 5 |
| III-209 | 5 | 5 | 5 |
| III-212 | 4 | 5 | 5 |
| III-213 | 4 | 5 | 5 |
| III-220 | 5 | 5 | 5 |
| III-221 | 4 | 5 | 5 |
| III-229 | 5 | 5 | 5 |
| III-230 | 5 | 5 | 5 |
| III-231 | 5 | 5 | 5 |
| III-232 | 5 | 5 | 5 |
| III-234 | 5 | 5 | 5 |
| III-235 | 5 | 5 | 5 |
| III-236 | 5 | 5 | 5 |
| III-237 | 5 | 5 | 5 |
| III-238 | 4 | 5 | 5 |
| III-239 | 4 | 5 | 5 |
| III-240 | 4 | 5 | 5 |
| III-241 | 5 | 5 | 5 |
| III-242 | 5 | 5 | 5 |
| III-243 | 5 | 5 | 5 |
| III-244 | 4 | 5 | 5 |
| III-245 | 4 | 5 | 5 |
| II-246 | 5 | 5 | 5 |
| III-247 | 5 | 5 | 5 |
| IV-1 | 5 | 5 | 5 |
| IV-2 | 5 | 5 | 5 |
| IV-3 | 5 | 5 | 5 |
| IV-4 | 5 | 5 | 5 |
| IV-6 | 4 | 5 | 5 |
| IV-7 | 5 | 5 | 5 |
| IV-8 | 5 | 5 | 5 |
| IV-9 | 5 | 5 | 5 |
| IV-11 | 5 | 5 | 5 |
| IV-13 | 5 | 5 | 5 |
| IV-17 | 5 | 5 | 5 |
| IV-18 | 5 | 5 | 5 |
| IV-19 | 5 | 5 | 5 |
| IV-20 | 5 | 5 | 5 |
| IV-21 | 5 | 5 | 5 |
| IV-23 | 5 | 5 | 5 |
| IV-24 | 5 | 5 | 5 |
| IV-30 | 5 | 5 | 5 |
| IV-33 | 5 | 5 | 5 |
| IV-34 | 5 | 5 | 5 |
| IV-39 | 5 | 5 | 5 |
| IV-40 | 5 | 5 | 5 |
| IV-41 | 5 | 5 | 5 |
| IV-44 | 5 | 5 | 5 |

TABLE 145

| Compound No. | Echinochloa oryzicola Vasing | Monochoria vaginalis (Burm. f.) Presl var. plantaginea (Roxb.) Solms-Laub. | Scirpus juncoides Roxb. var. ohwianus. T. Koyama |
|---|---|---|---|
| IV-52 | 5 | 5 | 5 |
| IV-57 | 4 | 5 | 5 |
| IV-62 | 5 | 5 | 5 |

TABLE 145-continued

| Compound No. | Echinochloa oryzicola Vasing | Monochoria vaginalis (Burm. f.) Presl var. plantaginea (Roxb.) Solms-Laub. | Scirpus juncoides Roxb. var. ohwianus. T. Koyama |
|---|---|---|---|
| IV-85 | 5 | 5 | 5 |
| IV-90 | 5 | 5 | 5 |
| IV-95 | 5 | 5 | 5 |
| IV-100 | 5 | 5 | 5 |
| IV-101 | 5 | 5 | 5 |
| IV-106 | 5 | 5 | 5 |
| IV-128 | 5 | 5 | 5 |
| IV-136 | 5 | 5 | 5 |
| IV-150 | 5 | 5 | 5 |
| IV-151 | 5 | 5 | 5 |
| IV-152 | 5 | 5 | 5 |
| IV-153 | 5 | 5 | 5 |
| IV-154 | 5 | 5 | 5 |
| IV-155 | 5 | 5 | 5 |
| IV-156 | 5 | 5 | 5 |
| IV-157 | 5 | 5 | 5 |
| IV-158 | 5 | 5 | 5 |
| IV-159 | 5 | 5 | 5 |
| IV-160 | 5 | 5 | 5 |
| IV-161 | 5 | 5 | 5 |
| IV-165 | 4 | 5 | 5 |
| IV-166 | 5 | 5 | 5 |
| IV-168 | 5 | 5 | 5 |
| IV-169 | 4 | 5 | 5 |
| IV-170 | 5 | 5 | 5 |
| IV-173 | 4 | 5 | 5 |
| IV-174 | 5 | 5 | 5 |
| IV-177 | 5 | 5 | 5 |
| IV-178 | 5 | 5 | 5 |
| IV-179 | 5 | 5 | 5 |
| IV-180 | 5 | 5 | 5 |
| IV-184 | 5 | 5 | 5 |
| IV-185 | 5 | 5 | 5 |
| IV-186 | 5 | 5 | 5 |
| IV-187 | 5 | 5 | 5 |
| IV-188 | 5 | 5 | 5 |
| IV-189 | 5 | 5 | 5 |
| IV-200 | 5 | 5 | 5 |
| IV-201 | 5 | 5 | 5 |
| IV-202 | 5 | 5 | 5 |
| IV-203 | 5 | 5 | 5 |
| IV-206 | 5 | 5 | 5 |
| IV-208 | 5 | 5 | 5 |
| IV-209 | 5 | 5 | 5 |
| IV-210 | 5 | 5 | 5 |
| IV-212 | 5 | 5 | 5 |
| IV-213 | 5 | 5 | 5 |
| IV-214 | 5 | 5 | 5 |

TABLE 146

| Compound No. | Echinochloa oryzicola Vasing | Monochoria vaginalis (Burm. f.) Presl var. plantaginea (Roxb.) Solms-Laub. | Scirpus juncoides Roxb. var. ohwianus. T. Koyama |
|---|---|---|---|
| IV-215 | 5 | 5 | 5 |
| IV-216 | 5 | 5 | 5 |
| IV-217 | 5 | 5 | 5 |
| IV-218 | 5 | 5 | 5 |
| IV-219 | 5 | 5 | 5 |
| IV-220 | 5 | 5 | 5 |
| IV-221 | 5 | 5 | 5 |
| IV-222 | 5 | 5 | 5 |
| IV-223 | 5 | 5 | 5 |
| IV-224 | 5 | 5 | 5 |
| IV-225 | 5 | 5 | 5 |
| IV-226 | 5 | 5 | 5 |
| IV-227 | 5 | 5 | 5 |
| IV-228 | 5 | 5 | 5 |
| IV-229 | 5 | 5 | 5 |
| IV-230 | 5 | 5 | 5 |

TABLE 146-continued

| Compound No. | Echinochloa oryzicola Vasing | Monochoria vaginalis (Burm. f.) Presl var. plantaginea (Roxb.) Solms-Laub. | Scirpus juncoides Roxb. var. ohwianus. T. Koyama |
|---|---|---|---|
| IV-231 | 5 | 5 | 5 |
| IV-232 | 5 | 5 | 5 |
| IV-233 | 5 | 5 | 5 |
| IV-234 | 5 | 5 | 5 |
| IV-235 | 5 | 5 | 5 |
| IV-236 | 5 | 5 | 5 |
| IV-237 | 5 | 5 | 5 |
| IV-238 | 5 | 5 | 5 |
| IV-239 | 5 | 5 | 5 |
| IV-240 | 5 | 5 | 5 |
| IV-241 | 5 | 5 | 5 |
| IV-242 | 4 | 5 | 5 |
| IV-243 | 5 | 5 | 5 |
| IV-244 | 5 | 5 | 5 |
| IV-245 | 5 | 5 | 5 |
| IV-247 | 5 | 5 | 5 |
| IV-248 | 5 | 5 | 5 |
| IV-249 | 5 | 5 | 5 |
| IV-250 | 3 | 5 | 5 |
| IV-251 | 5 | 5 | 5 |
| IV-252 | 5 | 5 | 5 |
| IV-253 | 5 | 5 | 5 |
| IV-254 | 5 | 5 | 5 |
| IV-255 | 5 | 5 | 5 |
| IV-256 | 5 | 5 | 5 |
| IV-257 | 5 | 5 | 5 |
| IV-258 | 5 | 5 | 5 |
| IV-259 | 5 | 5 | 5 |
| IV-260 | 5 | 5 | 5 |
| IV-262 | 4 | 5 | 5 |
| IV-265 | 5 | 5 | 5 |
| IV-266 | 5 | 5 | 5 |
| IV-267 | 5 | 5 | 5 |
| IV-268 | 5 | 5 | 5 |
| IV-269 | 5 | 5 | 5 |
| IV-270 | 5 | 5 | 5 |
| IV-271 | 5 | 5 | 5 |
| Comparative Compound A | 2 | 0 | 0 |
| Comparative Compound B | 0 | 0 | 0 |
| Comparative Compound C | 1 | 2 | 1 |
| Comparative Compound D | 1 | 4 | 2 |

Additionally, comparative compound A, comparative compound B, comparative compound C and comparative compound D in the tables are Compound No. 70, Compound No. 34, Compound No. 32 and Compound No. 31 described in EP 283261, respectively. The structural formulas of these compounds are shown below.

[Chemical Formula 35]

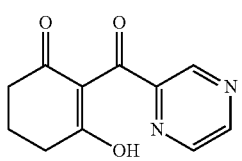

Comparative Compound A

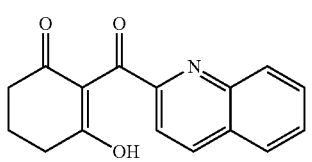

Comparative Compound B

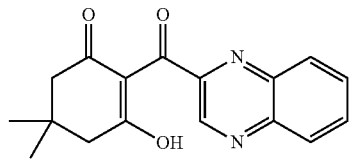

Comparative Compound C

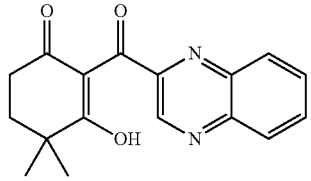

Comparative Compound D

Test Example 2

Test on Herbicidal Effects in Upland Field Soil Treatment

A 80-cm² plastic pot was filled with upland field soil. Seeds of *Abutilon theophrasti medicus* and *Amaranthus viridis* L. were sowed, and soil was covered. A wettable powder formulation prepared according to Preparation Example 1 was diluted with water, and was uniformly sprayed on the soil surface with a small sprayer, in an amount equivalent to 1000 liters per hectare, such that 1000 g of the active ingredient per hectare was applied. Thereafter, the plants were grown in a greenhouse, and on the 21$^{st}$ day after the treatment, the herbicidal effects were investigated according to the criteria described in the Table 138 shown above. The results are presented in the following Table 147 to Table 154.

TABLE 147

| Compound No. | Abutilon theophrasti medicus | Amaranthus viridis L. |
|---|---|---|
| I-2 | 5 | 5 |
| I-5 | 5 | 5 |
| I-7 | 5 | 5 |
| I-12 | 5 | 5 |
| I-13 | 5 | 5 |
| I-14 | 5 | 5 |
| I-15 | 5 | 5 |
| I-18 | 5 | 5 |
| I-21 | 5 | 5 |
| I-30 | 5 | 5 |
| I-40 | 5 | 5 |
| I-49 | 5 | 5 |
| I-50 | 5 | 5 |
| I-57 | 4 | 5 |
| I-58 | 5 | 5 |
| I-59 | 5 | 5 |
| I-62 | 5 | 5 |
| I-65 | 5 | 5 |
| I-68 | 5 | 5 |
| I-70 | 5 | 5 |
| I-71 | 5 | 5 |
| I-72 | 5 | 5 |
| I-80 | 5 | 5 |
| I-82 | 5 | 5 |
| I-88 | 5 | 5 |
| I-90 | 5 | 5 |
| I-93 | 4 | 5 |
| I-94 | 5 | 4 |
| I-99 | 5 | 5 |
| I-102 | 5 | 5 |
| I-103 | 5 | 5 |
| I-107 | 5 | 5 |

TABLE 147-continued

| Compound No. | Abutilon theophrasti medicus | Amaranthus viridis L. |
| --- | --- | --- |
| I-131 | 5 | 5 |
| I-139 | 5 | 5 |
| I-144 | 5 | 5 |
| I-145 | 5 | 5 |
| I-148 | 5 | 5 |
| I-149 | 5 | 5 |
| I-156 | 5 | 5 |
| I-158 | 5 | 5 |
| I-159 | 5 | 5 |
| I-160 | 5 | 5 |
| I-163 | 5 | 5 |
| I-165 | 5 | 5 |
| I-171 | 5 | 5 |
| I-173 | 5 | 5 |
| I-176 | 5 | 5 |
| I-177 | 5 | 5 |
| I-178 | 5 | 5 |
| I-179 | 5 | 5 |

TABLE 148

| Compound No. | Abutilon theophrasti medicus | Amaranthus viridis L. |
| --- | --- | --- |
| I-180 | 5 | 5 |
| I-182 | 5 | 5 |
| I-185 | 5 | 5 |
| I-189 | 5 | 5 |
| I-195 | 5 | 5 |
| I-197 | 5 | 5 |
| I-199 | 5 | 5 |
| I-201 | 4 | 5 |
| I-202 | 4 | 5 |
| I-207 | 5 | 5 |
| I-209 | 4 | 5 |
| I-211 | 5 | 5 |
| I-212 | 5 | 5 |
| I-213 | 5 | 5 |
| I-220 | 5 | 5 |
| I-221 | 5 | 5 |
| I-223 | 5 | 5 |
| I-225 | 5 | 5 |
| I-227 | 5 | 5 |
| I-229 | 5 | 5 |
| I-230 | 4 | 5 |
| I-238 | 5 | 4 |
| I-256 | 5 | 5 |
| I-263 | 5 | 5 |
| I-264 | 4 | 5 |
| I-265 | 4 | 5 |
| I-266 | 5 | 5 |
| I-267 | 5 | 5 |
| I-268 | 5 | 5 |
| I-269 | 5 | 5 |
| I-270 | 5 | 5 |
| I-271 | 5 | 5 |
| I-272 | 5 | 5 |
| I-273 | 5 | 5 |
| I-275 | 4 | 5 |
| I-277 | 4 | 5 |
| I-278 | 5 | 5 |
| I-279 | 5 | 5 |
| I-281 | 5 | 5 |
| I-283 | 5 | 5 |
| I-363 | 5 | 5 |
| I-364 | 5 | 5 |
| I-368 | 5 | 5 |
| I-371 | 5 | 5 |
| I-372 | 5 | 5 |
| I-373 | 5 | 5 |
| I-379 | 5 | 5 |
| I-380 | 5 | 5 |
| II-1 | 5 | 5 |
| II-4 | 4 | 5 |
| II-5 | 5 | 5 |
| II-6 | 5 | 5 |

TABLE 148-continued

| Compound No. | Abutilon theophrasti medicus | Amaranthus viridis L. |
| --- | --- | --- |
| II-7 | 5 | 5 |
| II-8 | 5 | 5 |
| II-9 | 5 | 4 |
| II-11 | 5 | 5 |

TABLE 149

| Compound No. | Abutilon theophrasti medicus | Amaranthus viridis L. |
| --- | --- | --- |
| II-13 | 5 | 5 |
| II-14 | 5 | 5 |
| II-15 | 5 | 5 |
| II-20 | 5 | 5 |
| II-21 | 5 | 5 |
| II-23 | 5 | 5 |
| II-24 | 5 | 5 |
| II-29 | 4 | 5 |
| II-33 | 4 | 5 |
| II-39 | 5 | 5 |
| II-44 | 5 | 5 |
| II-52 | 5 | 5 |
| II-57 | 5 | 5 |
| II-62 | 5 | 5 |
| II-63 | 5 | 5 |
| II-64 | 4 | 5 |
| II-68 | 5 | 5 |
| II-69 | 4 | 5 |
| II-75 | 4 | 5 |
| II-81 | 5 | 5 |
| II-90 | 5 | 5 |
| II-95 | 5 | 5 |
| II-101 | 5 | 5 |
| II-122 | 5 | 5 |
| II-125 | 5 | 5 |
| II-129 | 5 | 5 |
| II-130 | 5 | 5 |
| II-131 | 5 | 5 |
| II-136 | 5 | 5 |
| II-137 | 5 | 5 |
| II-146 | 4 | 5 |
| II-149 | 4 | 5 |
| II-167 | 5 | 5 |
| II-168 | 5 | 5 |
| II-173 | 4 | 5 |
| II-174 | 4 | 5 |
| II-180 | 4 | 5 |
| II-185 | 5 | 5 |
| II-186 | 5 | 5 |
| II-188 | 5 | 5 |
| II-189 | 5 | 5 |
| II-190 | 5 | 4 |
| II-193 | 5 | 5 |
| II-194 | 4 | 5 |
| II-196 | 4 | 5 |
| II-208 | 5 | 5 |
| II-211 | 5 | 5 |
| II-212 | 5 | 5 |
| II-213 | 5 | 5 |

TABLE 150

| Compound No. | Abutilon theophrasti medicus | Amaranthus viridis L. |
| --- | --- | --- |
| II-215 | 5 | 5 |
| II-216 | 4 | 5 |
| II-217 | 5 | 5 |
| II-218 | 5 | 5 |
| II-219 | 5 | 5 |
| II-220 | 5 | 5 |
| II-221 | 4 | 5 |
| II-222 | 5 | 5 |
| II-223 | 4 | 5 |
| II-224 | 5 | 5 |

TABLE 150-continued

| Compound No. | Abutilon theophrasti medicus | Amaranthus viridis L. |
|---|---|---|
| II-225 | 5 | 5 |
| II-226 | 5 | 5 |
| II-227 | 5 | 5 |
| II-228 | 5 | 5 |
| II-229 | 4 | 5 |
| II-230 | 4 | 5 |
| II-231 | 4 | 5 |
| II-232 | 4 | 5 |
| II-233 | 5 | 5 |
| II-234 | 5 | 5 |
| II-235 | 4 | 5 |
| II-236 | 4 | 5 |
| II-237 | 5 | 5 |
| II-238 | 5 | 5 |
| II-239 | 5 | 5 |
| II-240 | 5 | 5 |
| II-241 | 5 | 5 |
| II-242 | 4 | 5 |
| II-243 | 5 | 5 |
| II-244 | 5 | 5 |
| II-245 | 5 | 5 |
| II-247 | 5 | 5 |
| II-249 | 5 | 5 |
| II-250 | 5 | 5 |
| II-252 | 5 | 5 |
| II-254 | 4 | 5 |
| II-259 | 5 | 5 |
| II-260 | 5 | 5 |
| II-261 | 4 | 5 |
| II-262 | 4 | 5 |
| II-263 | 4 | 5 |
| II-301 | 5 | 5 |
| II-302 | 4 | 5 |
| II-303 | 5 | 5 |
| II-304 | 5 | 5 |
| II-305 | 5 | 5 |
| II-306 | 5 | 5 |
| III-2 | 5 | 5 |
| III-5 | 5 | 4 |
| III-7 | 5 | 5 |
| III-12 | 4 | 5 |
| III-13 | 5 | 5 |
| III-15 | 5 | 5 |
| III-30 | 5 | 5 |

TABLE 151

| Compound No. | Abutilon theophrasti medicus | Amaranthus viridis L. |
|---|---|---|
| III-35 | 5 | 5 |
| III-40 | 5 | 5 |
| III-45 | 4 | 5 |
| III-59 | 5 | 5 |
| III-70 | 5 | 5 |
| III-88 | 5 | 5 |
| III-90 | 5 | 5 |
| III-96 | 5 | 5 |
| III-99 | 5 | 5 |
| III-107 | 4 | 5 |
| III-108 | 5 | 5 |
| III-111 | 5 | 5 |
| III-117 | 5 | 5 |
| III-118 | 5 | 5 |
| III-120 | 4 | 5 |
| III-130 | 5 | 5 |
| III-139 | 5 | 5 |
| III-158 | 5 | 5 |
| III-173 | 5 | 5 |
| III-189 | 5 | 5 |
| III-201 | 5 | 5 |
| III-202 | 5 | 5 |
| III-207 | 5 | 5 |
| III-209 | 5 | 5 |
| III-212 | 4 | 5 |
| III-213 | 5 | 5 |
| III-220 | 5 | 4 |

TABLE 151-continued

| Compound No. | Abutilon theophrasti medicus | Amaranthus viridis L. |
|---|---|---|
| III-221 | 4 | 5 |
| III-229 | 5 | 5 |
| III-231 | 5 | 5 |
| III-232 | 5 | 5 |
| III-233 | 5 | 5 |
| III-234 | 5 | 5 |
| III-236 | 5 | 5 |
| III-237 | 5 | 5 |
| III-238 | 5 | 5 |
| III-239 | 5 | 5 |
| III-240 | 5 | 5 |
| III-242 | 4 | 5 |
| III-243 | 5 | 5 |
| III-244 | 5 | 5 |
| III-245 | 5 | 5 |
| III-246 | 4 | 5 |
| III-247 | 4 | 5 |
| IV-1 | 5 | 5 |
| IV-2 | 5 | 5 |
| IV-3 | 5 | 5 |
| IV-4 | 5 | 5 |

TABLE 152

| Compound No. | Abutilon theophrasti medicus | Amaranthus viridis L. |
|---|---|---|
| IV-6 | 5 | 5 |
| IV-7 | 5 | 5 |
| IV-8 | 5 | 5 |
| IV-9 | 5 | 5 |
| IV-11 | 5 | 5 |
| IV-13 | 5 | 5 |
| IV-17 | 5 | 5 |
| IV-18 | 5 | 5 |
| IV-19 | 5 | 5 |
| IV-20 | 5 | 5 |
| IV-21 | 5 | 5 |
| IV-23 | 5 | 5 |
| IV-24 | 5 | 5 |
| IV-30 | 4 | 5 |
| IV-33 | 5 | 5 |
| IV-34 | 5 | 5 |
| IV-39 | 5 | 5 |
| IV-40 | 5 | 5 |
| IV-41 | 5 | 5 |
| IV-44 | 5 | 5 |
| IV-52 | 5 | 4 |
| IV-57 | 5 | 5 |
| IV-62 | 5 | 5 |
| IV-85 | 5 | 5 |
| IV-90 | 5 | 5 |
| IV-95 | 5 | 5 |
| IV-100 | 5 | 5 |
| IV-101 | 5 | 5 |
| IV-106 | 5 | 5 |
| IV-128 | 5 | 5 |
| IV-136 | 5 | 5 |
| IV-150 | 5 | 5 |
| IV-151 | 5 | 5 |
| IV-152 | 5 | 5 |
| IV-153 | 5 | 5 |
| IV-154 | 5 | 5 |
| IV-155 | 5 | 5 |
| IV-156 | 5 | 5 |
| IV-157 | 5 | 5 |
| IV-158 | 5 | 5 |
| IV-159 | 5 | 5 |
| IV-160 | 5 | 5 |
| IV-161 | 5 | 5 |
| IV-165 | 5 | 5 |
| IV-166 | 5 | 5 |
| IV-168 | 5 | 5 |
| IV-169 | 5 | 5 |
| IV-170 | 5 | 5 |

TABLE 153

| Compound No. | Abutilon theophrasti medicus | Amaranthus viridis L. |
|---|---|---|
| IV-173 | 5 | 5 |
| IV-177 | 5 | 5 |
| IV-178 | 5 | 5 |
| IV-179 | 5 | 5 |
| IV-180 | 4 | 5 |
| IV-184 | 5 | 5 |
| IV-186 | 5 | 5 |
| IV-187 | 5 | 5 |
| IV-188 | 5 | 5 |
| IV-189 | 5 | 4 |
| IV-200 | 5 | 5 |
| IV-201 | 5 | 5 |
| IV-202 | 5 | 5 |
| IV-203 | 5 | 5 |
| IV-206 | 5 | 5 |
| IV-208 | 5 | 5 |
| IV-209 | 5 | 5 |
| IV-210 | 5 | 5 |
| IV-212 | 5 | 5 |
| IV-213 | 5 | 5 |
| IV-214 | 5 | 5 |
| IV-215 | 5 | 5 |
| IV-216 | 5 | 5 |
| IV-217 | 5 | 5 |
| IV-218 | 5 | 5 |
| IV-219 | 5 | 5 |
| IV-220 | 5 | 5 |
| IV-221 | 5 | 5 |
| IV-222 | 5 | 5 |
| IV-223 | 5 | 5 |
| IV-224 | 5 | 5 |
| IV-225 | 5 | 5 |
| IV-226 | 5 | 5 |
| IV-227 | 5 | 5 |
| IV-228 | 5 | 5 |
| IV-229 | 5 | 5 |
| IV-230 | 5 | 5 |
| IV-231 | 5 | 5 |
| IV-232 | 5 | 5 |
| IV-233 | 5 | 5 |
| IV-234 | 5 | 5 |
| IV-235 | 5 | 5 |
| IV-236 | 5 | 5 |
| IV-237 | 5 | 5 |
| IV-238 | 5 | 5 |
| IV-239 | 4 | 5 |
| IV-240 | 5 | 5 |
| IV-241 | 4 | 5 |
| IV-242 | 5 | 5 |
| IV-243 | 5 | 5 |

TABLE 154

| Compound No. | Abutilon theophrasti medicus | Amaranthus viridis L. |
|---|---|---|
| IV-244 | 5 | 5 |
| IV-245 | 5 | 5 |
| IV-247 | 5 | 5 |
| IV-248 | 5 | 5 |
| IV-249 | 4 | 5 |
| IV-250 | 4 | 5 |
| IV-251 | 4 | 5 |
| IV-252 | 5 | 5 |
| IV-253 | 5 | 5 |
| IV-254 | 5 | 5 |
| IV-255 | 5 | 5 |
| IV-256 | 5 | 5 |
| IV-257 | 5 | 5 |
| IV-258 | 5 | 5 |
| IV-259 | 5 | 5 |
| IV-260 | 5 | 5 |
| IV-262 | 5 | 5 |
| IV-266 | 5 | 5 |
| IV-267 | 5 | 5 |
| IV-268 | 5 | 5 |
| IV-269 | 5 | 5 |
| IV-271 | 4 | 5 |
| Comparative Compound A | 1 | 0 |
| Comparative Compound B | 2 | 2 |
| Comparative Compound C | 0 | 3 |
| Comparative Compound D | 0 | 3 |

Additionally, comparative compound A, comparative compound B, comparative compound C and comparative compound D in the tables are Compound Nos. 70, 34, 32 and 31 described in EP-283261, respectively. Additionally, comparative compound A and comparative compound B in the tables are Compound No. 70 and Compound No. 34 described in EP-283261, respectively.

Test Example 3

Test on Herbicidal Effects in Upland Field Foliar Treatment

A 80-cm$^2$ plastic pot was filled with upland field soil. Seeds of *Echinochloa crus-galli* (L.) P. Beauv. var. *crus-galli*, *Abutilon theophrasti medicus* and *Amaranthus viridis* L. were sowed, and the plants were grown for two weeks in a greenhouse. A wettable powder formulation prepared according to Preparation Example 1 was diluted with water, and was sprayed with a small sprayer to perform foliar application over the entirety of plants from the upper side, in an amount equivalent to 1000 liters per hectare, such that 1000 g of the active ingredient per hectare was applied. Thereafter, the plants were grown in a greenhouse, and on the 14$^{th}$ day after the treatment, the herbicidal effects were investigated according to the criteria described in the Table 138 shown above. The results are presented in the following Table 155 to Table 162.

TABLE 155

| Compound No. | Echinochloa crus-galli (L.) P. Beauv. var. crus-galli | Abutilon theophrasti medicus | Amaranthus viridis L. |
|---|---|---|---|
| I-2 | 4 | 5 | 5 |
| I-5 | 4 | 5 | 5 |
| I-7 | 4 | 5 | 5 |
| I-12 | 4 | 5 | 5 |
| I-13 | 5 | 5 | 5 |
| I-14 | 4 | 5 | 5 |
| I-15 | 5 | 5 | 5 |
| I-21 | 5 | 5 | 5 |
| I-22 | 4 | 5 | 5 |
| I-30 | 4 | 5 | 5 |
| I-35 | 4 | 5 | 5 |
| I-40 | 5 | 5 | 5 |
| I-49 | 4 | 5 | 5 |
| I-50 | 4 | 5 | 5 |
| I-58 | 5 | 5 | 5 |
| I-59 | 5 | 5 | 5 |
| I-62 | 5 | 5 | 5 |
| I-65 | 4 | 5 | 5 |
| I-67 | 4 | 5 | 5 |
| I-68 | 4 | 5 | 5 |
| I-70 | 5 | 5 | 5 |
| I-71 | 5 | 5 | 5 |
| I-72 | 5 | 5 | 5 |
| I-82 | 4 | 5 | 5 |

TABLE 155-continued

| Compound No. | Echinochloa crus-galli (L.) P. Beauv. var. crus-galli | Abutilon theophrasti medicus | Amaranthus viridis L. |
|---|---|---|---|
| I-88 | 5 | 5 | 5 |
| I-90 | 5 | 5 | 5 |
| I-91 | 5 | 5 | 5 |
| I-92 | 5 | 5 | 5 |
| I-93 | 5 | 5 | 5 |
| I-94 | 5 | 5 | 5 |
| I-99 | 5 | 5 | 5 |
| I-100 | 5 | 4 | 5 |
| I-102 | 5 | 5 | 5 |
| I-103 | 5 | 5 | 5 |
| I-107 | 4 | 5 | 5 |
| I-111 | 5 | 5 | 5 |
| I-112 | 4 | 5 | 5 |
| I-131 | 5 | 5 | 5 |
| I-136 | 4 | 5 | 5 |
| I-137 | 4 | 5 | 5 |
| I-139 | 4 | 5 | 5 |
| I-144 | 5 | 5 | 5 |
| I-145 | 5 | 5 | 5 |
| I-148 | 5 | 5 | 5 |
| I-149 | 5 | 5 | 5 |
| I-156 | 5 | 5 | 5 |
| I-158 | 5 | 5 | 5 |
| I-159 | 4 | 5 | 5 |
| I-160 | 5 | 5 | 5 |
| I-163 | 4 | 5 | 5 |

TABLE 156

| Compound No. | Echinochloa crus-galli (L.) P. Beauv. var. crus-galli | Abutilon theophrasti medicus | Amaranthus viridis L. |
|---|---|---|---|
| I-171 | 5 | 5 | 5 |
| I-173 | 5 | 5 | 5 |
| I-176 | 5 | 5 | 5 |
| I-177 | 5 | 5 | 5 |
| I-179 | 5 | 5 | 5 |
| I-180 | 4 | 5 | 5 |
| I-182 | 5 | 5 | 5 |
| I-185 | 5 | 5 | 5 |
| I-189 | 4 | 5 | 5 |
| I-195 | 5 | 5 | 5 |
| I-197 | 5 | 5 | 5 |
| I-199 | 5 | 5 | 5 |
| I-201 | 5 | 4 | 5 |
| I-202 | 4 | 5 | 5 |
| I-207 | 5 | 5 | 5 |
| I-211 | 5 | 5 | 5 |
| I-212 | 5 | 4 | 5 |
| I-213 | 5 | 5 | 5 |
| I-220 | 5 | 5 | 5 |
| I-221 | 4 | 5 | 5 |
| I-225 | 4 | 5 | 5 |
| I-227 | 4 | 5 | 5 |
| I-229 | 4 | 5 | 5 |
| I-230 | 5 | 5 | 5 |
| I-243 | 5 | 5 | 5 |
| I-247 | 4 | 5 | 5 |
| I-263 | 5 | 5 | 5 |
| I-266 | 5 | 5 | 5 |
| I-267 | 5 | 5 | 5 |
| I-268 | 5 | 5 | 5 |
| I-269 | 5 | 5 | 5 |
| I-270 | 5 | 5 | 5 |
| I-271 | 5 | 5 | 5 |
| I-272 | 5 | 5 | 5 |
| I-275 | 5 | 4 | 5 |
| I-277 | 5 | 5 | 5 |
| I-281 | 5 | 5 | 5 |
| I-283 | 4 | 5 | 5 |

TABLE 156-continued

| Compound No. | Echinochloa crus-galli (L.) P. Beauv. var. crus-galli | Abutilon theophrasti medicus | Amaranthus viridis L. |
|---|---|---|---|
| I-364 | 5 | 5 | 5 |
| I-371 | 5 | 5 | 5 |
| I-372 | 4 | 5 | 5 |
| I-373 | 5 | 5 | 5 |
| I-380 | 4 | 5 | 5 |
| II-1 | 5 | 5 | 5 |
| II-4 | 4 | 5 | 5 |
| II-5 | 5 | 5 | 5 |
| II-6 | 5 | 5 | 5 |
| II-7 | 5 | 5 | 5 |
| II-8 | 5 | 5 | 5 |
| II-9 | 5 | 5 | 5 |
| II-11 | 5 | 5 | 5 |
| II-13 | 5 | 5 | 5 |

TABLE 157

| Compound No. | Echinochloa crus-galli (L.) P. Beauv. var. crus-galli | Abutilon theophrasti medicus | Amaranthus viridis L. |
|---|---|---|---|
| II-14 | 5 | 4 | 5 |
| II-15 | 5 | 5 | 5 |
| II-20 | 5 | 5 | 5 |
| II-21 | 5 | 5 | 5 |
| II-23 | 5 | 5 | 5 |
| II-24 | 5 | 4 | 5 |
| II-33 | 5 | 5 | 5 |
| II-39 | 5 | 5 | 5 |
| II-44 | 5 | 5 | 5 |
| II-51 | 4 | 5 | 5 |
| II-52 | 5 | 5 | 5 |
| II-57 | 5 | 5 | 5 |
| II-62 | 4 | 5 | 5 |
| II-63 | 5 | 4 | 5 |
| II-64 | 5 | 5 | 5 |
| II-68 | 5 | 5 | 5 |
| II-69 | 5 | 5 | 5 |
| II-71 | 4 | 5 | 5 |
| II-74 | 3 | 4 | 4 |
| II-75 | 5 | 4 | 5 |
| II-84 | 4 | 4 | 5 |
| II-90 | 5 | 5 | 5 |
| II-95 | 5 | 5 | 5 |
| II-101 | 5 | 5 | 5 |
| II-116 | 4 | 4 | 5 |
| II-121 | 4 | 4 | 4 |
| II-122 | 5 | 4 | 5 |
| II-124 | 5 | 4 | 5 |
| II-125 | 5 | 5 | 5 |
| II-129 | 5 | 5 | 5 |
| II-130 | 5 | 5 | 5 |
| II-131 | 5 | 5 | 5 |
| II-136 | 5 | 5 | 5 |
| II-137 | 5 | 5 | 5 |
| II-149 | 5 | 5 | 5 |
| II-167 | 5 | 5 | 5 |
| II-168 | 4 | 5 | 5 |
| II-173 | 4 | 5 | 5 |
| II-178 | 5 | 5 | 5 |
| II-185 | 4 | 5 | 5 |
| II-188 | 4 | 5 | 5 |
| II-189 | 5 | 5 | 5 |
| II-190 | 4 | 5 | 5 |
| II-196 | 5 | 5 | 5 |
| II-197 | 5 | 4 | 5 |
| II-208 | 4 | 5 | 5 |
| II-210 | 4 | 5 | 5 |
| II-211 | 5 | 5 | 5 |

TABLE 158

| Compound No. | Echinochloa crus-galli (L.) P. Beauv. var. crus-galli | Abutilon theophrasti medicus | Amaranthus viridis L. |
| --- | --- | --- | --- |
| II-212 | 5 | 5 | 5 |
| II-213 | 4 | 5 | 5 |
| II-214 | 5 | 5 | 5 |
| II-215 | 5 | 5 | 5 |
| II-217 | 4 | 5 | 5 |
| II-218 | 4 | 5 | 5 |
| II-219 | 5 | 5 | 5 |
| II-220 | 5 | 5 | 5 |
| II-221 | 5 | 5 | 5 |
| II-222 | 5 | 5 | 5 |
| II-223 | 5 | 5 | 5 |
| II-224 | 5 | 5 | 5 |
| II-225 | 5 | 5 | 5 |
| II-226 | 5 | 5 | 5 |
| II-227 | 5 | 4 | 5 |
| II-228 | 5 | 5 | 5 |
| II-231 | 5 | 5 | 5 |
| II-233 | 5 | 5 | 5 |
| II-234 | 4 | 5 | 5 |
| II-237 | 5 | 5 | 5 |
| II-238 | 5 | 5 | 5 |
| II-239 | 4 | 5 | 5 |
| II-241 | 5 | 5 | 5 |
| II-242 | 5 | 4 | 5 |
| II-243 | 5 | 5 | 5 |
| II-244 | 5 | 5 | 5 |
| II-249 | 5 | 5 | 5 |
| II-252 | 5 | 5 | 5 |
| II-254 | 5 | 4 | 5 |
| II-255 | 5 | 4 | 5 |
| II-256 | 5 | 4 | 5 |
| II-257 | 5 | 4 | 5 |
| II-260 | 5 | 5 | 5 |
| II-261 | 5 | 5 | 5 |
| II-263 | 5 | 4 | 5 |
| II-303 | 5 | 5 | 5 |
| II-304 | 4 | 5 | 5 |
| II-305 | 5 | 5 | 5 |
| III-2 | 5 | 5 | 5 |
| III-5 | 5 | 5 | 5 |
| III-7 | 4 | 5 | 5 |
| III-12 | 4 | 5 | 5 |
| III-13 | 4 | 5 | 5 |
| III-15 | 5 | 5 | 5 |
| III-30 | 4 | 5 | 5 |
| III-35 | 4 | 5 | 5 |
| III-40 | 4 | 5 | 5 |
| III-45 | 5 | 5 | 5 |
| III-59 | 5 | 5 | 5 |
| III-88 | 5 | 5 | 5 |

TABLE 159

| Compound No. | Echinochloa crus-galli (L.) P. Beauv. var. crus-galli | Abutilon theophrasti medicus | Amaranthus viridis L. |
| --- | --- | --- | --- |
| III-90 | 5 | 5 | 5 |
| III-96 | 5 | 5 | 5 |
| III-99 | 4 | 5 | 5 |
| III-107 | 4 | 5 | 5 |
| III-108 | 5 | 5 | 5 |
| III-111 | 5 | 5 | 5 |
| III-117 | 5 | 5 | 5 |
| III-118 | 5 | 5 | 5 |
| III-120 | 5 | 5 | 5 |
| III-130 | 5 | 5 | 5 |
| III-139 | 4 | 5 | 5 |
| III-158 | 5 | 5 | 5 |
| III-173 | 5 | 5 | 5 |
| III-189 | 5 | 5 | 5 |
| III-201 | 5 | 5 | 5 |
| III-202 | 5 | 5 | 5 |
| III-207 | 5 | 5 | 5 |
| III-209 | 5 | 5 | 5 |
| III-212 | 5 | 5 | 5 |
| III-213 | 4 | 5 | 5 |
| III-221 | 4 | 5 | 5 |
| III-229 | 5 | 5 | 5 |
| III-230 | 5 | 5 | 5 |
| III-231 | 5 | 5 | 5 |
| III-232 | 5 | 5 | 5 |
| III-234 | 5 | 5 | 5 |
| III-235 | 5 | 5 | 5 |
| III-236 | 4 | 5 | 5 |
| III-237 | 5 | 5 | 5 |
| III-238 | 5 | 5 | 5 |
| III-239 | 4 | 5 | 5 |
| III-240 | 4 | 5 | 5 |
| III-241 | 4 | 5 | 5 |
| III-242 | 5 | 5 | 5 |
| III-243 | 5 | 5 | 5 |
| III-246 | 5 | 5 | 5 |
| III-247 | 5 | 5 | 5 |
| IV-1 | 5 | 5 | 5 |
| IV-2 | 5 | 5 | 5 |
| IV-3 | 5 | 5 | 5 |
| IV-4 | 5 | 5 | 5 |
| IV-6 | 4 | 5 | 5 |
| IV-7 | 5 | 5 | 5 |
| IV-8 | 5 | 5 | 5 |
| IV-9 | 5 | 5 | 5 |
| IV-11 | 5 | 5 | 5 |
| IV-13 | 5 | 5 | 5 |

TABLE 160

| Compound No. | Echinochloa crus-galli (L.) P. Beauv. var. crus-galli | Abutilon theophrasti medicus | Amaranthus viridis L. |
| --- | --- | --- | --- |
| IV-17 | 5 | 5 | 5 |
| IV-18 | 5 | 5 | 5 |
| IV-19 | 5 | 5 | 5 |
| IV-20 | 5 | 5 | 5 |
| IV-21 | 5 | 5 | 5 |
| IV-23 | 5 | 4 | 5 |
| IV-24 | 5 | 4 | 5 |
| IV-30 | 5 | 4 | 5 |
| IV-33 | 5 | 5 | 5 |
| IV-34 | 5 | 5 | 5 |
| IV-39 | 5 | 5 | 5 |
| IV-40 | 5 | 5 | 5 |
| IV-41 | 5 | 5 | 5 |
| IV-44 | 5 | 5 | 5 |
| IV-52 | 5 | 5 | 5 |
| IV-57 | 4 | 5 | 5 |
| IV-62 | 5 | 5 | 5 |
| IV-85 | 5 | 5 | 5 |
| IV-90 | 5 | 5 | 5 |
| IV-95 | 5 | 5 | 5 |
| IV-100 | 5 | 5 | 5 |
| IV-101 | 5 | 5 | 5 |
| IV-106 | 5 | 5 | 5 |
| IV-128 | 5 | 5 | 5 |
| IV-136 | 5 | 5 | 5 |
| IV-150 | 5 | 5 | 5 |
| IV-151 | 5 | 5 | 5 |
| IV-152 | 5 | 5 | 5 |
| IV-153 | 4 | 5 | 5 |
| IV-154 | 5 | 5 | 5 |
| IV-155 | 5 | 5 | 5 |
| IV-156 | 5 | 5 | 5 |
| IV-157 | 4 | 5 | 5 |

TABLE 160-continued

| Compound No. | Echinochloa crus-galli (L.) P. Beauv. var. crus-galli | Abutilon theophrasti medicus | Amaranthus viridis L. |
|---|---|---|---|
| IV-158 | 5 | 5 | 5 |
| IV-160 | 5 | 5 | 5 |
| IV-161 | 5 | 5 | 5 |
| IV-165 | 5 | 5 | 5 |
| IV-166 | 5 | 5 | 5 |
| IV-168 | 5 | 5 | 5 |
| IV-169 | 5 | 5 | 5 |
| IV-173 | 5 | 5 | 5 |
| IV-174 | 4 | 5 | 5 |
| IV-177 | 4 | 5 | 5 |
| IV-178 | 5 | 5 | 5 |
| IV-179 | 5 | 4 | 5 |
| IV-180 | 5 | 5 | 5 |
| IV-184 | 5 | 5 | 5 |

TABLE 161

| Compound No. | Echinochloa crus-galli (L.) P. Beauv. var. crus-galli | Abutilon theophrasti medicus | Amaranthus viridis L. |
|---|---|---|---|
| IV-185 | 5 | 4 | 5 |
| IV-186 | 5 | 5 | 5 |
| IV-187 | 5 | 5 | 5 |
| IV-188 | 5 | 5 | 5 |
| IV-189 | 5 | 5 | 5 |
| IV-200 | 5 | 5 | 5 |
| IV-201 | 5 | 5 | 5 |
| IV-202 | 5 | 5 | 5 |
| IV-203 | 5 | 5 | 5 |
| IV-206 | 5 | 5 | 5 |
| IV-208 | 5 | 4 | 5 |
| IV-209 | 5 | 5 | 5 |
| IV-210 | 5 | 5 | 5 |
| IV-212 | 5 | 5 | 5 |
| IV-213 | 5 | 5 | 5 |
| IV-214 | 5 | 5 | 5 |
| IV-215 | 5 | 5 | 5 |
| IV-216 | 5 | 5 | 5 |
| IV-217 | 5 | 5 | 5 |
| IV-218 | 5 | 5 | 5 |
| IV-219 | 5 | 5 | 5 |
| IV-220 | 5 | 5 | 5 |
| IV-221 | 5 | 5 | 5 |
| IV-222 | 5 | 5 | 5 |
| IV-223 | 5 | 5 | 5 |
| IV-224 | 5 | 5 | 5 |
| IV-225 | 5 | 5 | 5 |
| IV-226 | 5 | 5 | 5 |
| IV-227 | 5 | 5 | 5 |
| IV-228 | 5 | 5 | 5 |
| IV-229 | 5 | 5 | 5 |
| IV-230 | 5 | 5 | 5 |
| IV-231 | 5 | 5 | 5 |
| IV-232 | 5 | 5 | 5 |
| IV-233 | 5 | 5 | 5 |
| IV-234 | 5 | 5 | 5 |
| IV-235 | 5 | 5 | 5 |
| IV-236 | 5 | 5 | 5 |
| IV-237 | 5 | 5 | 5 |
| IV-238 | 5 | 5 | 5 |
| IV-239 | 5 | 5 | 5 |
| IV-240 | 5 | 5 | 5 |
| IV-241 | 5 | 4 | 5 |
| IV-242 | 5 | 5 | 5 |
| IV-243 | 5 | 5 | 5 |
| IV-244 | 5 | 5 | 5 |
| IV-245 | 5 | 5 | 5 |
| IV-247 | 5 | 5 | 5 |
| IV-248 | 5 | 5 | 5 |

TABLE 162

| Compound No. | Echinochloa crus-galli (L.) P. Beauv. var. crus-galli | Abutilon theophrasti medicus | Amaranthus viridis L. |
|---|---|---|---|
| IV-251 | 5 | 4 | 5 |
| IV-252 | 5 | 5 | 5 |
| IV-253 | 5 | 5 | 5 |
| IV-254 | 5 | 5 | 5 |
| IV-255 | 5 | 5 | 5 |
| IV-256 | 5 | 5 | 5 |
| IV-257 | 4 | 5 | 5 |
| IV-258 | 5 | 5 | 5 |
| IV-259 | 5 | 5 | 5 |
| IV-260 | 4 | 5 | 5 |
| IV-262 | 4 | 5 | 5 |
| IV-266 | 5 | 5 | 5 |
| IV-267 | 4 | 5 | 5 |
| IV-268 | 5 | 5 | 5 |
| IV-269 | 5 | 5 | 5 |
| IV-271 | 5 | 5 | 5 |
| Comparative Compound A | 0 | 2 | 1 |
| Comparative Compound B | 0 | 5 | 1 |
| Comparative Compound C | 0 | 4 | 0 |
| Comparative Compound D | 0 | 4 | 1 |

Additionally, comparative compound A, comparative compound B, comparative compound C and comparative compound D in the tables are Compound Nos. 70, 34, 32 and 31 described in EP-283261, respectively.

From the above results, it has been demonstrated that the compound of the present invention has an excellent herbicidal activity.

INDUSTRIAL APPLICABILITY

The present invention is to provide a novel compound having an excellent herbicidal activity, and thus the invention is useful in the fields of agrochemical and agriculture, and has industrial applicability.

The invention claimed is:

1. A compound represented by formula [I], or an agrochemically acceptable salt thereof:

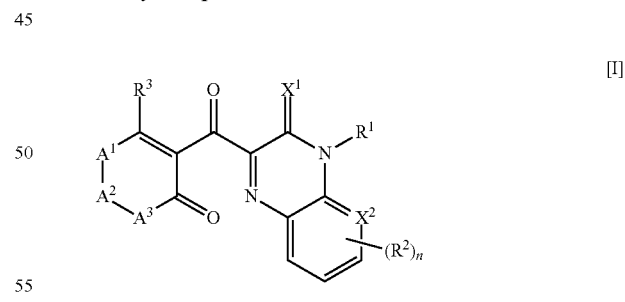

[I]

wherein $X^1$ represents an oxygen atom or a sulfur atom;
$X^2$ represents $N(O)_m$;
m represents 0 or 1;
$R^1$ represents a hydrogen atom; a $C_1$-$C_{12}$ alkyl group; a $C_2$-$C_6$ alkenyl group; a $C_2$-$C_6$ alkynyl group; a $C_3$-$C_8$ cycloalkyl group; a $C_3$-$C_8$ cycloalkyl-$C_1$-$C_6$ alkyl group; a $C_1$-$C_6$ haloalkyl group; a $C_2$-$C_6$ haloalkenyl group; a $C_2$-$C_6$ haloalkynyl group; a $C_3$-$C_8$ halocycloalkyl group; a $C_3$-$C_8$ halocycloalkyl-$C_1$-$C_6$ alkyl group; an amino-$C_1$-$C_6$ alkyl group; a nitro-$C_1$-$C_6$ alkyl group; a mono($C_1$-$C_6$ alkyl)amino-$C_1$-$C_6$ alkyl group; a di($C_1$-$C_6$ alkyl)amino-$C_1$-$C_6$ alkyl group; a $C_1$-$C_6$ alkylthio-$C_1$-$C_6$ alkyl group; a $C_1$-$C_6$ alkylsulfinyl-$C_1$-$C_6$ alkyl group; a $C_1$-$C_6$ alkylsulfonyl-$C_1$-$C_6$ alkyl group; a $C_1$-$C_6$ haloalkylthio-$C_1$-$C_6$ alkyl group; a $C_1$-$C_6$ haloalkylsulfinyl-$C_1$-$C_6$ alkyl group; a $C_1$-$C_6$ haloalkylsulfonyl-$C_1$-$C_6$ alkyl group; a $C_1$-$C_6$ alkoxy-$C_1$-$C_6$ alkyl group; a hydroxy-$C_1$-$C_6$ alkyl group; a phenyl-$C_1$-$C_6$ alkoxy-$C_1$-$C_6$ alkyl group (the phenyl moiety of the group may be substituted with one or two or more identical or different $R^4$s); a $C_1$-$C_6$ alkoxy-$C_1$-$C_6$ alkoxy-$C_1$-$C_6$ alkyl group; a $C_3$-$C_8$ cycloalkyloxy-$C_1$-$C_6$ alkyl group; a $C_3$-$C_8$ cycloalkyl-$C_1$-$C_6$ alkoxy-$C_1$-$C_6$ alkyl group; a phenyloxy-$C_1$-$C_6$ alkyl group (the phenyl moiety of the group may be substituted with one or two or more identical or different $R^4$s); a heterocyclic-oxy-$C_1$-$C_6$ alkyl group in which the heterocyclic moiety has 2 to 10 carbon atoms and 1 to 5 heteroatoms selected from an oxygen atom, a sulfur atom and a nitrogen atom (the heterocyclic moiety having 2 to 10 carbon atoms and having 1 to 5 heteroatoms selected from an oxygen atom, a sulfur atom and a nitrogen atom in the group, may be substituted with one or two or more identical or different $R^5$s); a phenylthio-$C_1$-$C_6$ alkyl group (the phenyl moiety of the group may be substituted with one or two or more identical or different $R^4$s); a phenylsulfinyl-$C_1$-$C_6$ alkyl group (a phenyl of the group may be substituted with one or two or more identical or different $R^4$s), a phenylsulfonyl-$C_1$-$C_6$ alkyl group (a phenyl of the group may be substituted with one or two or more identical or different $R^4$s); a $C_1$-$C_6$ haloalkoxy-$C_1$-$C_6$ alkyl group; a heterocyclic-$C_1$-$C_6$ alkoxy-$C_1$-$C_6$ alkyl group in which the heterocyclic moiety has 2 to 10 carbon atoms and 1 to 5 heteroatoms selected from an oxygen atom, a sulfur atom and a nitrogen atom (the heterocyclic moiety having 2 to 10 carbon atoms and having 1 to 5 heteroatoms selected from an oxygen atom, a sulfur atom and a nitrogen atom in the group, may be substituted with one or two or more identical or different $R^5$s); a $C_1$-$C_6$ alkylthio-$C_1$-$C_6$ alkoxy-$C_1$-$C_6$ alkyl group; a $C_1$-$C_6$ alkylsulfinyl-$C_1$-$C_6$ alkoxy-$C_1$-$C_6$ alkyl group; a $C_1$-$C_6$ alkylsulfonyl-$C_1$-$C_6$ alkoxy-$C_1$-$C_6$ alkyl group; a cyano-$C_1$-$C_6$ alkoxy-$C_1$-$C_6$ alkyl group; a cyano-$C_1$-$C_6$ alkyl group; a $C_1$-$C_6$ alkylcarbonyloxy-$C_1$-$C_6$ alkyl group; a $C_1$-$C_6$ acyl-$C_1$-$C_6$ alkyl group; a di($C_1$-$C_6$ alkoxy)-$C_1$-$C_6$ alkyl group; a $C_1$-$C_6$ alkoxycarbonyl-$C_1$-$C_6$ alkyl group; a $C_1$-$C_6$ alkoxyimino-$C_1$-$C_6$ alkyl group; a $C_1$-$C_6$ alkylideneaminooxy-$C_1$-$C_6$ alkyl group; a ($R^6R^7N$—C=O)—$C_1$-$C_6$ alkyl group; a $C_6$-$C_{10}$ aryl-$C_1$-$C_6$ alkyl group (the aryl moiety of the group may be substituted with one or two or more identical or different $R^8$s); a heterocyclic-$C_1$-$C_6$ alkyl group in which the heterocyclic moiety has 2 to 10 carbon atoms and 1 to 5 heteroatoms selected from an oxygen atom, a sulfur atom and a nitrogen atom (the heterocyclic moiety having 2 to 10 carbon atoms and 1 to 5 heteroatoms selected from an oxygen atom, a sulfur atom and a nitrogen atom in the group, may be substituted with one or two or more identical or different $R^9$s); an $NR^{10}R^{11}$ group; a $C_1$-$C_6$ alkoxy group; a $C_6$-$C_{10}$ aryl group (the group may be substituted with one or two or more identical or different $R^{12}$s); or a heterocyclic group having 2 to 10 carbon atoms and 1 to 5 heteroatoms selected from an oxygen atom, a sulfur atom and a nitrogen atom (the group may be substituted with one or two or more identical or different $R^{13}$s);

$R^2$ represents a halogen atom; a hydroxy group; a nitro group; a cyano group; a $C_1$-$C_6$ alkyl group; a $C_3$-$C_8$ cycloalkyl group; a $C_3$-$C_8$ cycloalkyl-$C_1$-$C_6$ alkyl group; a $C_2$-$C_6$ alkenyl group; a $C_2$-$C_6$ alkynyl group; a $C_1$-$C_6$ haloalkyl group; a $C_1$-$C_6$ haloalkenyl group; a $C_1$-$C_6$ haloalkynyl group; a $C_3$-$C_8$ halocycloalkyl group; a $C_3$-$C_8$ halocycloalkyl-$C_1$-$C_6$ alkyl group; a $C_1$-$C_6$ alkoxy group; a $C_3$-$C_8$ cycloalkyloxy group; a $C_3$-$C_8$ cycloalkyl-$C_1$-$C_6$ alkyloxy group; a $C_2$-$C_6$ alkenyloxy group; a $C_2$-$C_6$ alkynyloxy group; a $C_1$-$C_6$ haloalkoxy group; a $C_1$-$C_6$ alkoxy-$C_1$-$C_6$ alkoxy group; a $C_1$-$C_6$ alkylcarbonyloxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; an amino group; a mono($C_1$-$C_6$ alkyl)amino group; a di($C_1$-$C_6$ alkyl)amino group; a $C_1$-$C_6$ acylamino group; a hydroxy-$C_1$-$C_6$ alkyl group; a $C_1$-$C_6$ alkoxy-$C_1$-$C_6$ alkyl group; a $C_1$-$C_6$ alkylthio-$C_1$-$C_6$ alkyl group; a $C_1$-$C_6$ alkylsulfinyl-$C_1$-$C_6$ alkyl group; a $C_1$-$C_6$ alkylsulfonyl-$C_1$-$C_6$ alkyl group; a $C_1$-$C_6$ haloalkylthio-$C_1$-$C_6$ alkyl group; a $C_1$-$C_6$ haloalkylsulfinyl-$C_1$-$C_6$ alkyl group; a $C_1$-$C_6$ haloalkylsulfonyl-$C_1$-$C_6$ alkyl group; a cyano-$C_1$-$C_6$ alkyl group; a $C_1$-$C_6$ acyl group; a $C_1$-$C_6$ alkoxyimino-$C_1$-$C_6$ alkyl group; a carboxyl group; a $C_1$-$C_6$ alkoxycarbonyl group; a carbamoyl group; a mono($C_1$-$C_6$ alkyl)aminocarbonyl group; a di($C_1$-$C_6$ alkyl)aminocarbonyl group; or a heterocyclic group having 2 to 10 carbon atoms and 1 to 5 heteroatoms selected from an oxygen atom, a sulfur atom and a nitrogen atom (the heterocyclic moiety having 2 to 10 carbon atoms and 1 to 5 heteroatoms selected from an oxygen atom, a sulfur atom and a nitrogen atom in the group, may be substituted with one or two or more identical or different $R^{14}$s);

n represents 0, 1, 2, or 3;

$R^3$ represents a hydroxy group; $O^-M^+$ (wherein $M^+$ is an alkali metal cation or an ammonium cation); an amino group; a halogen atom; a $C_1$-$C_6$ alkylsulfonyloxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; a $C_2$-$C_6$ alkenylthio group; a $C_2$-$C_6$ alkenylsulfinyl group; a $C_2$-$C_6$ alkenylsulfonyl group; a $C_2$-$C_6$ alkynylthio group; a $C_2$-$C_6$ alkynylsulfinyl group; a $C_2$-$C_6$ alkynylsulfonyl group; a $C_1$-$C_6$ alkylcarbonyloxy group; a $C_2$-$C_6$ alkenylcarbonyloxy group; a $C_2$-$C_6$ alkynylcarbonyloxy group; a phenoxy group (the group may be substituted with one or two or more identical or different $R^{14}$s); a phenylthio group (the group may be substituted with one or two or more identical or different $R^{14}$s); a phenylsulfinyl group (the group may be substituted with one or two or more identical or different $R^{14}$s); a phenylsulfonyl group (the group may be substituted with one or two or more identical or different $R^{14}$s); a phenylsulfonyloxy group (the group may be substituted with one or two or more identical or different $R^{14}$s); a phenylcarbonyloxy group (the group may be substituted with one or two or more identical or different $R^{14}$s); a 1,2,4-triazol-1-yl group; a 1,2,3-triazol-1-yl group; a 1,2,3-triazol-2-yl group; an imidazol-1-yl group; a pyrazol-1-yl group; a tetrazol-1-yl group; or a tetrazol-2-yl group;

$R^4$ represents a halogen atom; a nitro group; a cyano group; a $C_1$-$C_6$ alkyl group; a $C_2$-$C_6$ alkenyl group; a $C_2$-$C_6$ alkynyl group; a $C_3$-$C_8$ cycloalkyl group; a $C_1$-$C_6$ haloalkyl group; a $C_1$-$C_6$ alkoxy group; a $C_2$-$C_6$ alkenyloxy group; a $C_2$-$C_6$ alkynyloxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; a $C_1$-$C_6$ alkoxycarbonyl group; a $C_1$-$C_6$ acyl group; or a $C_1$-$C_6$ alkoxy-$C_1$-$C_6$ alkyl group;

$R^5$ represents an oxo group; a halogen atom; a nitro group; a cyano group; a $C_1$-$C_6$ alkyl group; a $C_2$-$C_6$ alkenyl group; a $C_2$-$C_6$ alkynyl group; a $C_3$-$C_8$ cycloalkyl group; a $C_1$-$C_6$ haloalkyl group; a $C_1$-$C_6$ alkoxy group; a $C_2$-$C_6$ alkenyloxy group; a $C_2$-$C_6$ alkynyloxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; a $C_1$-$C_6$ alkoxycarbonyl group; a $C_1$-$C_6$ acyl group; or a $C_1$-$C_6$ alkoxy-$C_1$-$C_6$ alkyl group;

$R^6$ and $R^7$ each independently represent a $C_1$-$C_6$ alkyl group, or $R^6$ and $R^7$ may be joined with the nitrogen atom to which these are bound, to form a 5- to 6-membered ring, while the ring thus formed may have an oxygen atom interposed, in addition to the nitrogen atom to which $R^6$ and $R^7$ are bound;

$R^8$ represents a halogen atom; a nitro group; a cyano group; a $C_1$-$C_6$ alkyl group; a $C_2$-$C_6$ alkenyl group; a $C_2$-$C_6$ alkynyl group; a $C_3$-$C_8$ cycloalkyl group; a $C_1$-$C_6$ haloalkyl group; a $C_1$-$C_6$ alkoxy group; a $C_2$-$C_6$ alkenyloxy group; a $C_2$-$C_6$ alkynyloxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; a $C_1$-$C_6$ alkoxycarbonyl group; a $C_1$-$C_6$ acyl group; or a $C_1$-$C_6$ alkoxy-$C_1$-$C_6$ alkyl group;

$R^9$ represents an oxo group; a halogen atom; a nitro group; a cyano group; a $C_1$-$C_6$ alkyl group; a $C_2$-$C_6$ alkenyl group; a $C_2$-$C_6$ alkynyl group; a $C_3$-$C_8$ cycloalkyl group; a $C_1$-$C_6$ haloalkyl group; a $C_1$-$C_6$ alkoxy group; a $C_2$-$C_6$ alkenyloxy group; a $C_2$-$C_6$ alkynyloxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; a $C_1$-$C_6$ alkoxycarbonyl group; a $C_1$-$C_6$ acyl group; or a $C_1$-$C_6$ alkoxy-$C_1$-$C_6$ alkyl group;

$R^{10}$ and $R^{11}$ each independently represent a hydrogen atom; a $C_1$-$C_6$ alkyl group; or a $C_1$-$C_6$ alkoxycarbonyl group, and furthermore, $R^{10}$ and $R^{11}$ may be joined together with the nitrogen atom to which these are bound, to form a 5- to 6-membered ring, while the ring thus formed may have a sulfur atom and/or an oxygen atom interposed, in addition to the nitrogen atom to which $R^{10}$ and $R^{11}$ are bound;

$R^{12}$ represents a halogen atom; a hydroxy group; a nitro group; a cyano group; a $C_1$-$C_6$ alkyl group; a $C_3$-$C_8$ cycloalkyl group; a $C_3$-$C_8$ cycloalkyl-$C_1$-$C_6$ alkyl group; a $C_2$-$C_6$ alkenyl group; a $C_2$-$C_6$ alkynyl group; a $C_1$-$C_6$ haloalkyl group; a $C_2$-$C_6$ haloalkenyl group; a $C_3$-$C_8$ halocycloalkyl group; a $C_3$-$C_8$ halocycloalkyl-$C_1$-$C_6$ alkyl group; a $C_1$-$C_6$ alkoxy group; a $C_3$-$C_8$ cycloalkyloxy group; a $C_2$-$C_6$ alkenyloxy group; a $C_2$-$C_6$ alkynyloxy group; a $C_1$-$C_6$ alkylcarbonyloxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; an amino group; a $C_1$-$C_6$ acylamino group; a mono($C_1$-$C_6$ alkyl)amino group; a di($C_1$-$C_6$ alkyl)amino group; a hydroxy-$C_1$-$C_6$ alkyl group; a $C_1$-$C_6$ alkoxy-$C_1$-$C_6$ alkyl group; a $C_1$-$C_6$ alkylthio-$C_1$-$C_6$ alkyl group; a $C_1$-$C_6$ alkylsulfinyl-$C_1$-$C_6$ alkyl group; a $C_1$-$C_6$ alkylsulfonyl-$C_1$-$C_6$ alkyl group; a $C_1$-$C_6$ haloalkylthio-$C_1$-$C_6$ alkyl group; a $C_1$-$C_6$ haloalkylsulfinyl-$C_1$-$C_6$ alkyl group; a $C_1$-$C_6$ haloalkylsulfonyl-$C_1$-$C_6$ alkyl group; a cyano-$C_1$-$C_6$ alkyl group; a $C_1$-$C_6$ alkoxy-$C_1$-$C_6$ alkoxy group; a $C_3$-$C_8$ cycloalkyl-$C_1$-$C_6$ alkyloxy group; a $C_1$-$C_6$ haloalkoxy-$C_1$-$C_6$ alkoxy group; a cyano-$C_1$-$C_6$ alkoxy group; a $C_1$-$C_6$ acyl group; a $C_1$-$C_6$ alkoxyimino-$C_1$-$C_6$ alkyl group; a carboxyl group; a $C_1$-$C_6$ alkoxycarbonyl group; a carbamoyl group; a mono($C_1$-$C_6$ alkyl)aminocarbonyl group; a di($C_1$-$C_6$ alkyl)aminocarbonyl group; a heterocyclic group having 2 to 10 carbon atoms and 1 to 5 heteroatoms selected from an oxygen atom, a sulfur atom and a nitrogen atom (the heterocyclic moiety of the group may be substituted with one or two or more identical or different $R^{14}$s); or a heterocyclic-$C_1$-$C_6$ alkoxy group in which the heterocyclic moiety has 2 to 10 carbon atoms and 1 to 5 heteroatoms selected from an oxygen atom, a sulfur atom and a nitrogen atom (the heterocyclic moiety having 2 to 10 carbon atoms and having 1 to 5 heteroatoms selected from an oxygen atom, a sulfur atom and a nitrogen atom in the group, may be substituted with one or two or more identical or different $R^{14}$s), or two adjacent $R^{12}$s may be joined with the respective carbon atoms to which $R^{12}$s are directly bound, to form a 4- to 8-membered carbocyclic ring or a 4- to 8-membered heterocyclic ring having 1 to 4 heteroatoms selected from an oxygen atom, a sulfur atom and a nitrogen atom, while the ring thus formed may be substituted with a halogen atom, a cyano group, a nitro group, a $C_1$-$C_6$ alkyl group, a $C_1$-$C_6$ haloalkyl group, a $C_1$-$C_6$ alkoxy group, a $C_1$-$C_6$ haloalkoxy group or an oxo group;

$R^{13}$ represents an oxo group; a thioxo group; a hydroxy group; a halogen atom; a nitro group; a cyano group; a $C_1$-$C_6$ alkyl group; a $C_2$-$C_6$ alkenyl group; a $C_2$-$C_6$ alkynyl group; a $C_3$-$C_8$ cycloalkyl group; a $C_3$-$C_8$ cycloalkyl-$C_1$-$C_6$ alkyl group; a $C_1$-$C_6$ haloalkyl group; a $C_2$-$C_6$ haloalkenyl group; a $C_3$-$C_8$ halocycloalkyl group; a $C_3$-$C_8$ halocycloalkyl-$C_1$-$C_6$ alkyl group; a $C_1$-$C_6$ alkoxy group; a $C_2$-$C_6$ alkenyloxy group; a $C_2$-$C_6$ alkynyloxy group; a $C_3$-$C_8$ cycloalkyloxy group; a $C_3$-$C_8$ cycloalkyl-$C_1$-$C_6$ alkyloxy group; a $C_1$-$C_6$ haloalkoxy group; a $C_1$-$C_6$ alkoxy-$C_1$-$C_6$ alkoxy group; a $C_1$-$C_6$ haloalkoxy-$C_1$-$C_6$ alkoxy group; a cyano-$C_1$-$C_6$ alkoxy group; a $C_1$-$C_6$ alkylcarbonyloxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; an amino group; a mono($C_1$-$C_6$ alkyl)amino group; a di($C_1$-$C_6$ alkyl)amino group; a $C_1$-$C_6$ acylamino group; a carboxyl group; a $C_1$-$C_6$ alkoxycarbonyl group; a carbamoyl group; a mono($C_1$-$C_6$ alkyl)aminocarbonyl group; a di($C_1$-$C_6$ alkyl)aminocarbonyl group; a $C_1$-$C_6$ acyl group; a $C_1$-$C_6$ alkoxyimino-$C_1$-$C_6$ alkyl group; a $C_1$-$C_6$ alkoxy-$C_1$-$C_6$ alkyl group; a $C_1$-$C_6$ alkylthio-$C_1$-$C_6$ alkyl group; a $C_1$-$C_6$ alkyl sulfinyl-$C_1$-$C_6$ alkyl group; a $C_1$-$C_6$ alkylsulfonyl-$C_1$-$C_6$ alkyl group; a $C_1$-$C_6$ haloalkylthio-$C_1$-$C_6$ alkyl group; a $C_1$-$C_6$ haloalkylsulfinyl-$C_1$-$C_6$ alkyl group; a $C_1$-$C_6$ haloalkylsulfonyl-$C_1$-$C_6$ alkyl group; or a cyano-$C_1$-$C_6$ alkyl group; and further, two adjacent $R^{13}$s may be joined with the respective carbon atoms to which $R^{13}$s are directly bound, to form a 4- to 8-membered carbocyclic ring or a 4- to 8-membered heterocyclic ring having 1 to 4 heteroatoms selected from an oxygen atom, a sulfur atom and a nitrogen atom, while the ring thus formed may be substituted with a halogen atom, a cyano group, a nitro group, a $C_1$-$C_6$ alkyl group, a $C_1$-$C_6$ haloalkyl group, a $C_1$-$C_6$ alkoxy group, a $C_1$-$C_6$ haloalkoxy group or an oxo group;

$R^{14}$ represents a halogen atom; a nitro group; a cyano group; a $C_1$-$C_6$ alkyl group; a $C_1$-$C_6$ haloalkyl group; a $C_1$-$C_6$ alkoxy group; or a $C_1$-$C_6$ haloalkoxy group;

$A^1$ represents $C(R^{15}R^{16})$;

$A^2$ represents $C(R^{17}R^{18})$, or $C=O$;

$A^3$ represents $C(R^{19}R^{20})$; and $R^{15}$, $R^{16}$, $R^{17}$, $R^{18}$, $R^{19}$ and $R^{20}$ each independently represent a hydrogen atom or a $C_1$-$C_6$ alkyl group, and $R^{15}$ and $R^{20}$ may be joined together to form a $C_2$-$C_5$ alkylene chain, and may constitute a ring together with adjacent carbon atoms.

2. The compound or the agrochemically acceptable salt thereof according to claim 1, wherein $R^3$ is a hydroxy group; or $O^-M^+$ (wherein $M^+$ is an alkali metal cation or an ammonium cation).

3. The compound or the agrochemically acceptable salt thereof according to claim 1, wherein:

$X^2$ is a nitrogen atom;

$R^1$ represents a hydrogen atom; a $C_1$-$C_{12}$ alkyl group; a $C_2$-$C_6$ alkenyl group; a $C_2$-$C_6$ alkynyl group; a $C_3$-$C_8$ cycloalkyl group; a $C_1$-$C_6$ haloalkyl group; a $C_2$-$C_6$ haloalkenyl group; a $C_1$-$C_6$ alkylthio-$C_1$-$C_6$ alkyl group; a $C_1$-$C_6$ alkylsulfonyl-$C_1$-$C_6$ alkyl group; a $C_1$-$C_6$ alkoxy-$C_1$-$C_6$ alkyl group; a $C_1$-$C_6$ alkoxy-$C_1$-$C_6$ alkoxy-$C_1$-$C_6$ alkyl group; a phenoxy-$C_1$-$C_6$ alkyl group; a $C_1$-$C_6$ haloalkoxy-$C_1$-$C_6$ alkyl group; a tetrahydrofuran-$C_1$-$C_6$ alkoxy-$C_1$-$C_6$ alkyl group; a $C_1$-$C_6$ alkylsulfonyl-$C_1$-$C_6$ alkoxy-$C_1$-$C_6$ alkyl group; a cyano-$C_1$-$C_6$ alkoxy-$C_1$-$C_6$ alkyl group; a cyano-$C_1$-$C_6$ alkyl group; a $C_1$-$C_6$ alkylcarbonyloxy-$C_1$-$C_6$ alkyl group; a $C_1$-$C_6$ acyl-$C_1$-$C_6$ alkyl group; a $C_1$-$C_6$ alkoxycarbonyl-$C_1$-$C_6$ alkyl group; a $(R^6R^7N-C=O)$-$C_1$-$C_6$ alkyl group; a $C_6$-$C_{10}$ aryl-$C_1$-$C_6$ alkyl group (the aryl moiety of the group may be substituted with one or two or more identical or different $R^8$s); a Het$^1$-$C_1$-$C_6$ alkyl group (the group may be substituted with one or two or more identical or different $R^9$s); a $NR^{10}R^{11}$ group; a $C_6$-$C_{10}$ aryl group (the group may be substituted with one or two or more identical or different $R^{12}$s); or a Het$^1$ group (the group may be substituted with one or two or more identical or different $R^{13}$s);

Het$^1$ is tetrahydrofuran, tetrahydrothiophene, tetrahydrothiophene dioxide, tetrahydrothiopyrane, tetrahydrothiopyrane dioxide, 4,5-dihydroisoxazole, thiophene, pyrazole, oxazole, isoxazole, thiazole, isothiazole, 1,2,4-triazole, 1,2,4-oxadiazole, 1,3,4-thiadiazole, pyridine, pyridazine, pyrimidine, pyrazine, 2,3-dihydrobenzofuran, 1,3-benzodioxole, benzo-1,4-dioxane, benzofuran or indole;

$R^2$ is a halogen atom, a nitro group, a $C_1$-$C_6$ alkyl group, a $C_1$-$C_6$ haloalkyl group, a $C_1$-$C_6$ alkoxy group, a $C_1$-$C_6$ alkylthio group, a $C_1$-$C_6$ alkylsulfonyl group, or a $C_1$-$C_6$ alkoxy-$C_1$-$C_6$ alkyl group;

$R^3$ is a hydroxy group;

$R^8$ is a halogen atom, a $C_1$-$C_6$ haloalkyl group, a $C_1$-$C_6$ alkoxy group, or a $C_1$-$C_6$ haloalkoxy group;

$R^9$ is a $C_1$-$C_6$ alkyl group, a halogen atom, or a $C_1$-$C_6$ haloalkyl group;

$R^{10}$ and $R^{11}$ are each independently a $C_1$-$C_6$ alkyl group, or a $C_1$-$C_6$ alkoxycarbonyl group;

$R^{12}$ is a halogen atom, a hydroxy group, a nitro group, a cyano group, a $C_1$-$C_6$ alkyl group, a $C_3$-$C_8$ cycloalkyl group, a $C_1$-$C_6$ haloalkyl group, a $C_1$-$C_6$ alkoxy group, a $C_2$-$C_6$ alkenyloxy group, a $C_2$-$C_6$ alkynyloxy group, a $C_1$-$C_6$ haloalkoxy group, a $C_1$-$C_6$ alkylthio group, a $C_1$-$C_6$ alkylsulfonyl group, a $C_1$-$C_6$ haloalkylthio group, a $C_1$-$C_6$ alkoxy-$C_1$-$C_6$ alkyl group, a $C_3$-$C_8$ cycloalkyl-$C_1$-$C_6$ alkyloxy group, a cyano-$C_1$-$C_6$ alkoxy group, a $C_1$-$C_6$ acyl group, a $C_1$-$C_6$ alkoxycarbonyl group, a di($C_1$-$C_6$ alkyl)amino group, or a Het$^1$-$C_1$-$C_6$ alkoxy group, or two adjacent $R^{12}$s may be joined with the respective carbon atoms to which they are directly bound, to form a 4- to 8-membered carbocyclic ring or a 4- to 8-membered heterocyclic ring having 1 to 4 heteroatoms selected from an oxygen atom, a sulfur atom and a nitrogen atom, while the ring thus formed may be substituted with a halogen atom, a $C_1$-$C_6$ alkyl group or an oxo group; and $R^{13}$ is an oxo group, a halogen atom, a $C_1$-$C_6$ alkyl group, a $C_1$-$C_6$ haloalkyl group, a $C_1$-$C_6$ alkoxy group, or a mono($C_1$-$C_6$ alkyl)amino group.

4. The compound or the agrochemically acceptable salt thereof according to any one of claims 1, 2, and 3 wherein:

$X^1$ is an oxygen atom;

$X^2$ is a nitrogen atom;

$R^1$ is a hydrogen atom; a $C_1$-$C_{12}$ alkyl group; a $C_2$-$C_6$ alkenyl group; a $C_2$-$C_6$ alkynyl group; a $C_1$-$C_6$ haloalkyl group; a $C_2$-$C_6$ haloalkenyl group; a $C_1$-$C_6$ alkylthio-$C_1$-$C_6$ alkyl group; a $C_1$-$C_6$ alkoxy-$C_1$-$C_6$ alkyl group; a $C_1$-$C_6$ halo alkoxy-$C_1$-$C_6$ alkyl group; a $C_1$-$C_6$ alkoxycarbonyl-$C_1$-$C_6$ alkyl group; a $C_6$-$C_{10}$ aryl-$C_1$-$C_6$ alkyl group (the aryl moiety of the group may be substituted with one or two or more identical or different $R^8$s); a Het$^2$-$C_1$-$C_6$ alkyl group (the group may be substituted with one or two or more identical or different $R^9$s); a $C_6$-$C_{10}$ aryl group (the group may be substituted with one or two or more identical or different $R^{12}$s); or a Het$^2$ group (the group may be substituted with one or two or more identical or different $R^{13}$s);

Het$^2$ is 4,5-dihydroisoxazole, thiophene, pyrazole, isoxazole, pyridine, 2,3-dihydrobenzofuran, 1,3-benzodioxole or benzo-1,4-dioxane;

$R^2$ is a halogen atom, a $C_1$-$C_6$ alkyl group; $C_1$-$C_6$ alkylthio group; or a $C_1$-$C_6$ alkoxy group;

$R^3$ is a hydroxy group;

$R^8$ is a halogen atom, a $C_1$-$C_6$ haloalkyl group, a $C_1$-$C_6$ alkoxy group, or a $C_1$-$C_6$ haloalkoxy group;

$R^9$ is a $C_1$-$C_6$ alkyl group, a halogen atom or a $C_1$-$C_6$ haloalkyl group;

$R^{12}$ is a halogen atom, a cyano group, a $C_1$-$C_6$ alkyl group, a $C_3$-$C_8$ cycloalkyl group, a $C_1$-$C_6$ haloalkyl group, a $C_1$-$C_6$ alkoxy group, a $C_1$-$C_6$ haloalkoxy group or a $C_1$-$C_6$ haloalkylthio group, or two adjacent $R^{12}$s may be joined with the respective carbon atoms to which they are directly bound, to form a 4- to 8-membered carbocyclic ring or a 4- to 8-membered heterocyclic ring having 1 to 4 heteroatoms selected from an oxygen atom, a sulfur atom and a nitrogen atom, while the ring thus formed may be substituted with a halogen atom; and $R^{13}$ is a halogen atom, a $C_1$-$C_6$ alkyl group, a $C_1$-$C_6$ haloalkyl group, or a $C_1$-$C_6$ alkoxy group.

5. An agrochemical composition comprising the compound according to claim 1 or an agrochemically acceptable salt thereof, and an agrochemically acceptable carrier.

6. An agrochemical composition comprising the compound according to claim 2 or an agrochemically acceptable salt thereof, and an agrochemically acceptable carrier.

7. An agrochemical composition comprising the compound according to claim 3 or an agrochemically acceptable salt thereof, and an agrochemically acceptable carrier.

8. An agrochemical composition comprising the compound according to claim 4 or an agrochemically acceptable salt thereof, and an agrochemically acceptable carrier.

9. An agrochemical method for treating soil and/or plants comprising contacting said soil and/or said plant with an agrochemically effective amount of the agrochemical composition according to claim 3.

10. A compound represented by formula [J1]:

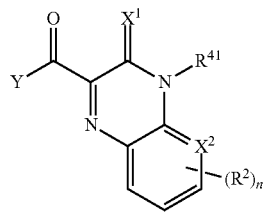

[J1]

wherein $X^1$ represents an oxygen atom or a sulfur atom;
$X^2$ represents a nitrogen atom;
$R^1$ represents a $C_1$-$C_{12}$ alkyl group; a $C_2$-$C_6$ alkenyl group; a $C_2$-$C_6$ alkynyl group; a $C_3$-$C_8$ cycloalkyl group; a $C_1$-$C_6$ haloalkyl group; a $C_2$-$C_6$ haloalkenyl group; a $C_1$-$C_6$ alkylthio-$C_1$-$C_6$ alkyl group; a $C_1$-$C_6$ alkylsulfonyl-$C_1$-$C_6$ alkyl group; a $C_1$-$C_6$ alkoxy-$C_1$-$C_6$ alkyl group; a $C_1$-$C_6$ alkoxy-$C_1$-$C_6$ alkoxy-$C_1$-$C_6$ alkyl group; a phenyloxy-$C_1$-$C_6$ alkyl group; a $C_1$-$C_6$ haloalkoxy-$C_1$-$C_6$ alkyl group; a tetrahydrofuran-$C_1$-$C_6$ alkoxy-$C_1$-$C_6$ alkyl group; a $C_1$-$C_6$ alkylsulfonyl-$C_1$-$C_6$ alkoxy-$C_1$-$C_6$ alkyl group; cyano-$C_1$-$C_6$ alkoxy-$C_1$-$C_6$ alkyl group; a cyano-$C_1$-$C_6$ alkyl group; a $C_1$-$C_6$ alkylcarbonyloxy-$C_1$-$C_6$ alkyl group; a $C_1$-$C_6$ acyl-$C_1$-$C_6$ alkyl group; a $C_1$-$C_6$ alkoxycarbonyl-$C_1$-$C_6$ alkyl group; a ($R^6R^7N$—C=O)—$C_1$-$C_6$ alkyl group; a $C_6$-$C_{10}$ aryl-$C_1$-$C_6$ alkyl group (the aryl moiety of the group may be substituted with one or two or more identical or different $R^8$s); a Het$^1$-$C_1$-$C_6$ alkyl group (the group may be substituted with one or two or more identical or different $R^9$s); a $NR^{10}R^{11}$ group; a $C_6$-$C_{10}$ aryl group (the group may be substituted with one or two or more identical or different $R^{12}$s); or a Het$^1$ group (the group may be substituted with one or two or more identical or different $R^{13}$s);
$R^2$ represents a halogen atom; a nitro group; a $C_1$-$C_6$ alkyl group; a $C_1$-$C_6$ haloalkyl group; a $C_1$-$C_6$ alkoxy group; a $C_1$-$C_6$ alkylthio group; a $C_1$-$C_6$ alkylsulfonyl group; or a $C_1$-$C_6$ alkoxy-$C_1$-$C_6$ alkyl group;
n represents 0, 1, 2, or 3;
$R^6$ and $R^7$ each independently represent a $C_1$-$C_6$ alkyl group, and furthermore, $R^6$ and $R^7$ may be joined with the nitrogen atom to which these are bound, to form a 5- to 6-membered ring, while the ring thus formed may have an oxygen atom interposed, in addition to the nitrogen atom to which $R^6$ and $R^7$ are bound;
$R^8$ represents a halogen atom; a $C_1$-$C_6$ haloalkyl group; a $C_1$-$C_6$ alkoxy group; or a $C_1$-$C_6$ haloalkoxy group;
$R^9$ represents a $C_1$-$C_6$ alkyl group; a halogen atom; or a $C_1$-$C_6$ haloalkyl group;

$R^{10}$ and $R^{11}$ each independently represent a $C_1$-$C_6$ alkyl group; or a $C_1$-$C_6$ alkoxycarbonyl group;
$R^{12}$ represents a halogen atom; a hydroxy group; a nitro group; a cyano group; a $C_1$-$C_6$ alkyl group; a $C_3$-$C_8$ cycloalkyl group; a $C_1$-$C_6$ haloalkyl group; a $C_1$-$C_6$ alkoxy group; a $C_2$-$C_6$ alkenyloxy group; a $C_2$-$C_6$ alkynyloxy group; a $C_1$-$C_6$ haloalkoxy group; a $C_1$-$C_6$ alkylthio group; a $C_1$-$C_6$ alkylsulfonyl group; a $C_1$-$C_6$ haloalkylthio group; a $C_1$-$C_6$ alkoxy-$C_1$-$C_6$ alkyl group; a $C_3$-$C_8$ cycloalkyl-$C_1$-$C_6$ alkyloxy group; a cyano-$C_1$-$C_6$ alkoxy group; a $C_1$-$C_6$ acyl group; a $C_1$-$C_6$ alkoxycarbonyl group; a di($C_1$-$C_6$ alkyl)amino group; or a Het$^1$-$C_1$-$C_6$ alkoxy group, and furthermore, two adjacent $R^{12}$s may be joined with the respective carbon atoms to which they are directly bound, to form a 4- to 8-membered carbocyclic ring or a 4- to 8-membered heterocyclic ring having 1 to 4 heteroatoms selected from an oxygen atom, a sulfur atom and a nitrogen atom, while the ring thus formed may be substituted with a halogen atom; a $C_1$-$C_6$ alkyl group; or an oxo group;
$R^{13}$ represents an oxo group; a halogen atom; a $C_1$-$C_6$ alkyl group; a $C_1$-$C_6$ haloalkyl group;
a $C_1$-$C_6$ alkoxy group; or a mono($C_1$-$C_6$ alkyl)amino group;
Y represents a halogen atom or a cyano group; and
Het$^1$ represents tetrahydrothiophene, tetrahydrothiophene dioxide, tetrahydrothiopyrane, tetrahydrothiopyrane dioxide, 4,5-dihydroisoxazole, thiophene, pyrazole, oxazole, isoxazole, thiazole, isothiazole, 1,2,4-triazole, 1,2,4-oxadiazole, 1,3,4-thiadiazole, pyridine, pyridazine, pyrimidine, pyrazine, 2,3-dihydrobenzofuran, 1,3-benzodioxole, benzo-1,4-dioxane, benzofuran or indole.

11. A compound represented by formula [J2]:

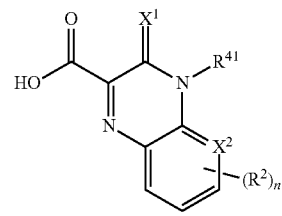

[J2]

wherein $X^1$ represents an oxygen atom or a sulfur atom;
$X^2$ represents a nitrogen atom;
$R^1$ represents a $C_2$-$C_6$ alkenyl group; a $C_2$-$C_6$ alkynyl group; a $C_3$-$C_8$ cycloalkyl group; a $C_1$-$C_6$ haloalkyl group; a $C_2$-$C_6$ haloalkenyl group; a $C_1$-$C_6$ alkylthio-$C_1$-$C_6$ alkyl group; a $C_1$-$C_6$ alkylsulfonyl-$C_1$-$C_6$ alkyl group; a $C_1$-$C_6$ alkoxy-$C_1$-$C_6$ alkyl group; a $C_1$-$C_6$ alkoxy-$C_1$-$C_6$ alkoxy-$C_1$-$C_6$ alkyl group; a phenyloxy-$C_1$-$C_6$ alkyl group; a $C_1$-$C_6$ haloalkoxy-$C_1$-$C_6$ alkyl group; a tetrahydrofuran-$C_1$-$C_6$ alkoxy-$C_1$-$C_6$ alkyl group; a $C_1$-$C_6$ alkylsulfonyl-$C_1$-$C_6$ alkoxy-$C_1$-$C_6$ alkyl group; cyano-$C_1$-$C_6$ alkoxy-$C_1$-$C_6$ alkyl group; a cyano-$C_1$-$C_6$ alkyl group; a $C_1$-$C_6$ alkylcarbonyloxy-$C_1$-$C_6$ alkyl group; a $C_1$-$C_6$ acyl-$C_1$-$C_6$ alkyl group; a $C_1$-$C_6$ alkoxycarbonyl-$C_1$-$C_6$ alkyl group; a ($R^6R^7N$—C=O)—$C_1$-$C_6$ alkyl group; a $C_6$-$C_{10}$ aryl-$C_1$-$C_6$ alkyl group (the aryl moiety of the group may be substituted with one or two or more identical or different $R^8$s); a Het$^1$-$C_1$-$C_6$ alkyl group (the group may be substituted with one or two or more identical or different $R^9$s); a $NR^{10}R^{11}$ group; a $C_6$-$C_{10}$ aryl group (the group may be substituted with one or two or more identical or different $R^{12}$s); or a $Het^1$ group (the group may be substituted with one or two or more identical or different $R^{13}$s);

$R^2$ represents a halogen atom; a nitro group; a $C_1$-$C_6$ alkyl group; a $C_1$-$C_6$ haloalkyl group; a $C_1$-$C_6$ alkoxy group; a $C_1$-$C_6$ alkylthio group; a $C_1$-$C_6$ alkylsulfonyl group; or a $C_1$-$C_6$ alkoxy-$C_1$-$C_6$ alkyl group;

n represents 0, 1, 2, or 3;

$R^6$ and $R^7$ each independently represent a $C_1$-$C_6$ alkyl group, and furthermore, $R^6$ and $R^7$ may be joined with the nitrogen atom to which these are bound, to form a 5- to 6-membered ring, while the ring thus formed may have an oxygen atom interposed, in addition to the nitrogen atom to which $R^6$ and $R^7$ are bound;

$R^8$ represents a halogen atom; a $C_1$-$C_6$ haloalkyl group; a $C_1$-$C_6$ alkoxy group; or a $C_1$-$C_6$ haloalkoxy group;

$R^9$ represents a $C_1$-$C_6$ alkyl group; a halogen atom; or a $C_1$-$C_6$ haloalkyl group;

$R^{10}$ and $R^{11}$ each independently represent a $C_1$-$C_6$ alkyl group; or a $C_1$-$C_6$ alkoxycarbonyl group;

$R^{12}$ represents a halogen atom; a hydroxy group; a nitro group; a cyano group; a $C_1$-$C_6$ alkyl group; a $C_3$-$C_8$ cycloalkyl group; a $C_1$-$C_6$ haloalkyl group; a $C_1$-$C_6$ alkoxy group; a $C_2$-$C_6$ alkenyloxy group; a $C_2$-$C_6$ alkynyloxy group; a $C_1$-$C_6$ haloalkoxy group; a $C_1$-$C_6$ alkylthio group; a $C_1$-$C_6$ alkylsulfonyl group; a $C_1$-$C_6$ haloalkylthio group; a $C_1$-$C_6$ alkoxy-$C_1$-$C_6$ alkyl group; a $C_3$-$C_8$ cycloalkyl-$C_1$-$C_6$ alkyloxy group; a cyano-$C_1$-$C_6$ alkoxy group; a $C_1$-$C_6$ acyl group; a $C_1$-$C_6$ alkoxycarbonyl group; a di($C_1$-$C_6$ alkyl)amino group; or a $Het^1$-$C_1$-$C_6$ alkoxy group, and furthermore, two adjacent $R^{12}$s may be joined with the respective carbon atoms to which they are directly bound, to form a 4- to 8-membered carbocyclic ring or a 4- to 8-membered heterocyclic ring having 1 to 4 heteroatoms selected from an oxygen atom, a sulfur atom and a nitrogen atom, while the ring thus formed may be substituted with a halogen atom; a $C_1$-$C_6$ alkyl group; or an oxo group;

$R^{13}$ represents an oxo group; a halogen atom; a $C_1$-$C_6$ alkyl group; a $C_1$-$C_6$ haloalkyl group; a $C_1$-$C_6$ alkoxy group; or a mono($C_1$-$C_6$ alkyl)amino group;

$Het^1$ represents tetrahydrothiophene, tetrahydrothiophene dioxide, tetrahydrothiopyrane, tetrahydrothiopyrane dioxide, 4,5-dihydroisoxazole, thiophene, pyrazole, oxazole, isoxazole, thiazole, isothiazole, 1,2,4-triazole, 1,2,4-oxadiazole, 1,3,4-thiadiazole, pyridine, pyridazine, pyrimidine, pyrazine, 2,3-dihydrobenzofuran, 1,3-benzodioxole, benzo-1,4-dioxane, benzofuran or indole.

12. The compound according to claim 11, wherein:

$R^1$ is a $C_2$-$C_6$ alkynyl group; a $C_3$-$C_8$ cycloalkyl group; a $C_1$-$C_6$ haloalkyl group; a $C_2$-$C_6$ haloalkenyl group; a $C_1$-$C_6$ alkylthio-$C_1$-$C_6$ alkyl group; a $C_1$-$C_6$ alkylsulfonyl-$C_1$-$C_6$ alkyl group; a $C_1$-$C_6$ alkoxy-$C_1$-$C_6$ alkoxy-$C_1$-$C_6$ alkyl group; a phenyloxy-$C_1$-$C_6$ alkyl group; a $C_1$-$C_6$ haloalkoxy-$C_1$-$C_6$ alkyl group; a tetrahydrofuran-$C_1$-$C_6$ alkoxy-$C_1$-$C_6$ alkyl group; a $C_1$-$C_6$ alkylsulfonyl-$C_1$-$C_6$ alkoxy-$C_1$-$C_6$ alkyl group; a cyano-$C_1$-$C_6$ alkoxy-$C_1$-$C_6$ alkyl group; a cyano-$C_1$-$C_6$ alkyl group; a $C_1$-$C_6$ alkylcarbonyloxy-$C_1$-$C_6$ alkyl group; a $C_1$-$C_6$ acyl-$C_1$-$C_6$ alkyl group; a $C_1$-$C_6$ alkoxycarbonyl-$C_1$-$C_6$ alkyl group; a $(R^6R^7N-C=O)-C_1$-$C_6$ alkyl group; a $C_6$-$C_{10}$ aryl-$C_1$-$C_6$ alkyl group (the aryl moiety of the group may be substituted with one or two or more identical or different $R^8$s), a $Het^1$-$C_1$-$C_6$ alkyl group (the group may be substituted with one or two or more identical or different $R^9$s); a $NR^{10}R^{11}$ group; or a $Het^1$ group (the group may be substituted with one or two or more identical or different $R^{13}$s).

13. The compound according to claim 1, wherein:

$R^1$ is a $C_6$-$C_{10}$ aryl group (the group may be substituted with one or two or more identical or different $R^{12}$s).

* * * * *